(12) United States Patent
Bradshaw et al.

(10) Patent No.: US 7,521,425 B2
(45) Date of Patent: Apr. 21, 2009

(54) ANTI-ANGIOGENIC COMPOUNDS

(75) Inventors: Curt W. Bradshaw, San Diego, CA (US); Venkata Ramana Doppalapudi, San Diego, CA (US); Jing-Yu Lai, San Diego, CA (US); John Rizzo, Oceanside, CA (US)

(73) Assignee: Covx Technologies Ireland Limited, Dublin (IE)

( * ) Notice: Subject to any disclaimer, the term of this patent is extended or adjusted under 35 U.S.C. 154(b) by 0 days.

(21) Appl. No.: 11/368,338

(22) Filed: Mar. 3, 2006

(65) Prior Publication Data

US 2006/0205670 A1 Sep. 14, 2006

Related U.S. Application Data

(60) Provisional application No. 60/658,654, filed on Mar. 3, 2005, provisional application No. 60/677,089, filed on May 2, 2005.

(51) Int. Cl.
*A61K 38/04* (2006.01)
(52) U.S. Cl. ................. 514/15; 530/328; 530/387.1; 424/1.49
(58) Field of Classification Search ............. None
See application file for complete search history.

(56) References Cited

U.S. PATENT DOCUMENTS

| | | | |
|---|---|---|---|
| 3,719,667 A | 3/1973 | Gutowski | |
| 3,840,556 A | 10/1974 | Kukolja | |
| 5,216,132 A | 6/1993 | Basi | |
| 5,229,275 A | 7/1993 | Goroff | |
| 5,565,332 A | 10/1996 | Hoogenboom et al. | |
| 5,567,610 A | 10/1996 | Borrebaeck et al. | |
| 5,573,905 A | 11/1996 | Lerner et al. | |
| 5,733,757 A | 3/1998 | Barbas, III et al. | |
| 5,739,277 A | 4/1998 | Presta et al. | |
| 5,932,545 A | 8/1999 | Henkin et al. | |
| 5,985,626 A | 11/1999 | Barbas, III et al. | |
| 6,013,625 A | 1/2000 | Pierschbacher et al. | |
| 6,080,840 A | 6/2000 | Slanetz et al. | |
| 6,210,938 B1 | 4/2001 | Barbas et al. | |
| 6,326,176 B1 | 12/2001 | Barbas et al. | |
| 6,368,839 B1 | 4/2002 | Barbas, III et al. | |
| 6,589,766 B1 | 7/2003 | Barbas et al. | |
| 6,696,245 B2 | 2/2004 | Winter et al. | |
| 6,716,963 B1 * | 4/2004 | Henkin et al. ............. | 530/328 |
| 6,753,408 B1 | 6/2004 | Haviv et al. | |
| 6,774,211 B1 | 8/2004 | Henkin et al. | |
| 2002/0183242 A1 | 12/2002 | Henkin et al. | |
| 2003/0045477 A1 | 3/2003 | Haviv et al. | |
| 2003/0175921 A1 * | 9/2003 | Barbas et al. ............ | 435/188.5 |

FOREIGN PATENT DOCUMENTS

| | | |
|---|---|---|
| WO | WO 95/14714 | 6/1995 |
| WO | WO 97/17852 | 5/1997 |
| WO | WO 99/61476 | 12/1999 |
| WO | WO 01/22922 | 4/2001 |
| WO | WO 01/38347 | 5/2001 |
| WO | WO 01/38397 | 5/2001 |
| WO | WO 03/002609 | 1/2003 |
| WO | WO 2004/003019 | 1/2004 |
| WO | WO 2004/058821 | 7/2004 |

OTHER PUBLICATIONS

Li, Lian-Sheng et al. Chemical Adaptor Immunotherapy: Design, Synthesis, and Evaluation of Novel Integrin-Targeting Devices. *Journal of Medicinal Chemistry*. Oct. 6, 2004, vol. 47, No. 23, pp. 5630-5640.

PCT International Search Report for International Application No. PCT/US06/07865 dated Oct. 20, 2006, 4 pages.

Barbas III, C.F., et al. Immune Versus Natural Selection: Antibody Aldolases with Enzymic Rates But Broader Scope. *Science* 278:2085-2092 (1997).

Basi, G.S. et al. Antibodies to Soluble Human T Cell Receptor γ Chain Recognize Multiple Epitopes on Cell Surface TcR. *J. Immunol. Methods* 155:175-191 (1992).

Bodor, N. Novel Approaches in Prodrug Design. *Drugs of the Future* 6:165-182 (1981).

Borrebaeck, C.A.K., et al. Human Monoclonal Antibodies Produced by Primary in vitro Immunication of Peripheral Blood Lymphocytes. *Proc. Natl. Acad. Sci. USA.* 85:3995-3999 (1988).

Brennan, M. et al. Preparation of Bispecific Antibodies by Chemical Recombination of Monoclonal Immunoglobulin G1 Fragments. *Science* 229:81-83 (1985).

Brooks, P. et al. Integrin $\alpha_v\beta_3$ Antagonists Promote Tumor Regression by Inducing Apoptosis of Angiogenic Blood Vessels. *Cell* 79:1157-1164 (1994).

Bruggemann, M. et al. A Repertoire of Monoclonal Antibodies with Human Heavy Chaims from Transgenic Mice. *Proc. Natl. Acad. Sci. USA.* 86:6709-6713 (1989).

Bruggemann, M. et al. Designer Mice: The Production of Human Antibody Repertoires in Transgenic Animals. *Year Immunol.* 7:33-40 (1993).

Cahn, R. S. et al. Specification of Molecular Chirality. *Angew. Chem. Intl. Edit. Engl.* 5:385-415 (1966).

Carter, P. et al. High Level *Escherichia coli* Expression and Production of a Bivalent Humanized Antibody Fragment. *Biotechnology* 10:163-167 (1992).

Carter, P. et al. Humanization of an Anti-p185[HER2] Antibody for Human Cancer Therapy. *Proc. Natl. Acad. Sci. USA.* 89:4285-4289 (1992).

(Continued)

*Primary Examiner*—Cecilia Tsang
*Assistant Examiner*—Satyanarayana Gudibande
(74) *Attorney, Agent, or Firm*—Michael J. Wise; Perkins Coie LLP

(57) ABSTRACT

The present invention provides AA targeting compounds which comprise AA targeting agent-linker conjugates which are linked to a combining site of an antibody. Various uses of the compounds are provided, including methods to treat disorders connected to abnormal angiogenesis.

12 Claims, 30 Drawing Sheets

OTHER PUBLICATIONS

Chin, J.W. and P.G. Schultz. In Vivo Photocrosslinking with Unnatural Amino Acid Mutagenesis. *ChemBioChem.* 3:1135-1137 (2002).

Chin, J.W. et al. Addition of a Photocrosslinking Amino Acide to the Genetic Code of *Escherichia coli. Proc. Natl. Acad. Sci. USA* 99:11020-11024 (2002).

Chin, J.W. et al. Addition of p-Azido-L-phenylalanine to the Genetic Code of *Escherichia coli. J. Am. Chem. Soc.* 124:9026-9027 (2002).

Chin, J.W. et al. An Expanded Eukryotic Genetic Code. *Science* 301:964-966 (2003).

Chothia, C. and Lesk, A.M. Canonical Structures for the Hypervariable Regions of Immunoglobulins. *J. Mol. Biol.* 196:901-917 (1987).

Chothia, C. et al. Conformations of Immunoglobulin Hypervariable Regions. *Nature* 342:877-883 (1989).

Clackson, T. et al. Making Antibody Fragments Using Phage Display Libraries. *Nature* 352:624-628 (1991).

Cohen, B.D. et al. Combination Therapy Enhances the Inhibition of Tumor Growth with the Fully Human Anti-Type 1 Insulin-Like Growth Factor Receptor Monoclonal Antibody CP-751,871. *Clin. Cancer Res.* 11:2063-2073 (2005).

Cunningham, B.C. and J.A. Wells. High-Resolution Epitope Mapping of hGH-Receptor Interacton by Alanine-Scanning Mutagenesis. *Science* 244:1081-1085 (1989).

de Haard, H.J. et al. A Large Non-immunized Human Fab Fragment Phage Library That Permits Rapid Isolation and Kinetic Analysis of High Affintiy Antibodies. *J. Biol. Chem.* 274:18218-18230 (1999).

Folkman, J. How is Blood Vessel Growth hRegulated in Normal and Neoplastic Tissue? *Cancer Research* 46:467-473 (1986).

Folkman, J. What is the Evidence that Tumors are Angiogenesis Dependent? *J. Natl. Cancer Inst.* 82:4-6 (1989).

Francis, G.E., et al. PEGylation of Cytokines and Other Therapeutic Proteins and Peptides: the Importance of Biological Optimisation of Coupling Techniques. *Intl. J. Hematol.* 68:1-18 (1998).

Glennie, M.J. and Stevenson, G.T. Univalent Antibodies Kill Tumour Cells in vivo. *Nature* 295:712-714 (1982).

Griffiths, A.D., et al. Human Anti-self Antibodies with High Specificity from Phage Display Libraries. *EMBO J.* 12:725-734 (1993).

Gutowski, G.E. 6-EPI-Penicillins and 7-EPI-Cephalosporins. *Tetrahedron Lett.* 21:1779-1782 (1970).

Hardman, N. et al. Generation of a Recombinant Mouse-Human Chimaeric Monoclonal Antibody Directed Against Human Carcinoembryonic Antigen. *Int. J. Cancer* 44:424-433 (1989).

Holler, P.D. et al. In Vitro Evolution of a T Cell Receptor with Affinity for Peptide/MHC. *Proc. Natl. Acad. Sci. USA* 97:5387-5392 (2000).

Huston, J.S. et al. Protein Engineering of Antibody Binding Sites: Recovery of Specific Activity in an Anti-digozin Sinle-chain Fv analogue Produced in *Escherichia coli. Proc. Natl. Acad. Sci. USA* 85:5879-5883 (1988).

IUPAC-IUB Commission on Biochemical Nomenclature. Abbreviated Nomenclature of Synthetic Polypeptides (Ploymerized Amino Acides). *Biochemistry* 11:942-944 (1972).

Jakobovits, A. et al. Analysis of Homozygous Mutant Chimeric Mice: Deletion of the Immunoglobulin Heavy-chain Joining Region Blocks B-cell Development and Antibody Production. *Proc. Natl. Acad. Sci. USA* 90:2551-2555 (1993).

Jakobovits, A. et al. Germ-like Transmission and Expression of a Human-derived Yeast Artificial Chromosome. *Nature* 362:255-258 (1993).

Janda, K.D. et al. Direct Selection for a catalytic Mechanism from Combinatorial Antibody Libraries. *Proc. Natl. Acad. Sci. USA* 91:2532-2536 (1994).

Jespers, L. S. et al. Guiding the Selection of Human Antibodies from Phage Display Repertoires to a Single Epitope of an Antigen. *Biotechnology* 12:899-903 (1994).

Johnson, K. S. and Chiswell, D.J. Human Antibody Engineering. *Curr. Opin. Struct. Biol.* 3:564-571 (1993).

Jones, P. T. et al. Replacing the Complementarity-determining Regions in a Human Antibody Those from a Mouse. *Nature* 321:522-525 (1986).

Karlstrom, A., et al. Using Antibody Catlysis to Study the Outcome of Multiple Evolutionary Trials of a Chemical Task. *Proc. Natl. Acad. Sci. USA* 97:3878-3883 (2000).

Katre, N. V. Immunogenicity of Recombinant IL-2 Modified by Covalent Attachment of Polyethylene Glycol. *J. Immunology* 144:209-213 (1990).

Knappik, A. et al. Fully Synthetic Human Combinatorial Antibody Libraries (HuCAL) Based on Mudular Consensus Framework and CDRs Reandomized with Trinucleotides. *J. Mol. Biol.* 296, 57-86 (2000).

Kukolja, S. Electrophilic Opening of the Thiazolidine Ring in Penicillins. *J. Am. Chem. Soc.* 93:6267-6269 (1971).

Lappi, D. Tumor Targeting Through Fibroblast Growth Factor Receptors. *Seminars in Cancer Biology* 6:279-288 (1995).

Lerner, R. A. and C. F. Barbas, III. Using the Process of Reactive Immunication to Induce Catalytic Antibodies with Complex Mechanism: Aldolases. *Acta Chemica Scand.* 50:672-678 (1996).

Lonberg, N. et al. Antigen-specific human Antibodies from Mice Comprising Four Distinct Genetic Modifications. *Nature* 368:856-859 (1994).

MacCallum, R. M. et al. Antibody-antigen Interactions: Contact Analysis and Binding Site Topography. *J. Mol. Biol.* 262:732-745 (1996).

Marks, J. D. et al. By-passing Immunization Human Antibodies from V-gene Libraries Displayed on Pahge. *J. Mol. Biol.* 222:581-597 (1991).

McCafferty J. et al. Phage Antibodies: Filamentous Phage Displaying Antibody Variable Domains. *Nature* 348:552-553 (1990).

Morimoto, K. and Inouye, K. Single-step Purification of F(ab')$_2$ Fragments of Mouse Monoclonal Antibodies (Immunoglobulines G1) by Hydrophobic Interaction High Performance Liquid Chromatography Using TSKgel Phenyl-5PW. *J. Biochem. Biophys. Methods* 24:107-117 (1992).

Mustonen, T. and Alitalo, K. Endothelial Receptor Tyrosine Kinases Involved in Angiogenesis. *J. Cell Biol.* 129:895-898 (1995).

Muyldermans et al. Recognition of Antigens by Single-Domain Antibody Fragments: The Superfluous Luxury of Paired Domains. *TRENDS in Biochem. Sci.* 26(4):230-235 (1991).

Notari, R.E., Theory and Practice of Prodrug Kinetics. *Methods Enzymol.* 112:309-323 (1985).

Olafsen, T., et al., Characterization of Engineered Anti-p185$^{HER-2}$ (scFv-C$_H$3)$_2$ Antibody Fragments (Minibodies) for Tumor Targeting. *Protein Eng. Des. Sel.* 17:315-323 (2004).

Polverini, P.J. et al. Assay and Purification of Naturally Occurring Inhibitor of Angiogenesis. *Methods Enzymol.* 198:440-450 (1991).

Presta, L.G. et al. Humanization of an Antibody Directed Against IgE. *J. Immunol.* 151:2623-2632 (1993).

Queen, C. et al. A Humanized Antibody That Binds to the Interleukin 2 Receptor. *Proc. Natl. Acad. Sci. USA* 86:10029-10033 (1989).

Rader, C. et al. A Humanized Aldolase Antibody for Selective Chemotherapy and Adaptor Immunotherapy. *J. Mol. Biol.* 332:889-899 (2003).

Rader, C. et al. A Phage Display Approach for Rapid Antibody Humanization: Designed Combinatorial V Gene Libraries. *Proc. Nat. Acad. Sci. USA* 95:8910-8915 (1998).

Rader, C. et al. Integrin αvβ3-Targeted Therapy for Kaposi's Sarcoma With an In Viro-Evolved Antibody. *The FASEB Journal*, published online Oct. 18, 2002.

Rader, C. et al. The Rabbit Antibody Repertoire as a Novel Source for the Generation of Therapeutic Human Antibodies. *J. Biol. Chem.* 275:13668-13676 (2000).

Riechmann, L. et al. Reshaping Human Antibodies for Therapy. *Nature* 332:323-327 (1988).

Roche, Edward B. *Bioreversible Carriers in Drug Design: Theory and Application* (E.B. Roche, ed.), Pergamon Press, New York (1987), pp. 14-21.

Roguska, M.A. et al. Humanization of Murine Monoclonal Antibodies Through Variable Domain Resurfacing. *Proc. Natl. Acad. Sci. USA* 91:969-973 (1994).

Seitz, O. and H. Kunz, HYCRON, an Allylic Anchor for High-Efficiency Solid Phase Synthesis of Protected Peptides and Glycopeptides. *J. Org. Chem.* 62:813-826 (1997).

Shusta. E.V., et al. Directed Evolution of a Stable Scaffold for T-Cell Receptor Engineering. *Nat. Biotechnol.* 18:754-759 (2000).

Sims, M.J. et al. A Humanized CD18 Antibody Can Block Function without Cell Destruction. *J. Immunol.* 151:2296-2308 (1993).

Slanetz, A.E. and Bothwell, A.L., Eur. Heterodimeric, Disulfide-Linked α/β T Cell Receptors in Solution. *J. Immunol.* 21:179-183 (1991).

Stevenson, G.T. et al. A Chimeric Antibody with Dual Fc Regions (*bis*FabFc) Prepared By Manipulations at the IgG Hinge. *Anti-cancer Drug Des.* 3:219-230 (1989).

Taylor, L.D. et al. A Transgenic Mouse That Expresses a Diversity og Human Sequence Heavy and Light Chain Immunoglobulins. *Nucleic Acids Res.* 20:6287-6295 (1992).

Tramontano, A., et al. Framework Residue 71 is a Major Determinant of the Position and Conformation of the Second Hypervariable Region in the $V_H$ Domains of Immunoglobulins. *J. Mol. Biol.* 215:175-182 (1990).

Vallejo, Luis Felipe and Rinas, Ursula. Strategies for the Recovery of active Proteins Through Refolding of Bacterial Inclusion Body Proteins. *Microbial Cell Factories* 3:11 (2004) and *Biomed Central* available at world wide web URL microbialcellfactories.com/content/3/1/11.

Verhoeyen, M. et al. Reshaping Human Antibodies: Grafting an Antilysozyme Activity. *Science* 239:1534-1536 (1988).

Wagner J. et al. Efficient Aldolase Catalytic Antibodies That Use the Enamine Mechanism of Natural Enzymes. *Science* 270:1797-1800 (1995).

Wang, L. and P.G. Schultz, Expanding the Genetic Code. *Chem. Commun.* (1):1-11 (2002).

Wang, L. et al. Adding L-3-(2-Naphthyl)alanine to the Genetic Code of *E. coli. J. Am. Chem. Soc.* 124:1836-1837 (2002).

Wang, L. et al. Addition of the Keto Functional Group to the Genetic Code of *Escherichia coli. Proc. Natl. Acad. Sci. USA* 100:56-61 (2003).

Wang, L. et al. Expanding the Genetic Code of *Escherichia coli. Science* 292:498-500 (2001).

Weidner, N. et al. Tumor Angiogenesis and Metastasis—Correlation in Invasive Breast Carcinoma. *N. Engl. J. Med.* 324:1-8 (1991).

Wirsching, P. et al. Reactive Immunization. *Science* 270:1775-1782 (1995).

Zhang, Z., et al. The Selective Incorporation of Alkenes into Proteins in *Escherichia coli. Angew. Chem. Intl. Edit. Engl.* 41:2840-2842 (2002).

Zhong, G. et al. Broadening the Aldolase Catalytic Antibody Repertoire by Combining Reactive Immunization and Transition State Theory: New Enantio- and Diastereoselectivities. *Angew. Chem. Intl. Edit. Engl.* 38:3738-3741 (1999).

* cited by examiner

FIGURE 1A
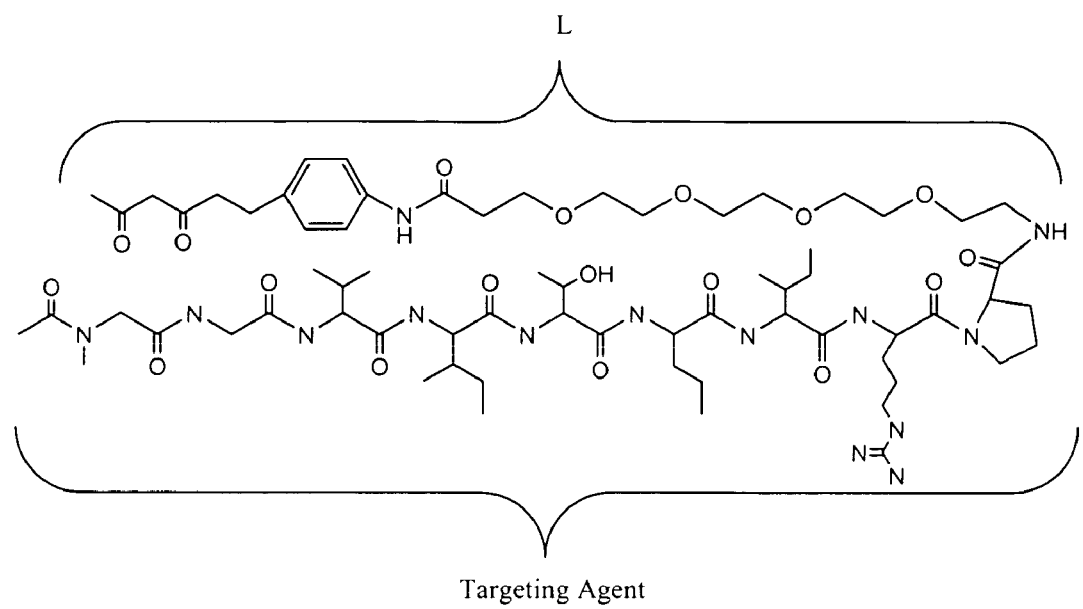
Targeting Agent
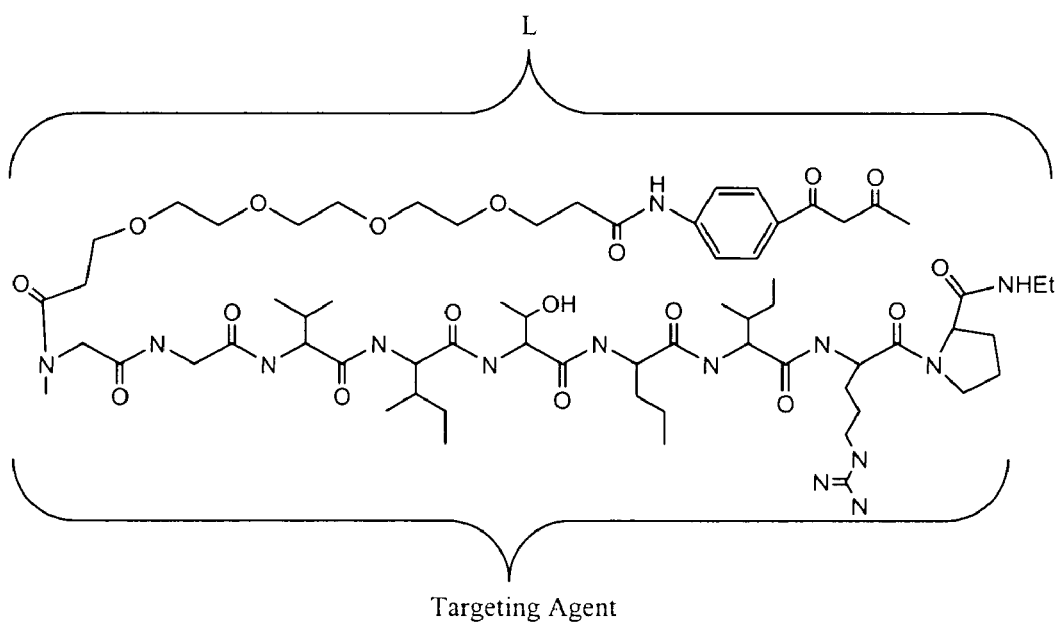
Targeting Agent

FIGURE 1B
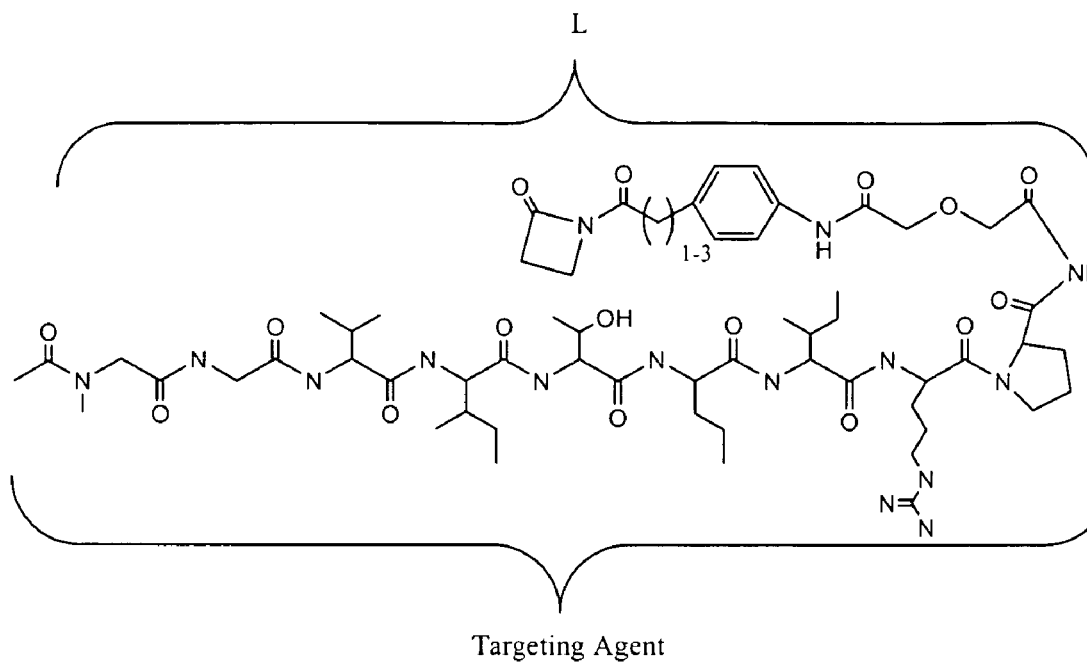
Targeting Agent
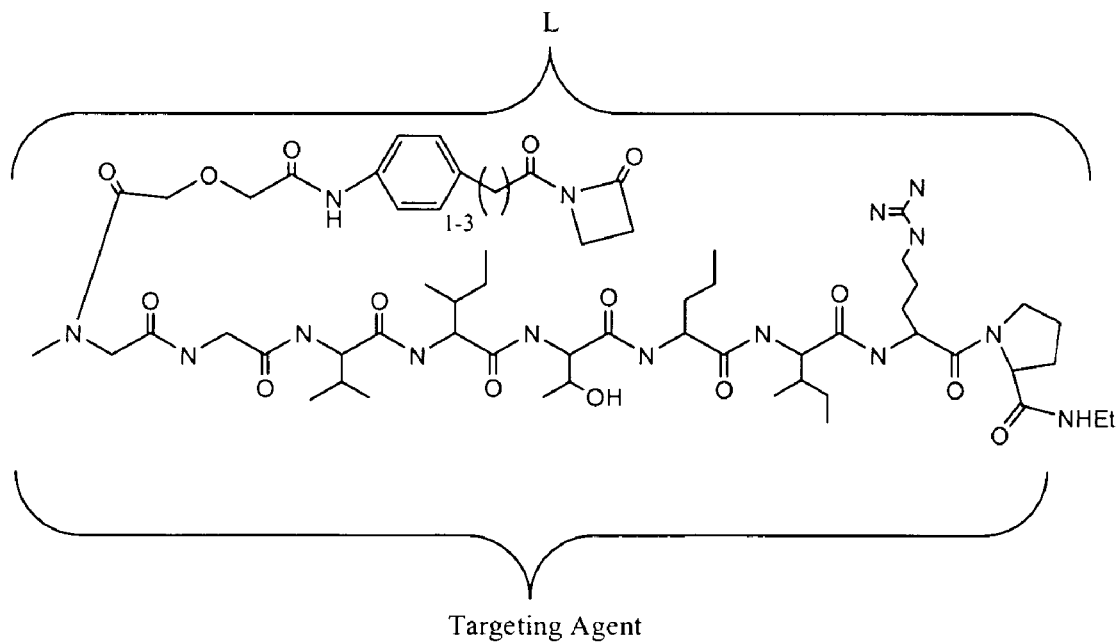
Targeting Agent

FIGURE 2
Targeting Agent
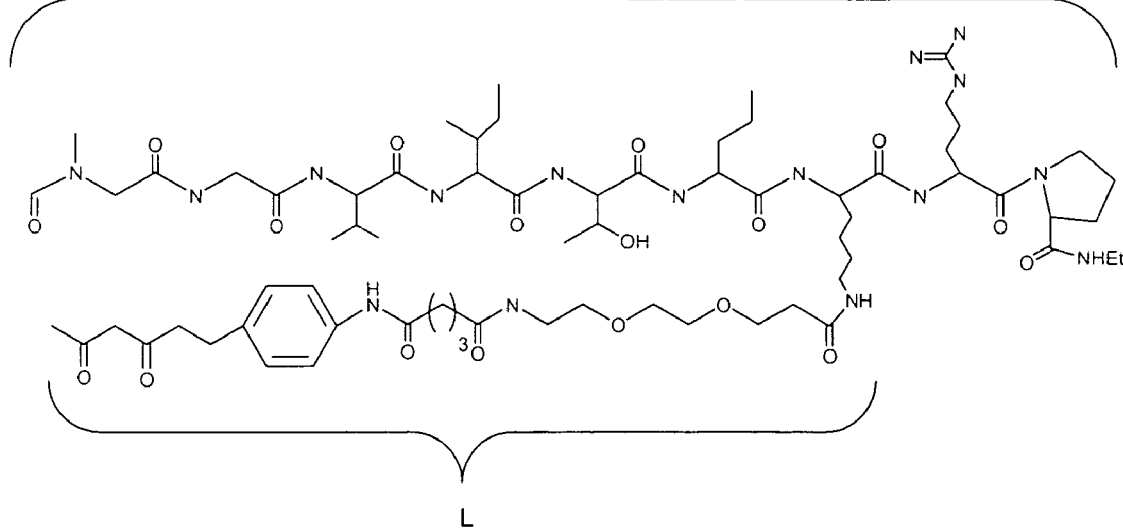
L
Targeting Agent
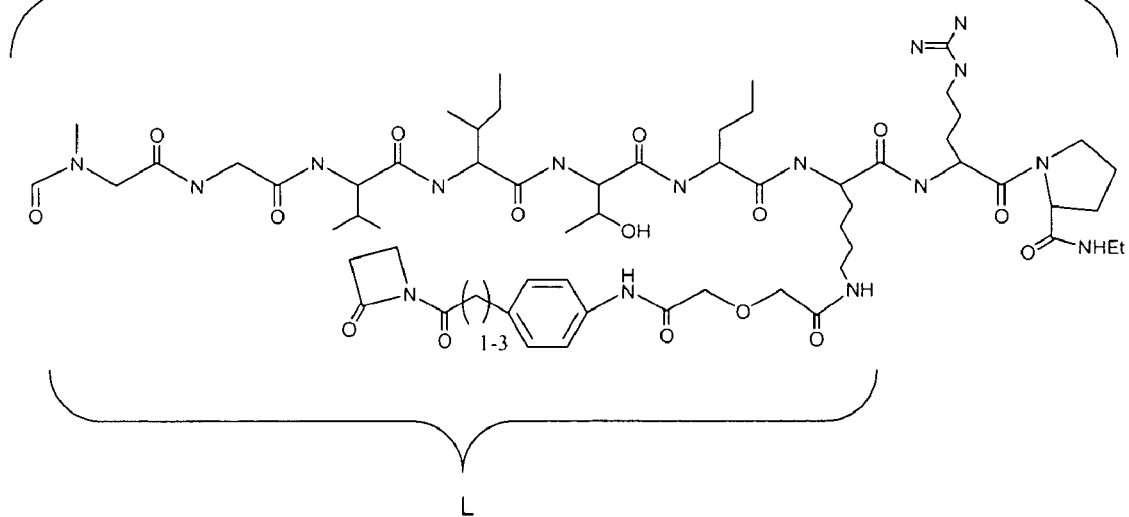
L

FIGURE 3
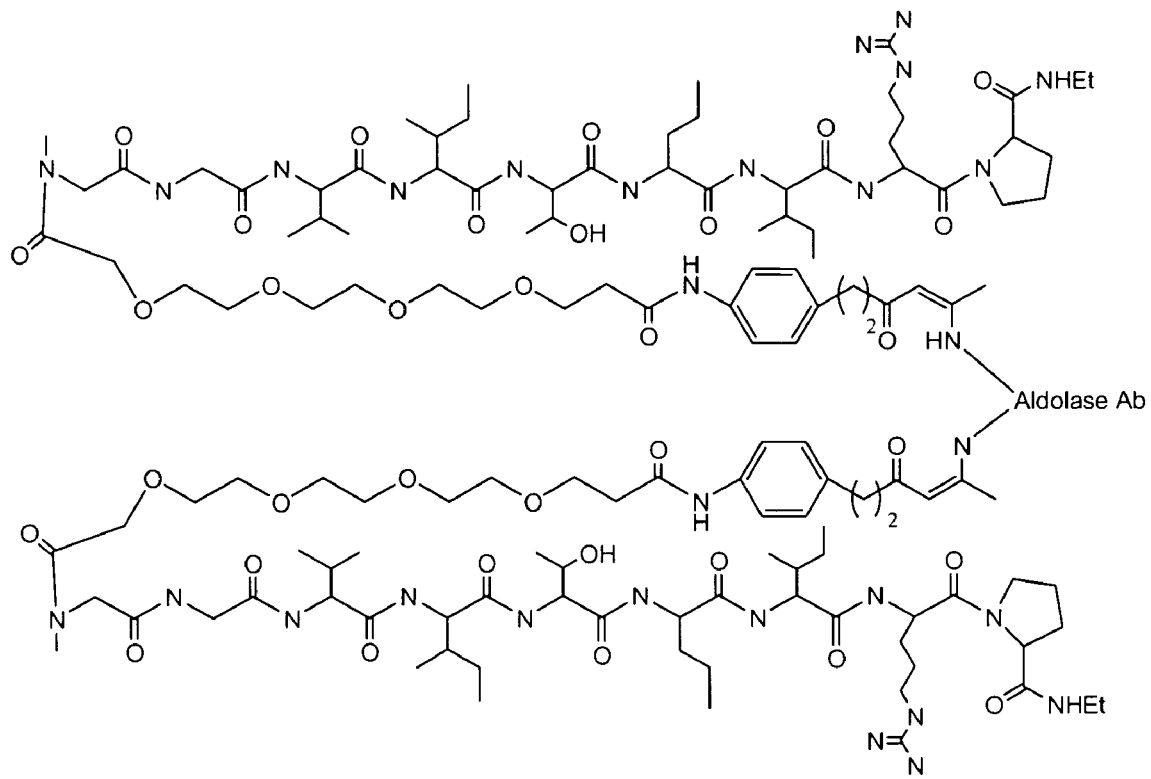
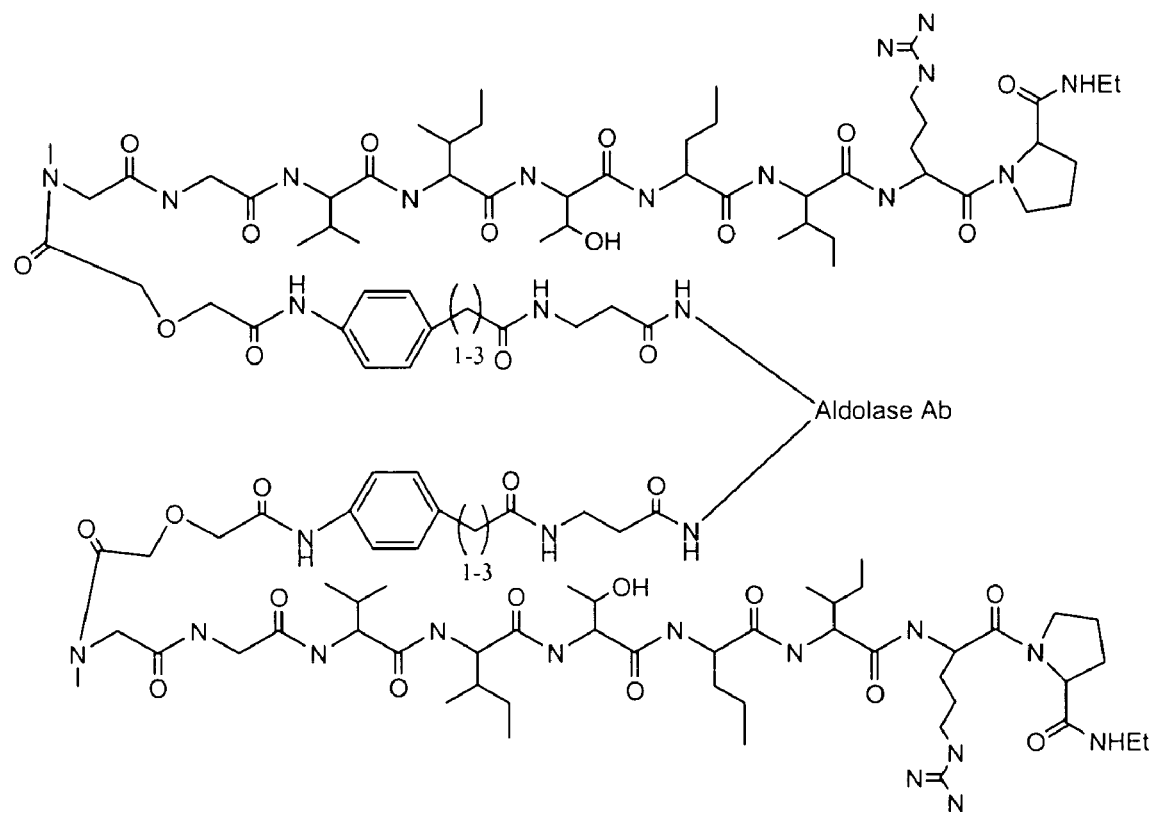

FIGURE 4
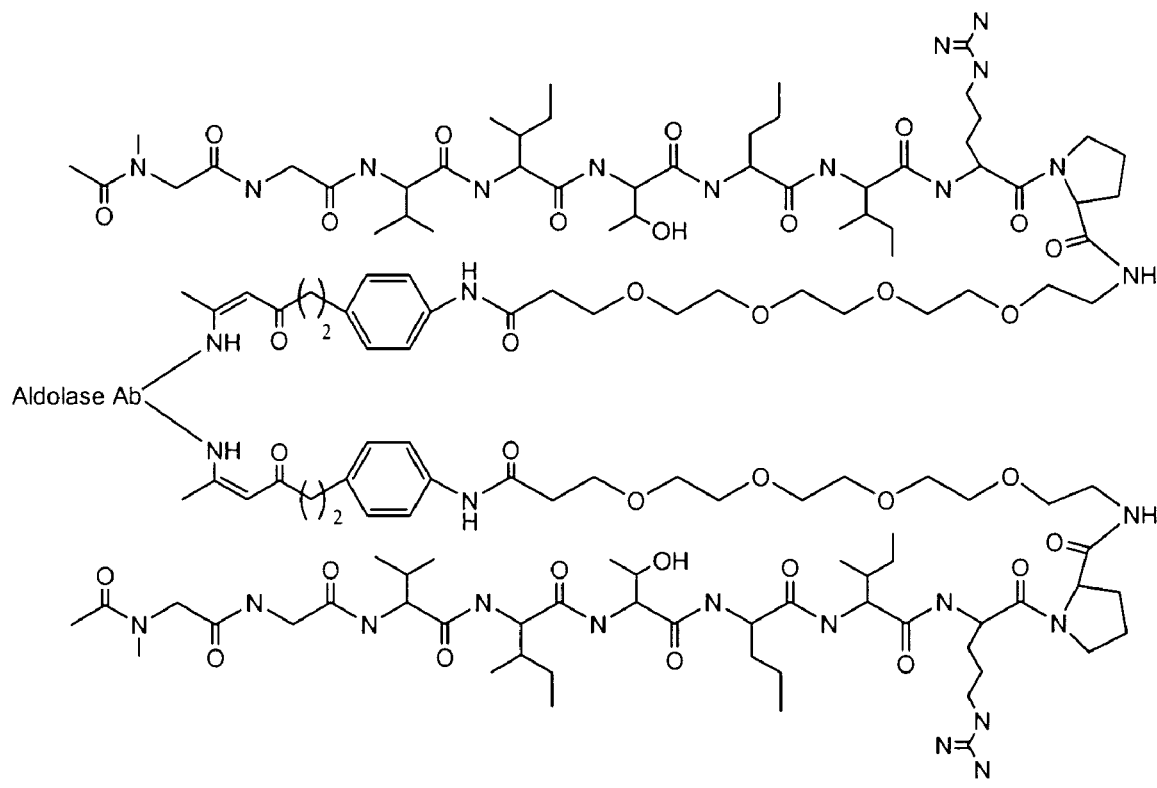
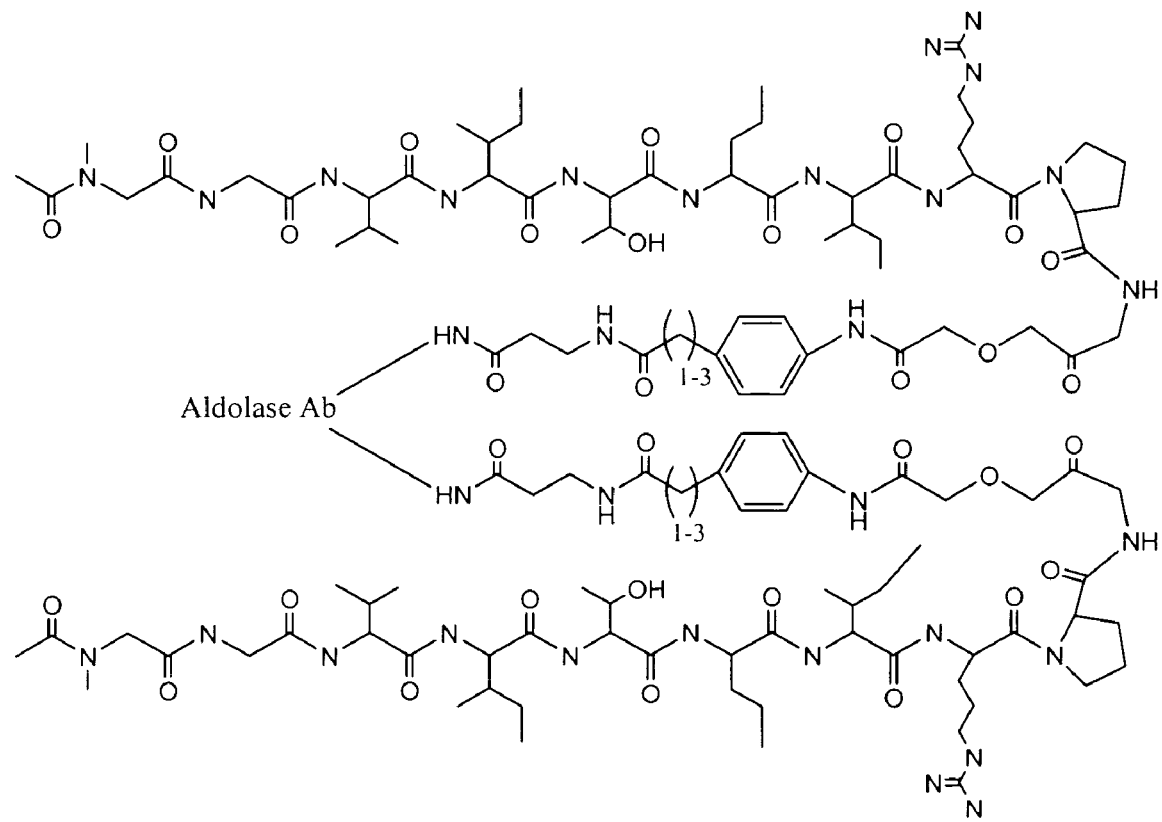

FIGURE 5
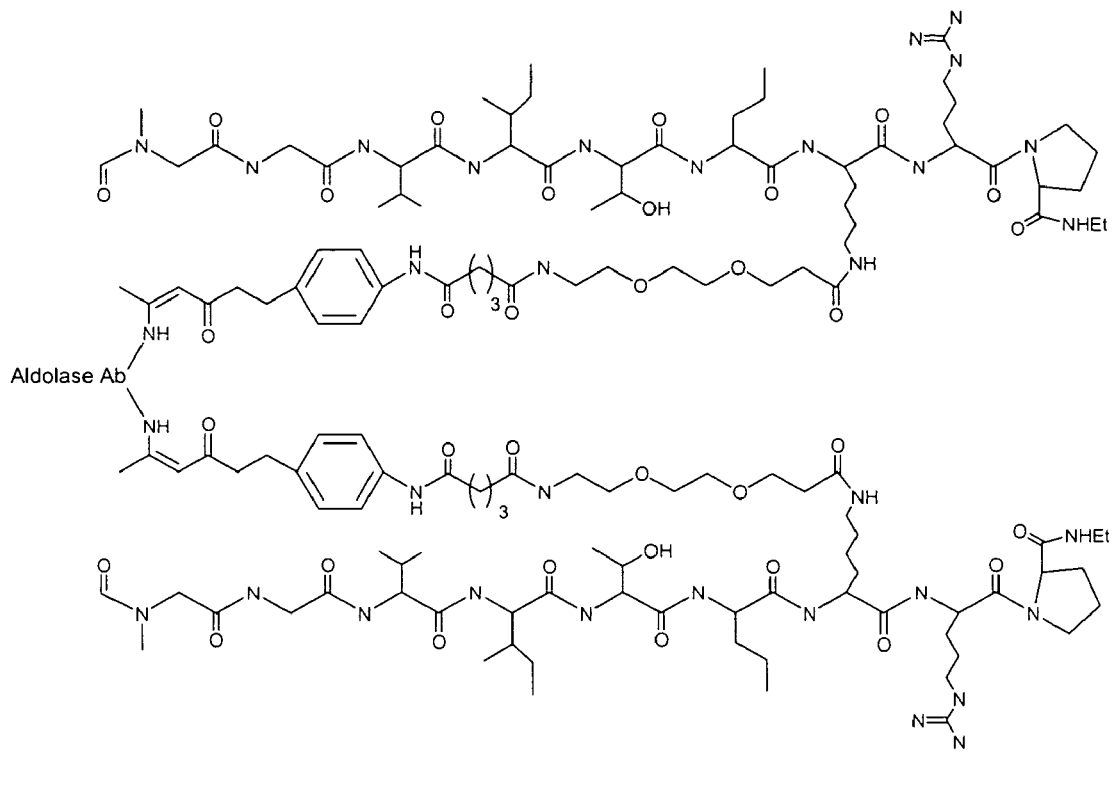
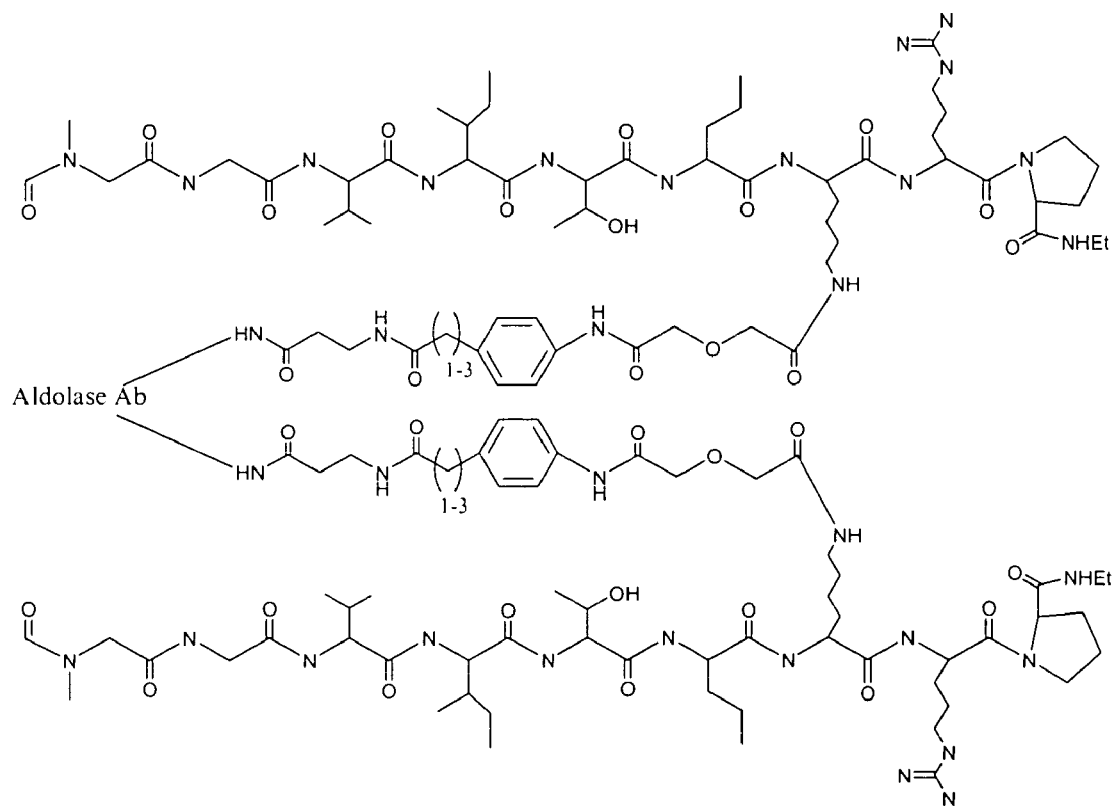

```
                FR1                     CDR1                    FR2            CDR2              FR3                                CDR3        FR4
          1         2         3                        4         5          6         7         8         9         0          1
       1234567890123 4567890labcde234 56789012345678 9 0123456 789012345678 901234567 8901234567
m38C2  DVVMTQTPLSLPVRLGDQASISC RSSQSLLHTYGSPYLN WYLQKPGQSPKLLIY KVSNRFS GVPDRFSGSGSGTDFTLRISRVEAEDLGVYFC SQGTHLPYT FGGGTKLEIK
       ***  * *  ****  ***   *         ********          *  *         *   * **** *   *    *           * ****   *
h38C2  ELQMTQSPSSLSASVGDRVTITC RSSQSLLHTYGSPYLN WYLQKPGQSPKLLIY KVSNRFS GVPSRFSGSGSGTDFTLTISSLQPEDFAVYFC SQGTHLPYT FGGGTKVEIK
       **                      *        ********           ** ***              * ****     **  *  *        * ****      *
DPK-9  DIQMTQSPSSLSASVGDRVTITC RASQSISS-----YLN WYQQKPGKAPKLLIY AASSLQS GVPSRFSGSGSGTDFTLTISSLQPEDFATYYC
JK4                                                                                                    LT FGGGTKVEIK
```

```
                FR1                       CDR1            FR2              CDR2                     FR3                               CDR3          FR4
          1         2         3                    4         5              6         7         8         9                  1          1
       1234567890123456789012345 1ab2345 67890123456789 012abc345678901234 56789012345678901234abc3456789012345      56789012 34567890123
m38C2  EVKLVESGGGLVQPGGSLRLSCEISGLTFR N--YWMS WVRQSPEKGLEWVA EIRLRSDNYATHYAESVKG KFTISRDDSKSRLYLQMNSLRTEDTGIYYCKT YFY-SFSY WGQGTLVTVSA
       **                     *** *  * *   *              *     * *  ****     *           *   *       *   **         * **           *
h38C2  EVOLVESGGGLVQPGGSLRLSCAASGFTFS N--YWMS WVRQSPEKGLEWVS EIRLRSDNYATHYAESVKG RFTISRDNSKNTLYLQMNSLRAEDTGIYYCKT YFY-SFSY WGQGTLVTVSS
        *                           *          *         *                     *    * *  *          *  *
DP-47  EVQLLESGGGLVQPGGSLRLSCAASGFTFS S--YAMS WVRQAPGKGLEWVS AISG--SGGSTYYADSVKG RFTISRDNSKNTLYLQMNSLRAEDTAVYYCAK
JH4                                                                                                              YFDY WGQGTLVTVSS
```

Light Chain (219 amino acids):
ELQMTQSPSSLSASVGDRVTITCRSSQSLLHTYGSPYLNWYLQKPGQSPKLLIY
KVSNRFSGVPSRFSGSGSGTDFTLTISSLQPEDFAVYFCSQGTHLPYTFGGGTKV
EIKRTVAAPSVFIFPPSDEQLKSGTASVVCLLNNFYPREAKVQWKVDNALQSG
NSQESVTEQDSKDSTYSLSSTLTLSKADYEKHKVYACEVTHQGLSSPVTKSFNR
GEC

Heavy chain (448 amino acids):
EVQLVESGGGLVQPGGSLRLSCAASGFTFSNYWMSWVRQSPEKGLEWVSEIRL
RSDNYATHYAESVKGRFTISRDNSKNTLYLQMNSLRAEDTGIYYCKTYFYSFS
YWGQGTLVTVSSASTKGPSVFPLAPSSKSTSGGTAALGCLVKDYFPEPVTVSW
NSGALTSGVHTFPAVLQSSGLYSLSSVVTVPSSSLGTQTYICNVNHKPSNTKVD
KRVEPKSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGKE
YKCKVSNKALPAPIEKTISKAKGQPREPQVYTLPPSREEMTKNQVSLTCLVKGF
YPSDIAVEWESNGQPENNYKTTPPVLDSDGSFFLYSKLTVDKSRWQQGNVFSC
SVMHEALHNHYTQKSLSLSPGK Linker Reactive Groups

FIGURE 9
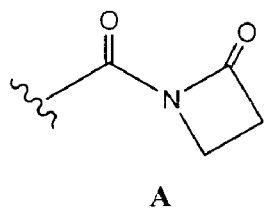
A
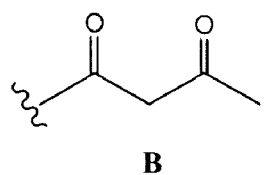
B
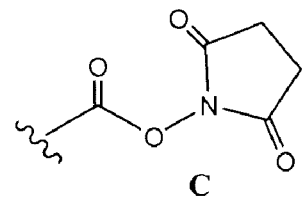
C
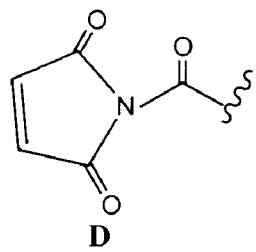
D
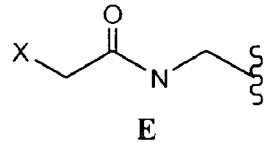
E
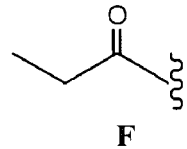
F
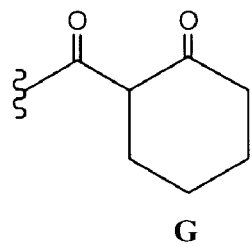
G
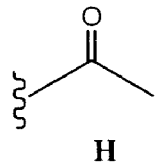
H

SEQUENCE LISTING

<160> NUMBER OF SEQ ID NOS: 41

<210> SEQ ID NO 1
<211> LENGTH: 11
<212> TYPE: PRT
<213> ORGANISM: Artificial
<220> FEATURE:
<223> OTHER INFORMATION: Peptide analog of thrombospondin-1
<220> FEATURE:

```
<221> NAME/KEY: MISC_FEATURE
<222> LOCATION: (1)..()
<223> OTHER INFORMATION: NH(CH3), N(CH3)C(O)CH3, N(CH3)C(O)CH2CH3,
      N(CH3)C(O)CH2CH2CH3, N(CH3)C(O)CH(CH3)CH3, N(CH3)C(O)CH2CH2CH2CH3,
      N(CH3)C(O)CH(CH3)CH2CH3, N(CH3)C(O)C6H5,
      N(CH3)C(O)CH2CH2(CH2CH2O)1-5Me, an amino protecting group, a
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: MISC_FEATURE
<222> LOCATION: (2)..()
<223> OTHER INFORMATION: Sarcosine
<220> FEATURE:
<221> NAME/KEY: MISC_FEATURE
<222> LOCATION: (5)..()
<223> OTHER INFORMATION: D-alloisoleucine
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (7)..()
<223> OTHER INFORMATION: Norvaline
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (11)..()
<223> OTHER INFORMATION: COOH, C(O)NH2, C(O)NH(CH3), C(O)NHCH2CH3,
      C(O)NHCH2CH2CH3, C(O)NHCH(CH3)CH3, C(O)NHCH2CH2CH2CH3,
      C(O)NHCH(CH3)CH2CH3, C(O)NHC6H5, C(O)NHCH2CH2OCH3, C(O)NHOCH3,
      C(O)NHOCH2CH3, a carboxy protecting group, a lipid fatty acid
      group, a carbohydrate, or
<220> FEATURE:
<221> NAME/KEY: misc_feature
<222> LOCATION: (11)..(11)
<223> OTHER INFORMATION: Xaa can be any naturally occurring amino acid

<400> SEQUENCE: 1

Xaa Xaa Gly Val Xaa Thr Xaa Ile Arg Pro Xaa
1               5                   10

<210> SEQ ID NO 2
<211> LENGTH: 11
<212> TYPE: PRT
<213> ORGANISM: Artificial
<220> FEATURE:
<223> OTHER INFORMATION: Peptide analog of thrombospondin-1
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (5)..()
<223> OTHER INFORMATION: D-alloisoleucine
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (7)..()
<223> OTHER INFORMATION: Norvaline
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (11)..()
<223> OTHER INFORMATION: COOH, C(O)NH2, C(O)NH(CH3), C(O)NHCH2CH3,
```

```
              C(O)NHCH2CH2CH3, C(O)NHCH(CH3)CH3, C(O)NHCH2CH2CH2CH3,
              C(O)NHCH(CH3)CH2CH3, C(O)NHC6H5, C(O)NHCH2CH2OCH3,C(O)NHOCH3,
              C(O)NHOCH2CH3, a carboxy protecting group, a lipid fatty acid
              group, a carbohydrate, or
<220>  FEATURE:
<221>  NAME/KEY: misc_feature
<222>  LOCATION: (11)..(11)
<223>  OTHER INFORMATION: Xaa can be any naturally occurring amino acid

<400>  SEQUENCE: 2

Xaa Pro Phe Val Xaa Thr Xaa Ile Arg Pro Xaa
1               5                   10

<210>  SEQ ID NO 3
<211>  LENGTH: 11
<212>  TYPE: PRT
<213>  ORGANISM: Artificial
<220>  FEATURE:
<223>  OTHER INFORMATION: Peptide analog of thrombospondin-1
<220>  FEATURE:
<221>  NAME/KEY: MISC_FEATURE
<222>  LOCATION: (1)..()
<223>  OTHER INFORMATION: NH(CH3), N(CH3)C(O)CH3, N(CH3)C(O)CH2CH3,
       N(CH3)C(O)CH2CH2CH3, N(CH3)C(O)CH(CH3)CH3, N(CH3)C(O)CH2CH2CH2CH3,
       N(CH3)C(O)CH(CH3)CH2CH3, N(CH3)C(O)C6H5,
       N(CH3)C(O)CH2CH2(CH2CH2O)1-5Me, an amino protecting group, a
<220>  FEATURE:
<221>  NAME/KEY: misc_feature
<222>  LOCATION: (1)..(2)
<223>  OTHER INFORMATION: Xaa can be any naturally occurring amino acid
<220>  FEATURE:
<221>  NAME/KEY: MISC_FEATURE
<222>  LOCATION: (2)..()
<223>  OTHER INFORMATION: Sarcosine
<220>  FEATURE:
<221>  NAME/KEY: MISC_FEATURE
<222>  LOCATION: (5)..()
<223>  OTHER INFORMATION: D-alloisoleucine
<220>  FEATURE:
<221>  NAME/KEY: misc_feature
<222>  LOCATION: (5)..(5)
<223>  OTHER INFORMATION: Xaa can be any naturally occurring amino acid
<220>  FEATURE:
<221>  NAME/KEY: MISC_FEATURE
<222>  LOCATION: (7)..()
<223>  OTHER INFORMATION: Norvaline
<220>  FEATURE:
<221>  NAME/KEY: misc_feature
<222>  LOCATION: (7)..(7)
<223>  OTHER INFORMATION: Xaa can be any naturally occurring amino acid
<220>  FEATURE:
<221>  NAME/KEY: MISC_FEATURE
<222>  LOCATION: (11)..()
<223>  OTHER INFORMATION: COOH, C(O)NH2, C(O)NH(CH3), C(O)NHCH2CH3,
       C(O)NHCH2CH2CH3, C(O)NHCH(CH3)CH3, C(O)NHCH2CH2CH2CH3,
       C(O)NHCH(CH3)CH2CH3, C(O)NHC6H5, C(O)NHCH2CH2OCH3,C(O)NHOCH3,
       C(O)NHOCH2CH3, a carboxy protecting group, a lipid fatty acid
       group, a carbohydrate, or
<220>  FEATURE:
<221>  NAME/KEY: misc_feature
<222>  LOCATION: (11)..(11)
<223>  OTHER INFORMATION: Xaa can be any naturally occurring amino acid

<400>  SEQUENCE: 3

Xaa Xaa Gly Val Xaa Thr Xaa Lys Arg Pro Xaa
1               5                   10

<210>  SEQ ID NO 4
<211>  LENGTH: 11
<212>  TYPE: PRT
<213>  ORGANISM: Artificial
<220>  FEATURE:
<223>  OTHER INFORMATION: Peptide analog of thrombospondin-1
<220>  FEATURE:
<221>  NAME/KEY: MISC_FEATURE
```

```
<222> LOCATION: (1)..()
<223> OTHER INFORMATION: NH(CH3), N(CH3)C(O)CH3, N(CH3)C(O)CH2CH3,
      N(CH3)C(O)CH2CH2CH3, N(CH3)C(O)CH(CH3)CH3, N(CH3)C(O)CH2CH2CH2CH3,
      N(CH3)C(O)CH(CH3)CH2CH3, N(CH3)C(O)C6H5,
      N(CH3)C(O)CH2CH2(CH2CH2O)1-5Me, an amino protecting group, a
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: MISC_FEATURE
<222> LOCATION: (2)..()
<223> OTHER INFORMATION: Sarcosine
<220> FEATURE:
<221> NAME/KEY: MISC_FEATURE
<222> LOCATION: (5)..()
<223> OTHER INFORMATION: D-alloisoleucine
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (11)..()
<223> OTHER INFORMATION: COOH, C(O)NH2, C(O)NH(CH3), C(O)NHCH2CH3,
      C(O)NHCH2CH2CH3, C(O)NHCH(CH3)CH3, C(O)NHCH2CH2CH2CH3,
      C(O)NHCH(CH3)CH2CH3, C(O)NHC6H5, C(O)NHCH2CH2OCH3,C(O)NHOCH3,
      C(O)NHOCH2CH3, a carboxy protecting group, a lipid fatty acid
      group, a carbohydrate, or
<220> FEATURE:
<221> NAME/KEY: misc_feature
<222> LOCATION: (11)..(11)
<223> OTHER INFORMATION: Xaa can be any naturally occurring amino acid

<400> SEQUENCE: 4

Xaa Xaa Gly Val Xaa Thr Lys Ile Arg Pro Xaa
1               5                   10

<210> SEQ ID NO 5
<211> LENGTH: 11
<212> TYPE: PRT
<213> ORGANISM: Artificial
<220> FEATURE:
<223> OTHER INFORMATION: Peptide analog of thrombospondin-1
<220> FEATURE:
<221> NAME/KEY: MISC_FEATURE
<222> LOCATION: (1)..()
<223> OTHER INFORMATION: NH(CH3), N(CH3)C(O)CH3, N(CH3)C(O)CH2CH3,
      N(CH3)C(O)CH2CH2CH3, N(CH3)C(O)CH(CH3)CH3, N(CH3)C(O)CH2CH2CH2CH3,
      N(CH3)C(O)CH(CH3)CH2CH3, N(CH3)C(O)C6H5,
      N(CH3)C(O)CH2CH2(CH2CH2O)1-5Me, an amino protecting group, a
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: MISC_FEATURE
<222> LOCATION: (2)..()
<223> OTHER INFORMATION: Sarcosine
<220> FEATURE:
<221> NAME/KEY: MISC_FEATURE
<222> LOCATION: (5)..()
<223> OTHER INFORMATION: D-alloisoleucine
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (11)..()
<223> OTHER INFORMATION: COOH, C(O)NH2, C(O)NH(CH3), C(O)NHCH2CH3,
      C(O)NHCH2CH2CH3, C(O)NHCH(CH3)CH3, C(O)NHCH2CH2CH2CH3,
      C(O)NHCH(CH3)CH2CH3, C(O)NHC6H5, C(O)NHCH2CH2OCH3,C(O)NHOCH3,
      C(O)NHOCH2CH3, a carboxy protecting group, a lipid fatty acid
      group, a carbohydrate, or
<220> FEATURE:
<221> NAME/KEY: misc_feature
```

```
<222> LOCATION: (11)..(11)
<223> OTHER INFORMATION: Xaa can be any naturally occurring amino acid

<400> SEQUENCE: 5

Xaa Xaa Gly Val Xaa Thr Gln Ile Arg Pro Xaa
1               5                   10

<210> SEQ ID NO 6
<211> LENGTH: 11
<212> TYPE: PRT
<213> ORGANISM: Artificial
<220> FEATURE:
<223> OTHER INFORMATION: Peptide analog of thrombospondin-1
<220> FEATURE:
<221> NAME/KEY: MISC_FEATURE
<222> LOCATION: (1)..()
<223> OTHER INFORMATION: NH(CH3), N(CH3)C(O)CH3, N(CH3)C(O)CH2CH3,
      N(CH3)C(O)CH2CH2CH3, N(CH3)C(O)CH(CH3)CH3, N(CH3)C(O)CH2CH2CH2CH3,
      N(CH3)C(O)CH(CH3)CH2CH3, N(CH3)C(O)C6H5,
      N(CH3)C(O)CH2CH2(CH2CH2O)1-5Me, an amino protecting group, a
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: MISC_FEATURE
<222> LOCATION: (2)..()
<223> OTHER INFORMATION: Sarcosine
<220> FEATURE:
<221> NAME/KEY: MISC_FEATURE
<222> LOCATION: (5)..()
<223> OTHER INFORMATION: D-alloisoleucine
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (7)..()
<223> OTHER INFORMATION: alpha-ally-glycine
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (11)..()
<223> OTHER INFORMATION: COOH, C(O)NH2, C(O)NH(CH3), C(O)NHCH2CH3,
      C(O)NHCH2CH2CH3, C(O)NHCH(CH3)CH3, C(O)NHCH2CH2CH2CH3,
      C(O)NHCH(CH3)CH2CH3, C(O)NHC6H5, C(O)NHCH2CH2OCH3, C(O)NHOCH3,
      C(O)NHOCH2CH3, a carboxy protecting group, a lipid fatty acid
      group, a carbohydrate, or
<220> FEATURE:
<221> NAME/KEY: misc_feature
<222> LOCATION: (11)..(11)
<223> OTHER INFORMATION: Xaa can be any naturally occurring amino acid

<400> SEQUENCE: 6

Xaa Xaa Gly Val Xaa Thr Xaa Ile Arg Pro Xaa
1               5                   10

<210> SEQ ID NO 7
<211> LENGTH: 11
<212> TYPE: PRT
<213> ORGANISM: Artificial
<220> FEATURE:
<223> OTHER INFORMATION: Peptide analog of thrombospondin-1
<220> FEATURE:
<221> NAME/KEY: MISC_FEATURE
<222> LOCATION: (1)..()
<223> OTHER INFORMATION: NH(CH3), N(CH3)C(O)CH3, N(CH3)C(O)CH2CH3,
      N(CH3)C(O)CH2CH2CH3, N(CH3)C(O)CH(CH3)CH3, N(CH3)C(O)CH2CH2CH2CH3,
      N(CH3)C(O)CH(CH3)CH2CH3, N(CH3)C(O)C6H5,
      N(CH3)C(O)CH2CH2(CH2CH2O)1-5Me, an amino protecting group, a
<220> FEATURE:
```

```
<221> NAME/KEY: misc_feature
<222> LOCATION: (1)..(2)
<223> OTHER INFORMATION: Xaa can be any naturally occurring amino acid
<220> FEATURE:
<221> NAME/KEY: MISC_FEATURE
<222> LOCATION: (2)..()
<223> OTHER INFORMATION: Sarcosine
<220> FEATURE:
<221> NAME/KEY: MISC_FEATURE
<222> LOCATION: (5)..()
<223> OTHER INFORMATION: D-alloisoleucine
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (7)..()
<223> OTHER INFORMATION: Norvaline
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (11)..()
<223> OTHER INFORMATION: COOH, C(O)NH2, C(O)NH(CH3), C(O)NHCH2CH3,
      C(O)NHCH2CH2CH3, C(O)NHCH(CH3)CH3, C(O)NHCH2CH2CH2CH3,
      C(O)NHCH(CH3)CH2CH3, C(O)NHC6H5, C(O)NHCH2CH2OCH3, C(O)NHOCH3,
      C(O)NHOCH2CH3, a carboxy protecting group, a lipid fatty acid
      group, a carbohydrate, or
<220> FEATURE:
<221> NAME/KEY: misc_feature
<222> LOCATION: (11)..(11)
<223> OTHER INFORMATION: Xaa can be any naturally occurring amino acid

<400> SEQUENCE: 7

Xaa Xaa Phe Val Xaa Thr Xaa Ile Arg Pro Xaa
1               5                   10

<210> SEQ ID NO 8
<211> LENGTH: 11
<212> TYPE: PRT
<213> ORGANISM: Artificial
<220> FEATURE:
<223> OTHER INFORMATION: Peptide analog of thrombospondin-1
<220> FEATURE:
<221> NAME/KEY: MISC_FEATURE
<222> LOCATION: (1)..()
<223> OTHER INFORMATION: NH2, NHC(O)CH3, NHC(O)CH2CH3,
      NHC(O)CH2CH2CH3, N HC(O)CH(CH3)CH3, NHC(O)CH2CH2CH2CH3,
      NHC(O)CH(CH3)CH2CH3, NHC(O)C6H5, NH(CH3)C(O)CH2CH2(CH2CH2O)
      1-5Me, an amino protecting group, a lipid fatty acid group, a
      carbohydrate, or absent
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (5)..()
<223> OTHER INFORMATION: D-alloisoleucine
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (7)..()
<223> OTHER INFORMATION: Norvaline
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (11)..()
```

```
<223> OTHER INFORMATION: COOH, C(O)NH2, C(O)NH(CH3), C(O)NHCH2CH3,
      C(O)NHCH2CH2CH3, C(O)NHCH(CH3)CH3, C(O)NHCH2CH2CH2CH3,
      C(O)NHCH(CH3)CH2CH3, C(O)NHC6H5, C(O)NHCH2CH2OCH3,C(O)NHOCH3,
      C(O)NHOCH2CH3, a carboxy protecting group, a lipid fatty acid
      group, a carbohydrate, or
<220> FEATURE:
<221> NAME/KEY: misc_feature
<222> LOCATION: (11)..(11)
<223> OTHER INFORMATION: Xaa can be any naturally occurring amino acid

<400> SEQUENCE: 8

Xaa Lys Gly Val Xaa Thr Xaa Ile Arg Pro Xaa
1               5                   10

<210> SEQ ID NO 9
<211> LENGTH: 11
<212> TYPE: PRT
<213> ORGANISM: Artificial
<220> FEATURE:
<223> OTHER INFORMATION: Peptide analog of thrombospondin-1
<220> FEATURE:
<221> NAME/KEY: MISC_FEATURE
<222> LOCATION: (1)..()
<223> OTHER INFORMATION: NH2, NHC(O)CH3, NHC(O)CH2CH3,
      NHC(O)CH2CH2CH3, NHC(O)CH(CH3)CH3, NHC(O)CH2CH2CH2CH3,
      NHC(O)CH(CH3)CH2CH3, NHC(O)C6H5, NH(CH3)C(O)CH2CH2(CH2CH2O)1-
      5Me, an amino protecting group, a lipid fatty acid group, a
      carbohydrate, or absent
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (5)..()
<223> OTHER INFORMATION: D-alloisoleucine
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (7)..()
<223> OTHER INFORMATION: Norvaline
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (11)..()
<223> OTHER INFORMATION: COOH, C(O)NH2, C(O)NH(CH3), C(O)NHCH2CH3,
      C(O)NHCH2CH2CH3, C(O)NHCH(CH3)CH3, C(O)NHCH2CH2CH2CH3,
      C(O)NHCH(CH3)CH2CH3, C(O)NHC6H5, C(O)NHCH2CH2OCH3,C(O)NHOCH3,
      C(O)NHOCH2CH3, a carboxy protecting group, a lipid fatty acid
      group, a carbohydrate, or
<220> FEATURE:
<221> NAME/KEY: misc_feature
<222> LOCATION: (11)..(11)
<223> OTHER INFORMATION: Xaa can be any naturally occurring amino acid

<400> SEQUENCE: 9

Xaa Glu Gly Val Xaa Thr Xaa Ile Arg Pro Xaa
1               5                   10

<210> SEQ ID NO 10
<211> LENGTH: 11
<212> TYPE: PRT
<213> ORGANISM: Artificial
<220> FEATURE:
<223> OTHER INFORMATION: Peptide analog of thrombospondin-1
<220> FEATURE:
<221> NAME/KEY: MISC_FEATURE
<222> LOCATION: (1)..()
<223> OTHER INFORMATION: NH2, NHC(O)CH3, NHC(O)CH2CH3,
```

```
        NHC(O)CH2CH2CH3, NHC(O)CH(CH3)CH3, NHC(O)CH2CH2CH2CH3,
        NHC(O)CH(CH3)CH2CH3, NHC(O)C6H5, NH(CH3)C(O)CH2CH2(CH2CH2O)
        1-5Me, an amino protecting group, a lipid fatty acid group, a
        carbohydrate, or absent
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (5)..()
<223> OTHER INFORMATION: D-alloisoleucine
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (7)..()
<223> OTHER INFORMATION: Norvaline
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (11)..()
<223> OTHER INFORMATION: COOH, C(O)NH2, C(O)NH(CH3), C(O)NHCH2CH3,
        C(O)NHCH2CH2CH3, C(O)NHCH(CH3)CH3, C(O)NHCH2CH2CH2CH3,
        C(O)NHCH(CH3)CH2CH3, C(O)NHC6H5, C(O)NHCH2CH2OCH3,C(O)NHOCH3,
        C(O)NHOCH2CH3, a carboxy protecting group, a lipid fatty acid
        group, a carbohydrate, or
<220> FEATURE:
<221> NAME/KEY: misc_feature
<222> LOCATION: (11)..(11)
<223> OTHER INFORMATION: Xaa can be any naturally occurring amino acid

<400> SEQUENCE: 10

Xaa Pro Gly Val Xaa Thr Xaa Ile Arg Pro Xaa
1               5                   10

<210> SEQ ID NO 11
<211> LENGTH: 11
<212> TYPE: PRT
<213> ORGANISM: Artificial
<220> FEATURE:
<223> OTHER INFORMATION: Peptide analog of thrombospondin-1
<220> FEATURE:
<221> NAME/KEY: MISC_FEATURE
<222> LOCATION: (1)..()
<223> OTHER INFORMATION: NH2, NHC(O)CH3, NHC(O)CH2CH3,
        NHC(O)CH2CH2CH3, NHC(O)CH(CH3)CH3, NHC(O)CH2CH2CH2CH3,
        NHC(O)CH(CH3)CH2CH3, NHC(O)C6H5, NH(CH3)C(O)CH2CH2(CH2CH2O)
        1-5Me, an amino protecting group, a lipid fatty acid group, a
        carbohydrate, or absent
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (3)..()
<223> OTHER INFORMATION: 4-Cyanophenylalanine
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (5)..()
<223> OTHER INFORMATION: D-alloisoleucine
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
```

```
<222> LOCATION: (7)..()
<223> OTHER INFORMATION: Norvaline
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (11)..()
<223> OTHER INFORMATION: COOH, C(O)NH2, C(O)NH(CH3), C(O)NHCH2CH3,
      C(O)NHCH2CH2CH3, C(O)NHCH(CH3)CH3, C(O)NHCH2CH2CH2CH3,
      C(O)NHCH(CH3)CH2CH3, C(O)NHC6H5, C(O)NHCH2CH2OCH3,C(O)NHOCH3,
      C(O)NHOCH2CH3, a carboxy protecting group, a lipid fatty acid
      group, a carbohydrate, or
<220> FEATURE:
<221> NAME/KEY: misc_feature
<222> LOCATION: (11)..(11)
<223> OTHER INFORMATION: Xaa can be any naturally occurring amino acid

<400> SEQUENCE: 11

Xaa Pro Xaa Val Xaa Thr Xaa Ile Arg Pro Xaa
1               5                   10

<210> SEQ ID NO 12
<211> LENGTH: 11
<212> TYPE: PRT
<213> ORGANISM: Artificial
<220> FEATURE:
<223> OTHER INFORMATION: Peptide analog of thrombospondin-1
<220> FEATURE:
<221> NAME/KEY: MISC_FEATURE
<222> LOCATION: (1)..()
<223> OTHER INFORMATION: NH2, NHC(O)CH3, NHC(O)CH2CH3,
      NHC(O)CH2CH2CH3, NHC(O)CH(CH3)CH3, NHC(O)CH2CH2CH2CH3,
      NHC(O)CH(CH3)CH2CH3, NHC(O)C6H5, NH(CH3)C(O)CH2CH2(CH2CH2O)
      1-5Me, an amino protecting group, a lipid fatty acid group, a
      carbohydrate, or absent
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (3)..()
<223> OTHER INFORMATION: 3,4-Dimethoxy-Phenylalanine
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (5)..()
<223> OTHER INFORMATION: D-alloisoleucine
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (7)..()
<223> OTHER INFORMATION: Norvaline
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (11)..()
<223> OTHER INFORMATION: COOH, C(O)NH2, C(O)NH(CH3), C(O)NHCH2CH3,
      C(O)NHCH2CH2CH3, C(O)NHCH(CH3)CH3, C(O)NHCH2CH2CH2CH3,
      C(O)NHCH(CH3)CH2CH3, C(O)NHC6H5, C(O)NHCH2CH2OCH3,C(O)NHOCH3,
      C(O)NHOCH2CH3, a carboxy protecting group, a lipid fatty acid
      group, a carbohydrate, or
<220> FEATURE:
<221> NAME/KEY: misc_feature
<222> LOCATION: (11)..(11)
<223> OTHER INFORMATION: Xaa can be any naturally occurring amino acid
```

```
<400> SEQUENCE: 12

Xaa Pro Xaa Val Xaa Thr Xaa Ile Arg Pro Xaa
1               5                   10

<210> SEQ ID NO 13
<211> LENGTH: 11
<212> TYPE: PRT
<213> ORGANISM: Artificial
<220> FEATURE:
<223> OTHER INFORMATION: Peptide analog of thrombospondin-1
<220> FEATURE:
<221> NAME/KEY: MISC_FEATURE
<222> LOCATION: (1)..()
<223> OTHER INFORMATION: NH2, NHC(O)CH3, NHC(O)CH2CH3,
      NHC(O)CH2CH2CH3, NHC(O)CH(CH3)CH3, NHC(O)CH2CH2CH2CH3,
      NHC(O)CH(CH3)CH2CH3, NHC(O)C6H5, NH(CH3)C(O)CH2CH2(CH2CH2O)
      1-5Me, an amino protecting group, a lipid fatty acid group, a
      carbohydrate, or absent
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (3)..()
<223> OTHER INFORMATION: 3-(4-thiazolyl)-L-Alanine
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (5)..()
<223> OTHER INFORMATION: D-alloisoleucine
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (7)..()
<223> OTHER INFORMATION: Norvaline
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (11)..()
<223> OTHER INFORMATION: COOH, C(O)NH2, C(O)NH(CH3), C(O)NHCH2CH3,
      C(O)NHCH2CH2CH3, C(O)NHCH(CH3)CH3, C(O)NHCH2CH2CH3,
      C(O)NHCH(CH3)CH2CH3, C(O)NHC6H5, C(O)NHCH2CH2OCH3,C(O)NHOCH3,
      C(O)NHOCH2CH3, a carboxy protecting group, a lipid fatty acid
      group, a carbohydrate, or
<220> FEATURE:
<221> NAME/KEY: misc_feature
<222> LOCATION: (11)..(11)
<223> OTHER INFORMATION: Xaa can be any naturally occurring amino acid

<400> SEQUENCE: 13

Xaa Pro Xaa Val Xaa Thr Xaa Ile Arg Pro Xaa
1               5                   10

<210> SEQ ID NO 14
<211> LENGTH: 11
<212> TYPE: PRT
<213> ORGANISM: Artificial
<220> FEATURE:
<223> OTHER INFORMATION: Peptide analog of thrombospondin-1
<220> FEATURE:
<221> NAME/KEY: MISC_FEATURE
<222> LOCATION: (1)..()
<223> OTHER INFORMATION: NH2, NHC(O)CH3, NHC(O)CH2CH3,
      NHC(O)CH2CH2CH3, NHC(O)CH(CH3)CH3, NHC(O)CH2CH2CH2CH3,
```

```
              NHC(O)CH(CH3)CH2CH3, NHC(O)C6H5, NH(CH3)C(O)CH2CH2(CH2CH2O)
              1-5Me, an amino protecting group, a lipid fatty acid group, a
              carbohydrate, or absent
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (3)..()
<223> OTHER INFORMATION: 2-furyl-Alanine
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (5)..()
<223> OTHER INFORMATION: D-alloisoleucine
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (7)..()
<223> OTHER INFORMATION: Norvaline
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (11)..()
<223> OTHER INFORMATION: COOH, C(O)NH2, C(O)NH(CH3), C(O)NHCH2CH3,
      C(O)NHCH2CH2CH3, C(O)NHCH(CH3)CH3, C(O)NHCH2CH2CH2CH3,
      C(O)NHCH(CH3)CH2CH3, C(O)NHC6H5, C(O)NHCH2OCH3,C(O)NHOCH3,
      C(O)NHOCH2CH3, a carboxy protecting group, a lipid fatty acid
      group, a carbohydrate, or
<220> FEATURE:
<221> NAME/KEY: misc_feature
<222> LOCATION: (11)..(11)
<223> OTHER INFORMATION: Xaa can be any naturally occurring amino acid

<400> SEQUENCE: 14

Xaa Pro Xaa Val Xaa Thr Xaa Ile Arg Pro Xaa
1               5                   10

<210> SEQ ID NO 15
<211> LENGTH: 11
<212> TYPE: PRT
<213> ORGANISM: Artificial
<220> FEATURE:
<223> OTHER INFORMATION: Peptide analog of thrombospondin-1
<220> FEATURE:
<221> NAME/KEY: MISC_FEATURE
<222> LOCATION: (1)..()
<223> OTHER INFORMATION: NH2, NHC(O)CH3, NHC(O)CH2CH3,
      NHC(O)CH2CH2CH3, NHC(O)CH(CH3)CH3, NHC(O)CH2CH2CH2CH3,
      NHC(O)CH(CH3)CH2CH3, NHC(O)C6H5, NH(CH3)C(O)CH2CH2(CH2CH2O)
      1-5Me, an amino protecting group, a lipid fatty acid group, a
      carbohydrate, or absent
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (3)..()
<223> OTHER INFORMATION: Cyclo-Leucine
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (5)..()
```

```
<223> OTHER INFORMATION: D-alloisoleucine
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (7)..()
<223> OTHER INFORMATION: Norvaline
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (11)..()
<223> OTHER INFORMATION: COOH, C(O)NH2, C(O)NH(CH3), C(O)NHCH2CH3,
      C(O)NHCH2CH2CH3, C(O)NHCH(CH3)CH3, C(O)NHCH2CH2CH2CH3,
      C(O)NHCH(CH3)CH2CH3, C(O)NHC6H5, C(O)NHCH2CH2OCH3,C(O)NHOCH3,
      C(O)NHOCH2CH3, a carboxy protecting group, a lipid fatty acid
      group, a carbohydrate, or
<220> FEATURE:
<221> NAME/KEY: misc_feature
<222> LOCATION: (11)..(11)
<223> OTHER INFORMATION: Xaa can be any naturally occurring amino acid

<400> SEQUENCE: 15

Xaa Pro Xaa Val Xaa Thr Xaa Ile Arg Pro Xaa
1               5                   10

<210> SEQ ID NO 16
<211> LENGTH: 9
<212> TYPE: PRT
<213> ORGANISM: Artificial
<220> FEATURE:
<223> OTHER INFORMATION: Peptide analog of thrombospondin-1
<220> FEATURE:
<221> NAME/KEY: MISC_FEATURE
<222> LOCATION: (1)..()
<223> OTHER INFORMATION: NH2, NHC(O)CH3, NHC(O)CH2CH3,
      NHC(O)CH2CH2CH3, NHC(O)CH(CH3)CH3, NHC(O)CH2CH2CH2CH3,
      NHC(O)CH(CH3)CH2CH3, NHC(O)C6H5, NH(CH3)C(O)CH2CH2(CH2CH2O)
      1-5Me, an amino protecting group, a lipid fatty acid group, a
      carbohydrate, or absent
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (4)..()
<223> OTHER INFORMATION: D-Isoleucine
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (9)..()
<223> OTHER INFORMATION: COOH, C(O)NH2, C(O)NH(CH3), C(O)NHCH2CH3,
      C(O)NHCH2CH2CH3, C(O)NHCH(CH3)CH3, C(O)NHCH2CH2CH2CH3,
      C(O)NHCH(CH3)CH2CH3, C(O)NHC6H5, C(O)NHCH2CH2OCH3,C(O)NHOCH3,
      C(O)NHOCH2CH3, a carboxy protecting group, a lipid fatty acid
      group, a carbohydrate, or
<220> FEATURE:
<221> NAME/KEY: misc_feature
<222> LOCATION: (9)..(9)
<223> OTHER INFORMATION: Xaa can be any naturally occurring amino acid

<400> SEQUENCE: 16

Xaa Gly Val Xaa Thr Arg Ile Arg Xaa
1               5

<210> SEQ ID NO 17
<211> LENGTH: 11
```

```
<212> TYPE: PRT
<213> ORGANISM: Artificial
<220> FEATURE:
<223> OTHER INFORMATION: Peptide analog of thrombospondin-1
<220> FEATURE:
<221> NAME/KEY: MISC_FEATURE
<222> LOCATION: (1)..()
<223> OTHER INFORMATION: NH(CH3), N(CH3)C(O)CH3, N(CH3)C(O)CH2CH3,
      N(CH3)C(O)CH2CH2CH3, N(CH3)C(O)CH(CH3)CH3, N(CH3)C(O)CH2CH2CH2CH3,
      N(CH3)C(O)CH(CH3)CH2CH3, N(CH3)C(O)C6H5,
      N(CH3)C(O)CH2CH2(CH2CH2O)1-5Me, an amino protecting group, a
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: MISC_FEATURE
<222> LOCATION: (2)..()
<223> OTHER INFORMATION: Sarcosine
<220> FEATURE:
<221> NAME/KEY: MISC_FEATURE
<222> LOCATION: (5)..()
<223> OTHER INFORMATION: D-alloisoleucine
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (7)..()
<223> OTHER INFORMATION: Norvaline
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (11)..()
<223> OTHER INFORMATION: COOH, C(O)NH2, C(O)NH(CH3), C(O)NHCH2CH3,
      C(O)NHCH2CH2CH3, C(O)NHCH(CH3)CH3, C(O)NHCH2CH2CH2CH3,
      C(O)NHCH(CH3)CH2CH3, C(O)NHC6H5, C(O)NHCH2CH2OCH3, C(O)NHOCH3,
      C(O)NHOCH2CH3, a carboxy protecting group, a lipid fatty acid
      group, a carbohydrate, or
<220> FEATURE:
<221> NAME/KEY: misc_feature
<222> LOCATION: (11)..(11)
<223> OTHER INFORMATION: Xaa can be any naturally occurring amino acid

<400> SEQUENCE: 17

Xaa Xaa Gly Val Xaa Thr Xaa Ile Arg Pro Xaa
1               5                   10

<210> SEQ ID NO 18
<211> LENGTH: 68
<212> TYPE: DNA
<213> ORGANISM: Artificial
<220> FEATURE:
<223> OTHER INFORMATION: PCR primer for generating humanized Vk

<400> SEQUENCE: 18
gagctccaga tgacccagtc tccatcctcc ctgtctgcat ctgtaggtga ccgcgtcacc      60
atcacttg                                                              68

<210> SEQ ID NO 19
<211> LENGTH: 69
<212> TYPE: DNA
<213> ORGANISM: Artificial
<220> FEATURE:
<223> OTHER INFORMATION: PCR primer for generating humanized Vk

<400> SEQUENCE: 19
attcagatat gggctgccat aagtgtgcag gaggctctga ctggagcggc aagtgatggt      60
```

```
                                       -continued
gacgcggtc                                                            69

<210> SEQ ID NO 20
<211> LENGTH: 66
<212> TYPE: DNA
<213> ORGANISM: Artificial
<220> FEATURE:
<223> OTHER INFORMATION: PCR primer for generating humanized Vk

<400> SEQUENCE: 20
tatggcagcc catatctgaa ttggtatctc cagaaaccag gccagtctcc taagctcctg    60
atctat                                                               66

<210> SEQ ID NO 21
<211> LENGTH: 65
<212> TYPE: DNA
<213> ORGANISM: Artificial
<220> FEATURE:
<223> OTHER INFORMATION: PCR primer for generating humanized Vk

<400> SEQUENCE: 21
ctgaaacgtg atgggacacc actgaaacga ttggacactt tatagatcag gagcttagga    60
gactg                                                                65

<210> SEQ ID NO 22
<211> LENGTH: 90
<212> TYPE: DNA
<213> ORGANISM: Artificial
<220> FEATURE:
<223> OTHER INFORMATION: PCR primer for generating humanized Vk

<400> SEQUENCE: 22
agtggtgtcc catcacgttt cagtggcagt ggttctggca cagatttcac tctcaccatc    60
agcagtctgc aacctgaaga ttttgcagtg                                     90

<210> SEQ ID NO 23
<211> LENGTH: 87
<212> TYPE: DNA
<213> ORGANISM: Artificial
<220> FEATURE:
<223> OTHER INFORMATION: PCR primer for generating humanized Vk

<400> SEQUENCE: 23
gatctccacc ttggtccctc cgccgaaagt ataagggagg tgggtgccct gactacagaa    60
gtacactgca aaatcttcag gttgcag                                        87

<210> SEQ ID NO 24
<211> LENGTH: 79
<212> TYPE: DNA
<213> ORGANISM: Artificial
<220> FEATURE:
<223> OTHER INFORMATION: PCR primer for generating humanized VH

<400> SEQUENCE: 24
gaggtgcagc tggtggagtc tggcggtggc ttggtacagc ctggcggttc cctgcgcctc    60
tcctgtgcag cctctggct                                                 79

<210> SEQ ID NO 25
<211> LENGTH: 81
<212> TYPE: DNA
<213> ORGANISM: Artificial
<220> FEATURE:
<223> OTHER INFORMATION: PCR primer for generating humanized VH
```

<400> SEQUENCE: 25
ctccaggccc ttctctggag actggcggac ccagctcatc aatagttgc taaaggtgaa    60 gccagaggct gcacaggaga g    81

<210> SEQ ID NO 26
<211> LENGTH: 81
<212> TYPE: DNA
<213> ORGANISM: Artificial
<220> FEATURE:
<223> OTHER INFORMATION: PCR primer for generating humanized VH

<400> SEQUENCE: 26
tctccagaga agggcctgga gtgggtctca gagattcgtc tgcgcagtga caactacgcc    60
acgcactatg cagagtctgt c    81

<210> SEQ ID NO 27
<211> LENGTH: 73
<212> TYPE: DNA
<213> ORGANISM: Artificial
<220> FEATURE:
<223> OTHER INFORMATION: PCR primer for generating humanized VH

<400> SEQUENCE: 27
cagatacagc gtgttcttgg aattgtcacg ggagatggtg aagcggccct tgacagactc    60
tgcatagtgc gtg    73

<210> SEQ ID NO 28
<211> LENGTH: 76
<212> TYPE: DNA
<213> ORGANISM: Artificial
<220> FEATURE:
<223> OTHER INFORMATION: PCR primer for generating humanized VH

<400> SEQUENCE: 28
caattccaag aacacgctgt atctgcaaat gaacagcctg cgcgccgagg acacgggcat    60
ttattactgt aaaacg    76

<210> SEQ ID NO 29
<211> LENGTH: 79
<212> TYPE: DNA
<213> ORGANISM: Artificial
<220> FEATURE:
<223> OTHER INFORMATION: PCR primer for generating humanized VH

<400> SEQUENCE: 29
tgaggagacg gtgaccaggg tgccctggcc ccagtagctg aaactgtaga agtacgtttt    60
acagtaataa atgcccgtg    79

<210> SEQ ID NO 30
<211> LENGTH: 48
<212> TYPE: DNA
<213> ORGANISM: Artificial
<220> FEATURE:
<223> OTHER INFORMATION: PCR primer for amplifying h38C2 VH coding
      sequence

<400> SEQUENCE: 30
gaggaggagg aggaggagct cactccgagg tgcagctggt ggagtctg    48

<210> SEQ ID NO 31
<211> LENGTH: 72

-continued

```
<212> TYPE: DNA
<213> ORGANISM: Artificial
<220> FEATURE:
<223> OTHER INFORMATION: PCR primer for amplifying h38C2 VL coding
      sequence

<400> SEQUENCE: 31
gaggaggagg aggagaagct tgttgctctg gatctctggt gcctacgggg agctccagat    60
gacccagtct cc                                                        72

<210> SEQ ID NO 32
<211> LENGTH: 112
<212> TYPE: PRT
<213> ORGANISM: Mus musculus
<220> FEATURE:
<221> NAME/KEY: MISC_FEATURE
<222> LOCATION: (1)..(23)
<223> OTHER INFORMATION: Framework region 1
<220> FEATURE:
<221> NAME/KEY: MISC_FEATURE
<222> LOCATION: (24)..(39)
<223> OTHER INFORMATION: Complementarity determining region 1
<220> FEATURE:
<221> NAME/KEY: MISC_FEATURE
<222> LOCATION: (40)..(54)
<223> OTHER INFORMATION: Framework region 2
<220> FEATURE:
<221> NAME/KEY: MISC_FEATURE
<222> LOCATION: (55)..(61)
<223> OTHER INFORMATION: Complementarity determining region 2
<220> FEATURE:
<221> NAME/KEY: MISC_FEATURE
<222> LOCATION: (62)..(93)
<223> OTHER INFORMATION: Framework region 3
<220> FEATURE:
<221> NAME/KEY: MISC_FEATURE
<222> LOCATION: (94)..(102)
<223> OTHER INFORMATION: Complementarity determining region 3
<220> FEATURE:
<221> NAME/KEY: MISC_FEATURE
<222> LOCATION: (103)..(112)
<223> OTHER INFORMATION: Framework region 4

<400> SEQUENCE: 32

Asp Val Val Met Thr Gln Thr Pro Leu Ser Leu Pro Val Arg Leu Gly
1               5                   10                  15

Asp Gln Ala Ser Ile Ser Cys Arg Ser Ser Gln Ser Leu Leu His Thr
            20                  25                  30

Tyr Gly Ser Pro Tyr Leu Asn Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Leu Gly Val Tyr Phe Cys Ser Gln Gly
                85                  90                  95

Thr His Leu Pro Tyr Thr Phe Gly Gly Gly Thr Lys Leu Glu Ile Lys
            100                 105                 110

<210> SEQ ID NO 33
<211> LENGTH: 118
<212> TYPE: PRT
<213> ORGANISM: Mus musculus
<220> FEATURE:
<221> NAME/KEY: MISC_FEATURE
<222> LOCATION: (1)..(30)
<223> OTHER INFORMATION: Framework region 1
<220> FEATURE:
```

```
<221> NAME/KEY: MISC_FEATURE
<222> LOCATION: (31)..(35)
<223> OTHER INFORMATION: Complementarity determining region 1
<220> FEATURE:
<221> NAME/KEY: MISC_FEATURE
<222> LOCATION: (36)..(49)
<223> OTHER INFORMATION: Framework region 2
<220> FEATURE:
<221> NAME/KEY: MISC_FEATURE
<222> LOCATION: (50)..(68)
<223> OTHER INFORMATION: Complementarity determining region 2
<220> FEATURE:
<221> NAME/KEY: MISC_FEATURE
<222> LOCATION: (69)..(100)
<223> OTHER INFORMATION: Framework region 3
<220> FEATURE:
<221> NAME/KEY: MISC_FEATURE
<222> LOCATION: (101)..(107)
<223> OTHER INFORMATION: Complementarity determining region 3
<220> FEATURE:
<221> NAME/KEY: MISC_FEATURE
<222> LOCATION: (108)..(118)
<223> OTHER INFORMATION: Framework region 4

<400> SEQUENCE: 33

Glu Val Lys Leu Val Glu Ser Gly Gly Gly Leu Val Gln Pro Gly Gly
1               5                   10                  15

Thr Met Lys Leu Ser Cys Glu Ile Ser Gly Leu Thr Phe Arg Asn Tyr
            20                  25                  30

Trp Met Ser Trp Val Arg Gln Ser Pro Glu Lys Gly Leu Glu Trp Val
        35                  40                  45

Ala Glu Ile Arg Leu Arg Ser Asp Asn Tyr Ala Thr His Tyr Ala Glu
    50                  55                  60

Ser Val Lys Gly Lys Phe Thr Ile Ser Arg Asp Asp Ser Lys Ser Arg
65                  70                  75                  80

Leu Tyr Leu Gln Met Asn Ser Leu Arg Thr Glu Asp Thr Gly Ile Tyr
                85                  90                  95

Tyr Cys Lys Thr Tyr Phe Tyr Ser Phe Ser Tyr Trp Gly Gln Gly Thr
            100                 105                 110

Leu Val Thr Val Ser Ala
        115

<210> SEQ ID NO 34
<211> LENGTH: 112
<212> TYPE: PRT
<213> ORGANISM: Homo sapiens
<220> FEATURE:
<221> NAME/KEY: MISC_FEATURE
<222> LOCATION: (1)..(23)
<223> OTHER INFORMATION: Framework region 1
<220> FEATURE:
<221> NAME/KEY: MISC_FEATURE
<222> LOCATION: (24)..(39)
<223> OTHER INFORMATION: Complementarity determining region 1
<220> FEATURE:
<221> NAME/KEY: MISC_FEATURE
<222> LOCATION: (40)..(54)
<223> OTHER INFORMATION: Framework region 2
<220> FEATURE:
<221> NAME/KEY: MISC_FEATURE
<222> LOCATION: (55)..(61)
<223> OTHER INFORMATION: Complementarity determining region 2
<220> FEATURE:
<221> NAME/KEY: MISC_FEATURE
<222> LOCATION: (62)..(93)
<223> OTHER INFORMATION: Framework region 3
<220> FEATURE:
<221> NAME/KEY: MISC_FEATURE
<222> LOCATION: (94)..(102)
<223> OTHER INFORMATION: Complementarity determining region 3
```

-continued

```
<220> FEATURE:
<221> NAME/KEY: MISC_FEATURE
<222> LOCATION: (103)..(112)
<223> OTHER INFORMATION: Framework region 4

<400> SEQUENCE: 34
```

Glu Leu Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Leu His Thr
            20                  25                  30

Tyr Gly Ser Pro Tyr Leu Asn Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Val Tyr Phe Cys Ser Gln Gly
                85                  90                  95

Thr His Leu Pro Tyr Thr Phe Gly Gly Gly Thr Lys Val Glu Ile Lys
            100                 105                 110

```
<210> SEQ ID NO 35
<211> LENGTH: 118
<212> TYPE: PRT
<213> ORGANISM: Homo sapiens
<220> FEATURE:
<221> NAME/KEY: MISC_FEATURE
<222> LOCATION: (1)..(30)
<223> OTHER INFORMATION: Framework region 1
<220> FEATURE:
<221> NAME/KEY: MISC_FEATURE
<222> LOCATION: (31)..(35)
<223> OTHER INFORMATION: Complementarity determining region 1
<220> FEATURE:
<221> NAME/KEY: MISC_FEATURE
<222> LOCATION: (36)..(49)
<223> OTHER INFORMATION: Framework region 2
<220> FEATURE:
<221> NAME/KEY: MISC_FEATURE
<222> LOCATION: (50)..(68)
<223> OTHER INFORMATION: Complementarity determining region 2
<220> FEATURE:
<221> NAME/KEY: MISC_FEATURE
<222> LOCATION: (69)..(100)
<223> OTHER INFORMATION: Framework region 3
<220> FEATURE:
<221> NAME/KEY: MISC_FEATURE
<222> LOCATION: (101)..(107)
<223> OTHER INFORMATION: Complementarity determining region 3
<220> FEATURE:
<221> NAME/KEY: MISC_FEATURE
<222> LOCATION: (108)..(118)
<223> OTHER INFORMATION: Framework region 4

<400> SEQUENCE: 35
```

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ser Pro Glu Lys Gly Leu Glu Trp Val
        35                  40                  45

Ser Glu Ile Arg Leu Arg Ser Asp Asn Tyr Ala Thr His Tyr Ala Glu
    50                  55                  60

Ser Val Lys Gly Arg Phe Thr Ile Ser Arg Asp Asn Ser Lys Asn Thr
65                  70                  75                  80

```
Leu Tyr Leu Gln Met Asn Ser Leu Arg Ala Glu Asp Thr Gly Ile Tyr
                85                  90                  95

Tyr Cys Lys Thr Tyr Phe Tyr Ser Phe Ser Tyr Trp Gly Gln Gly Thr
            100                 105                 110

Leu Val Thr Val Ser Ser
        115

<210> SEQ ID NO 36
<211> LENGTH: 95
<212> TYPE: PRT
<213> ORGANISM: Homo sapiens
<220> FEATURE:
<221> NAME/KEY: MISC_FEATURE
<222> LOCATION: (1)..(23)
<223> OTHER INFORMATION: Framework region 1
<220> FEATURE:
<221> NAME/KEY: MISC_FEATURE
<222> LOCATION: (24)..(34)
<223> OTHER INFORMATION: Complementarity determining region 1
<220> FEATURE:
<221> NAME/KEY: MISC_FEATURE
<222> LOCATION: (35)..(49)
<223> OTHER INFORMATION: Framework region 2
<220> FEATURE:
<221> NAME/KEY: MISC_FEATURE
<222> LOCATION: (50)..(56)
<223> OTHER INFORMATION: Complementarity determining region 2
<220> FEATURE:
<221> NAME/KEY: MISC_FEATURE
<222> LOCATION: (57)..(88)
<223> OTHER INFORMATION: Framework region 3
<220> FEATURE:
<221> NAME/KEY: MISC_FEATURE
<222> LOCATION: (89)..(95)
<223> OTHER INFORMATION: Complementarity determining region 3

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 37
<211> LENGTH: 98
<212> TYPE: PRT
<213> ORGANISM: Homo sapiens
<220> FEATURE:
<221> NAME/KEY: MISC_FEATURE
<222> LOCATION: (1)..(30)
<223> OTHER INFORMATION: Framework region 1
<220> FEATURE:
<221> NAME/KEY: MISC_FEATURE
```

```
<222> LOCATION: (31)..(35)
<223> OTHER INFORMATION: Complementarity determining region 1
<220> FEATURE:
<221> NAME/KEY: MISC_FEATURE
<222> LOCATION: (36)..(49)
<223> OTHER INFORMATION: Framework region 2
<220> FEATURE:
<221> NAME/KEY: MISC_FEATURE
<222> LOCATION: (50)..(66)
<223> OTHER INFORMATION: Complementarity determining region 2
<220> FEATURE:
<221> NAME/KEY: MISC_FEATURE
<222> LOCATION: (67)..(98)
<223> OTHER INFORMATION: Framework region 3

<400> SEQUENCE: 37

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys

<210> SEQ ID NO 38
<211> LENGTH: 12
<212> TYPE: PRT
<213> ORGANISM: Homo sapiens
<220> FEATURE:
<221> NAME/KEY: MISC_FEATURE
<222> LOCATION: (1)..(2)
<223> OTHER INFORMATION: Complementarity determining region 3
<220> FEATURE:
<221> NAME/KEY: MISC_FEATURE
<222> LOCATION: (3)..(12)
<223> OTHER INFORMATION: Framework region 4

<400> SEQUENCE: 38

Leu Thr Phe Gly Gly Gly Thr Lys Val Glu Ile Lys
1               5                   10

<210> SEQ ID NO 39
<211> LENGTH: 15
<212> TYPE: PRT
<213> ORGANISM: Homo sapiens
<220> FEATURE:
<221> NAME/KEY: MISC_FEATURE
<222> LOCATION: (1)..(4)
<223> OTHER INFORMATION: Complementarity determining region 3
<220> FEATURE:
<221> NAME/KEY: MISC_FEATURE
<222> LOCATION: (5)..(15)
<223> OTHER INFORMATION: Framework region 4
```

```
<400> SEQUENCE: 39

Tyr Phe Asp Tyr Trp Gly Gln Gly Thr Leu Val Thr Val Ser Ser
1               5                   10                  15

<210> SEQ ID NO 40
<211> LENGTH: 219
<212> TYPE: PRT
<213> ORGANISM: Homo sapiens

<400> SEQUENCE: 40

Glu Leu Gln Met Thr Gln Ser Pro Ser Ser Leu Ser Ala Ser Val Gly
1               5                   10                  15

Asp Arg Val Thr Ile Thr Cys Arg Ser Gln Ser Leu Leu His Thr
            20                  25                  30

Tyr Gly Ser Pro Tyr Leu Asn Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Val Tyr Phe Cys Ser Gln Gly
                85                  90                  95

Thr His Leu Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 41
<211> LENGTH: 448
<212> TYPE: PRT
<213> ORGANISM: Homo sapiens

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ser Pro Glu Lys Gly Leu Glu Trp Val
        35                  40                  45

Ser Glu Ile Arg Leu Arg Ser Asp Asn Tyr Ala Thr His Tyr Ala Glu
    50                  55                  60

Ser Val Lys Gly Arg Phe Thr Ile Ser Arg Asp Asn Ser Lys Asn Thr
65                  70                  75                  80
```

```
Leu Tyr Leu Gln Met Asn Ser Leu Arg Ala Glu Asp Thr Gly Ile Tyr
                85                  90                  95

Tyr Cys Lys Thr Tyr Phe Tyr Ser Phe Ser Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

ANTI-ANGIOGENIC COMPOUNDS

RELATED APPLICATIONS

The present application claims priority to U.S. Provisional Application No. 60/658,654, filed Mar. 3, 2005, and U.S. Provisional Application No. 60/677,089, filed May 2, 2005, the disclosures of both of which are incorporated by reference herein in their entirety, including drawings and sequence listings.

FIELD OF THE DISCLOSURE

The present invention relates to novel compounds that possess anti-angiogenic activity and methods of making and using these compounds.

BACKGROUND

Angiogenesis is the fundamental process by which new blood vessels are formed and is essential to a variety of normal body activities such as reproduction, development and wound repair. Although angiogenesis is a highly regulated process under normal conditions, many diseases (characterized as "angiogenic diseases") are caused or exacerbated by unregulated angiogenesis. For example, ocular neovascularization has been implicated as the most common cause of blindness. In certain existing conditions such as arthritis, newly formed capillary blood vessels invade the joints and destroy cartilage. In diabetes, new capillaries formed in the retina invade the vitreous, bleed, and cause blindness. Growth and metastasis of solid tumors are also angiogenesis-dependent (J. Folkman, Cancer Res., 46:467-473 (1986), J. Folkman, J. Natl. Cancer Inst., 82:4-6 (1989)). It has been shown, for example, that tumors which enlarge to greater than 2 mm obtain their own blood supply by inducing the growth of new capillary blood vessels. Once these new blood vessels become embedded in the tumor, they provide a means for tumor cells to enter the circulation and metastasize to distant sites such as the liver, lungs, and bones (N. Weidner, et. al., N. Engl. J. Med., 324:1-8 (1991)).

Thrombospondin-1 (TSP-1) is an extracellular matrix protein secreted in response to activation of platelets by thrombin. Various studies have demonstrated that certain peptide analogs of TSP-1 possess antiangiogenesic activity. See, e.g., WO 01/38397, WO 01/38347, WO 99/61476, U.S. Patent Application Pub. No. 2003/0045477, U.S. Patent Application Pub. No. 2002/0183242, U.S. Pat. Nos. 6,774,211, 6,716,963, 6,753,408, and 5,932,545. However, it is desirable to prepare antiangiogenic compounds having improved profiles of activity.

BRIEF SUMMARY

The present invention provides thrombospondin receptor targeting compounds (AA targeting compounds) with unique specificity and biological properties which are useful in many applications. The thrombospondin targeting compounds of the invention are formed by covalently linking a thrombospondin targeting agent to a combining site of an antibody. Pharmaceutical compositions comprising targeting compounds of the invention and a pharmaceutically acceptable carrier are also provided.

A first aspect of the invention is an AA targeting agent-linker conjugate having Formula I:

L-[AA targeting agent]  (I)

wherein:

[AA targeting agent] is a peptide selected from the group consisting of:

| | |
|---|---|
| $R^1$-Sar-Gly-Val-(D-alloIle)-Thr-Nva-Ile-Arg-Pro-$R^3$; | (SEQ ID NO:1) |
| $R^2$-Pro-Phe-Val-(D-alloIle)-Thr-Nva-Ile-Arg-Pro-$R^3$; | (SEQ ID NO:2) |
| $R^1$-Sar-Gly-Val-(D-alloIle)-Thr-Nva-Lys-Arg-Pro-$R^3$; | (SEQ ID NO:3) |
| $R^1$-Sar-Gly-Val-(D-alloIle)-Thr-Lys-Ile-Arg-Pro-$R^3$; | (SEQ ID NO:4) |
| $R^1$-Sar-Gly-Val-(D-alloIle)-Thr-Gln-Ile-Arg-Pro-$R^3$; | (SEQ ID NO:5) |
| $R^1$-Sar-Gly-Val-(D-alloIle)-Thr-(α-Ally-Gly)-Ile-Arg-Pro-$R^3$; | (SEQ ID NO:6) |
| $R^1$-Sar-Phe-Val-(D-alloIle)-Thr-Nva-Ile-Arg-Pro-$R^3$; | (SEQ ID NO:7) |
| $R^2$-Lys-Gly-Val-(D-alloIle)-Thr-Nva-Ile-Arg-Pro-$R^3$; | (SEQ ID NO:8) |
| $R^2$-Glu-Gly-Val-(D-alloIle)-Thr-Nva-Ile-Arg-Pro-$R^3$; | (SEQ ID NO:9) |
| $R^2$-Pro-Gly-Val-(D-alloIle)-Thr-Nva-Ile-Arg-Pro-$R^3$; | (SEQ ID NO:10) |
| $R^2$-Pro-(4-Cyano-Phe)-Val-(D-alloIle)-Thr-Nva-Ile-Arg-Pro-$R^3$; | (SEQ ID NO:11) |
| $R^2$-Pro-(3,4-Dimethoxy-Phe)-Val-(D-alloIle)-Thr-Nva-Ile-Arg-Pro-$R^3$; | (SEQ ID NO:12) |
| $R^2$-Pro-(3-(4-thiazolyl)-L-Ala)-Val-(D-alloIle)-Thr-Nva-Ile-Arg-Pro-$R^3$; | (SEQ ID NO:13) |
| $R^2$-Pro-(2-furyl-Ala)-Val-(D-alloIle)-Thr-Nva-Ile-Arg-Pro-$R^3$; | (SEQ ID NO:14) |
| $R^2$-Pro-(Cyclo-Leu)-Val-(D-alloIle)-Thr-Nva-Ile-Arg-Pro-$R^3$; | (SEQ ID NO:15) |
| $R^2$-Gly-Val-(D-Ile)-Thr-Arg-Ile-Arg-$R^3$; and | (SEQ ID NO:16) |
| $R^1$-Sar-Gly-Val-(D-Ile)-Thr-Nva-Ile-Arg-Pro-$R^3$; | (SEQ ID NO:17) | wherein $R^1$ is $NH(CH_3)$, $N(CH_3)C(O)CH_3$, $N(CH_3)C(O)CH_2CH_3$, $N(CH_3)C(O)CH_2CH_2CH_3$, $N(CH_3)C(O)CH(CH_3)CH_3$, $N(CH_3)C(O)CH_2CH_2CH_2CH_3$, $N(CH_3)C(O)CH(CH_3)CH_2CH_3$, $N(CH_3)C(O)C_6H_5$, $N(CH_3)C(O)CH_2CH_2(CH_2CH_2O)_{1-5}Me$, an amino protecting group, a lipid fatty acid group or a carbohydrate;

$R^2$ is $NH_2$, $NHC(O)CH_3$, $NHC(O)CH_2CH_3$, $NHC(O)CH_2CH_2CH_3$, $NHC(O)CH(CH_3)CH_3$, $NHC(O)CH_2CH_2CH_2CH_3$, $NHC(O)CH(CH_3)CH_2CH_3$, $NHC(O)C_6H_5$, $NH(CH_3)C(O)CH_2CH_2(CH_2CH_2O)_{1-5}Me$, an amino protecting group, a lipid fatty acid group or a carbohydrate;

$R^3$ is COOH, $C(O)NH_2$, $C(O)NH(CH_3)$, $C(O)NHCH_2CH_3$, $C(O)NHCH_2CH_2CH_3$, $C(O)NHCH(CH_3)CH_3$, $C(O)NHCH_2CH_2CH_2CH_3$, $C(O)NHCH(CH_3)$

CH$_2$CH$_3$, C(O)NHC$_6$H$_5$, C(O)NHCH$_2$CH$_2$OCH$_3$, C(O)NHOCH$_3$, C(O)NHOCH$_2$CH$_3$, a carboxy protecting group, a lipid fatty acid group or a carbohydrate; and L is a linker moiety having the formula —X—Y-Z, wherein:
  X is a biologically compatible polymer or block copolymer attached to one of the residues that comprises an AA targeting agent;
  Y is an optionally present recognition group comprising at least a ring structure; and
  Z is a reactive group that is capable of covalently linking to a side chain in a combining site of an antibody; and pharmaceutically acceptable salts, stereoisomers, tautomers, solvates, and prodrugs thereof.

In some embodiments of compounds of Formula I, X is:

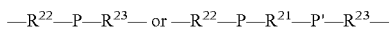

wherein:
  P and P' are independently selected from the group consisting of polyoxyalkylene oxides such as polyethylene oxide, polyethyloxazoline, poly-N-vinyl pyrrolidone, polyvinyl alcohol, polyhydroxyethyl acrylate, polyhydroxy ethylmethacrylate and polyacrylamide, polyamines having amine groups on either the polymer backbone or the polymer sidechains, such as polylysine, polyornithine, polyarginine, and polyhistidine, nonpeptide polyamines such as polyaminostyrene, polyaminoacrylate, poly(N-methyl aminoacrylate), poly(N-ethylaminoacrylate), poly(N,N-dimethyl aminoacrylate), poly(N,N-diethylaminoacrylate), poly(aminomethacrylate), poly(N-methyl amino-methacrylate), poly(N-ethyl aminomethacrylate), poly(N,N-dimethyl aminomethacrylate), poly(N,N-diethyl aminomethacrylate), poly(ethyleneimine), polymers of quaternary amines, such as poly(N,N,N-trimethylaminoacrylate chloride), poly(methyacrylamidopropyltrimethyl ammonium chloride), proteoglycans such as chondroitin sulfate-A (4-sulfate) chondroitin sulfate-C (6-sulfate) and chondroitin sulfate-B, polypeptides such as polyserine, polythreonine, polyglutamine, natural or synthetic polysaccharides such as chitosan, hydroxy ethyl cellulose, and lipids;
  $R^{21}$, $R^{22}$, and $R^{23}$ are each independently a covalent bond, —O—, —S—, —NR$^b$—, substituted or unsubstituted straight or branched chain C$_{1\text{-}50}$ alkylene, or substituted or unsubstituted straight or branched chain C$_{1\text{-}50}$ heteroalkylene;
  $R^b$ is hydrogen, substituted or unsubstituted C$_{1\text{-}10}$ alkyl, substituted or unsubstituted C$_{3\text{-}7}$ cycloalkyl-C$_{0\text{-}6}$ alkyl, or substituted or unsubstituted aryl-C$_{0\text{-}6}$ alkyl; and
  $R^{21}$, $R^{22}$, and $R^{23}$ are selected such that the backbone length of X remains about 200 atoms or less.

In some embodiments of compounds of Formula I, X is attached to an amino acid residue in [AA targeting agent], and is an optionally substituted —R$^{22}$—[CH$_2$—CH$_2$—O]$_t$—R$^{23}$—, —R$^{22}$-cycloalkyl-R$^{23}$—, —R$^{22}$-aryl-R$^{23}$—, or —R$^{22}$-heterocyclyl-R$^{23}$—, wherein t is 0 to 50.

In some embodiments of compounds of Formula I, $R^{22}$ is —(CH$_2$)$_v$—, —(CH$_2$)$_u$—C(O)—(CH$_2$)$_v$—, —(CH$_2$)$_u$—C(O)—O—(CH$_2$)$_v$—, —(CH$_2$)$_u$—C(S)—NR$^b$—(CH$_2$)$_v$—, —(CH$_2$)$_u$—C(O)—NR$^b$—(CH$_2$)$_v$—, —(CH$_2$)$_u$—NR$^b$—(CH$_2$)$_v$—, —(CH$_2$)$_u$—O—(CH$_2$)$_v$—, —(CH$_2$)$_u$—S(O)$_{0\text{-}2}$—(CH$_2$)$_v$—, —(CH$_2$)$_u$—S(O)$_{0\text{-}2}$—NR$^b$—(CH$_2$)$_v$—, or —(CH$_2$)$_u$—P(O)(OR$^b$)—O—(CH$_2$)$_v$—, wherein u and v are independently 0, 1, 2, 3, 4, 5, 6, 7, 8, 9, 10, 11, 12, 13, 14, 15, 16, 17, 18, 19 or 20.

In some embodiments of compounds of Formula I, $R^{21}$ and $R^{23}$ are independently —(CH$_2$)$_s$—, —(CH$_2$)$_r$—C(O)—(CH$_2$)$_s$—, —(CH$_2$)$_r$—C(O)—O—(CH$_2$)$_v$—, —(CH$_2$)$_r$—C(S)—NR$^b$—(CH$_2$)$_s$—, —(CH$_2$)$_r$—C(O)—NR$^b$—(CH$_2$)$_s$—, —(CH$_2$)$_r$—NR$^b$—(CH$_2$)$_s$—, —(CH$_2$)$_r$—O—(CH$_2$)$_s$—, —(CH$_2$)$_r$—S(O)$_{0\text{-}2}$—(CH$_2$)$_s$—, —(CH$_2$)$_r$—S(O)$_{0\text{-}2}$—NR$^b$—(CH$_2$)$_s$—, or —(CH$_2$)$_r$—P(O)(OR$^b$)—O—(CH$_2$)$_s$—, wherein r, s, and v are independently 0, 1, 2, 3, 4, 5, 6, 7, 8, 9, 10, 11, 12, 13, 14, 15, 16, 17, 18, 19 or 20.

In some embodiments of Formula I, if t>1 or if X is —R$^{22}$—[CH$_2$—CH$_2$—O]$_t$—R$^{23}$—, —R$^{22}$-cycloalkyl-R$^{23}$—, —R$^{22}$-aryl-R$^{23}$—, or —R$^{22}$-heterocyclyl-R$^{23}$—, Y is present. FIGS. 1A and 1B illustrate two embodiments according to Formula I that employ Ac-Sar-Gly-Val-(D-alloIle)-Thr-Nva-Ile-Arg-Pro (SEQ ID NO:1, wherein $R^1$ is Ac and $R^3$ is absent) and Sar-Gly-Val-(D-alloIle)-Thr-Nva-Ile-Arg-Pro-NHEt (SEQ ID NO:1, wherein $R^1$ is absent and $R^3$ is NHEt), respectively, as targeting agents. FIG. 2 illustrates other embodiments according to Formula I that employ Ac-Sar-Gly-Val-(D-alloIle)-Thr-Nva-Lys-Arg-Pro-NHEt (SEQ ID NO:3, wherein $R^1$ is Ac and $R^3$ is NHEt) as a targeting agent.

Another aspect of the invention, illustrated in Formula II, is an AA targeting compound comprising an AA targeting agent covalently linked to a combining site of an Antibody via an intervening linker L'. The Antibody portion of an AA targeting compound can include whole (full length) antibody, unique antibody fragments, or any other forms of an antibody as this term is used herein. In one embodiment, the Antibody is a humanized version of a murine aldolase antibody comprising a constant region from a human IgG, IgA, IgM, IgD, or IgE antibody. In another embodiment, the Antibody is a chimeric antibody comprising the variable region from a murine aldolase antibody and a constant region from a human IgG, IgA, IgM, IgD, or IgE antibody. In a further embodiment, the Antibody is a fully human version of a murine aldolase antibody comprising a polypeptide sequence from natural or native human IgG, IgA, IgM, IgD, or IgE antibody Antibody-L'-[AA targeting agent]    (II)

wherein:

[AA targeting agent] is a peptide selected from the group consisting of:

R$^1$-Sar-Gly-Val-(D-alloIle)-Thr-Nva-Ile-Arg-Pro-R$^3$;    (SEQ ID NO:1)

R$^2$-Pro-Phe-Val-(D-alloIle)-Thr-Nva-Ile-Arg-Pro-R$^3$;    (SEQ ID NO:2)

R$^1$-Sar-Gly-Val-(D-alloIle)-Thr-Nva-Lys-Arg-Pro-R$^3$;    (SEQ ID NO:3)

R$^1$-Sar-Gly-Val-(D-alloIle)-Thr-Lys-Ile-Arg-Pro-R$^3$;    (SEQ ID NO:4)

R$^1$-Sar-Gly-Val-(D-alloIle)-Thr-Gln-Ile-Arg-Pro-R$^3$;    (SEQ ID NO:5)

R$^1$-Sar-Gly-Val-(D-alloIle)-Thr-(α-Ally-Gly)-Ile-Arg-Pro-R$^3$;    (SEQ ID NO:6)

R$^1$-Sar-Phe-Val-(D-alloIle)-Thr-Nva-Ile-Arg-Pro-R$^3$;    (SEQ ID NO:7)

R$^2$-Lys-Gly-Val-(D-alloIle)-Thr-Nva-Ile-Arg-Pro-R$^3$;    (SEQ ID NO:8)

R$^2$-Glu-Gly-Val-(D-alloIle)-Thr-Nva-Ile-Arg-Pro-R$^3$;    (SEQ ID NO:9)

```
R²-Pro-Gly-Val-(D-alloIle)-Thr-Nva-    (SEQ ID NO:10)
Ile-Arg-Pro-R³;

R²-Pro-(4-Cyano-Phe)-Val-(D-           (SEQ ID NO:11)
alloIle)-Thr-Nva-Ile-Arg-Pro-R³;

R²-Pro-(3,4-Dimethoxy-Phe)-Val-(D-     (SEQ ID NO:12)
alloIle)-Thr-Nva-Ile-Arg-Pro-R³;

R²-Pro-(3-(4-thiazolyl)-L-Ala)-Val-    (SEQ ID NO:13)
(D-alloIle)-Thr-Nva-Ile-Arg-Pro-R³;

R²-Pro-(2-furyl-Ala)-Val-(D-           (SEQ ID NO:14)
alloIle)-Thr-Nva-Ile-Arg-Pro-R³;

R²-Pro-(Cyclo-Leu)-Val-(D-             (SEQ ID NO:15)
alloIle)-Thr-Nva-Ile-Arg-Pro-R³;

R²-Gly-Val-(D-Ile)-Thr-Arg-Ile-Arg-    (SEQ ID NO:16)
R³;
and

R¹-Sar-Gly-Val-(D-Ile)-Thr-Nva-Ile-    (SEQ ID NO:17)
Arg-Pro-R³;
wherein
```

$R^1$ is $NH(CH_3)$, $N(CH_3)C(O)CH_3$, $N(CH_3)C(O)CH_2CH_3$, $N(CH_3)C(O)CH_2CH_2CH_3$, $N(CH_3)C(O)CH(CH_3)CH_3$, $N(CH_3)C(O)CH_2CH_2CH_2CH_3$, $N(CH_3)C(O)CH(CH_3)CH_2CH_3$, $N(CH_3)C(O)C_6H_5$, $N(CH_3)C(O)CH_2CH_2(CH_2CH_2O)_{1-5}Me$, an amino protecting group, a lipid fatty acid group or a carbohydrate;

$R^2$ is $NH_2$, $NHC(O)CH_3$, $NHC(O)CH_2CH_3$, $NHC(O)CH_2CH_2CH_3$, $NHC(O)CH(CH_3)CH_3$, $NHC(O)CH_2CH_2CH_2CH_3$, $NHC(O)CH(CH_3)CH_2CH_3$, $NHC(O)C_6H_5$, $NH(CH_3)C(O)CH_2CH_2(CH_2CH_2O)_{1-5}Me$, an amino protecting group, a lipid fatty acid group or a carbohydrate;

$R^3$ is $COOH$, $C(O)NH_2$, $C(O)NH(CH_3)$, $C(O)NHCH_2CH_3$, $C(O)NHCH_2CH_2CH_3$, $C(O)NHCH(CH_3)CH_3$, $C(O)NHCH_2CH_2CH_2CH_3$, $C(O)NHCH(CH_3)CH_2CH_3$, $C(O)NHC_6H_5$, $C(O)NHCH_2CH_2OCH_3$, $C(O)NHOCH_3$, $C(O)NHOCH_2CH_3$, a carboxy protecting group, a lipid fatty acid group or a carbohydrate; and L' is a linker moiety having the formula —X—Y-Z', wherein:

X is a biologically compatible polymer or block copolymer attached to one of the residues that comprises an AA targeting agent;

Y is an optionally present recognition group comprising at least a ring structure; and Z is a group that is covalently linked to a side chain in a combining site of an antibody;

and pharmaceutically acceptable salts, stereoisomers, tautomers, solvates, and prodrugs thereof.

In some embodiments of compounds of Formula II, X is:

$$-R^{22}-P-R^{23}-\text{ or }-R^{22}-P-R^{21}-P'-R^{23}-$$

wherein:

P and P' are independently selected from the group consisting of polyoxyalkylene oxides such as polyethylene oxide, polyethyloxazoline, poly-N-vinyl pyrrolidone, polyvinyl alcohol, polyhydroxyethyl acrylate, polyhydroxy ethylmethacrylate and polyacrylamide, polyamines having amine groups on either the polymer backbone or the polymer side chains, such as polylysine, polyornithine, polyarginine, and polyhistidine, nonpeptide polyamines such as polyaminostyrene, polyaminoacrylate, poly(N-methyl aminoacrylate), poly(N-ethylaminoacrylate), poly(N,N-dimethyl aminoacrylate), poly(N,N-diethylaminoacrylate), poly(aminomethacrylate), poly(N-methyl amino-methacrylate), poly(N-ethyl aminomethacrylate), poly(N,N-dimethyl aminomethacrylate), poly(N,N-diethyl aminomethacrylate), poly(ethyleneimine), polymers of quaternary amines, such as poly(N,N,N-trimethylaminoacrylate chloride), poly(methyacrylamidopropyltrimethyl ammonium chloride), proteoglycans such as chondroitin sulfate-A (4-sulfate) chondroitin sulfate-C (6-sulfate) and chondroitin sulfate-B, polypeptides such as polyserine, polythreonine, polyglutamine, natural or synthetic polysaccharides such as chitosan, hydroxy ethyl cellulose, and lipids;

$R^{21}$, $R^{22}$, and $R^{23}$ are each independently a covalent bond, —O—, —S—, $-NR^b-$, substituted or unsubstituted straight or branched chain $C_{1-50}$ alkylene, or substituted or unsubstituted straight or branched chain $C_{1-50}$ heteroalkylene;

$R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl; and $R^{21}$, $R^{22}$, and $R^{23}$ are selected such that the backbone length of X remains about 200 atoms or less.

In some embodiments of compounds of Formula II, X is attached to an amino acid residue in [AA targeting agent], and is an optionally substituted $-R^{22}-[CH_2-CH_2-O]_t-R^{23}-$, $-R^{22}$-cycloalkyl-$R^{23}-$, $-R^{22}$-aryl-$R^{23}-$, or $-R^{22}$-heterocyclyl-$R^{23}-$, wherein t is 0 to 50.

In some embodiments of compounds of Formula II, $R^{22}$ is $-(CH_2)_v-$, $-(CH_2)_u-C(O)-(CH_2)_v-$, $-(CH_2)_u-C(O)-O-(CH_2)_v-$, $-(CH_2)_u-C(S)-NR^b-(CH_2)_v-$, $-(CH_2)_u-C(O)-NR^b-(CH_2)_v-$, $-(CH_2)_u-NR^b-(CH_2)_v-$, $-(CH_2)_u-O-(CH_2)_v-$, $-(CH_2)_u-S(O)_{0-2}-(CH_2)_v-$, $-(CH_2)_u-S(O)_{0-2}-NR^b-(CH_2)_v-$, or $-(CH_2)_u-P(O)(OR^b)-O-(CH_2)_v-$, wherein u and v are independently 0, 1, 2, 3, 4, 5, 6, 7, 8, 9, 10, 11, 12, 13, 14, 15, 16, 17, 18, 19 or 20.

In some embodiments of compounds of Formula II, $R^{21}$ and $R^{23}$ are independently $-(CH_2)_s-$, $-(CH_2)_r-C(O)-(CH_2)_s-$, $-(CH_2)_r-C(O)-O-(CH_2)_v-$, $-(CH_2)_r-C(S)-NR^b-(CH_2)_s-$, $-(CH_2)_r-C(O)-NR^b-(CH_2)_s-$, $-(CH_2)_r-NR^b-(CH_2)_s-$, $-(CH_2)_r-O-(CH_2)_s-$, $-(CH_2)_r-S(O)_{0-2}-(CH_2)_s-$, $-(CH_2)_r-S(O)_{0-2}-NR^b-(CH_2)_s-$, or $-(CH_2)_r-P(O)(OR^b)-O-(CH_2)_s-$, wherein r, s, and v are independently 0, 1, 2, 3, 4, 5, 6, 7, 8, 9, 10, 11, 12, 13, 14, 15, 16, 17, 18, 19 or 20.

Exemplary compounds in accordance with Formula II, wherein Antibody is the humanized aldolase antibody h38c2 IgG1, include:

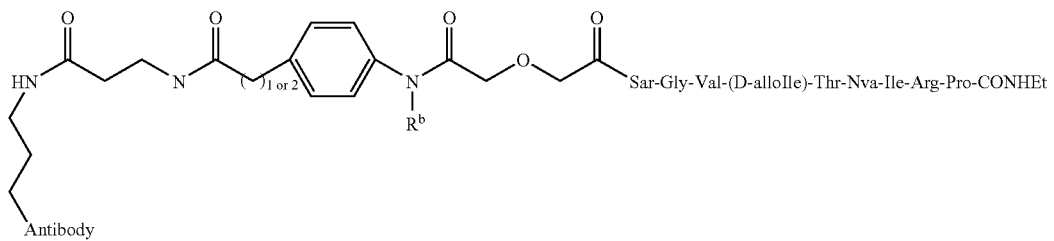
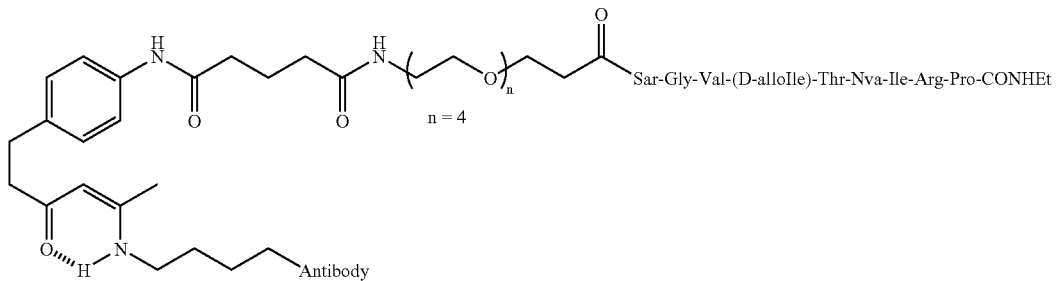
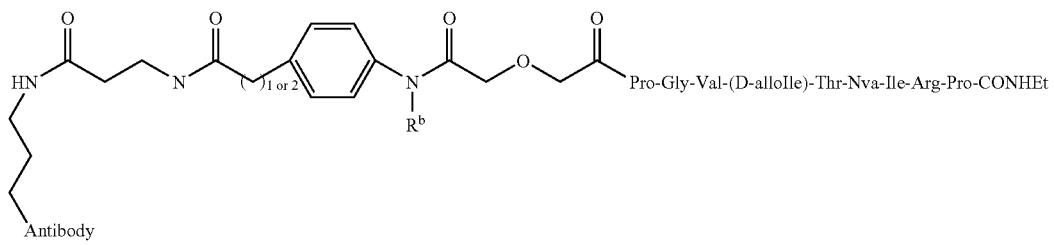
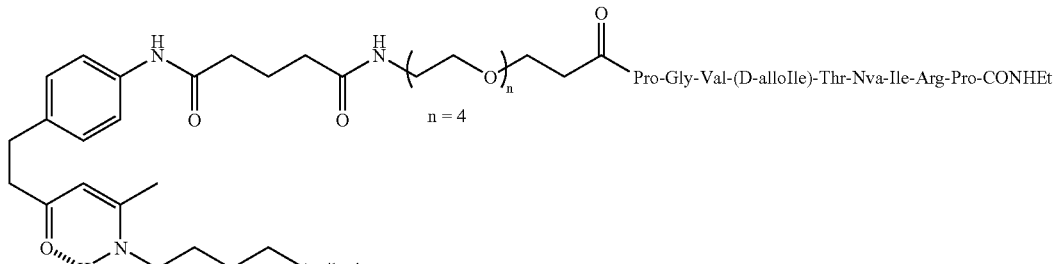
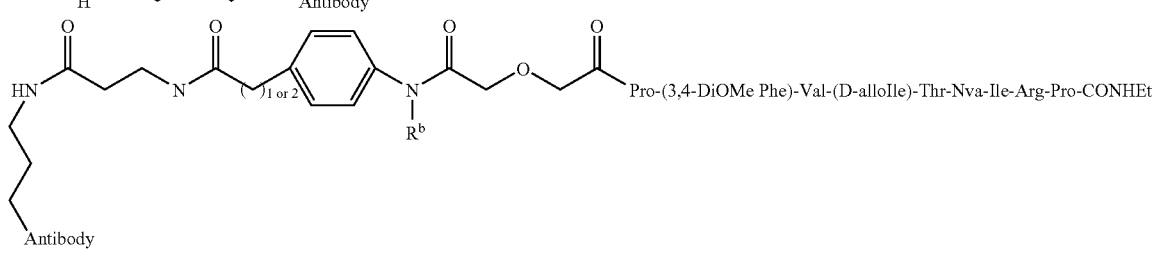
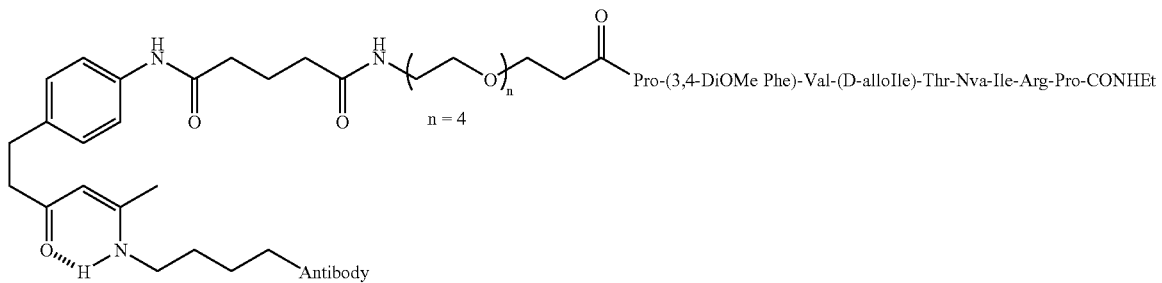

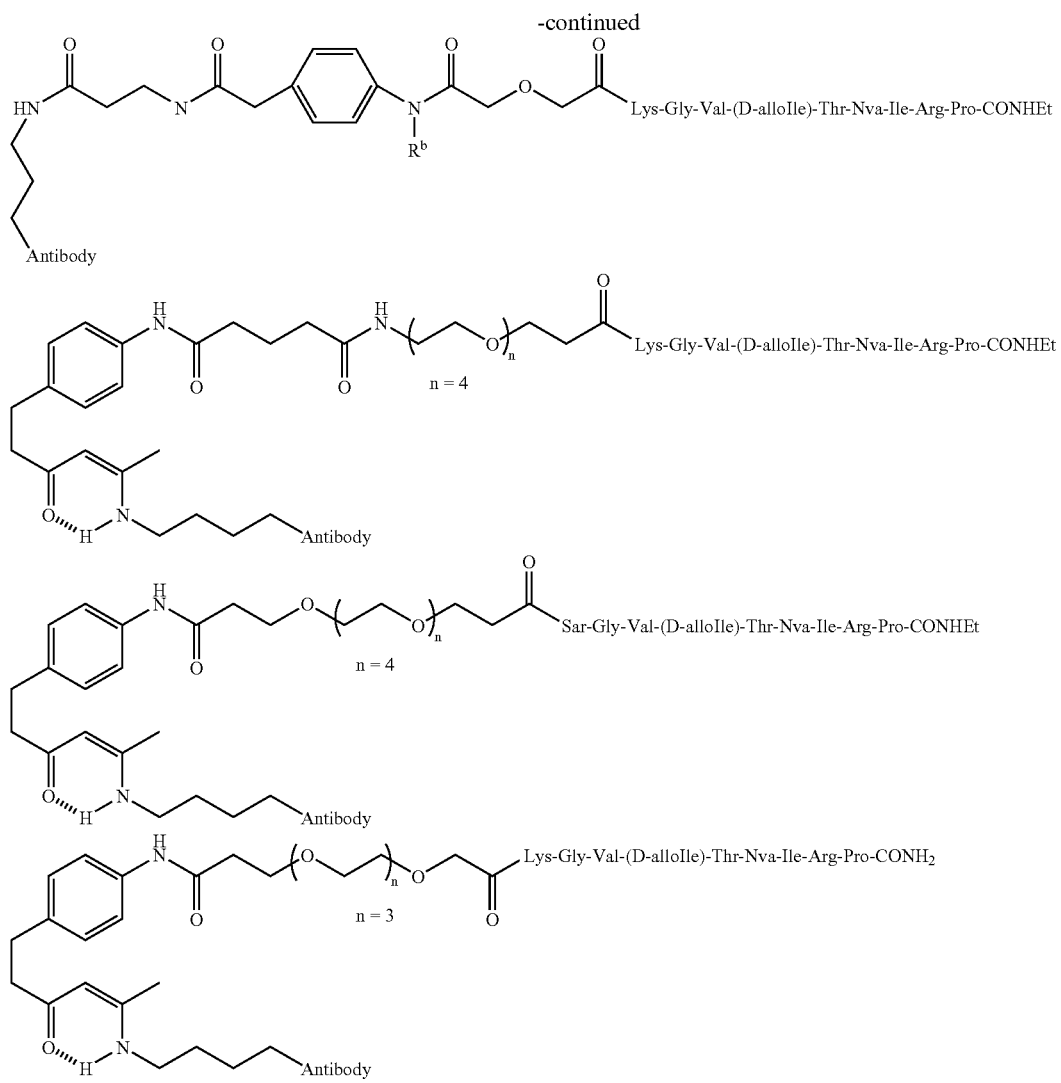

Another aspect of the invention, illustrated in Formula III, is an AA targeting compound in which two AA targeting agents, which may be the same or different, are each covalently linked to a combining site of an antibody. The Antibody portion of an AA targeting compound can include whole (full length) antibody, unique antibody fragments, or any other forms of an antibody as this term is used herein. In one embodiment, the Antibody is a humanized version of a murine aldolase antibody comprising a constant region from a human IgG, IgA, IgM, IgD, or IgE antibody. In another embodiment, the Antibody is a chimeric antibody comprising the variable region from a murine aldolase antibody and a constant region from a human IgG, IgA, IgM, IgD, or IgE antibody. In a further embodiment, the Antibody is a fully human version of a murine aldolase antibody comprising a polypeptide sequence from natural or native human IgG, IgA, IgM, IgD, or IgE antibody.

Antibody[-L'-[AA targeting agent]]$_2$ (III)

wherein:

[AA targeting agent], Antibody, and L' are as defined according to Formula II. FIG. 3 illustrates embodiments according to Formula III that employ Sar-Gly-Val-(D-alloIle)-Thr-Nva-Ile-Arg-Pro-NHEt (SEQ ID NO:1, wherein $R^1$ is absent and $R^3$ is NHEt) as a targeting agent. FIG. 4 illustrates other embodiments according to Formula III that employ Ac-Sar-Gly-Val-(D-alloIle)-Thr-Nva-Ile-Arg-Pro (SEQ ID NO:1) as a targeting agent. FIG. 5 illustrates other embodiments according to Formula III that employ Ac-Sar-Gly-Val-(D-alloIle)-Thr-Nva-Lys-Arg-Pro-NHEt (SEQ ID NO:3) as a targeting agent.

Also provided are methods of delivering or administering AA targeting compounds of the invention and methods of treatment using AA targeting compounds of the invention. For example, methods of treating (including preventing) a disease or condition associated with abnormal angiogenesis in a subject include administering a therapeutically effective amount of an AA targeting compound of the invention to the subject. Diseases and conditions that may be treated include cancer, arthritis, hypertension, kidney disease, psoriasis, angiogenesis of the eye associated with ocular disorder, infection or surgical intervention, macular degeneration, diabetic retinopathy, and the like.

Another aspect of the invention includes methods of using AA targeting compounds of the invention for diagnostic purposes. For example, the AA targeting compounds can be used for the diagnosis of a disease or condition associated with abnormal angiogenesis, including cancer, arthritis, psoriasis, angiogenesis of the eye associated with an ocular disorder, infection or surgical intervention, macular degeneration, diabetic retinopathy, and the like.

DESCRIPTION OF THE DRAWINGS

FIGS. 1A and 1B illustrate embodiments according to Formula I.

FIG. 2 illustrate additional embodiments according to Formula I.

FIG. 3 illustrates embodiments according to Formula III. Aldolase Ab-N-represents a covalent bond to a side of an amino acid in a combining site of an antibody.

FIG. 4 illustrates additional embodiments according to Formula III. Aldolase Ab-N-represents a covalent bond to a side of an amino acid in a combining site of an antibody.

FIG. 5 illustrates additional embodiments according to Formula III. Antibody-N-represents a covalent bond to a side of an amino acid in a combining site of an antibody.

FIG. 7A illustrates the amino acid sequence alignment of the variable domains of m38c2, h38c2, and human germlines. Framework regions (FR) and complementarity determining regions (CDR) are defined according to Kabat et al. Asterisks mark differences between m38c2 and h38c2 or between h38c2 and the human germlines. FIG. 7B illustrates the amino acid sequence of the light and heavy chains of h38c2 IgG1.

FIG. 9 shows various electrophiles that are suitable for reactive modification with a reactive amino acid side chain in a combining site of an antibody and thus may serve as linker reactive groups. Key: (A) acyl beta-lactam; (B) simple diketone; (C) succinimide active ester; (D) maleimide; (E) haloacetamide with linker; (F) haloketone; (G) cyclohexyl diketone; and (H) aldehyde. The squiggle line indicates the point of attachment to the rest of the linker or targeting agent. X refers to a halogen.

FIG. 12 shows a synthesis of:

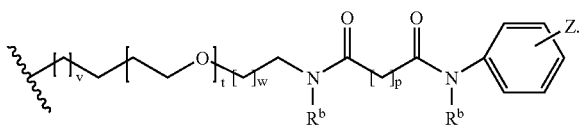

Figure 13:
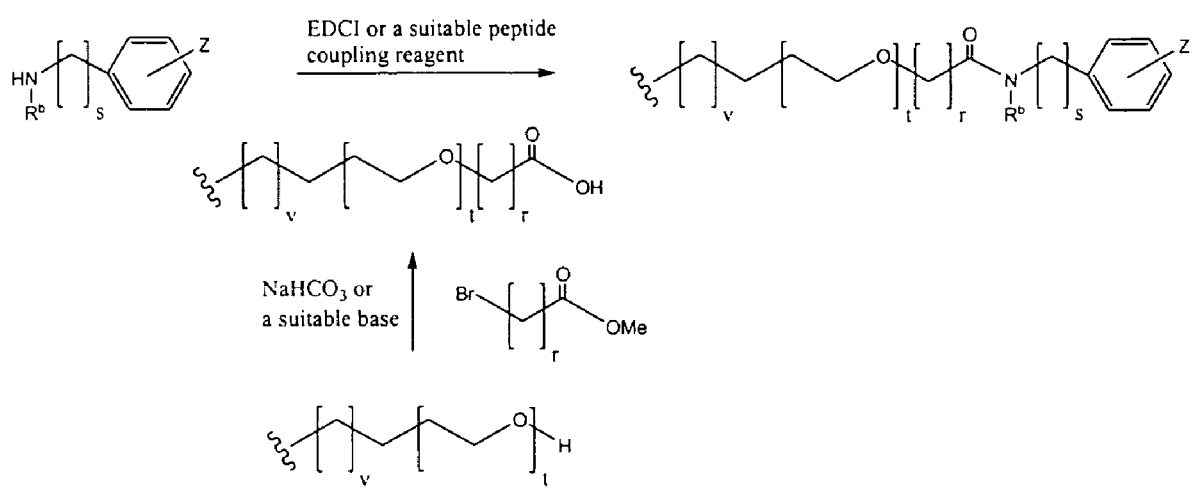

FIG. 13 shows a synthesis of:

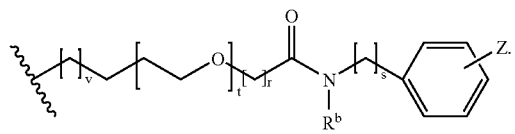

Figure 14:
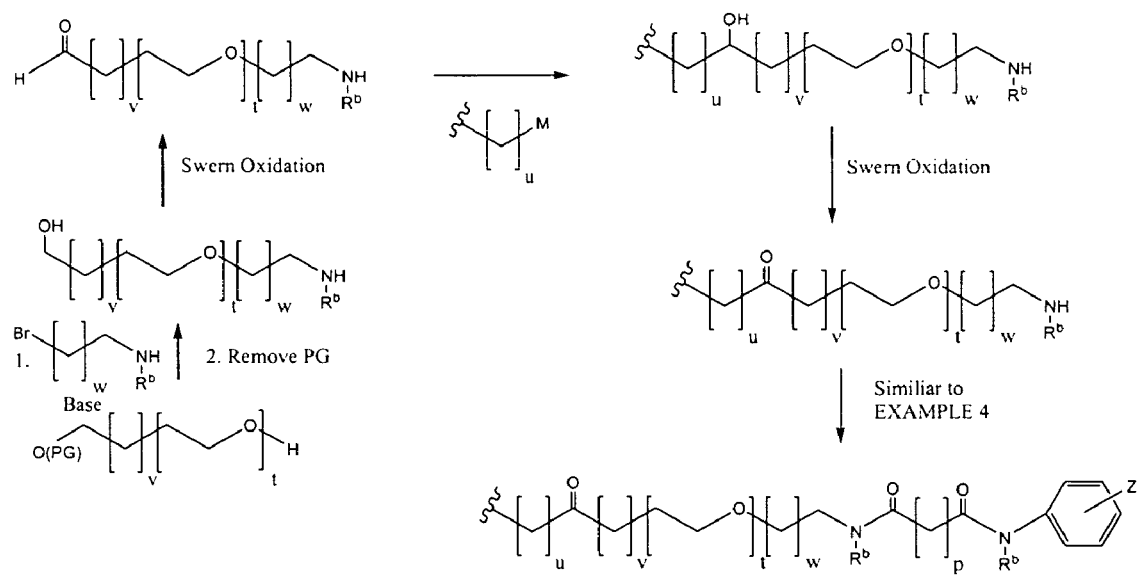

FIG. 14 shows a synthesis of:

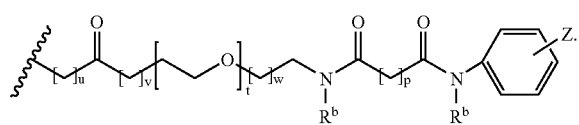

Figure 15:
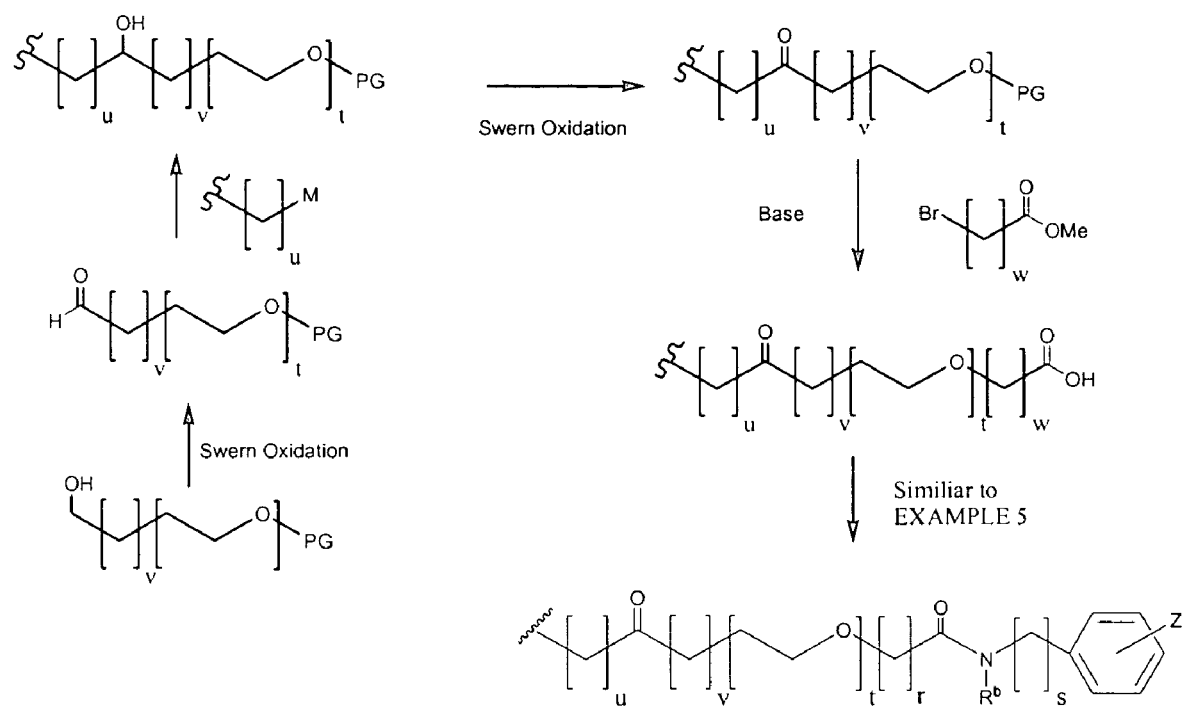

FIG. 15 shows a synthesis of:

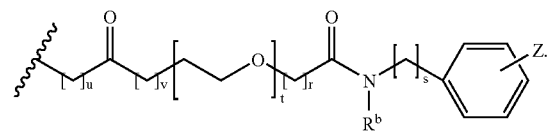

Figure 16:
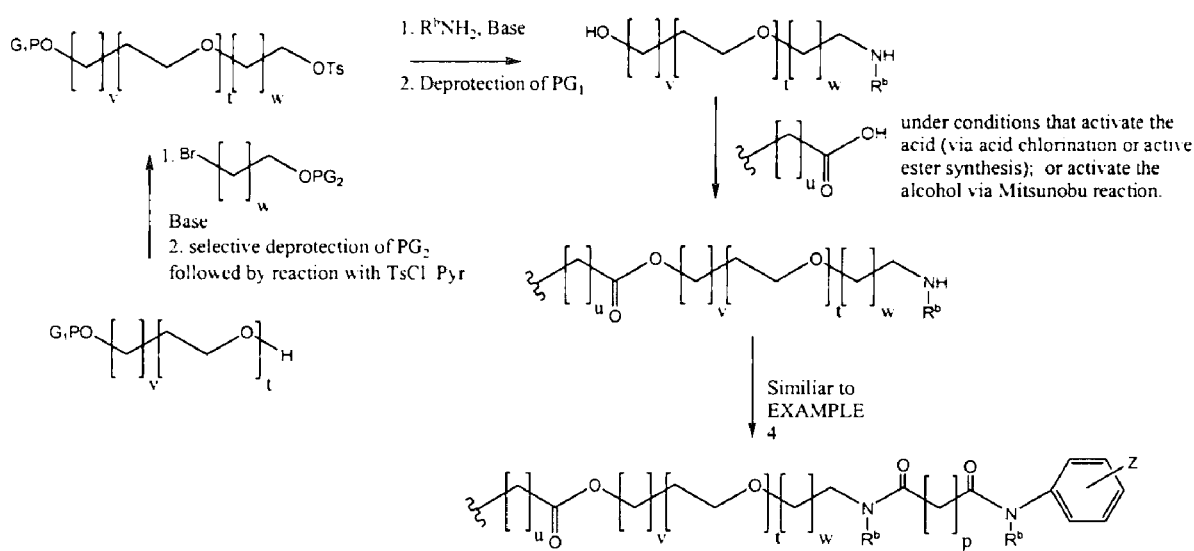

FIG. 16 shows a synthesis of:

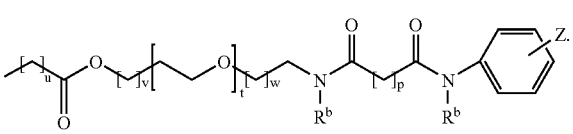

Figure 17:
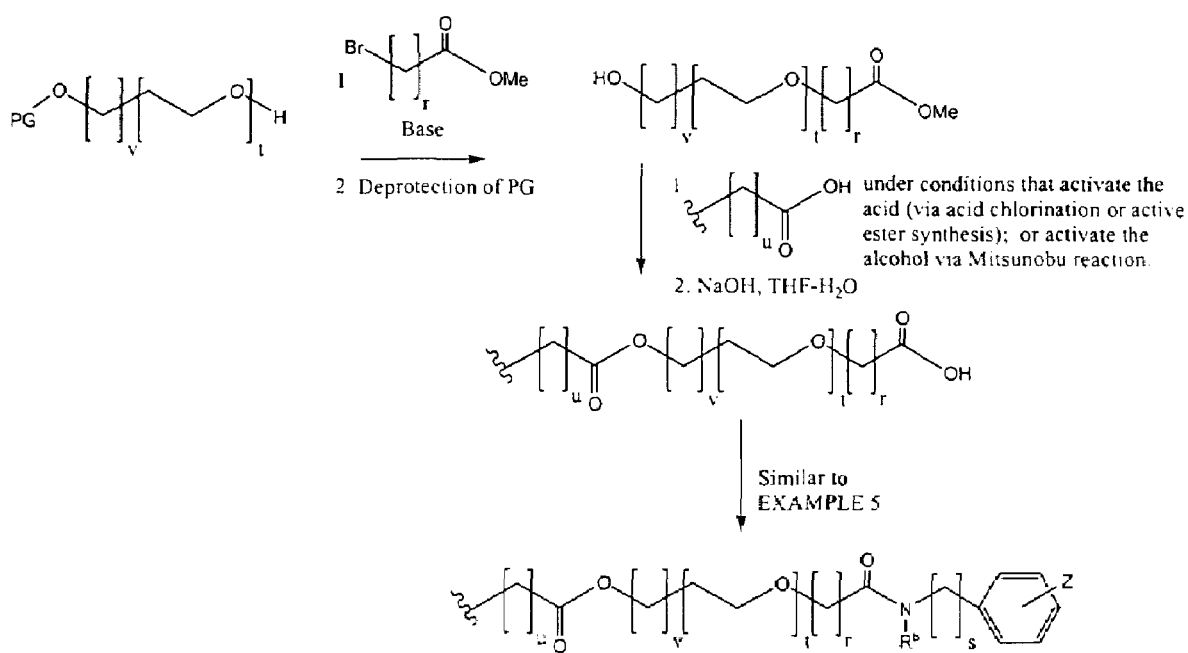

FIG. 17 shows a synthesis of:

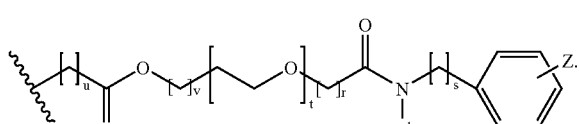

Figure 18:
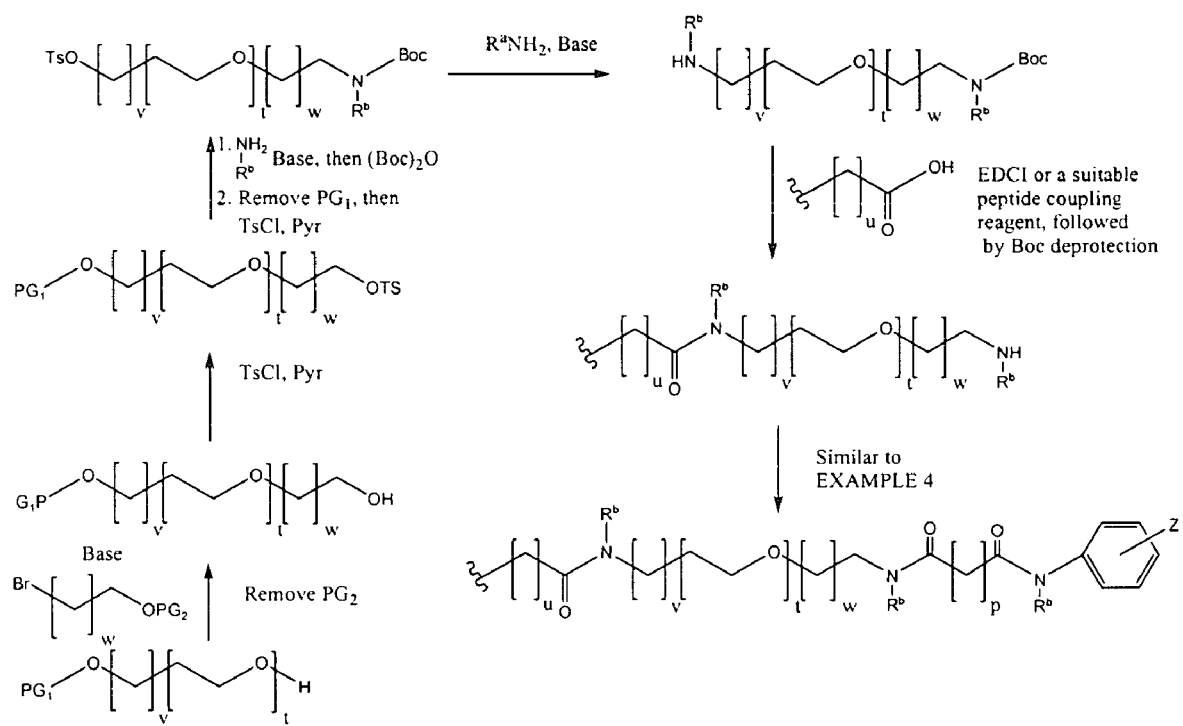

FIG. 18 shows a synthesis of:

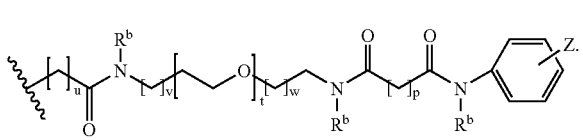

Figure 19:
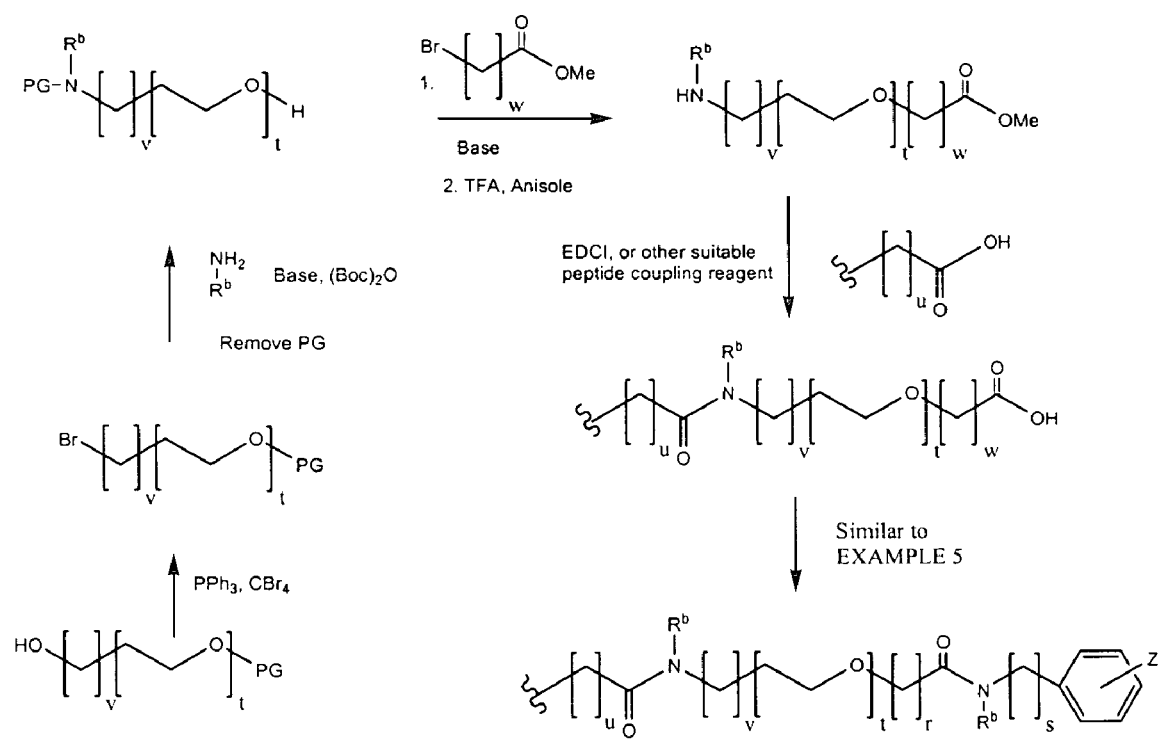
Figure 20:
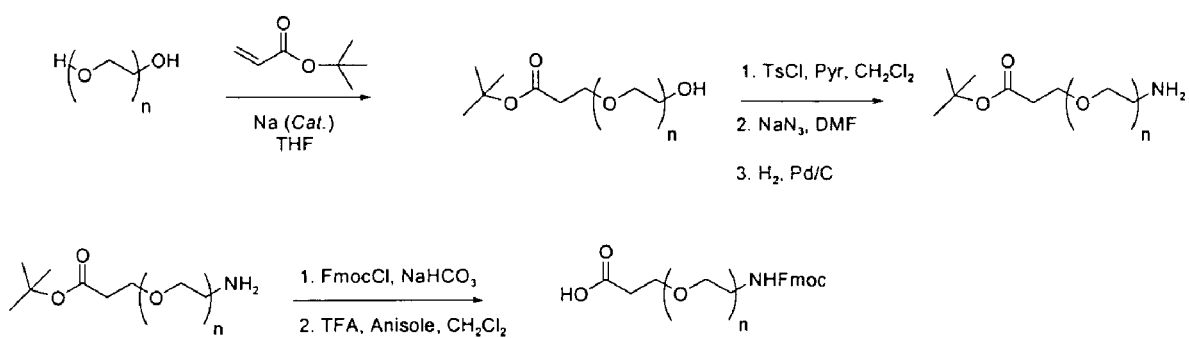
Figure 21:
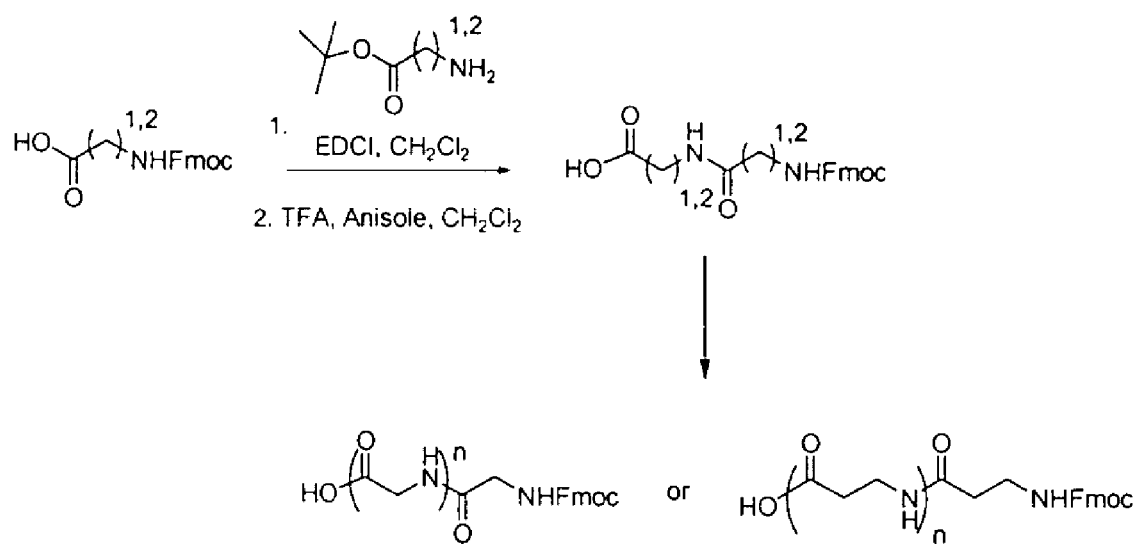
Figure 22:
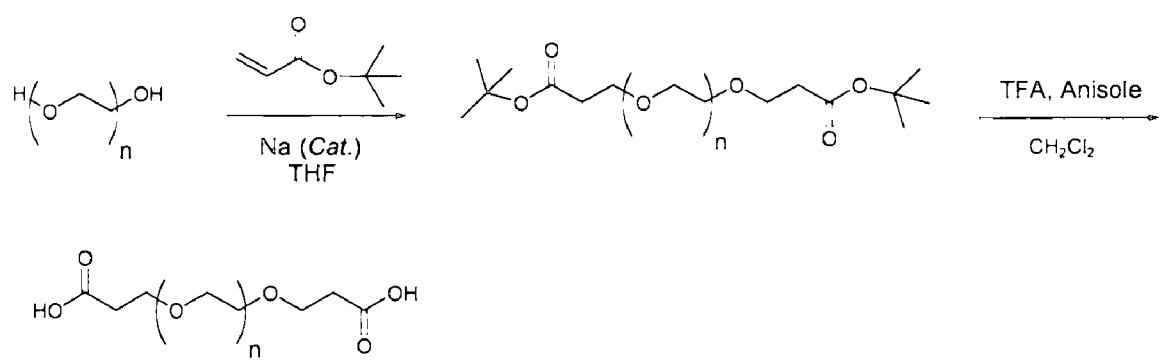
Figure 23:
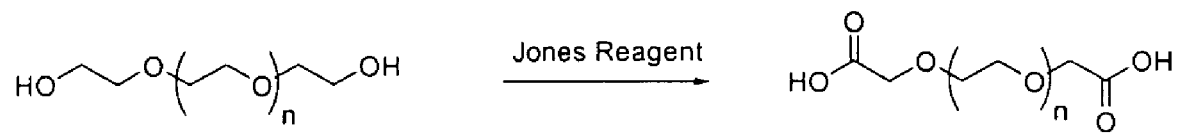
Figure 24:
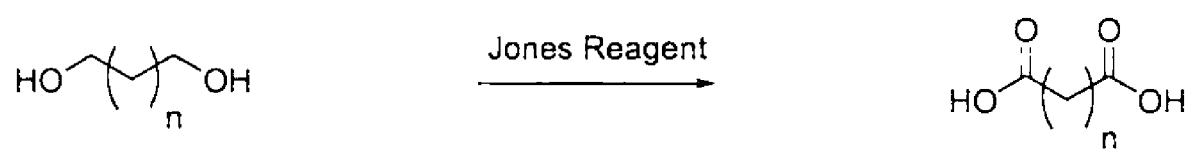
Figure 25:
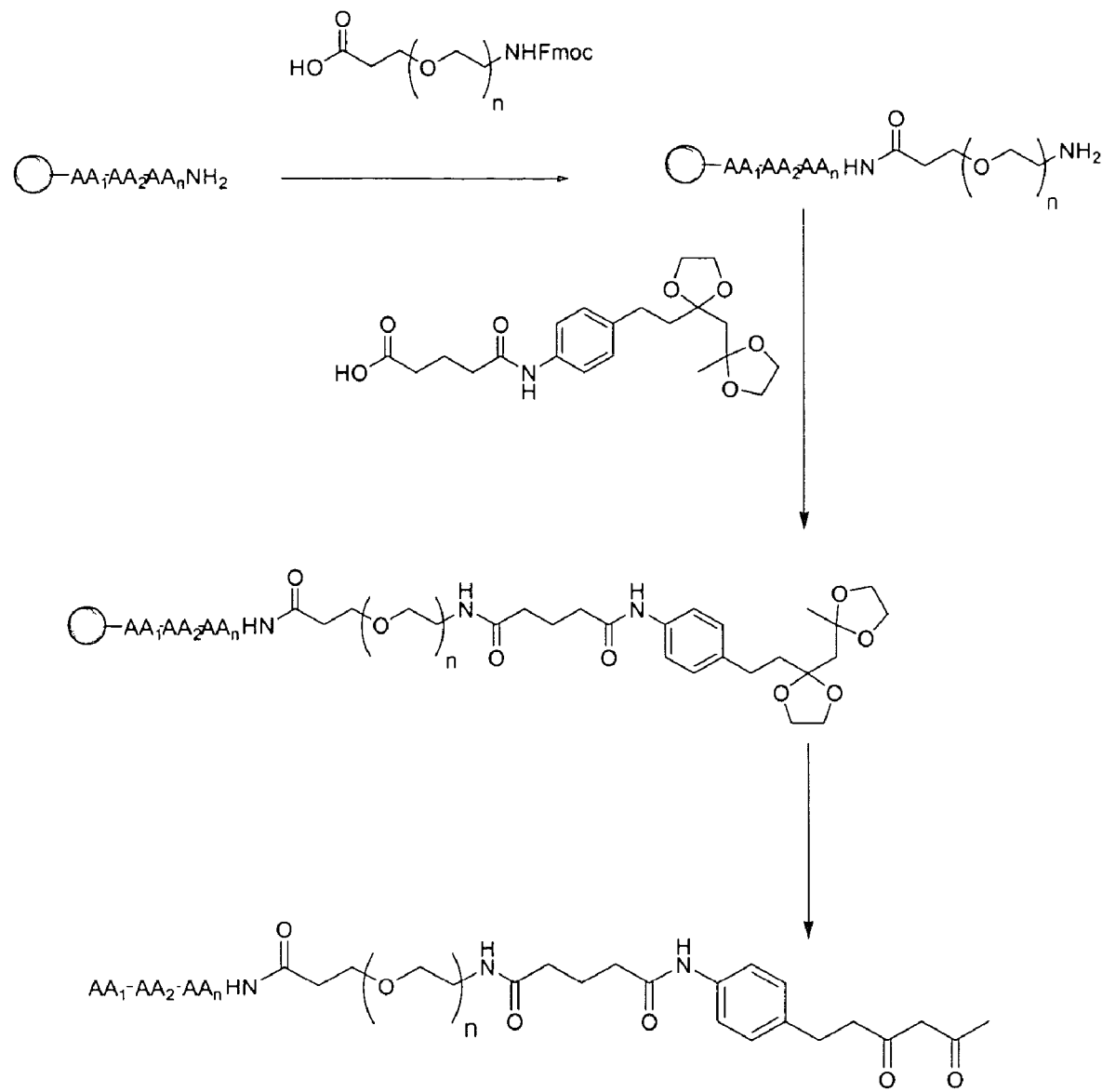
Figure 26:
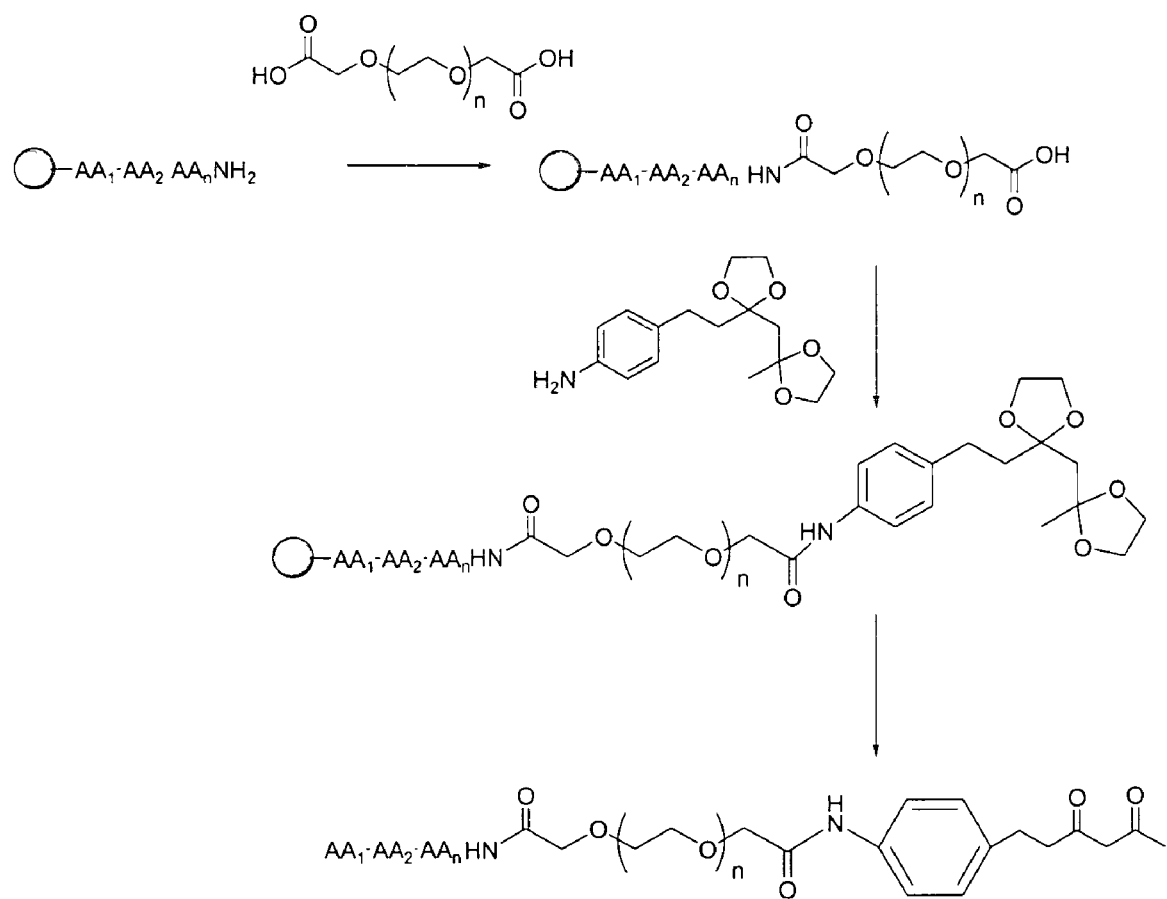
Figure 27:
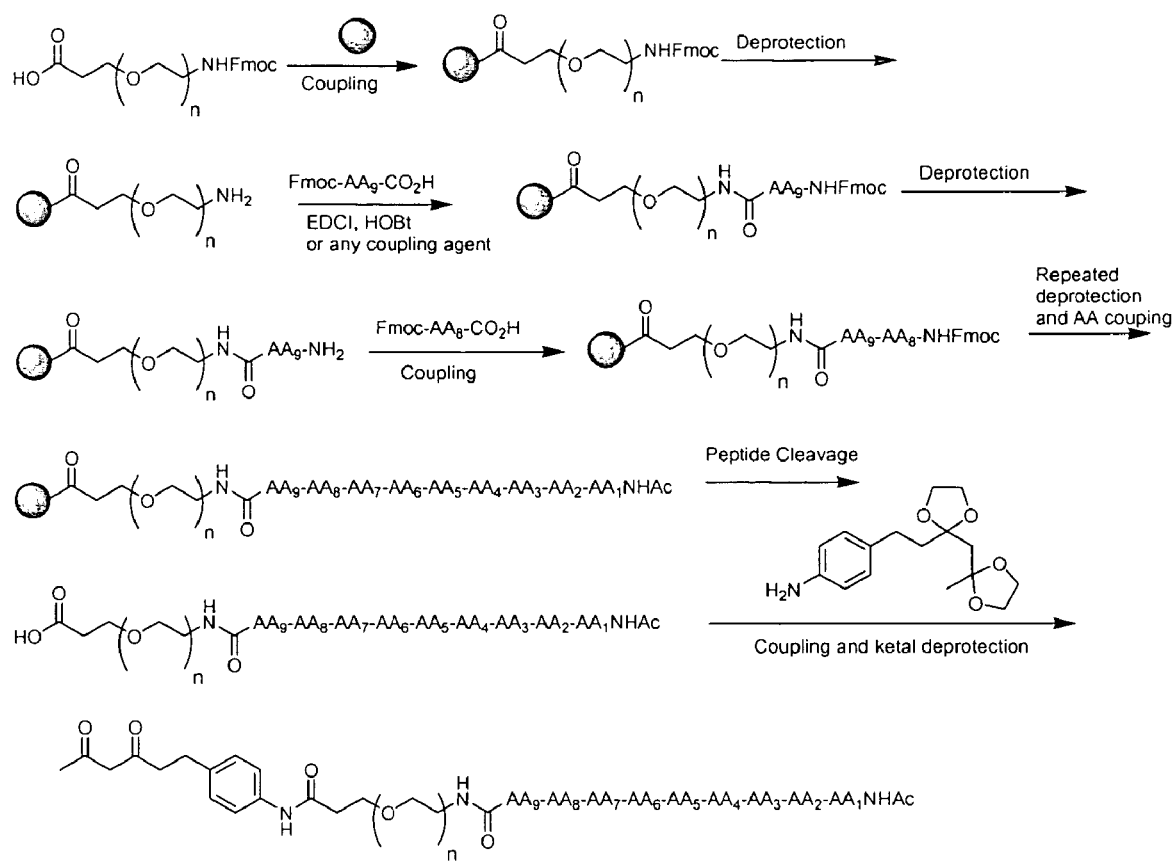

FIG. 19 shows a synthesis of:
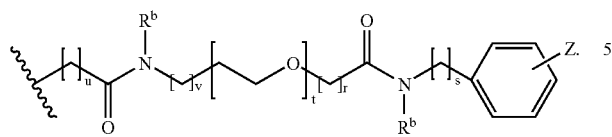
FIG. 20 shows a synthesis of:
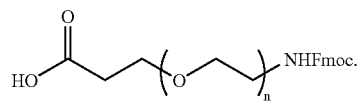
FIG. 21 shows syntheses of:
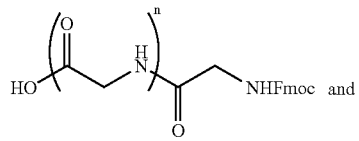
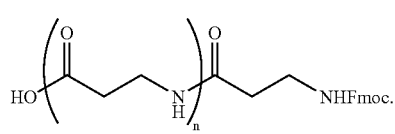
FIG. 22 shows a synthesis of:
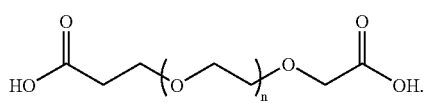
FIG. 23 shows a synthesis of:
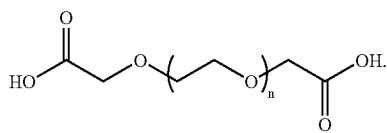
FIG. 24 shows a synthesis of:
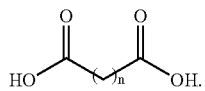
FIG. 25 shows a synthesis of:
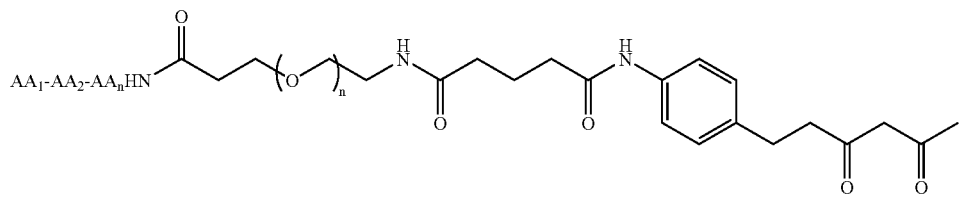
FIG. 26 shows a synthesis of:
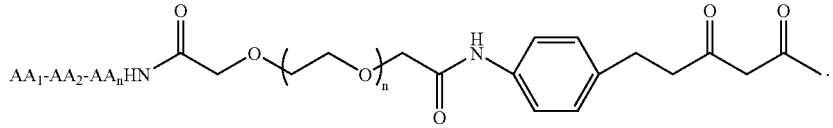
FIG. 27 shows a synthesis of:
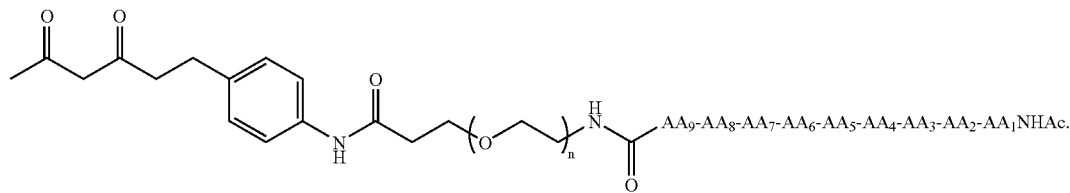

Figure 28:
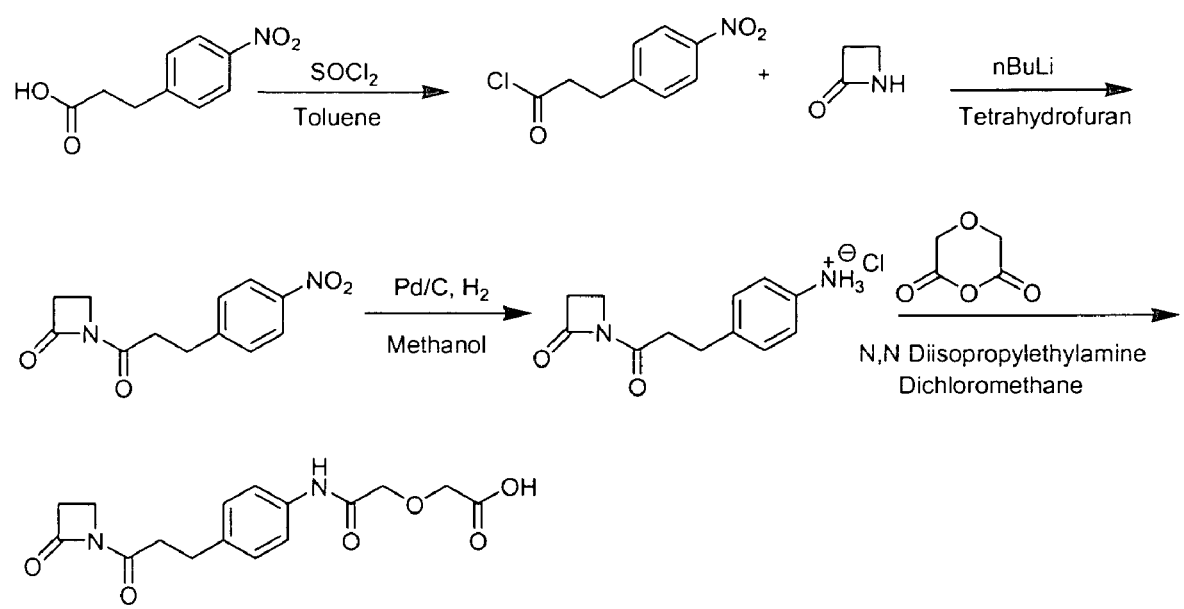

FIG. 28 shows a synthesis of:

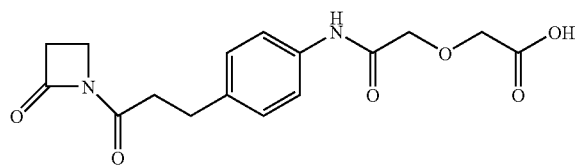

DETAILED DESCRIPTION

Definitions

The following abbreviations, terms and phrases are used herein as defined below.

TABLE 1

Amino acid abbreviations

| Amino acid | One letter abbreviation | Three letter abbreviation |
|---|---|---|
| Alanine | A | Ala |
| Arginine | R | Arg |
| Asparagine | N | Asn |
| Aspartic acid | D | Asp |
| Cysteine | C | Cys |
| Glutamic acid | E | Glu |
| Glutamine | Q | Gln |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |
| Norleucine | — | Nle |
| Norvaline | — | Nva |
| Sarcosine | — | Sar |

Every amino-bearing side chain of a targeting agent can be terminated by $R_1$ or $R_2$ as defined herein. Every COOH/COO$^-$-bearing side chain of a targeting agent can be terminated by $R_3$ as defined herein.

Sarcosine refers to N-methyl glycine.

Norvaline refers to:

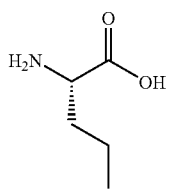

3-(4-thiazolyl)-L-Alanine or 3-(4-thiazolyl)-L-Ala refers to:

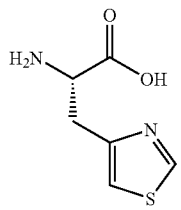

3,4-Dimethoxy-Phenylalanine or 3,4-Dimethoxy-Phe refers to:

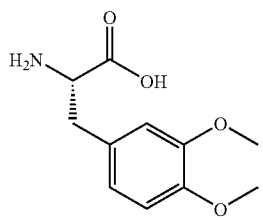

4-Cyanophenylalanine or 4-Cyano-Phe refers to:

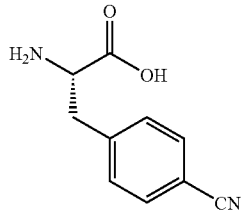

D-alloisoleucine or D-alloIle or D-aIle refers to:

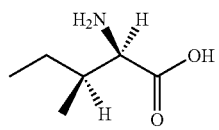

α-ally-glycine or α-ally-Gly refers to:

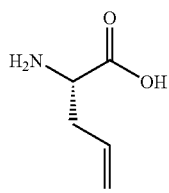

Cycloleucine or Cyclo-Leu refers to:

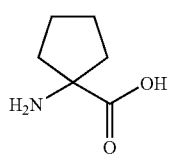

2-furyl-alanine or 2-furyl-Ala refers to:

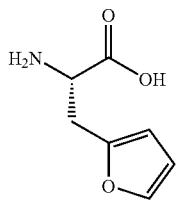

Unless indicated otherwise by a "D" prefix, e.g., D-Ala or N-Me-D-Ile, the stereochemistry of the alpha-carbon of the amino acids and aminoacyl residues in peptides described in this specification and the appended claims is the natural or "L" configuration. The Cahn-Ingold-Prelog "R" and "S" designations are used to specify the stereochemistry of chiral centers in certain acyl substituents at the N-terminus of the peptides. The designation "R,S" is meant to indicate a racemic mixture of the two enantiomeric forms. This nomenclature follows that described in R. S. Cahn, et al., Angew. Chem. Int. Ed. Engl., 5:385-415 (1966).

"Polypeptide," "peptide," and "protein" are used interchangeably to refer to a polymer of amino acid residues. As used herein, these terms apply to amino acid polymers in which one or more amino acid residues is an artificial chemical analog of a corresponding naturally occurring amino acid. These terms also apply to naturally occurring amino acid polymers. Amino acids can be in the L or D form as long as the binding function of the peptide is maintained. Peptides may be cyclic, having an intramolecular bond between two non-adjacent amino acids within the peptide, e.g., backbone to backbone, side-chain to backbone and side-chain to side-chain cyclization. Cyclic peptides can be prepared by methods well know in the art. See e.g., U.S. Pat. No. 6,013,625.

All peptide sequences are written according to the generally accepted convention whereby the alpha-N-terminal amino acid residue is on the left and the alpha-C-terminal amino acid residue is on the right. As used herein, the term "N-terminus" refers to the free alpha-amino group of an amino acid in a peptide, and the term "C-terminus" refers to the free α-carboxylic acid terminus of an amino acid in a peptide. A peptide which is N-terminated with a group refers to a peptide bearing a group on the alpha-amino nitrogen of the N-terminal amino acid residue. An amino acid which is N-terminated with a group refers to an amino acid bearing a group on the alpha-amino nitrogen.

In general, "substituted" refers to a group as defined below in which one or more bonds to a hydrogen atom contained therein are replaced by a bond to non-hydrogen or non-carbon atoms such as, but not limited to, a halogen atom such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups and also substituted cycloalkyl groups and others also include groups in which one or more bonds to a carbon(s) or hydrogen(s) atom is replaced by a bond to a heteroatom such as oxygen in carbonyl, carboxyl, and ester groups; nitrogen in groups such as imines, oximes, hydrazones, and nitriles. As employed herein, a group which is "optionally substituted" may be substituted or unsubstituted. Thus, e.g., "optionally substituted alkyl" refers to both substituted alkyl groups and unsubstituted alkyl groups.

The phrase "unsubstituted alkyl" refers to alkyl groups that do not contain heteroatoms. Thus, the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$CH(CH$_3$)$_2$, —CH(CH$_3$)CH(CH$_3$)CH(CH$_3$)$_2$, —CH(CH$_2$CH$_3$)CH(CH$_3$)CH(CH$_3$)(CH$_2$CH$_3$), and others. The phrase does not include cycloalkyl groups. Thus, the phrase unsubstituted alkyl groups includes primary alkyl groups, secondary alkyl groups, and tertiary alkyl groups. Unsubstituted alkyl groups may be bonded to one or more carbon atom(s), oxygen atom(s), nitrogen atom(s), and/or sulfur atom(s) in the parent compound. Possible unsubstituted alkyl groups include straight and branched chain alkyl groups having 1 to 20 carbon atoms. Alternatively, such unsubstituted alkyl groups have from 1 to 10 carbon atoms or are lower alkyl groups having from 1 to about 6 carbon atoms. Other unsubstituted alkyl groups include straight and branched chain alkyl groups having from 1 to 3 carbon atoms and include methyl, ethyl, propyl, and —CH(CH$_3$)$_2$.

The phrase "substituted alkyl" refers to an alkyl group in which one or more bonds to a carbon(s) or hydrogen(s) are replaced by a bond to non-hydrogen and non-carbon atoms such as, but not limited to, a halogen atom in halides such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups also include groups in which one or more bonds to a carbon(s) or hydrogen(s) atom is replaced by a bond to a heteroatom such as oxygen in carbonyl, carboxyl, and ester groups; nitrogen in groups such as imines, oximes, hydrazones, and nitriles. Substituted alkyl groups include, among others, alkyl groups in which one or more bonds to a carbon or hydrogen atom is/are replaced by one or more bonds to fluorine atoms. One example of a substituted alkyl group is the trifluoromethyl group and other alkyl groups that contain the trifluoromethyl group. Other alkyl groups include those in which one or more bonds to a carbon or hydrogen atom is replaced by a bond to an oxygen atom such that the substituted alkyl group contains a hydroxyl, alkoxy, aryloxy group, or heterocyclyloxy group. Still other alkyl groups include alkyl groups that have an amine, alkylamine, dialkylamine, arylamine, (alkyl)(aryl)amine, diarylamine, heterocyclylamine, (alkyl)(heterocyclyl)amine, (aryl)(heterocyclyl)amine, or diheterocyclylamine group.

The phrase "unsubstituted alkylene" refers to a divalent unsubstituted alkyl group as defined above. Thus methylene, ethylene, and propylene are each examples of unsubstituted alkylenes. The phrase "substituted alkylene" refers to a divalent substituted alkyl group as defined above. Substituted or unsubstituted lower alkylene groups have from 1 to about 6 carbons.

The phrase "unsubstituted cycloalkyl" refers to cyclic alkyl groups such as cyclopropyl, cyclobutyl, cyclopentyl, cyclohexyl, cycloheptyl, and cyclooctyl and such rings substituted with straight and branched chain alkyl groups as defined above. The phrase also includes polycyclic alkyl groups such as, but not limited to, adamantyl norbornyl, and bicyclo [2.2.2]octyl and the like, as well as such rings substituted with straight and branched chain alkyl groups as defined above. Thus, the phrase would include methylcylcohexyl groups among others. The phrase does not include cyclic alkyl groups containing heteroatoms. Unsubstituted cycloalkyl groups may be bonded to one or more carbon atom(s), oxygen atom(s), nitrogen atom(s), and/or sulfur atom(s) in the parent compound. In some embodiments unsubstituted cycloalkyl groups have from 3 to 20 carbon atoms. In other embodiments, such unsubstituted alkyl groups have from 3 to 8 carbon atoms while in others, such groups have from 3 to 7 carbon atoms.

The phrase "substituted cycloalkyl"" has the same meaning with respect to unsubstituted cycloalkyl groups that substituted alkyl groups have with respect to unsubstituted alkyl groups. Thus, the phrase includes, but is not limited to, oxocyclohexyl, chlorocyclohexyl, hydroxycyclopentyl, and chloromethylcyclohexyl groups.

The phrase "unsubstituted aryl" refers to aryl groups that do not contain heteroatoms. Thus the phrase includes, but is not limited to, groups such as phenyl, biphenyl, anthracenyl, and naphthenyl by way of example. Although the phrase "unsubstituted aryl" includes groups containing condensed rings such as naphthalene, it does not include aryl groups that have other groups such as alkyl or halo groups bonded to one of the ring members, as aryl groups such as tolyl are considered herein to be substituted aryl groups as described below. Typically, an unsubstituted aryl may be a lower aryl, having from 6 to about 10 carbon atoms. One unsubstituted aryl group is phenyl. Unsubstituted aryl groups may be bonded to one or more carbon atom(s), oxygen atom(s), nitrogen atom(s), and/or sulfur atom(s) in the parent compound, however.

The phrase "substituted aryl group" has the same meaning with respect to unsubstituted aryl groups that substituted alkyl groups have with respect to unsubstituted alkyl groups. However, a substituted aryl group also includes aryl groups in which one of the aromatic carbons is bonded to one of the non-carbon or non-hydrogen atoms described above and also includes aryl groups in which one or more aromatic carbons of the aryl group is bonded to a substituted and/or unsubstituted alkyl, alkenyl, or alkynyl group as defined herein. This includes bonding arrangements in which two carbon atoms of an aryl group are bonded to two atoms of an alkyl, alkenyl, or alkynyl group to define a fused ring system (e.g., dihydronaphthyl or tetrahydronaphthyl). Thus, the phrase "substituted aryl" includes, but is not limited to tolyl and hydroxyphenyl among others.

The phrase "unsubstituted alkenyl" refers to straight and branched chain and cyclic groups such as those described with respect to unsubstituted alkyl groups as defined above, except that at least one double bond exists between two carbon atoms. Examples include, but are not limited to vinyl, —CH═C(H)(CH$_3$), —CH═C(CH$_3$)$_2$, —C(CH$_3$)═C(H)$_2$, —C(CH$_3$)═C(H)(CH$_3$), —C(CH$_2$CH$_3$)═CH$_2$, cyclohexenyl, cyclopentenyl, cyclohexadienyl, butadienyl, pentadienyl, and hexadienyl among others. Lower unsubstituted alkenyl groups have from 1 to about 6 carbons.

The phrase "substituted alkenyl" has the same meaning with respect to unsubstituted alkenyl groups that substituted alkyl groups have with respect to unsubstituted alkyl groups. A substituted alkenyl group includes alkenyl groups in which a non-carbon or non-hydrogen atom is bonded to a carbon double bonded to another carbon and those in which one of the non-carbon or non-hydrogen atoms is bonded to a carbon not involved in a double bond to another carbon. For example, —CH═CH—OCH$_3$ and —CH═CH—CH$_2$—OH are both substituted alkenyls. Oxoalkenyls wherein a CH$_2$ group is replaced by a carbonyl, such as —CH═CH—C(O)—CH$_3$, are also substituted alkenyls.

The phrase "unsubstituted alkenylene" refers to a divalent unsubstituted alkenyl group as defined above. For example, —CH═CH— is an exemplary unsubstituted alkenylene. The phrase "substituted alkenylene" refers to a divalent substituted alkenyl group as defined above.

The phrase "unsubstituted alkynyl" refers to straight and branched chain groups such as those described with respect to unsubstituted alkyl groups as defined above, except that at least one triple bond exists between two carbon atoms. Examples include, but are not limited to, —C≡C(H), —C≡C(CH$_3$), —C≡C(CH$_2$CH$_3$), —C(H$_2$)C≡C(H), —C(H)$_2$C≡C(CH$_3$), and —C(H)$_2$C≡C(CH$_2$CH$_3$) among others. Unsubstituted lower alkynyl groups have from 1 to about 6 carbons.

The phrase "substituted alkynyl" has the same meaning with respect to unsubstituted alkynyl groups that substituted alkyl groups have with respect to unsubstituted alkyl groups. A substituted alkynyl group includes alkynyl groups in which a non-carbon or non-hydrogen atom is bonded to a carbon triple bonded to another carbon and those in which a non-carbon or non-hydrogen atom is bonded to a carbon not involved in a triple bond to another carbon. Examples include, but are not limited to, oxoalkynyls wherein a CH$_2$ group is replaced by a carbonyl, such as —C(O)—CH═CH—CH$_3$ and —C(O)—CH$_2$—CH═CH.

The phrase "unsubstituted alkynylene" refers to a divalent unsubstituted alkynyl group as defined above. A —C≡C— is an example of an unsubstituted alkynylene. The phrase "substituted alkynylene" refers to a divalent substituted alkynyl group as defined above.

The phrase "unsubstituted aralkyl" refers to unsubstituted alkyl groups as defined above in which a hydrogen or carbon bond of the unsubstituted alkyl group is replaced with a bond to an aryl group as defined above. For example, methyl (—CH$_3$) is an unsubstituted alkyl group. If a hydrogen atom of the methyl group is replaced by a bond to a phenyl group, such as if the carbon of the methyl were bonded to a carbon of benzene, then the compound is an unsubstituted aralkyl group (i.e., a benzyl group). Thus, the phrase includes, but is not limited to, groups such as benzyl, diphenylmethyl, and 1-phenylethyl (—CH(C$_6$H$_5$)(CH$_3$)).

The phrase "substituted aralkyl" has the same meaning with respect to unsubstituted aralkyl groups that substituted aryl groups have with respect to unsubstituted aryl groups. However, substituted aralkyls also include groups in which a carbon or hydrogen bond of the alkyl part of the group is replaced by a bond to a non-carbon or a non-hydrogen atom. Examples of substituted aralkyl groups include, but are not limited to, —CH$_2$C(═O)(C$_6$H$_5$), and —CH$_2$(2-methylphenyl).

The phrase "unsubstituted aralkenyl" refers to unsubstituted alkenyl groups as defined above in which a hydrogen or carbon bond of the unsubstituted alkenyl group is replaced with a bond to an aryl group as defined above. For example, vinyl is an unsubstituted alkenyl group. If a hydrogen atom of the vinyl group is replaced by a bond to a phenyl group, such as if a carbon of the vinyl were bonded to a carbon of benzene, then the compound is an unsubstituted aralkenyl group (i.e., a styryl group). Thus, the phrase includes, but is not limited to, groups such as styryl, diphenylvinyl, and 1-phenylethenyl (—C($C_6H_5$)($CH_2$)).

The phrase "substituted aralkenyl" has the same meaning with respect to unsubstituted aralkenyl groups that substituted aryl groups have with respect to unsubstituted aryl groups. A substituted aralkenyl group also includes groups in which a carbon or hydrogen bond of the alkenyl part of the group is replaced by a bond to a non-carbon or a non-hydrogen atom. Examples of substituted aralkenyl groups include, but are not limited to, —CH=C(Cl)($C_6H_5$), and —CH=CH (2-methylphenyl).

The phrase "unsubstituted aralkynyl" refers to unsubstituted alkynyl groups as defined above in which a hydrogen or carbon bond of the unsubstituted alkynyl group is replaced with a bond to an aryl group as defined above. For example, acetylene is an unsubstituted alkynyl group. If a hydrogen atom of the acetylene group is replaced by a bond to a phenyl group, such as if a carbon of the acetylene were bonded to a carbon of benzene, then the compound is an unsubstituted aralkynyl group. Thus, the phrase includes, but is not limited to, groups such as —C≡C-phenyl and —$CH_2$—C≡C-phenyl.

The phrase "substituted aralkynyl" has the same meaning with respect to unsubstituted aralkynyl groups that substituted aryl groups have with respect to unsubstituted aryl groups. However, a substituted aralkynyl group also includes groups in which a carbon or hydrogen bond of the alkynyl part of the group is replaced by a bond to a non-carbon or a non-hydrogen atom. Examples of substituted aralkynyl groups include, but are not limited to, —C≡C—C(Br) ($C_6H_5$) and —C≡C(2-methylphenyl).

The phrase "unsubstituted heteroalkyl" refers to unsubstituted alkyl groups as defined above in which the carbon chain is interrupted by one or more heteroatoms chosen from N, O, and S. Unsubstituted heteroalkyls containing N may have NH or N(unsubstituted alkyl) in the carbon chain. For example, unsubstituted heteroalkyls include alkoxy, alkoxyalkyl, alkoxyalkoxy, thioether, alkylaminoalkyl, aminoalkyoxy, and other such groups. Typically, unsubstituted heteroalkyl groups contain 1-5 heteroatoms, and particularly 1-3 heteroatoms. In some embodiments unsubstituted heteroalkyls include, for example, alkoxyalkoxyalkoxy groups such as ethyloxyethyloxyethyloxy.

The phrase "substituted heteroalkyl" has the same meaning with respect to unsubstituted heteroalkyl groups that substituted alkyl groups have with respect to unsubstituted alkyl groups.

The phrase "unsubstituted heteroalkylene" refers to a divalent unsubstituted heteroalkyl group as defined above. For example, —$CH_2$—O—$CH_2$— and —$CH_2$—NH—$CH_2CH_2$— are both exemplary unsubstituted heteroalkylenes. The phrase "substituted heteroalkylene" refers to a divalent substituted heteroalkyl group As defined above.

The phrase "unsubstituted heteroalkenyl" refers to unsubstituted alkene groups as defined above in which the carbon chain is interrupted by one or more heteroatoms chosen from N, O, and S. Unsubstituted heteroalkenyls containing N may have NH or N(unsubstituted alkyl or alkene) in the carbon chain. The phrase "substituted heteroalkenyl" has the same meaning with respect to unsubstituted heteroalkenyl groups that substituted heteroalkyl groups have with respect to unsubstituted heteroalkyl groups.

The phrase "unsubstituted heteroalkenylene" refers to a divalent unsubstituted heteroalkenyl group as defined above. Thus —$CH_2$—O—CH=CH— is an example of an unsubstituted heteroalkenylene. The phrase "substituted heteroalkenylene" refers to a divalent substituted heteroalkenyl group as defined above.

The phrase "unsubstituted heteroalkynyl" refers to unsubstituted alkynyl groups as defined above in which the carbon chain is interrupted by one or more heteroatoms chosen from N, O, and S. Unsubstituted heteroalkynyls containing N may have NH or N(unsubstituted alkyl, alkene, or alkyne) in the carbon chain. The phrase "substituted heteroalkynyl" has the same meaning with respect to unsubstituted heteroalkynyl groups that substituted heteroalkyl groups have with respect to unsubstituted heteroalkyl groups.

The phrase "unsubstituted heteroalkynylene" refers to a divalent unsubstituted heteroalkynyl group as defined above. Thus —$CH_2$—O—$CH_2$—C≡C— is an example of an unsubstituted heteroalkynylene. The phrase "substituted heteroalkynylene" refers to a divalent substituted heteroalkynyl group as defined above.

The phrase "unsubstituted heterocyclyl" refers to both aromatic and nonaromatic ring compounds including monocyclic, bicyclic, and polycyclic ring compounds such as, but not limited to, quinuclidyl, containing 3 or more ring members of which one or more is a heteroatom such as, but not limited to, N, O, and S. Although the phrase "unsubstituted heterocyclyl" includes condensed heterocyclic rings such as benzimidazolyl, it does not include heterocyclyl groups that have other groups such as alkyl or halo groups bonded to one of the ring members as compounds such as 2-methylbenzimidazolyl are substituted heterocyclyl groups. Examples of heterocyclyl groups include, but are not limited to: unsaturated 3 to 8 membered rings containing 1 to 4 nitrogen atoms such as, but not limited to pyrrolyl, pyrrolinyl, imidazolyl, pyrazolyl, pyridyl, dihydropyridyl, pyrimidyl, pyrazinyl, pyridazinyl, triazolyl (e.g., 4H-1,2,4-triazolyl, 1H-1,2,3-triazolyl, 2H-1,2, 3-triazolyl etc.), tetrazolyl, (e.g., 1H-tetrazolyl, 2H tetrazolyl, etc.); saturated 3 to 8 membered rings containing 1 to 4 nitrogen atoms such as, but not limited to, pyrrolidinyl, imidazolidinyl, piperidinyl, piperazinyl; condensed unsaturated heterocyclic groups containing 1 to 4 nitrogen atoms such as, but not limited to, indolyl, isoindolyl, indolinyl, indolizinyl, benzimidazolyl, quinolyl, isoquinolyl, indazolyl, benzotriazolyl; unsaturated 3 to 8 membered rings containing 1 to 2 oxygen atoms and 1 to 3 nitrogen atoms such as, but not limited to, oxazolyl, isoxazolyl, oxadiazolyl (e.g., 1,2,4-oxadiazolyl, 1,3,4-oxadiazolyl, 1,2,5-oxadiazolyl, etc.); saturated 3 to 8 membered rings containing 1 to 2 oxygen atoms and 1 to 3 nitrogen atoms such as, but not limited to, morpholinyl; unsaturated condensed heterocyclic groups containing 1 to 2 oxygen atoms and 1 to 3 nitrogen atoms, for example, benzoxazolyl, benzoxadiazolyl, benzoxazinyl (e.g., 2H-1,4-benzoxazinyl, etc.); unsaturated 3 to 8 membered rings containing 1 to 3 sulfur atoms and 1 to 3 nitrogen atoms such as, but not limited to, thiazolyl, isothiazolyl, thiadiazolyl (e.g., 1,2,3-thiadiazolyl, 1,2,4-thiadiazolyl, 1,3,4-thiadiazolyl, 1,2,5-thiadiazolyl, etc.); saturated 3 to 8 membered rings containing 1 to 2 sulfur atoms and 1 to 3 nitrogen atoms such as, but not limited to, thiazolodinyl; saturated and unsaturated 3 to 8 membered rings containing 1 to 2 sulfur atoms such as, but not limited to, thienyl, dihydrodithiinyl, dihydrodithionyl, tetrahydrothiophene, tetrahydrothiopyran; unsaturated condensed heterocyclic rings containing 1 to 2 sulfur atoms and 1 to 3 nitrogen atoms such as, but not limited to, benzothiazolyl, benzothiadiazolyl, benzothiazinyl (e.g., 2H-1,4-benzothiazinyl, etc.), dihydrobenzothiazinyl (e.g., 2H-3,4-dihydrobenzothiazinyl, etc.), unsaturated 3 to 8 membered rings containing oxygen atoms such as, but not limited to furyl; unsaturated condensed heterocyclic rings containing 1 to 2 oxygen atoms such as benzodioxolyl (e.g., 1,3-benzodioxoyl, etc.); unsaturated 3 to 8 membered rings containing an oxygen atom and 1 to 2 sulfur atoms such as, but not limited to, dihydrooxathiinyl; saturated 3 to 8 membered rings containing 1 to 3 oxygen atoms and 1 to 2 sulfur atoms such as 1,4-oxathiane; unsaturated condensed rings containing 1 to 2 sulfur atoms such as benzothienyl, benzodithiinyl; and unsaturated condensed heterocyclic rings containing an oxygen atom and 1 to 3 oxygen atoms such as benzoxathiinyl. Heterocyclyl group also include those described above in which one or more S atoms in the ring is double-bonded to one or two oxygen atoms (sulfoxides and sulfones). For example, heterocyclyl groups include tetrahydrothiophene, tetrahydrothiophene oxide, and tetrahydrothiophene 1,1-dioxide. In some embodiments heterocyclyl groups contain 5 or 6 ring members. In other embodiments heterocyclyl groups include morpholine, piperazine, piperidine, pyrrolidine, imidazole, pyrazole, 1,2,3-triazole, 1,2,4-triazole, tetrazole, thiomorpholine, thiomorpholine in which the S atom of the thiomorpholine is bonded to one or more O atoms, pyrrole, homopiperazine, oxazolidin-2-one, pyrrolidin-2-one, oxazole, quinuclidine, thiazole, isoxazole, furan, and tetrahydrofuran.

The phrase "substituted heterocyclyl" refers to an unsubstituted heterocyclyl group as defined above in which one of the ring members is bonded to a non-hydrogen atom such as described above with respect to substituted alkyl groups and substituted aryl groups. Examples include, but are not limited to, 2-methylbenzimidazolyl, 5-methylbenzimidazolyl, 5-chlorobenzthiazolyl, 1-methyl piperazinyl, and 2-chloropyridyl.

The phrase "unsubstituted heteroaryl" refers to unsubstituted aromatic heterocyclyl groups as defined above. Thus, unsubstituted heteroaryl groups include but are not limited to furyl, imidazolyl, oxazolyl, isoxazolyl, pyridinyl, benzimidazolyl, and benzothiazolyl. The phrase "substituted heteroaryl" refers to substituted aromatic heterocyclyl groups as defined above.

The phrase "unsubstituted heterocyclylalkyl" refers to unsubstituted alkyl groups as defined above in which a hydrogen or carbon bond of the unsubstituted alkyl group is replaced with a bond to a heterocyclyl group as defined above. For example, methyl (—$CH_3$) is an unsubstituted alkyl group. If a hydrogen atom of the methyl group is replaced by a bond to a heterocyclyl group, such as if the carbon of the methyl were bonded to carbon 2 of pyridine (one of the carbons bonded to the N of the pyridine) or carbons 3 or 4 of the pyridine, then the compound is an unsubstituted heterocyclylalkyl group.

The phrase "substituted heterocyclylalkyl" has the same meaning with respect to unsubstituted heterocyclylalkyl groups that substituted aralkyl groups have with respect to unsubstituted aralkyl groups. A substituted heterocyclylalkyl group also includes groups in which a non-hydrogen atom is bonded to a heteroatom in the heterocyclyl group of the heterocyclylalkyl group such as, but not limited to, a nitrogen atom in the piperidine ring of a piperidinylalkyl group.

The phrase "unsubstituted heterocyclylalkenyl" refers to unsubstituted alkenyl groups as defined above in which a hydrogen or carbon bond of the unsubstituted alkenyl group is replaced with a bond to a heterocyclyl group as defined above. For example, vinyl is an unsubstituted alkenyl group. If a hydrogen atom of the vinyl group is replaced by a bond to a heterocyclyl group, such as if the carbon of the vinyl were bonded to carbon 2 of pyridine or carbons 3 or 4 of the pyridine, then the compound is an unsubstituted heterocyclylalkenyl group.

The phrase "substituted heterocyclylalkenyl" has the same meaning with respect to unsubstituted heterocyclylalkenyl groups that substituted aralkenyl groups have with respect to unsubstituted aralkenyl groups. However, a substituted heterocyclylalkenyl group also includes groups in which a non-hydrogen atom is bonded to a heteroatom in the heterocyclyl group of the heterocyclylalkenyl group such as, but not limited to, a nitrogen atom in the piperidine ring of a piperidinylalkenyl group.

The phrase "unsubstituted heterocyclylalkynyl" refers to unsubstituted alkynyl groups as defined above in which a hydrogen or carbon bond of the unsubstituted alkynyl group is replaced with a bond to a heterocyclyl group as defined above. For example, acetylene is an unsubstituted alkynyl group. If a hydrogen atom of the acetylene group is replaced by a bond to a heterocyclyl group, such as if the carbon of the acetylene were bonded to carbon 2 of pyridine or carbons 3 or 4 of the pyridine, then the compound is an unsubstituted heterocyclylalkynyl group.

The phrase "substituted heterocyclylalkynyl" has the same meaning with respect to unsubstituted heterocyclylalkynyl groups that substituted aralkynyl groups have with respect to unsubstituted aralkynyl groups. A substituted heterocyclylalkynyl group also includes groups in which a non-hydrogen atom is bonded to a heteroatom in the heterocyclyl group of the heterocyclylalkynyl group such as, but not limited to, a nitrogen atom in the piperidine ring of a piperidinylalkynyl group.

The phrase "unsubstituted alkoxy" refers to a hydroxyl group (—OH) in which the bond to the hydrogen atom is replaced by a bond to a carbon atom of an otherwise unsubstituted alkyl group as defined above.

The phrase "substituted alkoxy" refers to a hydroxyl group (—OH) in which the bond to the hydrogen atom is replaced by a bond to a carbon atom of an otherwise substituted alkyl group as defined above.

A "pharmaceutically acceptable salt" includes a salt with an inorganic base, organic base, inorganic acid, organic acid, or basic or acidic amino acid. Salts of inorganic bases include, for example, alkali metals such as sodium or potassium; alkaline earth metals such as calcium and magnesium or aluminum; and ammonia. Salts of organic bases include, for example, trimethylamine, triethylamine, pyridine, picoline, ethanolamine, diethanolamine, and triethanolamine. Salts of inorganic acids include for example, hydrochloric acid, hydroboric acid, nitric acid, sulfuric acid, and phosphoric acid. Salts of organic acids include for example, formic acid, acetic acid, trifluoroacetic acid, fumaric acid, oxalic acid, tartaric acid, maleic acid, citric acid, scenic acid, malic acid, methanesulfonic acid, benzenesulfonic acid, and p-toluenesulfonic acid. Salts of basic amino acids include, for example, arginine, lysine and ornithine. Acidic amino acids include, for example, aspartic acid and glutamic acid.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, ketones are typically in equilibrium with their enol forms. Thus, ketones and their enols are referred to as tautomers of each other. As readily understood by one skilled in the art, a wide variety of functional groups and other structures may exhibit tautomerism, and all tautomers of compounds of Formulas I, II, and III are within the scope of the present invention.

The compounds according to the invention may be solvated, especially hydrated. Hydration may occur during manufacturing of the compounds or compositions comprising the compounds, or the hydration may occur over time due to the hygroscopic nature of the compounds.

Certain embodiments are derivatives referred to as prodrugs. The expression "prodrug" denotes a derivative of a pharmaceutically or therapeutically active drug, e.g., esters and amides, wherein the derivative has an enhanced characteristic such as, for example, enhanced delivery and therapeutic value as compared to the drug and can be transformed into the drug by an enzymatic or chemical process. See, for example, R. E. Notari, Methods Enzymol. 112:309-323 (1985); N. Bodor, Drugs of the Future 6:165-182 (1981); H. Bundgaard, Chapter 1 in *Design of Prodrugs* (H. Bundgaard, ed.), Elsevier, N.Y. (1985); and A. G. Gilman et al., *Goodman And Gilman's The Pharmacological Basis of Therapeutics*, $8^{th}$ ed., McGraw-Hill (1990). Thus, the prodrug may be designed to alter the metabolic stability or transport characteristics of a drug, mask side effects or toxicity of a drug, improve the flavor of a drug, or to alter other characteristics or properties of a drug.

Compounds of the present invention include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners. All such stereoisomers are within the scope of the invention.

The term "carboxy protecting group" as used herein refers to a carboxylic acid protecting ester group employed to block or protect the carboxylic acid functionality while the reactions involving other functional sites of the compound are carried out. Carboxy protecting groups are disclosed in, for example, Greene, *Protective Groups in Organic Synthesis*, pp. 152-186, John Wiley & Sons, New York (1981), which is hereby incorporated herein by reference. In addition, a carboxy protecting group can be used as a prodrug, whereby the carboxy protecting group can be readily cleaved in vivo by, for example, enzymatic hydrolysis to release the biologically active parent. T. Higuchi and V. Stella provide a discussion of the prodrug concept in "Pro-drugs as Novel Delivery Systems", Vol. 14 of the A.C.S. Symposium Series, American Chemical Society (1975), which is hereby incorporated herein by reference. Such carboxy protecting groups are well known to those skilled in the art, having been extensively used in the protection of carboxyl groups in the penicillin and cephalosporin fields, as described in U.S. Pat. Nos. 3,840,556 and 3,719,667, S. Kukolja, J. Am. Chem. Soc. 93:6267-6269 (1971), and G. E. Gutowski, Tetrahedron Lett. 21:1779-1782 (1970), the disclosures of which are hereby incorporated herein by reference. Examples of esters useful as prodrugs for compounds containing carboxyl groups can be found, for example, at pp. 14-21 in *Bioreversible Carriers in Drug Design: Theory and Application* (E. B. Roche, ed.), Pergamon Press, New York (1987), which is hereby incorporated herein by reference. Representative carboxy protecting groups are $C_1$ to $C_8$ alkyl (e.g., methyl, ethyl or tertiary butyl and the like); haloalkyl; alkenyl; cycloalkyl and substituted derivatives thereof such as cyclohexyl, cyclopentyl and the like; cycloalkylalkyl and substituted derivatives thereof such as cyclohexylmethyl, cyclopentylmethyl and the like; arylalkyl, for example, phenethyl or benzyl and substituted derivatives thereof such as alkoxybenzyl or nitrobenzyl groups and the like; arylalkenyl, for example, phenylethenyl and the like; aryl and substituted derivatives thereof, for example, 5-indanyl and the like; dialkylaminoalkyl (e.g., dimethylaminoethyl and the like); alkanoyloxyalkyl groups such as acetoxymethyl, butyryloxymethyl, valeryloxymethyl, isobutyryloxymethyl, isovaleryloxymethyl, 1-(propionyloxy)-1-ethyl, 1-(pivaloyloxyl)-1-ethyl, 1-methyl-1-(propionyloxy)-1-ethyl, pivaloyloxymethyl, propionyloxymethyl and the like; cycloalkanoyloxyalkyl groups such as cyclopropylcarbonyloxymethyl, cyclobutylcarbonyloxymethyl, cyclopentylcarbonyloxymethyl, cyclohexylcarbonyloxymethyl and the like; aroyloxyalkyl, such as benzoyloxymethyl, benzoyloxyethyl and the like; arylalkylcarbonyloxyalkyl, such as benzylcarbonyloxymethyl, 2-benzylcarbonyloxyethyl and the like; alkoxycarbonylalkyl, such as methoxycarbonylmethyl, cyclohexyloxycarbonylmethyl, 1-methoxycarbonyl-1-ethyl, and the like; alkoxycarbonyloxyalkyl, such as methoxycarbonyloxymethyl, t-butyloxycarbonyloxymethyl, 1-ethoxycarbonyloxy-1-ethyl, 1-cyclohexyloxycarbonyloxy-1-ethyl and the like; alkoxycarbonylaminoalkyl, such as t-butyloxycarbonylaminomethyl and the like; alkylaminocarbonylaminoalkyl, such as methylaminocarbonylaminomethyl and the like; alkanoylaminoalkyl, such as acetylaminomethyl and the like; heterocycliccarbonyloxyalkyl, such as 4-methylpiperazinylcarbonyloxymethyl and the like; dialkylaminocarbonylalkyl, such as dimethylaminocarbonylmethyl, diethylaminocarbonylmethyl and the like; (5-(alkyl)-2-oxo-1,3-dioxolen-4-yl)alkyl, such as (5-t-butyl-2-oxo-1,3-dioxolen-4-yl)methyl and the like; and (5-phenyl-2-oxo-1,3-dioxolen-4-yl)alkyl, such as (5-phenyl-2-oxo-1,3-dioxolen-4-yl) methyl and the like.

The term "N-protecting group" or "N-protected" as used herein refers to those groups intended to protect the N-terminus of an amino acid or peptide or to protect an amino group against undesirable reactions during synthetic procedures. Commonly used N-protecting groups are disclosed in, for example, Greene, *Protective Groups in Organic Synthesis*, John Wiley & Sons, New York (1981), which is hereby incorporated by reference. For example, N-protecting groups can comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, a-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-di methyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, triphenylmethyl, benzyloxymethyl and the like; and silyl groups such as trimethylsilyl and the like. In some embodiments N-protecting groups are formyl, acetyl, benzoyl, pivaloyl, t-butylacetyl, phenylsulfonyl, benzyl, 9-fluorenylmethyloxycarbonyl (Fmoc), t-butyloxycarbonyl (Boc), and benzyloxycarbonyl (Cbz).

As used herein, "halo," "halogen" or "halide" refers to F, Cl, Br or I.

As used herein, the abbreviations for any protective groups, amino acids or other compounds, are, unless indicated otherwise, in accord with their common usage, recognized abbreviations, or the IUPAC-IUB Commission on Biochemical Nomenclature, Biochem. 11:942-944 (1972).

As used herein, "substantially pure" means sufficiently homogeneous to appear free of readily detectable impurities as determined by standard methods of analysis, such as thin layer chromatography (TLC), gel electrophoresis, and high performance liquid chromatography (HPLC), used by those of skill in the art to assess such purity, or sufficiently pure such that further purification would not detectably alter the physical and chemical properties, such as enzymatic and biological activities, of the substance. Substantially pure includes compositions in which the AA targeting agent or AA targeting compound forms the major component of the composition, such as constituting about 50%, about 60%, about 70%, about 80%, about 90%, or about 95% or more of the substances in the composition. Methods for purification of compounds to produce substantially chemically pure compounds are known to those of skill in the art. A substantially chemically pure compound may, however, be a mixture of stereoisomers. In such instances, further purification may increase the specific activity of the compound. However, AA targeting agents need not always be provided in a specific purified state. Partially purified compositions will have utility in certain embodiments and depending on the desired use. For example, purification methods that may yield a greater total recovery of AA-targeting agent may produce a lower degree of relative purification.

As used herein, "biological activity" refers to the in vivo activities of a compound, composition, or other mixture, or physiological responses that result upon ill vivo administration of a compound, composition or other mixture. Biological activity thus encompasses therapeutic effects, diagnostic effects and pharmaceutical activity of such compounds, compositions, and mixtures. The term "biologically active" or "functional" when used as a modifier of invention AA targeting agent containing polypeptides or compositions thereof refers to a polypeptide that exhibits at least one activity that is characteristic of or similar to an AA targeting agent.

As used herein, "pharmacokinetics" refers to the concentration of an administered compound in the serum over time. Pharmacodynamics refers to the concentration of an administered compound in target and nontarget tissues over time and the effects on the target tissue (e.g., efficacy) and the non-target tissue (e.g., toxicity). Improvements in, for example, pharmacokinetics or pharmacodynamics can be designed for a particular targeting agent or biological agent, such as by using labile linkages or by modifying the chemical nature of any linker (e.g., changing solubility, charge, and the like).

As employed herein, the phrases "an effective amount" and "therapeutically effective amount" refer to an amount of an AA targeting agent or compound comprising an AA targeting agent that is useful or able to support an observable change in the level of one or more biological activity characteristic of an AA targeting agent, or a dose sufficient to impart a beneficial effect, e.g., an amelioration of a symptom on the recipient thereof. The specific therapeutically effective dose level for any particular subject will depend upon a variety of factors including the symptom or disorder being treated, the severity of the symptom or disorder, the activity of the specific compound, the route of administration, the rate of clearance of the compound, the duration of treatment, the drugs used in combination or coincident with the compound, the age, body weight, sex, diet, and general health of the subject, and like, as well as other factors well known in the medical arts and sciences. A therapeutically effective amount can be an amount of AA targeting compound sufficient to produce a measurable inhibition of angiogenesis in the tissue being treated, i.e., an angiogenesis-inhibiting amount. Inhibition of angiogenesis can be measured in situ by immunohistochemistry, or by other methods known to one skilled in the art. Various general considerations taken into account in determining the "therapeutically effective amount" are known to those of skill in the art and are described, e.g., in Gilman, A. G., et al., *Goodman And Gilman's The Pharmacological Basis of Therapeutics*, $8^{th}$ ed., McGraw-Hill (1990); and *Remington's Pharmaceutical Sciences*, $17^{th}$ ed., Mack Publishing Co., Easton, Pa. (990).

In one aspect, the present invention provides various targeting compounds in which AA targeting agents are covalently linked to a combining site of an antibody.

In another aspect, the present invention includes methods of altering at least one physical or biological characteristic of an AA targeting agent. The methods include covalently linking an AA targeting agent to a combining site of an antibody, either directly or though a linker. Characteristics of an AA targeting agent that may be modified include, but are not limited to, binding affinity, susceptibility to degradation (e.g., by proteases), pharmacokinetics, pharmacodynamics, immunogenicity, solubility, lipophilicity, hydrophilicity, hydrophobicity, stability (either more or less stable, as well as planned degradation), rigidity, flexibility, modulation of antibody binding, and the like. Also, the biological potency of a particular AA targeting agent may be increased by the addition of the effector function(s) provided by the antibody. For example, an antibody provides effector functions such as complement mediated effector functions. Without wishing to be bound by any theory, the antibody portion of an AA targeting compound may generally extend the half-life of a smaller sized AA targeting agent in vivo. Thus, in one aspect, the invention provides a method for increasing the effective circulating half-life of an AA targeting agent.

In another aspect, the present invention provides methods for modulating the binding activity of an antibody by covalently attaching an AA targeting agent to a combining site of the antibody. Although not wishing to be bound by any theory, substantially reduced antibody binding to an antigen may result from the linked AA targeting agent(s) sterically hindering the antigen from contacting the antibody combining site. Alternatively, substantially reduced antigen binding may result if the amino acid side chain of the antibody combining site modified by covalent linkage is important for binding to the antigen. By contrast, substantially increased antibody binding to an antigen may result when a linked AA targeting agent(s) does not sterically hinder the antigen from contacting the antibody combining site and/or when the amino acid side chain of the antibody combining site modified by covalent linkage is not important for binding to the antigen.

In another aspect, the present invention includes methods of modifying a combining site of an antibody to generate binding specificity for the thrombospondin binding cognate. Such methods include covalently linking a reactive amino acid side chain in a combining site of the antibody to a chemical moiety on a linker of an AA targeting agent-linker compound as described herein where an AA targeting agent is based upon a thrombospondin peptide. The chemical moiety of the linker is sufficiently distanced from the AA targeting agent so that an AA targeting agent can bind its cognate when an AA targeting agent-linker compound is covalently linked to an antibody combining site. Typically, the antibody will not be considered specific for the target molecule. In certain embodiments, an antibody prior to covalent linking would have an affinity for the thrombospondin binding cognate of less than about $1 \times 10^{-5}$ moles/liter. However, after the antibody is covalently linked to the AA targeting agent-linker compound, the modified antibody preferably has an affinity for the target molecule of at least about $1 \times 10^{-6}$ moles/liter, alternatively, at least about $1 \times 10^{-7}$ moles/liter, alternatively, at least $1 \times 10^{-8}$ moles/liter, alternatively at least $1 \times 10^{-9}$ moles/liter, or alternatively, at least about $1 \times 10^{-10}$ moles/liter.

AA Targeting Agents

An AA targeting agent is a peptide selected from the group consisting of:

| | |
|---|---|
| $R^1$-Sar-Gly-Val-(D-alloIle)-Thr-Nva-Ile-Arg-Pro-$R^3$; | (SEQ ID NO:1) |
| $R^2$-Pro-Phe-Val-(D-alloIle)-Thr-Nva-Ile-Arg-Pro-$R^3$; | (SEQ ID NO:2) |
| $R^1$-Sar-Gly-Val-(D-alloIle)-Thr-Nva-Lys-Arg-Pro-$R^3$; | (SEQ ID NO:3) |
| $R^1$-Sar-Gly-Val-(D-alloIle)-Thr-Lys-Ile-Arg-Pro-$R^3$; | (SEQ ID NO:4) |
| $R^1$-Sar-Gly-Val-(D-alloIle)-Thr-Gln-Ile-Arg-Pro-$R^3$; | (SEQ ID NO:5) |
| $R^1$-Sar-Gly-Val-(D-alloIle)-Thr-(α-Ally-Gly)-Ile-Arg-Pro-$R^3$; | (SEQ ID NO:6) |
| $R^1$-Sar-Phe-Val-(D-alloIle)-Thr-Nva-Ile-Arg-Pro-$R^3$; | (SEQ ID NO:7) |
| $R^2$-Lys-Gly-Val-(D-alloIle)-Thr-Nva-Ile-Arg-Pro-$R^3$; | (SEQ ID NO:8) |
| $R^2$-Glu-Gly-Val-(D-alloIle)-Thr-Nva-Ile-Arg-Pro-$R^3$; | (SEQ ID NO:9) |
| $R^2$-Pro-Gly-Val-(D-alloIle)-Thr-Nva-Ile-Arg-Pro-$R^3$; | (SEQ ID NO:10) |
| $R^2$-Pro-(4-Cyano-Phe)-Val-(D-alloIle)-Thr-Nva-Ile-Arg-Pro-$R^3$; | (SEQ ID NO:11) |
| $R^2$-Pro-(3,4-Dimethoxy-Phe)-Val-(D-alloIle)-Thr-Nva-Ile-Arg-Pro-$R^3$; | (SEQ ID NO:12) |
| $R^2$-Pro-(3-(4-thiazolyl)-L-Ala)-Val-(D-alloIle)-Thr-Nva-Ile-Arg-Pro-$R^3$; | (SEQ ID NO:13) |
| $R^2$-Pro-(2-furyl-Ala)-Val-(D-alloIle)-Thr-Nva-Ile-Arg-Pro-$R^3$; | (SEQ ID NO:14) |
| $R^2$-Pro-(Cyclo-Leu)-Val-(D-alloIle)-Thr-Nva-Ile-Arg-Pro-$R^3$; | (SEQ ID NO:15) |
| $R^2$-Gly-Val-(D-Ile)-Thr-Arg-Ile-Arg-$R^3$; and | (SEQ ID NO:16) |
| $R^1$-Sar-Gly-Val-(D-Ile)-Thr-Nva-Ile-Arg-Pro-$R^3$; wherein | (SEQ ID NO:17) |

$R^1$ is $NH(CH_3)$, $N(CH_3)C(O)CH_3$, $N(CH_3)C(O)CH_2CH_3$, $N(CH_3)C(O)CH_2CH_2CH_3$, $N(CH_3)C(O)CH(CH_3)CH_3$, $N(CH_3)C(O)CH_2CH_2CH_2CH_3$, $N(CH_3)C(O)CH(CH_3)CH_2CH_3$, $N(CH_3)C(O)C_6H_5$, $N(CH_3)C(O)CH_2CH_2(CH_2CH_2O)_{1-5}Me$, an amino protecting group, a lipid fatty acid group or a carbohydrate;

$R^2$ is $NH_2$, $NHC(O)CH_3$, $NHC(O)CH_2CH_3$, $NHC(O)CH_2CH_2CH_3$, $NHC(O)CH(CH_3)CH_3$, $NHC(O)CH_2CH_2CH_2CH_3$, $NHC(O)CH(CH_3)CH_2CH_3$, $NHC(O)C_6H_5$, $NH(CH_3)C(O)CH_2CH_2(CH_2CH_2O)_{1-5}Me$, an amino protecting group, a lipid fatty acid group or a carbohydrate; and $R^3$ is $COOH$, $C(O)NH_2$, $C(O)NH(CH_3)$, $C(O)NHCH_2CH_3$, $C(O)NHCH_2CH_2CH_3$, $C(O)NHCH(CH_3)CH_3$, $C(O)NHCH_2CH_2CH_2CH_3$, $C(O)NHCH(CH_3)CH_2CH_3$, $C(O)NHC_6H_5$, $C(O)NHCH_2CH_2OCH_3$, $C(O)NHOCH_3$, $C(O)NHOCH_2CH_3$, a carboxy protecting group, a lipid fatty acid group or a carbohydrate.

An AA targeting compound can be prepared using techniques well known in the art. Typically, synthesis of the peptidyl AA targeting agent is the first step and is carried out as described herein. The targeting agent is then derivatized for linkage to a connecting component (the linker), which is then combined with the antibody. One of skill in the art will readily appreciate that the specific synthetic steps used depend upon the exact nature of the three components. Thus, AA targeting agent—linker conjugates and AA targeting compounds described herein can be readily synthesized.

AA targeting agent peptides may be synthesized by many techniques that are known to those skilled in the art. For solid phase peptide synthesis, a summary of exemplary techniques may be found in *Chemical Approaches to the Synthesis of Peptides and Proteins* (Williams et al., eds.), CRC Press, Boca Raton, Fla. (1997).

Figure 6A:
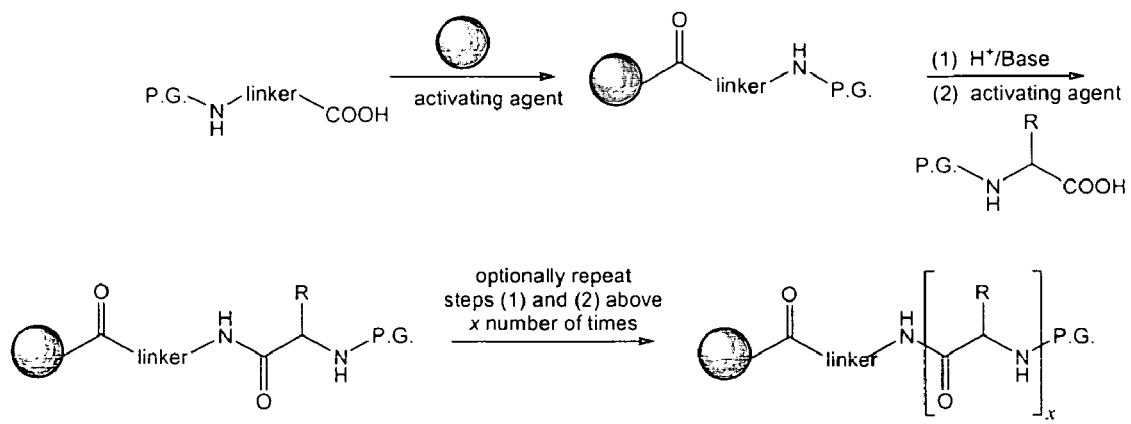
FIG. 6A and FIG. 6B illustrate the solid phase synthesis of targeting agent-linker conjugates of the present invention.
Figure 6B:
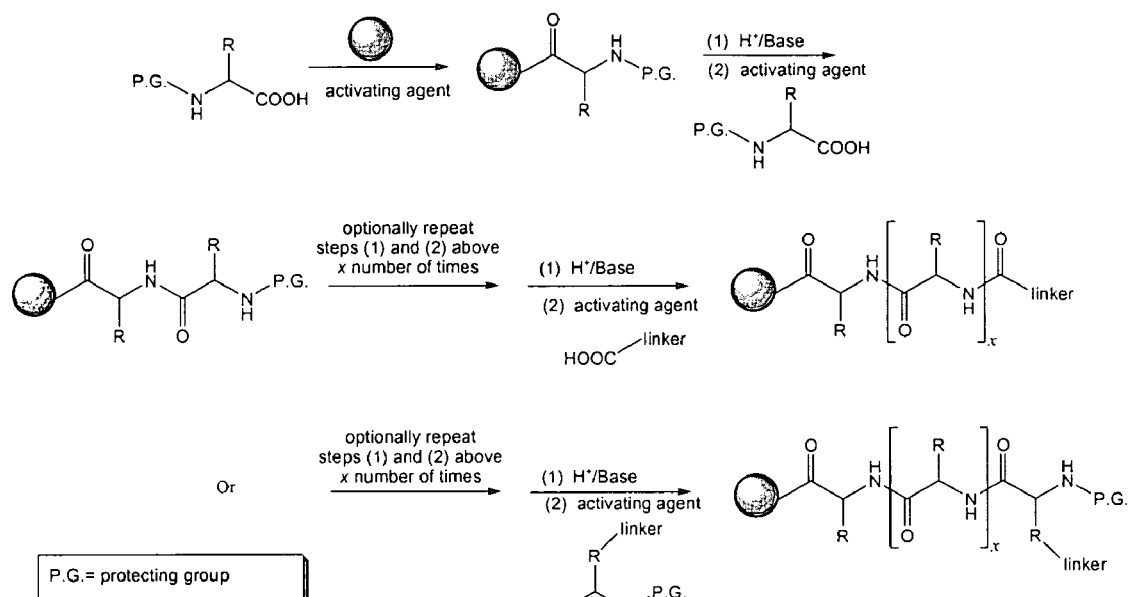

Typically, the desired peptidic AA targeting agent is synthesized sequentially on solid phase according to procedures well known in the art. See, e.g., U.S. Patent Application No. 2003/0045477). The linker may be attached to the peptide in part or in full on the solid phase, or may be added using solution phase techniques after the removal of the peptide from the resin (see FIGS. 6A and 6B). For example, an N-protected amino and carboxylic acid-containing linking moiety may be attached to a resin such as 4-hydroxymethyl-phenoxymethyl-poly(styrene-1% divinylbenzene). The N-protecting group may be removed by the appropriate acid (e.g., TFA for Boc) or base (e.g., piperidine for Fmoc), and the peptide sequence developed in the normal C-terminus to N-terminus fashion (see FIG. 6A). Alternatively, the peptide sequence may be synthesized first and the linker added to the N-terminal amino acid residue last (see FIG. 6B). Yet another method entails deprotecting an appropriate side chain during synthesis and derivatizing with a suitably reactive linker. For example, a lysine side chain may be deprotected and reacted with a linker having an active ester. Alternatively, an amino acid derivative with a suitably protected linker moiety already attached to the side chain (see FIG. 6B) or, in some cases, the alpha-amino nitrogen, may be added as part of the growing peptide sequence.

At the end of the solid phase synthesis, the targeting agent-linker conjugate is removed from the resin and deprotected, either in succession or in a single operation. Removal of the targeting agent-linker conjugate and deprotection can be accomplished in a single operation by treating the resin-bound peptide-linker conjugate with a cleavage reagent, for example, trifluoroacetic acid containing scavengers such as thianisole, water, or ethanedithiol. After deprotection and release of the targeting agent, further derivatization of the targeting agent peptide may be carried out.

The fully deprotected targeting agent-linker conjugate is purified by a sequence of chromatographic steps employing any or all of the following types: ion exchange on a weakly basic resin in the acetate form; hydrophobic adsorption chromatography on underivatized polystyrene-divinylbenzene (e.g., AMBERLITE XAD); silica gel adsorption chromatography; ion exchange chromatography on carboxymethylcellulose; partition chromatography, e.g., on SEPHADEX G-25, LH-20 or countercurrent distribution; high performance liquid chromatography (HPLC), especially reverse-phase HPLC on octyl- or octadecylsilyl-silica bonded phase column packing.

Antibodies

"Antibody" as used herein includes polypeptide molecules comprising heavy and/or light chains which have immunoreactive activity. Antibodies include immunoglobulins which are the product of B cells and variants thereof, as well as the T cell receptor (TcR) which is the product of T cells and variants thereof. An immunoglobulin is a protein comprising one or more polypeptides substantially encoded by the immunoglobulin kappa and lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. Subclasses of heavy chains are also known. For example, IgG heavy chains in humans can be any of IgG1, IgG2, IgG3, and IgG4 subclasses.

A typical immunoglobulin structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively. The amino acids of an antibody may be naturally or nonnaturally occurring.

Antibodies that contain two combining sites are bivalent in that they have two complementarity or antigen recognition sites. A typical natural bivalent antibody is an IgG. Although vertebrate antibodies generally comprise two heavy chains and two light chains, heavy chain only antibodies are also known. See Muyldermans et al., TRENDS in Biochem. Sci. 26(4):230-235 (1991). Such antibodies are bivalent and are formed by the pairing of heavy chains. Antibodies may also be multi-valent, as in the case of dimeric forms of IgA and the pentameric IgM molecule. Antibodies also include hybrid antibodies wherein the antibody chains are separately homologous with referenced mammalian antibody chains. One pair of heavy and light chain has a combining site specific to one antigen and the other pair of heavy and light chains has a combining site specific to a different antigen. Such antibodies are referred to as bi-specific because they are able to bind two different antigens at the same time. Antibodies may also be univalent, such as, for example, in the case of Fab or Fab' fragments.

Antibodies exist as full length intact antibodies or as a number of well-characterized fragments produced by digestion with various peptidases or chemicals. Thus, for example, pepsin digests an antibody below the disulfide linkages in the hinge region to produce F(ab')$_2$, a dimer of Fab which itself is a light chain joined to $V_H$—CH$_1$ by a disulfide bond. F(ab')$_2$ may be reduced under mild conditions to break the disulfide linkage in the hinge region, thereby converting the F(ab')$_2$ dimer into a Fab' monomer. The Fab' monomer is essentially a Fab fragment with part of the hinge region (see, e.g., *Fundamental Immunology* (W. E. Paul, ed.), Raven Press, N.Y. (1993) for a more detailed description of other antibody fragments). As another example, partial digestion with papain can yield a monovalent Fab/c fragment. See M. J. Glennie et al., Nature 295:712-714 (1982). While various antibody fragments are defined in terms of the digestion of an intact antibody, one of skill in the art will appreciate that any of a variety of antibody fragments may be synthesized de novo either chemically or by utilizing recombinant DNA methodology. Thus, the term antibody as used herein also includes antibody fragments produced by the modification of whole antibodies, synthesized de novo, or obtained from recombinant DNA methodologies. One skilled in the art will recognize that there are circumstances in which it is advantageous to use antibody fragments rather than whole antibodies. For example, the smaller size of the antibody fragments allows for rapid clearance and may lead to improved access to solid tumors.

Recombinant antibodies may be conventional full length antibodies, hybrid antibodies, heavy chain antibodies, antibody fragments known from proteolytic digestion, antibody fragments such as Fv or single chain Fv (scFv), single domain fragments such as $V_H$ or $V_L$, diabodies, domain deleted antibodies, minibodies, and the like. An Fv antibody is about 50 kD in size and comprises the variable regions of the light and heavy chain. The light and heavy chains may be expressed in bacteria where they assemble into an Fv fragment. Alternatively, the two chains can be engineered to form an interchain disulfide bond to give a dsFv. A single chain Fv ("scFv") is a single polypeptide comprising $V_H$ and $V_L$ sequence domains linked by an intervening linker sequence, such that when the polypeptide folds the resulting tertiary structure mimics the structure of the antigen binding site. See J. S. Huston et al., Proc. Nat. Acad. Sci. U.S.A. 85:5879-5883 (1988). One skilled in the art will recognize that depending on the particular expression method and/or antibody molecule desired, appropriate processing of the recombinant antibodies may be performed to obtain a desired reconstituted or reassembled antibody. See, e.g., Vallejo and Rinas, Biomed Central., available at world wide web URL microbialcellfactories.com/content/3/1/11.

Single domain antibodies are the smallest functional binding units of antibodies (approximately 13 kD in size), corresponding to the variable regions of either the heavy $V_H$ or light $V_L$ chains. See U.S. Pat. No. 6,696,245, WO04/058821, WO04/003019 and WO03/002609. Single domain antibodies are well expressed in bacteria, yeast, and other lower eukaryotic expression systems. Domain deleted antibodies have a domain, such as CH2, deleted relative to the full length antibody. In many cases such domain deleted antibodies, particularly CH2 deleted antibodies, offer improved clearance relative to their full length counterparts. Diabodies are formed by the association of a first fusion protein comprising two $V_H$ domains with a second fusion protein comprising two $V_L$ domains. Diabodies, like full length antibodies, are bivalent and may be bi-specific. Minibodies are fusion proteins comprising a $V_H$, $V_L$, or scFv linked to CH3, either directly or via an intervening IgG hinge. See T. Olafsen et al., Protein Eng. Des. Sel. 17:315-323 (2004). Minibodies, like domain deleted antibodies, are engineered to preserve the binding specificity of full-length antibodies but with improved clearance due to their smaller molecular weight.

The T cell receptor (TcR) is a disulfide linked heterodimer composed of two chains. The two chains are generally disulfide-bonded just outside the T cell plasma membrane in a short extended stretch of amino acids resembling the antibody hinge region. Each TcR chain is composed of one antibody-like variable domain and one constant domain. The full TcR has a molecular mass of about 95 kD, with the individual chains varying in size from 35 to 47 kD. Also encompassed within the meaning of TcR are portions of the receptor, such as, for example, the variable region, which can be produced as a soluble protein using methods well known in the art. For example, U.S. Pat. No. 6,080,840 and A. E. Slanetz and A. L. Bothwell, Eur. J. Immunol. 21:179-183 (1991) describe a soluble T cell receptor prepared by splicing the extracellular domains of a TcR to the glycosyl phosphatidylinositol (GPI) membrane anchor sequences of Thy-1. The molecule is expressed in the absence of CD3 on the cell surface, and can be cleaved from the membrane by treatment with phosphatidylinositol specific phospholipase C (PI-PLC). The soluble TcR also may be prepared by coupling the TcR variable domains to an antibody heavy chain $CH_2$ or $CH_3$ domain, essentially as described in U.S. Pat. No. 5,216,132 and G. S. Basi et al., J. Immunol. Methods 155:175-191 (1992), or as soluble TcR single chains, as described by E. V. Shusta et al., Nat. Biotechnol. 18:754-759 (2000) or P. D. Holler et al., Proc. Natl. Acad. Sci. U.S.A. 97:5387-5392 (2000). Certain embodiments of the invention use TcR "antibodies" as a soluble antibody. The combining site of the TcR can be identified by reference to CDR regions and other framework residues using the same methods discussed above for antibodies.

The combining site refers to the part of an antibody molecule that participates in antigen binding. The antigen binding site is formed by amino acid residues of the N-terminal variable ("V") regions of the heavy ("H") and light ("L") chains. The antibody variable regions comprise three highly divergent stretches referred to as "hypervariable regions" or "complementarity determining regions" (CDRs), which are interposed between more conserved flanking stretches known as "framework regions" (FRs). The three hypervariable regions of a light chain (LCDR1, LCDR2, and LCDR3) and the three hypervariable regions of a heavy chain (HCDR1, HCDR2, and HCDR3) are disposed relative to each other in three dimensional space to form an antigen binding surface or pocket. In heavy-chain antibodies or $V_H$ domains, the antigen binding site is formed by the three hypervariable regions of the heavy chains. In $V_L$ domains, the antigen binding site is formed by the three hypervariable regions of the light chain.

The identity of the amino acid residues in a particular antibody that make up a combining site can be determined using methods well known in the art. For example, antibody CDRs may be identified as the hypervariable regions originally defined by Kabat et al. See E. A. Kabat et al., *Sequences of Proteins of Immunological Interest*, 5$^{th}$ ed., Public Health Service, NIH, Washington D.C. (1992). The positions of the CDRs may also be identified as the structural loop structures originally described by Chothia and others. See, e.g., C. Chothia and A. M. Lesk, J. Mol. Biol. 196:901-917 (1987); C. Chothia et al., Nature 342:877-883 (1989); and A. Tramontano et al., J. Mol. Biol. 215:175-182 (1990). Other methods include the "AbM definition," which is a compromise between Kabat and Chothia and is derived using Oxford Molecular's AbM antibody modeling software (now Accelrys), or the "contact definition" of CDRs set forth in R. M. MacCallum et al., J. Mol. Biol. 262:732-745 (1996). Table 2 identifies CDRs based upon various known definitions:

TABLE 2

| CDR definitions | | | | |
|---|---|---|---|---|
| CDR | Kabat | AbM | Chothia | Contact |
| L1 | L24-L34 | L24-L34 | L24-L34 | L30-L36 |
| L2 | L50-L56 | L50-L56 | L50-L56 | L46-L55 |
| L3 | L89-L97 | L89-L97 | L89-L97 | L89-L96 |
| H1 (Kabat numbering) | H31-H35B | H26-H35B | H26-H32..H34 | H30-H35B |
| H1 (Chothia numbering) | H31-H35 | H26-H35 | H26-H32 | H30-H35 |
| H2 | H50-H56 | H50-H58 | H52-H56 | H47-H58 |
| H3 | H95-H102 | H95-H102 | H95-H102 | H93-H101 |

General guidelines by which one may identify the CDRs in an antibody from sequence alone are as follows:
LCDR1:
Start—Approximately residue 24.
Residue before is always a Cys.
Residue after is always a Trp, typically followed by Tyr-Gln, but also followed by Leu-Gln, Phe-Gln, or Tyr-Leu.
Length is 10 to 17 residues.
LCDR2:
Start—16 residues after the end of L1.
Sequence before is generally Ile-Tyr, but also may be Val-Tyr, Ile-Lys, or Ile-Phe.
Length is generally 7 residues.
LCDR3:
Start—33 residues after end of L2.
Residue before is a Cys.
Sequence after is Phe-Gly-X-Gly.
Length is 7 to 11 residues.
HCDR1:
Start—approximately residue 26, four residues after a Cys under Chothia/AbM definitions; start is 5 residues later under Kabat definition.
Sequence before is Cys-X—X—X.
Residue after is a Trp, typically followed by Val, but also followed by Ile or Ala.
Length is 10 to 12 residues under AbM definition; Chothia definition excludes the last 4 residues.
HCDR2:
Start—15 residues after the end of Kabat/AbM definition of CDR-H1.
Sequence before is typically Leu-Glu-Trp-Ile-Gly, but a number of variations are possible.
Sequence after is Lys/Arg-Leu/Ile/Val/Phe/Thr/Ala-Thr/Ser/Ile/Ala.
Length is 16 to 19 residues under Kabat definition; AbM definition excludes the last 7 residues.
HCDR3:
Start—33 residues after end of CDR-H2 (two residues after a Cys).
Sequence before is Cys-X—X (typically Cys-Ala-Arg).
Sequence after is Trp-Gly-X-Gly.
Length is 3 to 25 residues.

The identity of the amino acid residues in a particular antibody that are outside the CDRs, but nonetheless make up part of the combining site by having a side chain that is part of the lining of the combining site (i.e., that is available to linkage through the combining site), can be determined using methods well known in the art, such as molecular modeling and X-ray crystallography. See, e.g., L. Riechmann et al., Nature 332:323-327 (1988).

As discussed, antibodies that can be used in preparing antibody-based AA targeting compounds require a reactive side chain in the antibody combining site. A reactive side chain may be present naturally or may be placed in an antibody by mutation. The reactive residue of the antibody combining site may be associated with the antibody, such as when the residue is encoded by nucleic acid present in the lymphoid cell first identified to make the antibody. Alternatively, the amino acid residue may arise by purposely mutating the DNA so as to encode the particular residue (see, e.g., WO 01/22922 to Meares et al.). The reactive residue may be a non-natural residue arising, for example, by biosynthetic incorporation using a unique codon, tRNA, and aminoacyl-tRNA as discussed herein. In another approach, the amino acid residue or its reactive functional groups (e.g., a nucleophilic amino group or sulfhydryl group) may be attached to an amino acid residue in the antibody combining site. Thus, covalent linkage with the antibody occurring "through an amino acid residue in a combining site of an antibody" as used herein means that linkage can be directly to an amino acid residue of an antibody combining site or through a chemical moiety that is linked to a side chain of an amino acid residue of an antibody combining site.

Catalytic antibodies are one source of antibodies with combining sites that comprise one or more reactive amino acid side chains. Such antibodies include aldolase antibodies, beta lactamase antibodies, esterase antibodies, amidase antibodies, and the like.

One embodiment comprises an aldolase antibody such as the mouse monoclonal antibody mAb 38C2 or mAb 33F12, as well as suitably humanized and chimeric versions of such antibodies. Mouse mAb 38C2 has a reactive lysine near to but outside HCDR3, and is the prototype of a new class of catalytic antibodies that were generated by reactive immunization and mechanistically mimic natural aldolase enzymes. See C. F. Barbas $3^{rd}$ et al., Science 278:2085-2092 (1997)). Other aldolase catalytic antibodies that may be used include the antibodies produced by the hybridoma 85A2, having ATCC accession number PTA-1015; hybridoma 85C7, having ATCC accession number PTA-1014; hybridoma 92F9, having ATCC accession number PTA-1017; hybridoma 93F3, having ATCC accession number PTA-823; hybridoma 84G3, having ATCC accession number PTA-824; hybridoma 84G11, having ATCC accession number PTA-1018; hybridoma 84H9, having ATCC accession number PTA-1019; hybridoma 85H6, having ATCC accession number PTA-825; hybridoma 90G8, having ATCC accession number PTA-1016. Through a reactive lysine, these antibodies catalyze aldol and retro-aldol reactions using the enamine mechanism of natural aldolases. See, e.g., J. Wagner et al., Science 270:1797-1800 (1995); C. F. Barbas $3^{rd}$ et al., Science 278:2085-2092 (1997); G. Zhong et al., Angew. Chem. Int. Ed. Engl. 38:3738-3741 (1999); A. Karlstrom et al., Proc. Natl. Acad. Sci. U.S.A., 97:3878-3883 (2000). Aldolase antibodies and methods of generating aldolase antibodies are disclosed in U.S. Pat. Nos. 6,210,938, 6,368,839, 6,326,176, 6,589,766, 5,985,626, and 5,733,757.

AA targeting compounds may also be formed by linking an AA targeting agent to a reactive cysteine, such as those found in the combining sites of thioesterase and esterase catalytic antibodies. Suitable thioesterase catalytic antibodies are described by K. D. Janda et al., Proc. Natl. Acad. Sci. U.S.A. 91:2532-2536 (1994). Suitable esterase antibodies are described by P. Wirsching et al., Science 270:1775-1782 (1995). Reactive amino acid-containing antibodies may be prepared by means well known in the art, including mutating an antibody combining site residue to encode for the reactive amino acid or chemically derivatizing an amino acid side chain in an antibody combining site with a linker that contains the reactive group.

Antibodies suitable for use herein may be obtained by conventional immunization, reactive immunization in vivo, or by reactive selection in vitro, such as with phage display. Antibodies may also be obtained by hybridoma or cell fusion methods or in vitro host cells expression system. Antibodies may be produced in humans or in other animal species. Antibodies from one species of animal may be modified to reflect another species of animal. For example, human chimeric antibodies are those in which at least one region of the antibody is from a human immunoglobulin. A human chimeric antibody is typically understood to have variable region amino acid sequences homologous to a non-human animal, e.g., a rodent, with the constant region having amino acid sequence homologous to a human immunoglobulin In contrast, a humanized antibody uses CDR sequences from a non-human antibody with most or all of the variable framework region sequence and all the constant region sequence from a human immunoglobulin. Chimeric and humanized antibodies may be prepared by methods well known in the art including CDR grafting approaches (see, e.g., N. Hardman et al., Int. J. Cancer 44:424-433 (1989); C. Queen et al., Proc. Natl. Acad. Sci. U.S.A. 86:10029-10033 (1989)), chain shuffling strategies (see, e.g., Rader et al., Proc. Natl. Acad. Sci. U.S.A. 95:8910-8915 (1998), genetic engineering molecular modeling strategies (see, e.g., M. A. Roguska et al., Proc. Natl. Acad. Sci. U.S.A. 91:969-973 (1994)), and the like.

Methods for humanizing non-human antibodies have been described in the art. Preferably, a humanized antibody has one or more amino acid residues introduced into it from a source which is non-human. These non-human amino acid residues are often referred to as "import" residues, which are typically taken from an "import" variable domain. Humanization can be essentially performed following the methods of Winter and colleagues (see, e.g., P. T. Jones et al., Nature 321:522-525 (1986); L. Riechmann et al., Nature 332:323-327 (1988); M. Verhoeyen et al., Science 239:1534-1536 (1988)) by substituting hypervariable region sequences for the corresponding sequences of a human antibody. Accordingly, such "humanized" antibodies are chimeric antibodies wherein substantially less than an intact human variable domain has been substituted by the corresponding sequence from a non-human species. In practice, humanized antibodies are typically human antibodies in which some hypervariable region residues and possibly some framework (FR) residues are substituted by residues from analogous sites in rodent antibodies.

The choice of human variable domains, both light and heavy, to be used in making humanized antibodies is very important to reduce antigenicity and human anti-mouse antibody (HAMA) response when the antibody is intended for human therapeutic use. According to the so-called "best-fit" method, the human variable domain utilized for humanization is selected from a library of known domains based on a high degree of homology with the rodent variable region of interest (M. J. Sims et al., J. Immunol., 151:2296-2308 (1993); M. Chothia and A. M. Lesk, J. Mol. Biol. 196:901-917 (1987)). Another method uses a framework region derived from the consensus sequence of all human antibodies of a particular subgroup of light or heavy chains. The same framework may be used for several different humanized antibodies (see, e.g., P. Carter et al., Proc. Natl. Acad. Sci. U.S.A. 89:4285-4289 (1992); L. G. Presta et al., J. Immunol., 151:2623-2632 (1993)).

It is further important that antibodies be humanized with retention of high linking affinity for the Z group. To achieve this goal, according to one method, humanized antibodies are prepared by analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence with respect to linking to the Z group. In this way, FR residues can be selected and combined from the recipient and import sequences so that the desired antibody characteristic, such as increased affinity for the target antigen(s), is achieved.

Various forms of humanized murine aldolase antibodies are contemplated. One embodiment uses the humanized aldolase catalytic antibody h38c2 IgG1 or h38c2 Fab with human constant domains $C_\kappa$ and $C_{\gamma1}$. C. Rader et al., J. Mol. Bio. 332:889-899 (2003) discloses the gene sequences and vectors that may be used to produce h38c2 Fab and h38c2 IgG1. Human germline $V_k$ gene DPK-9 (SEQ ID NO:36) and human $J_k$ gene JK4 (SEQ ID NO:38) were used as frameworks for the humanization of the kappa light chain variable domain of m38c2, and human germline gene DP-47 (SEQ ID NO:37) and human $J_H$ gene JH4 (SEQ ID NO:39) were used as frameworks for the humanization of the heavy chain variable domain of m38c2. FIG. 7A illustrates a sequence alignment between the variable light and heavy chains in m38c2 (SEQ ID NOs: 32 and 33, respectively), h38c2 (SEQ ID NOs: 34 and 35, respectively), and human germlines. h38c2 may utilize IgG1, IgG2, IgG3, or IgG4 constant domains, including any of the allotypes thereof. FIG. 7B illustrates one embodiment of h38c2 IgG1 using the G1m(f) allotype. The light and heavy chain amino acid sequences of this h38c2 IgG1 are set forth in SEQ ID NOs:40 and 41, respectively. In certain embodiments of AA targeting compounds of formula II or III wherein Antibody is h38c2 IgG1 with the G1m(f) allotype, Z binds to the side chain of the lysine residue at position 99 of SEQ ID NO:41. This residue is denoted by bold print in FIG. 7B. Another embodiment uses a chimeric antibody comprising the variable domains ($V_L$ and $V_H$) of h38c2 and the constant domains from an IgG1, IgG2, IgG3, or IgG4.

Various forms of humanized aldolase antibody fragments are also contemplated. One embodiment uses h38c2 F(ab')$_2$. h38c2 F(ab')$_2$ may be produced by the proteolytic digestion of h38c2 IgG1. Another embodiment uses an h38c2 scFv comprising the $V_L$ and $V_H$ domains from h38c2 which are optionally connected by the intervening linker (Gly$_4$Ser)$_3$.

As an alternative to humanization, human antibodies can be generated. For example, it is now possible to produce transgenic animals (e.g., mice) that are capable, upon immunization (or reactive immunization in the case of catalytic antibodies) of producing a full repertoire of human antibodies in the absence of endogenous immunoglobulin production. For example, it has been described that the homozygous deletion of the antibody heavy-chain joining region ($J_H$) gene in chimeric and germ-line immunoglobulin gene array into such germ-line mutant mice will result in the production of human antibodies upon antigen challenge. See, e.g., B. D. Cohen et al, Clin. Cancer Res. 11:2063-2073 (2005); J. L. Teeling et al., Blood 104:1793-1800 (2004); N. Lonberg et al., Nature 368:856-859 (1994); A. Jakobovits et al., Proc. Natl. Acad. Sci. U.S.A. 90:2551-2555 (1993); A. Jakobovits et al., Nature 362:255-258 (1993); M. Bruggemann et al., Year Immunol. 7:33-40 (1993); L. D. Taylor, et al. Nucleic Acids Res. 20:6287-6295 (1992); M. Bruggemann et al., Proc. Natl. Acad. Sci. U.S.A. 86:6709-6713 (1989)); and WO 97/17852.

Alternatively, phage display technology (see, e.g., J. McCafferty et al., Nature 348:552-553 (1990); H. J. de Haard et al., J Biol Chem 274, 18218-18230 (1999); and A. Kanppik et al., J Mol Biol, 296, 57-86 (2000)) can be used to produce human antibodies and antibody fragments in vitro using immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, and is reviewed in, e.g., K. S. Johnson and D. J. Chiswell, Curr. Opin. Struct. Biol. 3:564-571 (1993). Several sources of V-gene segments can be used for phage display. T. Clackson et al., Nature, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by J. D. Marks et al., J. Mol. Biol. 222:581-597 (1991) or A. D. Griffiths et al., EMBO J. 12:725-734 (1993). See also U.S. Pat. Nos. 5,565,332 and 5,573,905; and L. S. Jespers et al., Biotechnology 12:899-903 (1994).

As indicated above, human antibodies may also be generated by in vitro activated B cells. See, e.g., U.S. Pat. Nos. 5,567,610 and 5,229,275; and C. A. K. Borrebaeck et al., Proc. Natl. Acad. Sci. U.S.A. 85:3995-3999 (1988).

Amino acid sequence modification(s) of the antibodies described herein are contemplated. For example, it may be desirable to improve the binding affinity and/or other biological properties of the antibody. Amino acid sequence variants of an antibody are prepared by introducing appropriate nucleotide changes into the antibody nucleic acid, or by peptide synthesis. Such modifications include, for example, deletions from, insertions into, and/or substitutions of residues within the amino acid sequences of the antibody. Any combination of deletion, insertion, and substitution is made to arrive at the final construct, provided that the final construct possesses the desired characteristics. The amino acid changes also may alter post-translational processes of the antibody, such as changing the number or position of glycosylation sites.

A useful method for identification of certain residues or regions of an antibody that are preferred locations for mutagenesis is called "alanine scanning mutagenesis," as described in B. C. Cunningham and J. A. Wells, Science 244:1081-1085 (1989). Here, a residue or group of target residues are identified (e.g., charged residues such as Arg, Asp, His, Lys, and Glu) and replaced by a neutral or negatively charged amino acid (most preferably Ala or Polyalanine) to affect the interaction of the amino acids with the Z group of the linker. Those amino acid locations demonstrating functional sensitivity to the substitutions are then refined by introducing further or other variants at, or for, the sites of substitution. Thus, while the site for introducing an amino acid sequence variation is predetermined, the nature of the mutation per se need not be predetermined. For example, to analyze the performance of a mutation at a given site, alanine scanning or random mutagenesis is conducted at the target codon or region and the expressed antibody variants are screened for the ability to form a covalent bond with Z.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of an antibody molecule include the fusion to the N- or C-terminus of an anti-antibody to an enzyme or a polypeptide which increases the serum half-life of the antibody.

Another type of variant is an amino acid substitution variant. These variants have at least one amino acid residue in an antibody molecule replaced by a different residue. The sites of greatest interest for substitutional mutagenesis include the hypervariable regions, but FR alterations are also contemplated. Conservative substitutions are shown in Table 3 below under the heading of "preferred substitutions." If such substitutions result in a change in biological activity, then more substantial changes, denominated "exemplary substitutions" as further described below in reference to amino acid classes, may be introduced and the products screened.

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: Nle, Met, Ala, Val, Leu, Ile;
(2) neutral hydrophilic: Cys, Ser, Thr;
(3) acidic: Asp, Glu;
(4) basic: Asn, Gln, His, Lys, Arg;
(5) residues that influence chain orientation: Gly, Pro; and
(6) aromatic: Trp, Tyr, Phe.

Non-conservative substitutions will entail exchanging a member of one of these classes for a member of another class.

Any cysteine residue not involved in maintaining the proper conformation of the antibody may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

One type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a structure of the antibody conjugate complex to identify contact points between the antibody and the Z group. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody by deleting one or more carbohydrate moieties found in the antibody and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences Asn-X"-Ser and Asn-X"-Thr, where X" is any amino acid except proline, are generally the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of or substitution by one or more serine or threonine residues to the sequence of the original antibody (for O-linked glycosylation sites).

It may be desirable to modify an antibody with respect to effector function, for example to enhance antigen-dependent cell-mediated cytotoxicity (ADCC) and/or complement dependent cytotoxicity (CDC) of the antibody. This may be achieved by introducing one or more amino acid substitutions in an Fc region of the antibody. Alternatively, an antibody can be engineered which has dual Fc regions and may thereby have enhanced complement lysis and ADCC capabilities. See G. T. Stevenson et al., Anticancer Drug Des. 3:219-230 (1989).

To increase the serum half life of an antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

TABLE 3

Amino acid substitutions

| Original Residue | Exemplary Substitutions | Preferred Substitutions |
|---|---|---|
| Ala (A) | Val; Leu; Ile | Val |
| Arg I | Lys; Gln; Asn | Lys |
| Asn (N) | Gln; His; Asp; Lys; Arg | Gln |
| Asp (D) | Glu; Asn | Glu |
| CI(C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Nle | Leu |
| Leu (L) | Nle; Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Tyr |
| Pro (P) | Ala | Ala |

TABLE 3-continued

Amino acid substitutions

| Original Residue | Exemplary Substitutions | Preferred Substitutions |
|---|---|---|
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Nle | Leu |

Various techniques have been developed for the production of whole antibodies and antibody fragments. Traditionally, antibody fragments were derived via proteolytic digestion of intact antibodies (see, e.g., K. Morimoto and K. Inouye, J. Biochem. Biophys. Methods 24:107-117 (1992); M. Brennan et al., Science 229:81-83 (1985)). However, these fragments can now be produced directly by recombinant host cells. Fab, Fv, $V_H$, $V_L$, and scFv antibody fragments can all be expressed in and secreted from E. coli as is detailed below, thus allowing the facile production of large amounts of these fragments. Antibody fragments can be isolated from the antibody phage libraries discussed above. Alternatively, Fab'-SH fragments can be directly recovered from E. coli and chemically coupled to form F(ab')$_2$ fragments (P. Carter et al., Biotechnology 10:163-167 (1992)). According to another approach, F(ab')$_2$ fragments can be isolated directly from recombinant host cell culture.

A variety of expression vector/host systems may be utilized to express antibodies. These systems include but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); or animal cell systems.

Mammalian cells that are useful in recombinant antibody expression include but are not limited to VERO cells, HeLa cells, Chinese hamster ovary (CHO) cell lines, COS cells (such as COS-7), W138, BHK, HepG2, 3T3, RIN, MDCK, A549, PC12, K562 and 293 cells, as well as hybridoma cell lines as described herein. Mammalian cells are preferred for preparation of those antibodies that are typically glycosylated and require proper refolding for activity. Preferred mammalian cells include CHO cells, hybridoma cells, and myeloid cells.

Some exemplary protocols for the recombinant expression of antibodies are described herein below.

The term "expression vector" or "vector" refers to a plasmid, phage, virus or vector, for expressing a polypeptide from a DNA (RNA) sequence. An expression vector may comprise a transcriptional unit comprising (1) one or more regulatory sequences controlling gene expression, for example, promoters or enhancers, (2) one or more sequences that encode one or more polypeptides, and (3) appropriate transcription initiation and termination sequences. Expression vectors intended for use in yeast or eukaryotic expression systems preferably include a leader sequence enabling extracellular secretion of translated protein by a host cell. Alternatively, where an antibody polypeptide(s) is expressed without a leader or transport sequence, it may include an amino terminal methionine residue. This residue may or may not be subsequently cleaved from the expressed recombinant protein to provide a final antibody product.

Antibodies, specifically antibody fragments, may be expressed in prokaryotic systems such as E. coli. In another example, the DNA sequence encoding the specific binding agent peptide can be amplified by PCR and cloned into an appropriate vector, such as for example pGEX-3x (Pharmacia). The pGEX vector is designed to produce a fusion protein comprising glutathione-S-transferase (GST), encoded by the vector, and a peptide encoded by a DNA fragment inserted into the vector's cloning site. The primers for PCR can be generated to include for example, an appropriate cleavage site. The pGEX-3x antibody peptide construct is transformed into E. coli XL-1 Blue cells (Stratagene, La Jolla Calif.), and individual transformants are isolated and grown. The expressed peptide fusion protein may then be cleaved from the GST portion of the fusion protein.

Expression of polynucleotides encoding antibodies using the recombinant systems described above may result in production of antibodies or fragments thereof that must be "refolded" (to properly create various disulphide bridges) in order to be biologically active.

Antibodies, specifically antibody fragments, made in bacterial cells may be produced as an insoluble inclusion body in the bacteria. Such antibodies can be purified as follows. Host cells can be sacrificed by centrifugation; washed in 0.15 M NaCl, 10 mM Tris, pH 8, 1 mM EDTA; and treated with 0.1 mg/ml lysozyme (Sigma, St. Louis, Mo.) for 15 minutes at room temperature. The lysate can be cleared by sonication, and cell debris can be pelleted by centrifugation for 10 minutes at 12,000×g. The antibody containing pellet can be resuspended in 50 mM Tris, pH 8, and 10 mM EDTA, layered over 50% glycerol, and centrifuged for 30 min. at 6000×g. The pellet can be resuspended in standard phosphate buffered saline solution (PBS) free of Mg and Ca ions. The antibody can be further purified by fractionating the resuspended pellet in a denaturing SDS polyacrylamide gel (Sambrook et al., supra). The gel can be soaked in 0.4 M KCl to visualize the protein, which can be excised and electroeluted in gel-running buffer lacking SDS.

Mammalian host systems for the expression of antibodies are well known to those of skill in the art. Host cell strains can be chosen for a particular ability to process the expressed protein or produce certain post-translation modifications that will be useful in providing protein activity. Such modifications of the polypeptide include, but are not limited to, acetylation, carboxylation, glycosylation, phosphorylation, lipidation and acylation. Different host cells such as CHO, HeLa, MDCK, 293, W138, as well as hybridoma cell lines, and the like have specific cellular machinery and characteristic mechanisms for such post-translational activities and can be chosen to ensure the correct modification and processing of the introduced, foreign protein.

A number of selection systems can be used to recover the cells that have been transformed for recombinant antibody production. Such selection systems include, but are not limited to, HSV thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection for DHFR which confers resistance to methotrexate; gpt which confers resistance to mycophenolic acid; neo which confers resistance to the aminoglycoside G418 and confers resistance to chlorsulfuron; and hygro which that confers resistance to hygromycin. Additional selectable genes that may be useful include trpB, which allows cells to utilize indole in place of tryptophan, or hisD, which allows cells to utilize histinol in place of histidine. Markers that give a visual indication for identification of transformants include anthocyanins, beta.-glucuronidase and its substrate, GUS, and luciferase and its substrate, luciferin.

In some cases, antibodies produced using procedures described above may need to be "refolded" and oxidized into a proper tertiary structure and allowed to generate disulfide linkages in order to be biologically active. Refolding can be accomplished using a number of procedures well known in the art. Such methods include, for example, exposing the solubilized polypeptide agent to a pH usually above 7 in the presence of a chaotropic agent. The selection of chaotrope is similar to the choices used for inclusion body solubilization. However a chaotrope is typically used at a lower concentration. An exemplary chaotropic agent is guanidine. In most cases, the refolding/oxidation solution will also contain a reducing agent plus its oxidized form in a specific ratio to generate a particular redox potential which allows for disulfide shuffling to occur for the formation of cysteine bridges. Some commonly used redox couples include cysteine/cystamine, glutathione/dithiobisGSH, cupric chloride, dithiothreitol DTT/dithiane DTT, and 2-mercaptoethanol (bME)/dithiobME. In many instances, a co-solvent may be used to increase the efficiency of the refolding. Commonly used cosolvents include glycerol, polyethylene glycol of various molecular weights, and arginine.

Linkers and Linked Compounds

An AA targeting agent may be covalently linked to a combining site in an antibody either directly or via a linker. An appropriate linker can be chosen to provide sufficient distance between the targeting agent and the antibody The general design of an embodiment of a linker for use in preparing AA targeting compounds is represented by the formula: —X—Y—Z, wherein X is a connecting chain, Y is a recognition group and Z is a reactive group. The linker may be linear or branched, and optionally includes one or more carbocyclic or heterocyclic groups. Linker length may be viewed in terms of the number of linear atoms, with cyclic moieties such as aromatic rings and the like to be counted by taking the shortest route around the ring. In some embodiments, the linker has a linear stretch of between 5-15 atoms, in other embodiments 15-30 atoms, in still other embodiments 30-50 atoms, in still other embodiments 50-100 atoms, and in still other embodiments 100-200 atoms. Other linker considerations include the effect on physical or pharmacokinetic properties of the resulting AA targeting compound or AA targeting agent-linker, such as solubility, lipophilicity, hydrophilicity, hydrophobicity, stability (more or less stable as well as planned degradation), rigidity, flexibility, immunogenicity, modulation of antibody binding, the ability to be incorporated into a micelle or liposome, and the like.

The connecting chain X of the linker includes any atom from the group C, H, N, O, P, S, halogen (F, Cl, Br, I), or a salt thereof. X also may include a group such as an alkyl, alkenyl, alkynyl, oxoalkyl, oxoalkenyl, oxoalkynyl, aminoalkyl, aminoalkenyl, aminoalkynyl, sulfoalkyl, sulfoalkenyl, sulfoalkynyl, phosphoalkyl, phosphoalkenyl, or phosphoalkynyl group. In some embodiments, X may include one or more ring structures. In some embodiments, the linker is a repeating polymer such as polyethylene glycol comprising 2-100 units.

The recognition group Y of the linker is optional, and if present is located between the reactive group and the connecting chain. In some embodiments, Y is located from 1-20 atoms from Z. Although not wishing to be bound by any theory, it is believed that the recognition group acts to properly position the reactive group into the antibody combining site so that it may react with a reactive amino acid side chain. Exemplary recognition groups include carbocyclic and heterocyclic rings, preferably having five or six atoms. However, larger ring structures also may be used. In some embodiments, an AA targeting agent is linked directly to Y without the use of an intervening linker.

Z is capable of forming a covalent bond with a reactive side chain in an antibody combining site. In some embodiments, Z includes one or more C=O groups arranged to form a diketone, an acyl beta-lactam, an active ester, a haloketone, a cyclohexyl diketone group, an aldehyde, a maleimide, an activated alkene, an activated alkyne or, in general, a molecule comprising a leaving group susceptible to nucleophilic or electrophilic displacement. Other groups may include a lactone, an anhydride, an alpha-haloacetamide, an imine, a hydrazide, or an epoxide. Exemplary linker electrophilic reactive groups that can covalently bond to a reactive nucleophilic group (e.g., a lysine or cysteine side chain) in a combining site of antibody include acyl beta-lactam, simple diketone, succinimide active ester, maleimide, haloacetamide with linker, haloketone, cyclohexyl diketone, aldehyde, amidine, guanidine, imine, eneamine, phosphate, phosphonate, epoxide, aziridine, thioepoxide, a masked or protected diketone (a ketal for example), lactam, sulfonate, and the like, masked C=O groups such as imines, ketals, acetals, and any other known electrophilic group. In certain embodiments, the reactive group includes one or more C=O groups arranged to form an acyl beta-lactam, simple diketone, succinimide active ester, maleimide, haloacetamide with linker, haloketone, cyclohexyl diketone, or aldehyde.

The linker reactive group or similar such reactive group is chosen for use with a reactive residue in a particular combining site. For example, a chemical moiety for modification by an aldolase antibody may be a ketone, diketone, beta lactam, active ester haloketone, lactone, anhydride, maleimide, alpha-haloacetamide, cyclohexyl diketone, epoxide, aldehyde, amidine, guanidine, imine, eneamine, phosphate, phosphonate, epoxide, aziridine, thioepoxide, masked or protected diketone (ketal for example), lactam, haloketone, aldehyde, and the like.

A linker reactive group chemical moiety suitable for covalent modification by a reactive sulfhydryl group in an antibody may be a disulfide, aryl halide, maleimide, alpha-haloacetamide, isocyanate, epoxide, thioester, active ester, amidine, guanidine, imine, eneamine, phosphate, phosphonate, epoxide, aziridine, thioepoxide, masked or protected diketone (ketal for example), lactam, haloketone, aldehyde, and the like.

One of skill in the art will readily appreciate that reactive amino acid side chains in antibody combining sites may possess an electrophilic group that reacts with a nucleophilic group on an AA targeting agent or its linker, whereas in other embodiments a reactive nucleophilic group in an amino acid side chain reacts with an electrophilic group in an AA targeting agent or linker.

An AA targeting compound may be prepared by several approaches. In one approach, an AA targeting agent-linker compound is synthesized with a linker that includes one or more reactive groups designed for covalent reaction with a side chain of an amino acid in a combining site of an antibody. The targeting agent-linker compound and antibody are combined under conditions where the linker reactive group forms a covalent bond with the amino acid side chain.

In another approach, linking can be achieved by synthesizing an antibody-linker compound comprising an antibody and a linker wherein the linker includes one or more reactive groups designed for covalent reaction with an appropriate chemical moiety of an AA targeting agent. An AA targeting agent may need to be modified to provide the appropriate moiety for reaction with the linker reactive group. The antibody-linker and AA targeting agent are combined under conditions where the linker reactive group covalently links to the targeting and/or biological agent.

A further approach for forming an antibody-AA targeting compound uses a dual linker design. In certain embodiments, an AA targeting agent-linker compound is synthesized which comprises an AA targeting agent and a linker with a reactive group. An antibody-linker compound is synthesized which comprises an antibody and a linker with a chemical group susceptible to reactivity with the reactive group of the AA targeting agent-linker of the first step. These two linker containing compounds are then combined under conditions whereby the linkers covalently link, forming the antibody-AA-targeting compound.

Exemplary functional groups that can be involved in the linkage include, for example, esters, amides, ethers, phosphates, amino, keto, amidine, guanidine, imines, eneamines, phosphates, phosphonates, epoxides, aziridines, thioepoxides, masked or protected diketones (ketals for example), lactams, haloketones, aldehydes, thiocarbamate, thioamide, thioester, sulfide, disulfide, phosphoramide, sulfonamide, urea, thioruea, carbamate, carbonate, hydroxamide, and the like.

The linker includes any atom from the group C, H, N, O, P, S, halogen (F, Cl, Br, I), or a salt thereof. The linker also may include a group such as an alkyl, alkenyl, alkynyl, oxoalkyl, oxoalkenyl, oxoalkynyl, aminoalkyl, aminoalkenyl, aminoalkynyl, sulfoalkyl, sulfoalkenyl, sulfoalkynyl group, phosphoalkyl, phosphoalkenyl, or phosphoalkynyl group. The linker also may include one or more ring structures. As used herein, a "ring structure" includes saturated, unsaturated, and aromatic carbocyclic rings and saturated, unsaturated, and aromatic heterocyclic rings. The ring structures may be mono-, bi-, or polycyclic, and include fused or unfused rings. Further, the ring structures are optionally substituted with functional groups well known in the art, including but not limited to halogen, oxo, —OH, —CHO, —COOH, —NO$_2$, —CN, —NH$_2$, —C(O)NH$_2$, C$_{1-6}$ alkyl, C$_{2-6}$ alkenyl, C$_{2-6}$ alkynyl, C$_{1-6}$ oxoalkyl, oxoalkenyl, oxoalkynyl, aminoalkyl, aminoalkenyl, aminoalkynyl, sulfoalkyl, sulfoalkenyl, sulfoalkynyl, phosphoalkyl, phosphoalkenyl, or phosphoalkynyl group. Combinations of the above groups and rings may also be present in the linkers of AA targeting compounds.

One aspect of the invention is an AA targeting agent-linker conjugate having Formula I:

L-[AA targeting agent]　(I)

wherein [AA targeting agent] is an AA targeting agent peptide.

The linker moiety L in compounds of Formula I may be attached to the amino terminus, carboxy terminus or any amino acid side chain of an AA targeting agent. In certain embodiments, L is linked to the carboxy terminus of an AA targeting agent. In certain other embodiments, L is linked to the amino terminus of an AA targeting agent. In still other embodiments, L is linked to either a nucleophilic or electrophilic side chain. For the case of linking to an electrophilic side chain, L should possess a nucleophilic group susceptible to covalent reaction with the electrophilic side chain. Exemplary electrophilic side chains are Asp and Glu. Exemplary nucleophilic side chains are Cys, Lys, Ser, Thr, and Tyr. For the case of linking to a nucleophilic side chain, L should comprise an electrophilic group susceptible to covalent reaction with the nucleophilic side chain. In another embodiment, a nucleophilic amino acid is added to either the carboxy terminus or the amino terminus of an AA targeting agent and the linker L is covalently attached to the side chain of this additional amino acid. In certain embodiments, Lys is added to the amino terminus of an AA targeting agent. In certain other embodiments, Lys is added to the carboxy terminus of an AA targeting agent.

Thus, in those embodiments comprising R$^1$-Sar-Gly-Val-(D-alloIle)-Thr-Nva-Ile-Arg-Pro-R$^3$ (SEQ ID NO:1) based AA targeting agents, exemplary compounds of Formula I formed by linking to either i) the side chains of D, E, C, K, S, T, and Y or ii) the amino or carboxy termini, include:

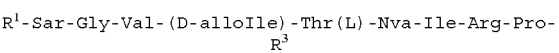
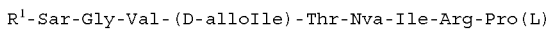

Similarly, in those embodiments comprising R$^1$-Sar-Gly-Val-(D-alloIle)-Thr-Lys-Ile-Arg-Pro-R$^3$ (SEQ ID NO:4) based AA targeting agents, exemplary compounds of Formula I formed by linking to either i) the side chains of D, E, C, K, S, T, and Y or ii) the amino or carboxy termini, include:

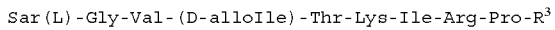
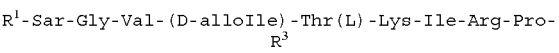
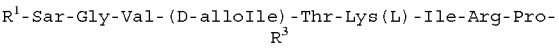
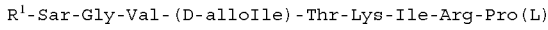

In compounds of Formula I, L is a linker moiety having the formula —X—Y-Z, wherein:

X is a biologically compatible polymer or block copolymer attached to one of the residues that comprises an AA targeting agent;

Y is an optionally present recognition group comprising at least a ring structure; and Z is a reactive group that is capable of covalently linking to a side chain in a combining site of an antibody.

In some embodiments of compounds in Formula I, X is:

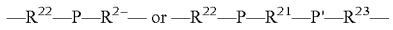

wherein:

P and P' are independently selected from the group consisting of polyoxyalkylene oxides such as polyethylene oxide, polyeth noacrylate chloride), poly(methyacrylamidopropyltrimethyl ammonium chloride), proteoglycans such as chondroitin sulfate-A (4-sulfate) chondroitin sulfate-C (6-sulfate) and chondroitin sulfate-B, polypeptides such as polyserine, polythreonine, polyglutamine, natural or synthetic polysaccharides such as chitosan, hydroxy ethyl cellulose, and lipids;

$R^{21}$, $R^{22}$, and $R^{23}$ are each independently a covalent bond, —O—, —S—, —$NR^b$—, substituted or unsubstituted straight or branched chain $C_{1-50}$ alkylene, or substituted or unsubstituted straight or branched chain $C_{1-50}$ heteroalkylene;

$R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl; and $R^{21}$, $R^{22}$, and $R^{23}$ are selected such that the backbone length of X remains about 200 atoms or less.

In some embodiments of compounds of Formula I, $R^{22}$ is —(CH$_2$)$_v$—, —(CH$_2$)$_u$—C(O)—(CH$_2$)$_v$—, —(CH$_2$)$_u$—C(O)—O—(CH$_2$)$_v$—, —(CH$_2$)$_u$—C(S)—$NR^b$—(CH$_2$)$_v$—, —(CH$_2$)$_u$—C(O)—$NR^b$—(CH$_2$)$_v$—, —(CH$_2$)$_u$—$NR^b$—(CH$_2$)$_v$—, —(CH$_2$)$_u$—O—(CH$_2$)$_v$—, —(CH$_2$)$_u$—S(O)$_{0-2}$—(CH$_2$)$_v$—, —(CH$_2$)$_u$—S(O)$_{0-2}$—$NR^b$—(CH$_2$)$_v$, or —(CH$_2$)$_u$—P(O)(OR$^b$)—O—(CH$_2$)$_v$—, wherein u and v are each independently 0, 1, 2, 3, 4, 5, 6, 7, 8, 9, 10, 11, 12, 13, 14, 15, 16, 17, 18, 19 or 20.

In yet other embodiments of compounds of Formula I, $R^{22}$ is —(CH$_2$)$_v$—, —(CH$_2$)$_u$—C(O)—(CH$_2$)$_v$—, —(CH$_2$)$_u$—C(O)—O—(CH$_2$)$_v$—, —(CH$_2$)$_u$—C(O)—$NR^b$—(CH$_2$)$_v$—, or —(CH$_2$)$_u$—$NR^b$—(CH$_2$)$_v$. In still other embodiments, $R^{-2}$ is —(CH$_2$)$_u$—C(O)—$NR^b$—(CH$_2$)$_v$—.

In some embodiments of compounds of Formula I, $R^{21}$ and $R^{23}$ are each independently —(CH$_2$)$_s$—, —(CH$_2$)$_r$—C(O)—(CH$_2$)$_s$—, —(CH$_2$)$_r$—C(O)—O—(CH$_2$)$_v$—, —(CH$_2$)$_r$—C(S)—$NR^b$—(CH$_2$)$_s$—, —(CH$_2$)$_r$—C(O)—$NR^b$—(CH$_2$)$_s$—, —(CH$_2$)$_r$—$NR^b$—(CH$_2$)$_s$—, —(CH$_2$)$_r$—O—(CH$_2$)$_s$—, —(CH$_2$)$_r$—S(O)$_{0-2}$—(CH$_2$)$_s$—, —(CH$_2$)$_r$—S(O)$_{0-2}$—$NR^b$—(CH$_2$)$_s$—, or —(CH$_2$)$_r$—P(O)(OR$^b$)—O—(CH$_2$)$_s$—, wherein r, s, and v are each independently 0, 1, 2, 3, 4, 5, 6, 7, 8, 9, 10, 11, 12, 13, 14, 15, 16, 17, 18, 19 or 20.

In yet other embodiments, $R^{21}$ and $R^{23}$ are each independently —(CH$_2$)$_s$—, —(CH$_2$)$_r$—C(O)—(CH$_2$)$_s$—, —(CH$_2$)$_r$—C(O)—O—(CH$_2$)$_s$—, —(CH$_2$)$_r$—C(O)—$NR^b$—(CH$_2$)$_s$—, or —(CH$_2$)$_r$—$NR^b$—(CH$_2$)$_s$, and —(CH$_2$)$_r$—C(O)—$NR^b$—(CH$_2$)$_s$—.

In still other embodiments, $R^{21}$ and $R^{23}$ each independently have the structure:

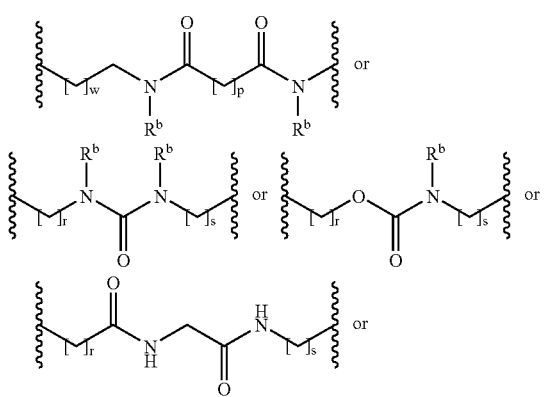

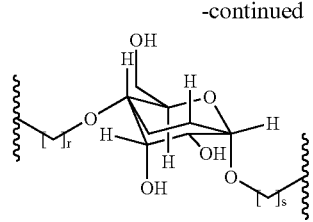

wherein p is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 32, 43, 44, or 45; w, r, and s are each independently 0, 1, 2, 3, 4, 5, 6, 7, 8, 9, 10, 11, 12, 13, 14, 15, 16, 17, 18, 19 or 20; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl.

In certain embodiments of compounds of Formula I, X has the structure:

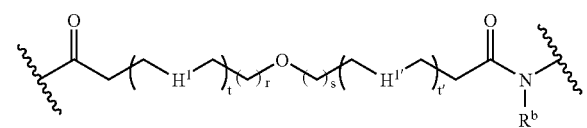

wherein $H^1$ and $H^{1'}$ at each occurrence are independently N, O, S, or CH$_2$; r and s are each independently 1, 2, 3, 4, 5, 6, 7, 8, 9, 10, 11, 12, 13, 14, 15, 16, 17, 18, 19, or 20; t and t' are each independently 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 32, 43, 44, 45, 46, 47, 48, 49 or 50; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl.

In certain embodiments of compounds of Formula I, X has the structure:

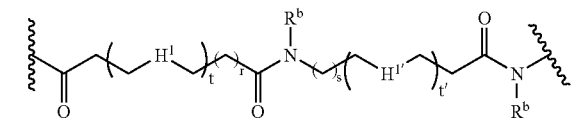

wherein $H^1$ and $H^{1'}$ at each occurrence are independently N, O, S, or CH$_2$; r and s are each independently 1, 2, 3, 4, 5, 6, 7, 8, 9, 10, 11, 12, 13, 14, 15, 16, 17, 18, 19, or 20; t and t' are each independently 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 32, 43, 44, 45, 46, 47, 48, 49 or 50; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl.

In certain embodiments of compounds of Formula I, X has the structure:

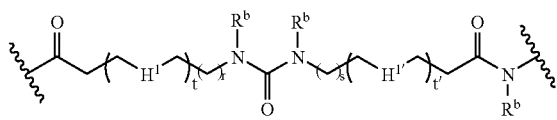

wherein $H^1$ and $H^{1'}$ at each occurrence are independently N, O, S, or $CH_2$; r and s are each independently 1, 2, 3, 4, 5, 6, 7, 8, 9, 10, 11, 12, 13, 14, 15, 16, 17, 18, 19, or 20; t and t' are each independently 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 32, 43, 44, 45, 46, 47, 48, 49 or 50; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl.

In certain embodiments of compounds of Formula I, X has the structure:

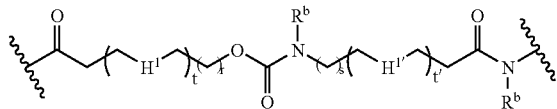

wherein $H^1$ and $H^{1'}$ at each occurrence are independently N, O, S, or $CH_2$; r and s are each independently 1, 2, 3, 4, 5, 6, 7, 8, 9, 10, 11, 12, 13, 14, 15, 16, 17, 18, 19, or 20; t and t' are each independently 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 32, 43, 44, 45, 46, 47, 48, 49 or 50; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl.

In certain embodiments of compounds of Formula I, X has the structure:

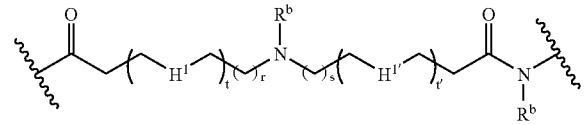

wherein $H^1$ and $H^{1'}$ at each occurrence are independently N, O, S, or $CH_2$; r and s are each independently 1, 2, 3, 4, 5, 6, 7, 8, 9, 10, 11, 12, 13, 14, 15, 16, 17, 18, 19, or 20; t and t' are each independently 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 32, 43, 44, 45, 46, 47, 48, 49 or 50; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl.

In certain embodiments of compounds of Formula I, X has the structure:

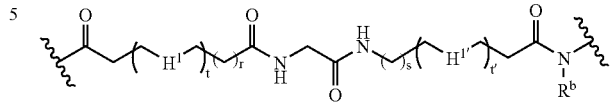

wherein $H^1$ and $H^{1'}$ at each occurrence are independently N, O, S, or $CH_2$; r and s are each independently 1, 2, 3, 4, 5, 6, 7, 8, 9, 10, 11, 12, 13, 14, 15, 16, 17, 18, 19, or 20; t and t' are each independently 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 32, 43, 44, 45, 46, 47, 48, 49 or 50; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl.

In certain embodiments of compounds of Formula I, X has the structure:

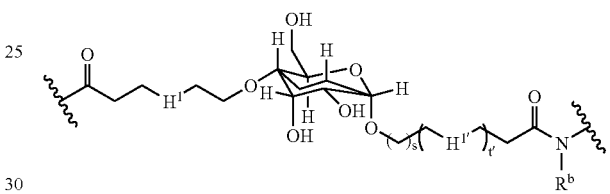

wherein $H^1$ and $H^{1'}$ at each occurrence are independently N, O, S, or $CH_2$; r and s are each independently 1, 2, 3, 4, 5, 6, 7, 8, 9, 10, 11, 12, 13, 14, 15, 16, 17, 18, 19, or 20; t and t' are each independently 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 32, 43, 44, 45, 46, 47, 48, 49 or 50; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl.

In certain embodiments of compounds of Formula I, X has the structure:

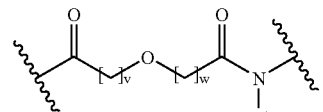

wherein v and w are each independently 1, 2, 3, 4, or 5 and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain of these embodiments, v is 1, 2 or 3, w is 1, 2, or 3, and $R^b$ is hydrogen.

In certain embodiments of Formula I, L is a linker moiety having the formula —X—Y-Z, wherein:
X is attached to one of the residues that comprises an AA targeting agent, and is an optionally substituted —$R^{22}$—[$CH_2$—$CH_2$—O]$_t$—$R^{23}$—, —$R^{22}$-cycloalkyl-$R^{23}$—, —$R^{22}$-aryl-$R^{23}$—, or —$R^{22}$-heterocyclyl-$R^{23}$—, wherein;
$R^{22}$ and $R^{23}$ are each independently a covalent bond, —O—, —S—, —$NR^b$—, substituted or unsubstituted straight or branched chain $C_{1-50}$ alkylene, substituted or unsubstituted straight or branched chain $C_{1-50}$ heteroalkylene, substituted or unsubstituted straight or branched chain $C_{2-50}$ alkenylene, or substituted or unsubstituted $C_{2-50}$ heteroalkenylene;

$R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl;

t is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 32, 43, 44, 45, 46, 47, 48, 49 or 50;

and the size of $R^{22}$ and $R^{23}$ are such that the backbone length of X remains about 200 atoms or less;

Y is an optionally present recognition group comprising at least a ring structure; and Z is a reactive group that is capable of covalently linking to a side chain in a combining site of an antibody. In some embodiments of compounds of Formula I, if t>1 or if —X is —$R^{22}$-cycloalkyl-$R^{23}$—, —$R^{22}$-aryl-$R^{23}$—, or —$R^{22}$-heterocyclyl-$R^{23}$—, Y is present.

In some embodiments of compounds of Formula I, X is:

$$—R^{22}—[CH_2—CH_2—O]_t—R^{2}—,$$

wherein:

$R^{22}$ is —$(CH_2)_v$—, —$(CH_2)_u$—C(O)—$(CH_2)_v$—, —$(CH_2)_u$—C(O)—O—$(CH_2)_v$—, —$(CH_2)_u$—C(O)—$NR^b$—$(CH_2)_v$—, —$(CH_2)_u$—C(S)—$NR^b$—$(CH_2)_v$—, —$(CH_2)_u$—$NR^b$—$(CH_2)_v$—, —$(CH_2)_u$—O—$(CH_2)_v$—, —$(CH_2)_u$—$S(O)_{0-2}$—$(CH_2)_v$—, —$(CH_2)_u$—$S(O)_{0-2}$—$NR^b$—$(CH_2)_v$—, or —$(CH_2)_u$—$P(O)(OR^b)$—O—$(CH_2)_v$—;

u and v are each independently 0, 1, 2, 3, 4, 5, 6, 7, 8, 9, 10, 11, 12, 13, 14, 15, 16, 17, 18, 19 or 20 and t is 0 to 50.

$R^{23}$ has the structure:

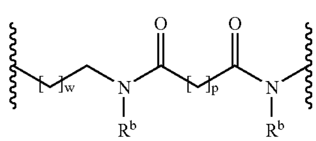

or 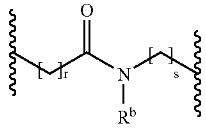 wherein:

p is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 32, 43, 44, or 45;

w and r are each independently 1, 2, 3, 4, 5, 6, 7, 8, 9, 10, 11, 12, 13, 14, 15, 16, 17, 18, 19 or 20;

s is 0, 1, 2, 3, 4, 5, 6, 7, 8, 9, 10, 11, 12, 13, 14, 15, 16, 17, 18, 19 or 20; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl;

and the values of t, u, w, p, v, r and s are such that the backbone length of X remains about 200 atoms or less.

In certain embodiments of compounds of Formula I, X has the formula:

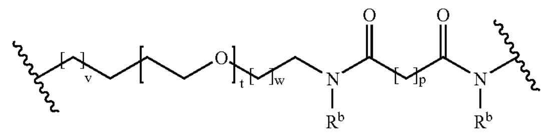

wherein the values of v, t, w, and p are selected such that the backbone length of X is less than 200 atoms, alternatively is less than 100 atoms, alternatively is less than 75 atoms, alternatively is less than 50 atoms, alternatively is less than 25 atoms, or alternatively is less than 15 atoms.

In certain embodiments of compounds of Formula I, X has the structure:

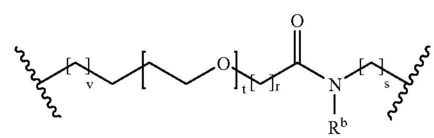

wherein the values of v, t, r, and s are selected such that the backbone length of X is less than 200 atoms, alternatively is less than 100 atoms, alternatively is less than 75 atoms, alternatively is less than 50 atoms, alternatively is less than 25 atoms, or alternatively is less than 15 atoms.

In certain embodiments of compounds of Formula I, X has the structure:

wherein the values of u, v, t, w, and p are selected such that the backbone length of X is less than 200 atoms, alternatively is less than 100 atoms, alternatively is less than 75 atoms, alternatively is less than 50 atoms, alternatively is less than 25 atoms, or alternatively is less than 15 atoms.

In certain embodiments of compounds of Formula I, X has the structure:

wherein the values of u, v, t, r, and s are selected such that the backbone length of X is less than 200 atoms, alternatively is less than 100 atoms, alternatively is less than 75 atoms, alternatively is less than 50 atoms, alternatively is less than 25 atoms, or alternatively is less than 15 atoms.

In certain embodiments of compounds of Formula I, X has the structure:

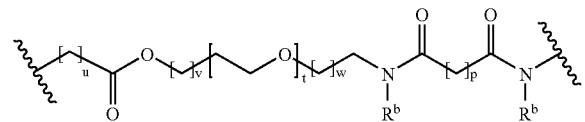

wherein the values of u, v, t, w, and p are selected such that the backbone length of X is less than 200 atoms, alternatively is less than 100 atoms, alternatively is less than 75 atoms, alternatively is less than 50 atoms, alternatively is less than 25 atoms, or alternatively is less than 15 atoms.

In certain embodiments of compounds of Formula I, X has the structure:

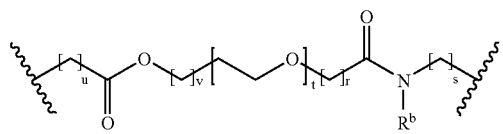

wherein the values of u, v, t, r, and s are selected such that the backbone length of X is less than 200 atoms, alternatively is less than 100 atoms, alternatively is less than 75 atoms, alternatively is less than 50 atoms, alternatively is less than 25 atoms, or alternatively is less than 15 atoms.

In certain embodiments of compounds of Formula I, X has the structure:

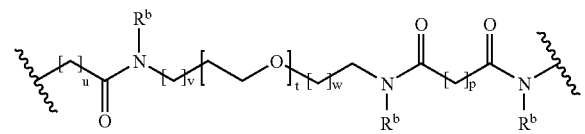

wherein the values of u, v, t, w, and p are selected such that the backbone length of X is less than 200 atoms, alternatively is less than 100 atoms, alternatively is less than 75 atoms, alternatively is less than 50 atoms, alternatively is less than 25 atoms, or alternatively is less than 15 atoms.

In certain embodiments of compounds of Formula I, X has the structure:

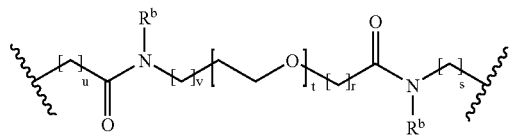

wherein the values of u, v, t, r, and s are selected such that the backbone length of X is less than 200 atoms, alternatively is less than 100 atoms, alternatively is less than 75 atoms, alternatively is less than 50 atoms, alternatively is less than 25 atoms, or alternatively is less than 15 atoms.

In certain embodiments of compounds of Formula I, X has the structure:

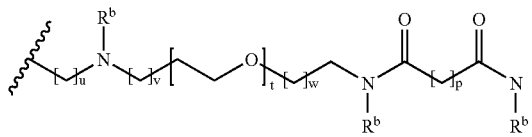

wherein the values of u, v, t, w, and p are selected such that the backbone length of X is less than 200 atoms, alternatively is less than 100 atoms, alternatively is less than 75 atoms, alternatively is less than 50 atoms, alternatively is less than 25 atoms, or alternatively is less than 15 atoms.

In certain embodiments of compounds of Formula I, X has the structure:

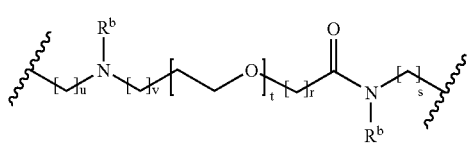

wherein the values of u, v, t, r, and s are selected such that the backbone length of X is less than 200 atoms, alternatively is less than 100 atoms, alternatively is less than 75 atoms, alternatively is less than 50 atoms, alternatively is less than 25 atoms, or alternatively is less than 15 atoms.

In certain embodiments of compounds of Formula I, X has the structure:

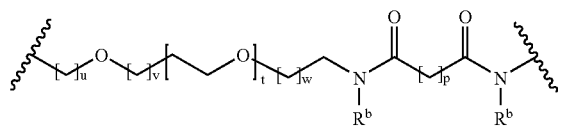

wherein the values of u, v, t, w, and p are selected such that the backbone length of X is less than 200 atoms, alternatively is less than 100 atoms, alternatively is less than 75 atoms, alternatively is less than 50 atoms, alternatively is less than 25 atoms, or alternatively is less than 15 atoms.

In certain embodiments of compounds of Formula I, X has the structure:

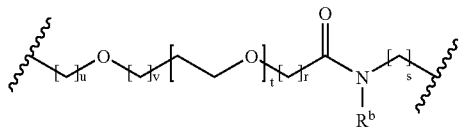

wherein the values of u, v, t, r, and s are selected such that the backbone length of X is less than 200 atoms, alternatively is less than 100 atoms, alternatively is less than 75 atoms, alternatively is less than 50 atoms, alternatively is less than 25 atoms, or alternatively is less than 15 atoms.

In compounds having Formula I wherein L has the formula —X—Y-Z, the ring structure of Y includes saturated, unsaturated, and aromatic carbocyclic rings and saturated, unsaturated, and aromatic heterocyclic rings. The ring structure(s) may be mono-, bi-, or polycyclic, and include fused or unfused rings. Further, the ring structure(s) is optionally substituted with functional groups well known in the art including, but not limited to halogen, oxo, —OH, —CHO, —COOH, —NO$_2$, —CN, —NH$_2$, amidine, guanidine, hydroxylamine, —C(O)NH$_2$, secondary and tertiary amides, sulfonamides, substituted or unsubstituted alkyl, substituted or unsubstituted alkenyl, substituted or unsubstituted alkynyl, oxoalkyl, oxoalkenyl, oxoalkynyl, aminoalkyl, aminoalkenyl, aminoalkynyl, sulfoalkyl, sulfoalkenyl, sulfoalkynyl, phosphoalkyl, phosphoalkenyl, and phosphoalkynyl groups.

In some embodiments of compounds having Formula I, the ring structure of Y has the optionally substituted structure:

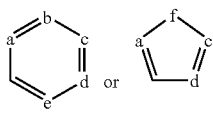

wherein a, b, c, d, and e are each independently carbon or nitrogen; f is carbon, nitrogen, oxygen, or sulfur; Y is attached to X and Z independently at any two ring positions of sufficient valence; and no more than four of a, b, c, d, e, or f are simultaneously nitrogen.

Any open valences remaining on atoms constituting the ring structure may be filled by hydrogen or other substituents, or by the covalent attachments to X and Z. For example, if b is carbon, its valence may be filled by hydrogen, a substituent such as halogen, a covalent attachment to X, or a covalent attachment to Z. In some embodiments, a, b, c, d, and e are each carbon, while in others, a, c, d and f are each carbon. In other embodiments, at least one of a, b, c, d, or e is nitrogen, and in still others, f is oxygen or sulfur. In yet another embodiment, the ring structure of Y is unsubstituted. In certain embodiments, Y is phenyl.

In certain embodiments of compounds of Formula I, X—Y has the structure:

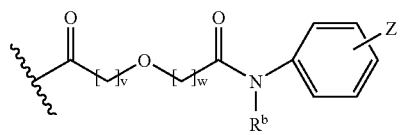

In certain of these embodiments, v is 1, 2, 3, 4, or 5; w is 1, 2, 3, 4, or 5; and R$^b$ is hydrogen, substituted or unsubstituted C$_{1-10}$ alkyl, substituted or unsubstituted C$_{3-7}$ cycloalkyl-C$_{0-6}$ alkyl, or substituted or unsubstituted aryl-C$_{0-6}$ alkyl. In certain other embodiments, v is 1, 2 or 3 and w is 1, 2, or 3. In still other embodiments, v is 1 or 2 and w is 1 or 2.

In certain embodiments of compounds of Formula I, X has the structure:

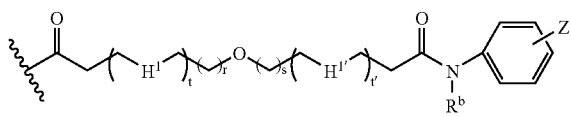

wherein H$^1$ and H$^{1'}$ are each independently N, O, S, or CH$_2$; r and s are each independently 1, 2, 3, 4, or 5; and t and t' are each independently 0, 1, 2, 3, 4, or 5. In certain of these embodiments, H$^1$ and H$^{1'}$ are each independently O or CH$_2$; r and s are each independently 1 or 2; and t and t' are each independently 0 or 1.

In certain embodiments of compounds of Formula I, X has the structure:

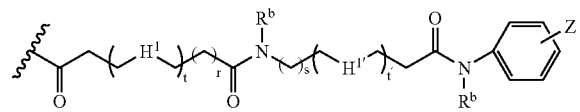

wherein H$^1$ and H$^{1'}$ are each independently N, O, S, or CH$_2$; r and s are each independently 1, 2, 3, 4, or 5; t and t' are each independently 0, 1, 2, 3, 4, or 5, and R$^b$ at each occurrence is independently hydrogen, substituted or unsubstituted C$_{1-10}$ alkyl, substituted or unsubstituted C$_{3-7}$ cycloalkyl-C$_{0-6}$ alkyl, or substituted or unsubstituted aryl-C$_{0-6}$ alkyl In certain of these embodiments, H$^1$ and H$^1$ are each independently O or CH$_2$; r and s are each independently 1 or 2; and t and t' are each independently 0 or 1.

In certain embodiments of compounds of Formula I, X has the structure:

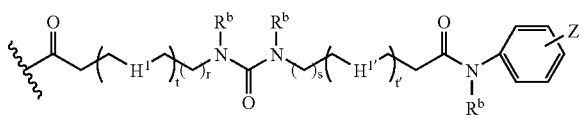

wherein H$^1$ and H$^{1'}$ are each independently N, O, S, or CH$_2$; r and s are each independently 1, 2, 3, 4, or 5; t and t' are each independently 0, 1, 2, 3, 4, or 5, and R$^b$ at each occurrence is independently hydrogen, substituted or unsubstituted C$_{1-10}$ alkyl, substituted or unsubstituted C$_{3-7}$ cycloalkyl-C$_{0-6}$ alkyl, or substituted or unsubstituted aryl-C$_{0-6}$ alkyl. In certain of these embodiments, H$^1$ and H$^{1'}$ are each independently O or CH$_2$; r and s are each independently 1 or 2; and t and t' are each independently 0 or 1.

In certain embodiments of compounds of Formula I, X has the structure:

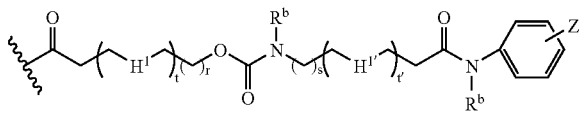

wherein H$^1$ and H$^{1'}$ are each independently N, O, S, or CH$_2$; r and s are each independently 1, 2, 3, 4, or 5; t and t' are each independently 0, 1, 2, 3, 4, or 5, and R$^b$ at each occurrence is independently hydrogen, substituted or unsubstituted C$_{1-10}$ alkyl, substituted or unsubstituted C$_{3-7}$ cycloalkyl-C$_{0-6}$ alkyl, or substituted or unsubstituted aryl-C$_{0-6}$ alkyl. In certain of these embodiments, H$^1$ and H$^{1'}$ are each independently O or CH$_2$; r and s are each independently 1 or 2; and t and t' are each independently 0 or 1.

In certain embodiments of compounds of Formula I, X has the structure:

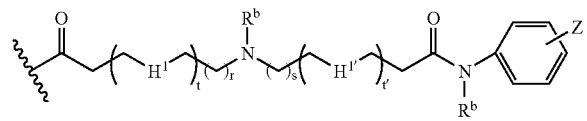

wherein $H^1$ and $H^{1'}$ are each independently N, O, S, or $CH_2$; r and s are each independently 1, 2, 3, 4, or 5; t and t' are each independently 0, 1, 2, 3, 4, or 5, and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain of these embodiments, $H^1$ and $H^{1'}$ are each independently O or $CH_2$; r and s are each independently 1 or 2; and t and t' are each independently 0 or 1.

In certain embodiments of compounds of Formula I, X has the structure:

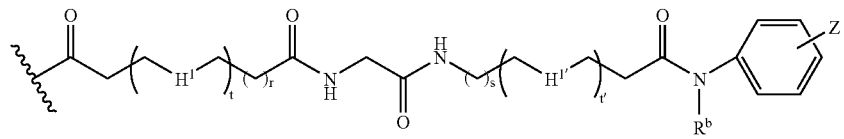

wherein $H^1$ and $H^{1'}$ are each independently N, O, S, or $CH_2$; r and s are each independently 1, 2, 3, 4, or 5; t and t' are each independently 0, 1, 2, 3, 4, or 5, and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain of these embodiments, $H^1$ and $H^{1'}$ are each independently O or $CH_2$; r and s are each independently 1 or 2; and t and t' are each independently 0 or 1.

In certain embodiments of compounds of Formula I, X has the structure:

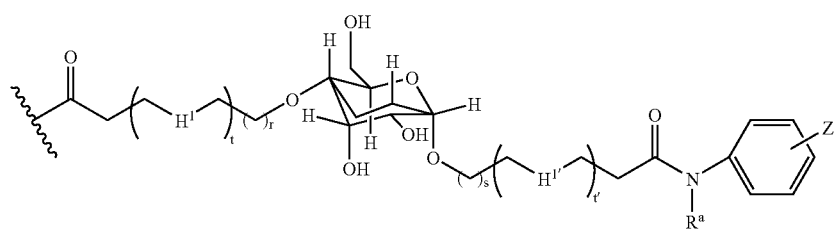

wherein $H^1$ and $H^{1'}$ are each independently N, O, S, or $CH_2$; r and s are each independently 1, 2, 3, 4, or 5; and t and t' are each independently 0, 1, 2, 3, 4, or 5. In certain of these embodiments, $H^1$ and $H^{1'}$ are each independently O or $CH_2$; r and s are each independently 1 or 2; and t and t' are each independently 0 or 1.

In certain of these embodiments of compounds of Formula I, X—Y has the structure:

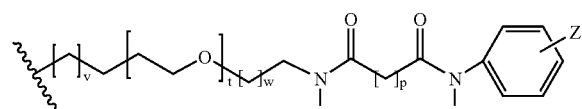

In certain of these embodiments, v is 0, 1, 2, 3, 4, or 5; t is 1, 2, 3, 4, 5, or 6; w is 1, 2, 3, 4, or 5; p is 1, 2, 3, 4, or 5, and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; and p is 3. In some embodiments, v is 0; t is 1, 2, or 3, w is 1; and p is 1 or 2.

In certain embodiments of compounds of Formula I, X—Y has the structure:

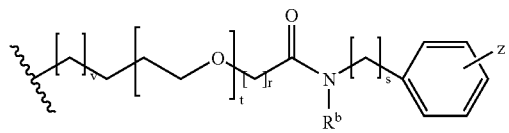

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; and s is 3. In some embodiments, v is 0; t is 1, 2, or 3, r is 1; and s is 1 or 2.

In certain embodiments of compounds of Formula I, X—Y has the structure:

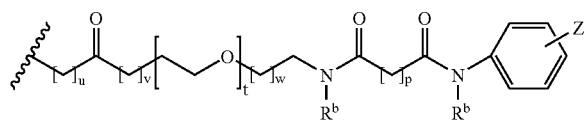

In certain of these embodiments, u is 0, 1, 2, 3, 4, or 5; v is 0, 1, 2, 3, 4, or 5; t is 1, 2, 3, 4, 5, or 6; w is 1, 2, 3, 4, or 5; p is 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, u is 0; v is 0; t is 1, 2, 3, 4, 5, or 6; w is 1; and p is 3. In some embodiments, u is 0 or 1; v is 0; t is 1 or 2; w is 1; and p is 1 or 2.

In certain embodiments of compounds of Formula I, X—Y has the structure:

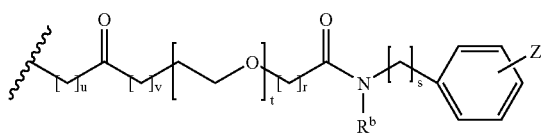

In certain of these embodiments, u is 0, 1, 2, 3, 4, or 5; v is 0, 1, 2, 3, 4, or 5; t is 1, 2, 3, 4, 5, or 6; r is 1, 2, 3, 4, or 5; s is 0, 1, 2, 3, 4, or 5; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, u is 0; v is 0; t is 1, 2, 3, 4, 5, or 6; r is 1 or 2; and s is 3. In some embodiments, u is 0 or 1; v is 0; t is 1, 2, or 3; r is 1; and s is 1 or 2.

In certain embodiments of compounds of Formula I, X—Y has the structure:

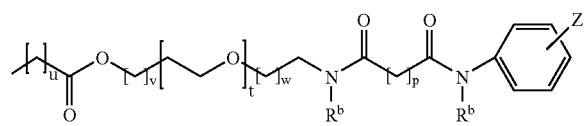

In certain of these embodiments, u is 0, 1, 2, 3, 4, or 5; v is 0, 1, 2, 3, 4, or 5; t is 1, 2, 3, 4, 5, or 6; w is 1, 2, 3, 4, or 5; p is 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, u is 0; v is 0; t is 1, 2, 3, 4, 5, or 6; w is 1; and p is 3. In some embodiments, u is 0 or 1; v is 0; t is 1 or 2; w is 1; and p is 1 or 2.

In certain embodiments of compounds of Formula I, X—Y has the structure:

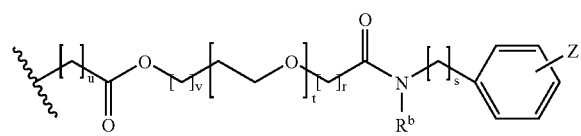

In certain of these embodiments, u is 0, 1, 2, 3, 4, or 5; v is 0, 1, 2, 3, 4, or 5; t is 1, 2, 3, 4, 5, or 6; r is 1, 2, 3, 4, or 5; s is 0, 1, 2, 3, 4, or 5; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, u is 0; v is 0; t is 1, 2, 3, 4, 5, or 6; r is 1 or 2; and s is 3. In some embodiments, u is 0 or 1; v is 0; t is 1, 2, or 3, r is 1; and s is 1 or 2.

In certain embodiments of compounds of Formula I, X—Y has the structure:

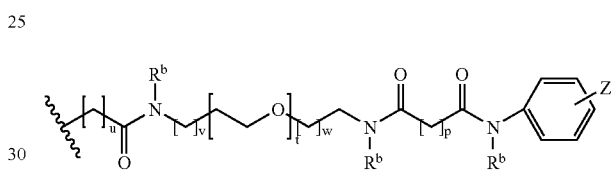

In certain of these embodiments, u is 0, 1, 2, 3, 4, or 5; v is 0, 1, 2, 3, 4, or 5; t is 1, 2, 3, 4, 5, or 6; w is 1, 2, 3, 4, or 5; p is 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, u is 0; v is 0; t is 1, 2, 3, 4, 5, or 6; w is 1; and p is 3. In some embodiments, u is 0 or 1; v is 0; t is 1 or 2; w is 1; and p is 1 or 2.

In certain embodiments of compounds of Formula I, X—Y has the structure:

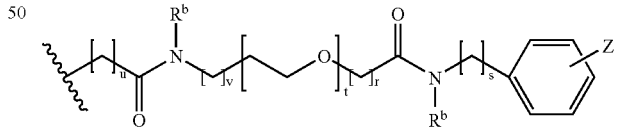

In certain of these embodiments, u is 0, 1, 2, 3, 4, or 5; v is 0, 1, 2, 3, 4, or 5; t is 1, 2, 3, 4, 5, or 6; r is 1, 2, 3, 4, or 5; s is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, u is 0; v is 0; t is 1, 2, 3, 4, 5, or 6; r is 1 or 2; and s is 3. In some embodiments, u is 0 or 1; v is 0; t is 1, 2, or 3, r is 1; and s is 1 or 2.

In certain embodiments of compounds of Formula I, X—Y has the structure:

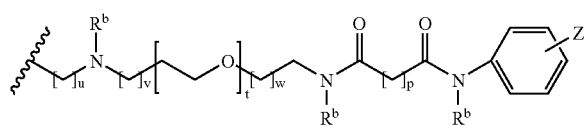

In certain of these embodiments, u is 0, 1, 2, 3, 4, or 5; v is 0, 1, 2, 3, 4, or 5; t is 1, 2, 3, 4, 5, or 6; w is 1, 2, 3, 4, or 5; p is 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, u is 0; v is 0; t is 1, 2, 3, 4, 5, or 6; w is 1; and p is 3. In some embodiments, u is 0 or 1; v is 0; t is 1 or 2; w is 1; and p is 1 or 2.

In certain embodiments of compounds of Formula I, X—Y has the structure:

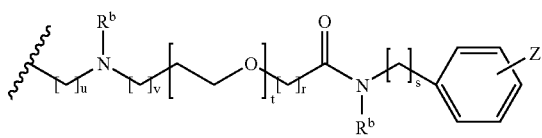

In certain of these embodiments, u is 0, 1, 2, 3, 4, or 5; v is 0, 1, 2, 3, 4, or 5; t is 1, 2, 3, 4, 5, or 6; r is 1, 2, 3, 4, or 5; s is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl In certain embodiments, u is 0; v is 0; t is 1, 2, 3, 4, 5, or 6; r is 1 or 2; and s is 3. In some embodiments, u is 0 or 1; v is 0; t is 1, 2, or 3, r is 1; and s is 1 or 2.

In certain embodiments of compounds of Formula I, X—Y has the structure:

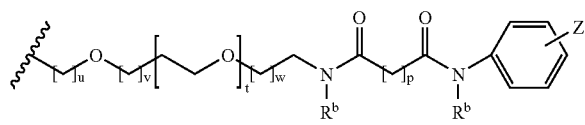

In certain of these embodiments, u is 0, 1, 2, 3, 4, or 5; v is 0, 1, 2, 3, 4, or 5; t is 1, 2, 3, 4, 5, or 6; w is 1, 2, 3, 4, or 5; p is 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, u is 0; v is 0; t is 1, 2, 3, 4, 5, or 6; w is 1; and p is 3. In some embodiments, u is 0 or 1; v is 0; t is 1 or 2; w is 1; and p is 1 or 2.

In certain embodiments of compounds of Formula I, X—Y has the structure:

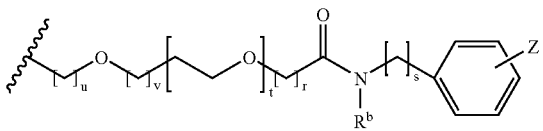

In certain of these embodiments, u is 0, 1, 2, 3, 4, or 5; v is 0, 1, 2, 3, 4, or 5; t is 1, 2, 3, 4, 5, or 6; r is 1, 2, 3, 4, or 5; s is 0, 1, 2, 3, 4, or 5; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiment, u is 0; v is 0; t is 1, 2, 3, 4, 5, or 6; r is 1 or 2; and s is 3. In some embodiments, u is 0 or 1; v is 0; t is 1, 2, or 3, r is 1; and s is 1 or 2.

In compounds having Formula I wherein L has the formula —X—Y-Z, the reactive group Z contains a moiety capable of forming a covalent linkage with an amino acid in a combining site of an antibody. For example, Z may be substituted alkyl, substituted cycloalkyl, substituted aryl, substituted arylalkyl, substituted heterocyclyl, or substituted heterocyclylalkyl, wherein at least one substituent is a 1,3-diketone moiety, an acyl beta-lactam, an active ester, an alpha-haloketone, an aldehyde, a maleimide, a lactone, an anhydride, an alpha-haloacetamide, an amine, a hydrazide, or an epoxide. In some such embodiments, Z is substituted alkyl.

Figure 8:
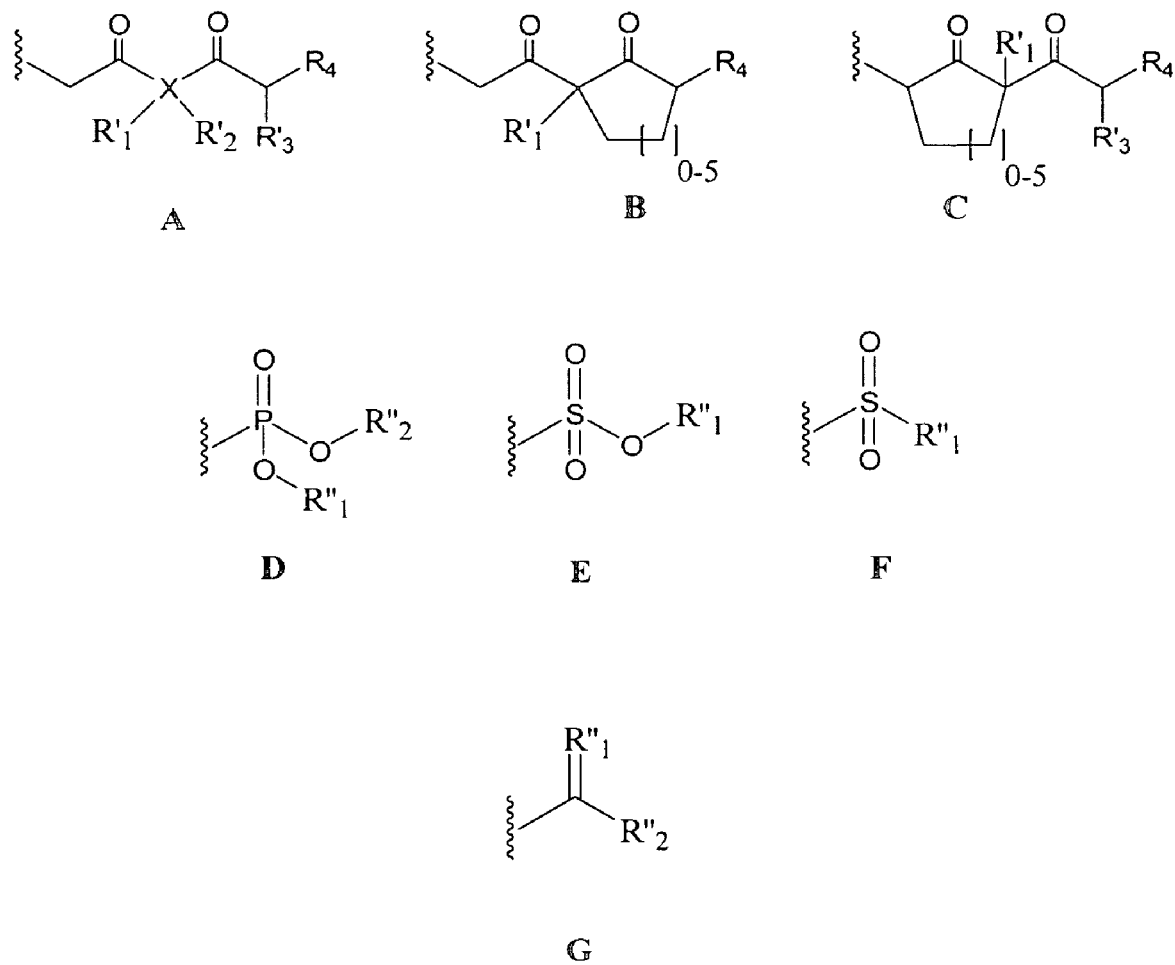
FIG. 8 shows various structures that may serve as linker reactive groups. Structures A-C form reversible covalent bonds with surface accessible reactive nucleophilic groups (e.g., lysine or cysteine side chain) of a combining site of an antibody. $R'_1$, $R'_2$, $R'_3$, and $R_4$ in structures A-C represent substituents which include, for example, C, H, N, O, P, S, halogen (F, Cl, Br, I) or a salt thereof. X is N, C, or any other heteroatom. These substituents may also include a group such as an alkyl, alkenyl, alkynyl, oxoalkyl, oxoalkenyl, oxoalkynyl, aminoalkyl, aminoalkenyl, aminoalkynyl, sulfoalkyl, sulfoalkenyl, or sulfoalkynyl group, phosphoalkyl, phosphoalkenyl, phosphoalkynyl group. $R'_2$ and $R'_3$ could be cyclic as exemplified in structures B and C while X could be a heteroatom. For example, structure A could form an irreversible covalent bond with a reactive nucleophile if X is N and if $R'_1$ and $R_3$ form part of a cyclic structure. Structures D-G may form nonreversible covalent bonds with reactive nucleophilic groups in a combining site of an antibody. In these structures, $R''_1$ and $R''_2$ represent C, O, N, halide or leaving groups such as mesyl or tosyl.

Z may be a group that forms a reversible or irreversible covalent bond. In some embodiments, reversible covalent bonds may be formed using diketone Z groups such as those shown in FIG. 8. Thus, structures A-C may form reversible covalent bonds with reactive nucleophilic groups (e.g. lysine or cysteine side chain) in a combining site of an antibody. $R'_1$, $R'_2$, $R'_3$, and $R_4$ in structures A-C of FIG. 8 represent substituents which can be C, H, N, O, P, S, halogen (F, Cl, Br, I) or a salt thereof. These substituents also may include a group such as an alkyl, alkenyl, alkynyl, oxoalkyl, oxoalkenyl, oxoalkynyl, aminoalkyl, aminoalkenyl, aminoalkynyl, sulfoalkyl, sulfoalkenyl, or sulfoalkynyl group, phosphoalkyl, phosphoalkenyl, phosphoalkynyl group. $R'_2$ and $R'_3$ also could from a ring structure as exemplified in structures B and C. X in FIG. 8 could be a heteroatom. Other Z groups that form reversible covalent bonds include the amidine, imine, and other reactive groups encompassed by structure G of FIG. 8. FIG. 9 includes the structures of other linker reactive groups that form reversible covalent bonds, e.g., structures B, G, H, and, where X is not a leaving group, E and F.

Z reactive groups that form an irreversible covalent bond with a combining site of an antibody include structures D-G in FIG. 8 (e.g., when G is an imidate) and structures A, C and D of FIG. 9. When X is a leaving group, structures E and F of FIG. 9 may also form irreversible covalent bonds. Such structures are useful for irreversibly attaching a targeting agent-linker to a reactive nucleophilic group to a combining site of an antibody.

In other such embodiments, Z is a 1,3-diketone moiety. In still other such embodiments, Z is alkyl substituted by a 1,3-diketone moiety. In certain embodiments, Z has the structure:

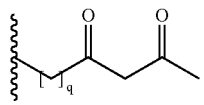

wherein q=0-5. In certain other embodiments, Z has the structure:

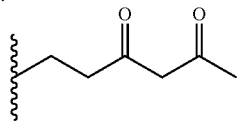

One linker for use in AA targeting compounds and for preparing AA targeting agent-linker compounds includes a 1,3-diketone reactive group as Z. In certain embodiments of Formula I, L has the structure:

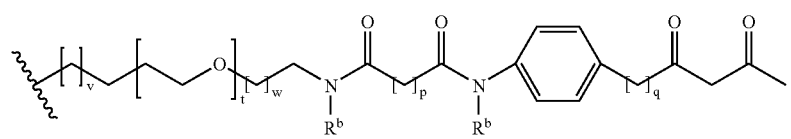

In certain of these embodiments, v is 0, 1, 2, 3, 4, or 5; t is 1, 2, 3, 4, 5, or 6; w is 1, 2, 3,4, or 5; p is 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments v is 0; t is 1, 2, 3, 4, 5, or 6; w is 1; p is 3; and q is 0, 1, 2, or 3. In some embodiments, v is 0; t is 1 or 2; w is 1; p is 1 or 2; and q is 1 or 2.

In certain embodiments of Formula I, L has the structure:

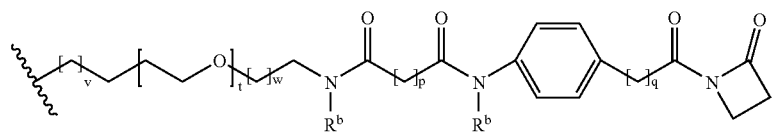

In certain of these embodiments, v is 0, 1, 2, 3, 4, or 5; t is 1, 2, 3, 4, 5, or 6; w is 1, 2, 3, 4, or 5; p is 1, 2, 3, 4, or 5; q is 0, 1, 2, or 3; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; p is 3; and q is 0, 1, 2, or 3. In some embodiments, v is 0; t is 1 or 2; w is 1; p is 1 or 2; and q is 2 or 3.

In certain embodiments of Formula I, L has the structure:

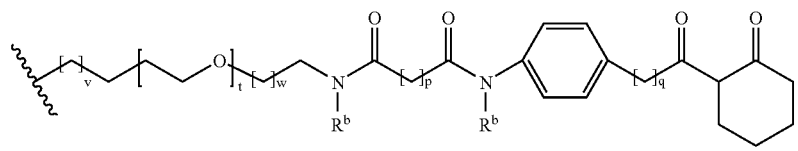

In certain of these embodiments, v is 0, 1, 2, 3, 4, or 5; t is 1, 2, 3, 4, 5, or 6; w is 1, 2, 3, 4, or 5; p is 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; p is 3; and q is 0, 1, 2, or 3. In some embodiments, v is 0; t is 1 or 2; w is 1; p is 1 or 2; and q is 1 or 2.

In certain embodiments of Formula I, L has the structure:

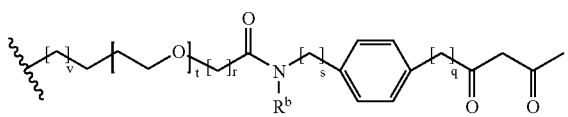

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, 3, 4, or 5; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; s is 3; and q is 0, 1, 2, or 3. In some embodiments, v is 0; t is 1, 2, or 3, r is 1; s is 1 or 2; and q is 1 or 2.

In certain embodiments of Formula I, L has the structure:

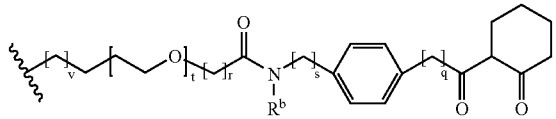

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, 3, 4, or 5; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; s is 3; and q is 0, 1, 2, or 3. In some embodiments, v is 0; t is 1, 2, or 3, r is 1; s is 1 or 2; and q is 1 or 2.

In certain embodiments of Formula I, L has the structure:

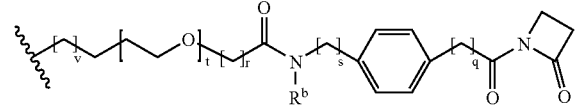

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, or 3; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; s is 3; and q is 0, 1, 2, or 3. In some embodiments, v is 0; t is 1, 2, or 3, r is 1; s is 1 or 2; and q is 2 or 3.

In certain embodiments of Formula I, L has the structure:

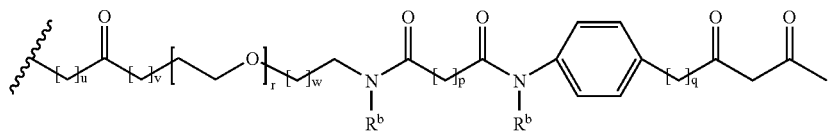

In certain of these embodiments, u is 0, 1, 2, 3, 4, or 5; v is 0, 1, 2, 3, 4, or 5; t is 1, 2, 3, 4, 5, or 6; w is 1, 2, 3, 4, or 5; p is 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, u is 0; v is 0; t is 1, 2, 3, 4, 5, or 6; w is 1; p is 3; and q is 0, 1, 2, or 3. In some embodiments, u is 0 or 1; v is 0; t is 1 or 2; w is 1; p is 1 or 2; and q is 1 or 2.

In certain embodiments of Formula I, L has the structure:

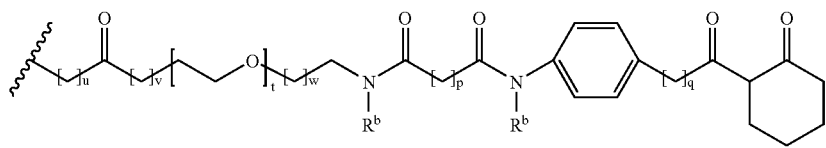

In certain of these embodiments, u is 0, 1, 2, 3, 4, or 5; v is 0, 1, 2, 3, 4, or 5; t is 1, 2, 3, 4, 5, or 6; w is 1, 2, 3, 4, or 5; p is 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, u is 0; v is 0; t is 1, 2, 3, 4, 5, or 6; w is 1; p is 3; and q is 0, 1, 2, or 3. In some embodiments, v is 0; t is 1 or 2; w is 1; p is 1 or 2; and q is 1 or 2.

In certain embodiments of Formula I, L has the structure:

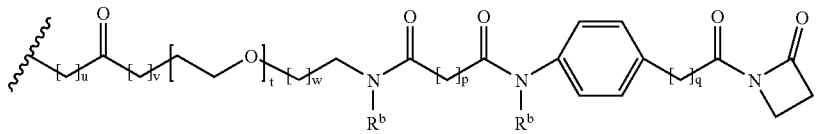

In certain of these embodiments, u is 0, 1, 2, 3, 4, or 5; v is 0, 1, 2, 3, 4, or 5; t is 1, 2, 3, 4, 5, or 6; w is 1, 2, 3, 4, or 5; p is 1, 2, 3, 4, or 5; q is 0, 1, 2, or 3; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, u is 0; v is 0; t is 1, 2, 3, 4, 5, or 6; w is 1; p is 3; and q is 0, 1, 2, or 3. In some embodiments, v is 0; t is 1 or 2; w is 1; p is 1 or 2; and q is 2 or 3.

In certain embodiments of Formula I, L has the structure:

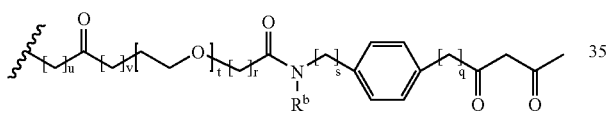

In certain of these embodiments, u is 0, 1, 2, 3, 5, or 5; v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, 3, 4, or 5; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, u is 0; v is 0; t is 1, 2, 3, 4, 5, or 6; r is 1 or 2; s is 3; and q is 0, 1, 2, or 3. In some embodiments, u is 0 or 1; v is 0; t is 1 or 2; w is 1; p is 1 or 2; and q is 1 or 2.

In certain embodiments of Formula I, L has the structure:

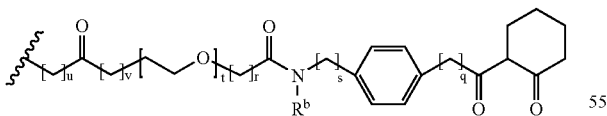

In certain of these embodiments u is 0, 1, 2, 3, 5, or 5; v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, 3, 4, or 5; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, u is 0; v is 0; t is 1, 2, 3, 4, 5, or 6; r is 1 or 2; s is 3; and q is 0, 1, 2, or 3. In some embodiments, u is 0 or 1; v is 0; t is 1, 2, or 3, r is 1; s is 1 or 2; and q is 1 or 2.

In certain embodiments of Formula I, L has the structure:

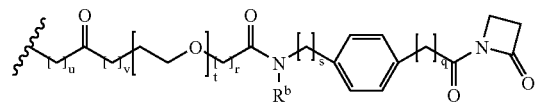

In certain of these embodiments, u is 0, 1, 2, 3, 5, or 5; v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, or 3; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, u is 0; v is 0; t is 1, 2, 3, 4, 5, or 6; r is 1 or 2; s is 3; and q is 0, 1, 2, or 3. In some embodiments, u is 0 or 1; v is 0; t is 1, 2, or 3, r is 1; s is 1 or 2; and q is 2 or 3.

In certain embodiments of Formula I, L has the structure:

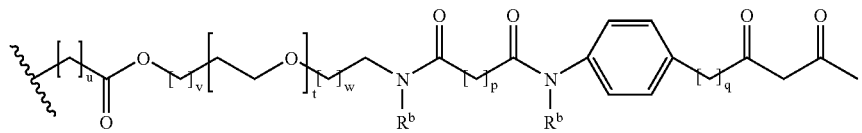

In certain of these embodiments, u is 0, 1, 2, 3, 4, or 5; v is 0, 1, 2, 3, 4, or 5; t is 1, 2, 3, 4, 5, or 6; w is 1, 2, 3, 4, or 5; p is 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, u is 0; v is 0; t is 1, 2, 3, 4, 5, or 6; w is 1; p is 3; and q is 0, 1, 2, or 3. In some embodiments, u is 0 or 1; v is 0; t is 1 or 2; w is 1; p is 1 or 2; and q is 1 or 2.

In certain embodiments of Formula I, L has the structure:

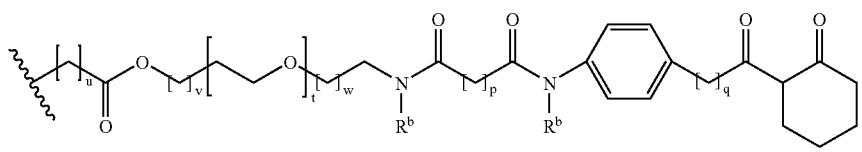

In certain of these embodiments, u is 0, 1, 2, 3, 4, or 5; v is 0, 1, 2, 3, 4, or 5; t is 1, 2, 3, 4, 5, or 6; w is 1, 2, 3, 4, or 5; p is 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, u is 0; v is 0; t is 1, 2, 3, 4, 5, or 6; w is 1; p is 3; and q is 0, 1, 2, or 3. In some embodiments, u is 0 or 1; v is 0; t is 1 or 2; w is 1; p is 1 or 2; and q is 1 or 2.

In certain embodiments of Formula I, L has the structure:

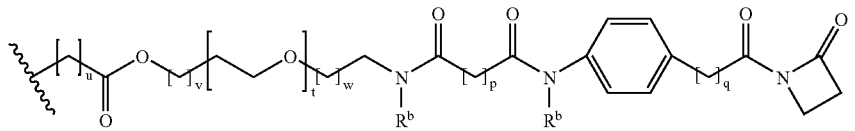

In certain of these embodiments, u is 0, 1, 2, 3, 4, or 5; v is 0, 1, 2, 3, 4, or 5; t is 1, 2, 3, 4, 5, or 6; w is 1, 2, 3, 4, or 5; p is 1, 2, 3, 4, or 5; q is 0, 1, 2, or 3; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, u is 0; v is 0; t is 1, 2, 3, 4, 5, or 6; w is 1; p is 3; and q is 0, 1, 2, or 3. In some embodiments, u is 0 or 1; v is 0; t is 1 or 2; w is 1; p is 1 or 2; and q is 2 or 3.

In certain embodiments of Formula I, L has the structure:

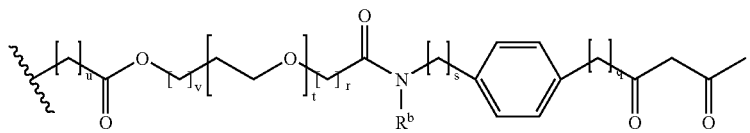

In certain of these embodiments, u is 0, 1, 2, 3, 5, or 5; v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, 3, 4, or 5; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, u is 0; v is 0; t is 1, 2, 3, 4, 5, or 6; r is 1 or 2; s is 3; and q is 0, 1, 2, or 3. In some embodiments, u is 0 or 1; v is 0; t is 1, 2, or 3, r is 1; s is 1 or 2; and q is 1 or 2.

In certain embodiments of Formula I, L has the structure:

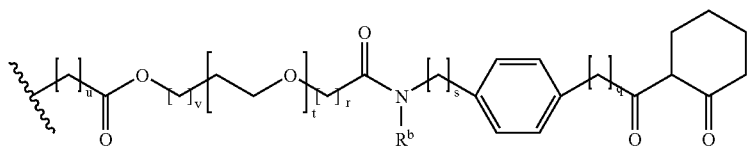

In certain of these embodiments, u is 0, 1, 2, 3, 5, or 5; v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, 3, 4, or 5; and $R^b$ is hydrogen, substituted or unsubstituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, u is 0; v is 0; t is 1, 2, 3, 4, 5, or 6; r is 1 or 2; s is 3; and q is 0, 1, 2, or 3. In some embodiments, u is 0 or 1; v is 0; t is 1, 2, or 3, r is 1; s is 1 or 2; and q is 1 or 2.

In certain embodiments of Formula I, L has the structure:

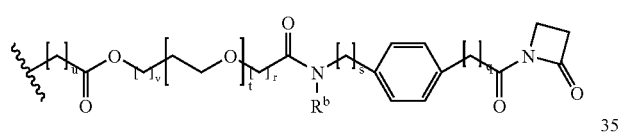

In certain of these embodiments, u is 0, 1, 2, 3, 5, or 5; v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, or 3; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, u is 0; v is 0; t is 1, 2, 3, 4, 5, or 6; r is 1 or 2; s is 3; and q is 0, 1, 2, or 3. In some embodiments, u is 0 or 1; v is 0; t is 1, 2, or 3, r is 1; s is 1 or 2; and q is 2 or 3.

In certain embodiments of Formula I, L has the structure:

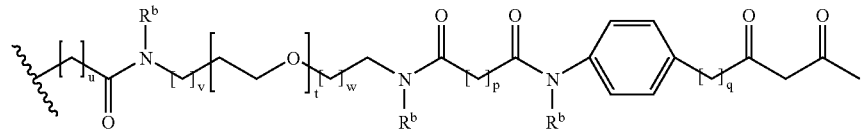

In certain of these embodiments, u is 0, 1, 2, 3, 4, or 5; v is 0, 1, 2, 3, 4, or 5; t is 1, 2, 3, 4, 5, or 6; w is 1, 2, 3, 4, or 5; p is 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, u is 0; v is 0; t is 1, 2, 3, 4, 5, or 6; w is 1; p is 3; and q is 0, 1, 2, or 3. In some embodiments, u is 0 or 1; v is 0; t is 1 or 2; w is 1; p is 1 or 2; and q is 1 or 2.

In certain embodiments of Formula I, L has the structure:

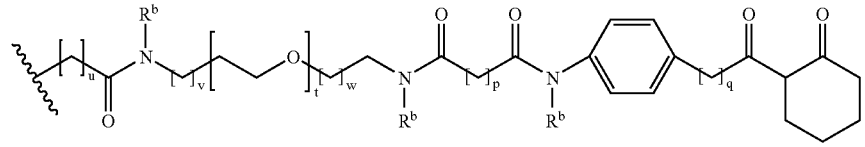

In certain of these embodiments, u is 0, 1, 2, 3, 4, or 5; v is 0, 1, 2, 3, 4, or 5; t is 1, 2, 3, 4, 5, or 6; w is 1, 2, 3, 4, or 5; p is 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, u is 0; v is 0; t is 1, 2, 3, 4, 5, or 6; w is 1; p is 3; and q is 0, 1, 2, or 3. In some embodiments, u is 0 or 1; v is 0; t is 1 or 2; w is 1; p is 1 or 2; and q is 1 or 2.

In certain embodiments of Formula I, L has the structure:

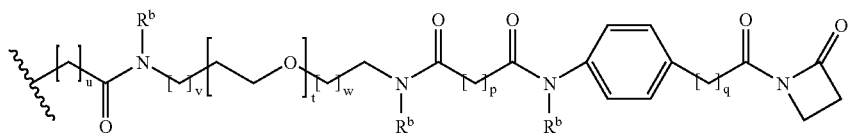

In certain of these embodiments, u is 0, 1, 2, 3, 4, or 5; v is 0, 1, 2, 3, 4, or 5; t is 1, 2, 3, 4, 5, or 6; w is 1, 2, 3, 4, or 5; p is 1, 2, 3, 4, or 5; q is 0, 1, 2, or 3; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, u is 0; v is 0; t is 1, 2, 3, 4, 5, or 6; w is 1; p is 3; and q is 0, 1, 2, or 3. In some embodiments, u is 0 or 1; v is 0; t is 1 or 2; w is 1; p is 1 or 2; and q is 2 or 3.

In certain embodiments of Formula I, L has the structure:

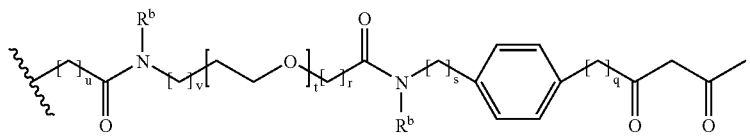

In certain of these embodiments, u is 0, 1, 2, 3, 5, or 5; v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, u is 0; v is 0; t is 1, 2, 3, 4, 5, or 6; r is 1 or 2; s is 3; and q is 0, 1, 2, or 3. In some embodiments, u is 0 or 1; v is 0; t is 1, 2, or 3, r is 1; s is 1 or 2; and q is 1 or 2.

In certain embodiments of Formula I, L has the structure:

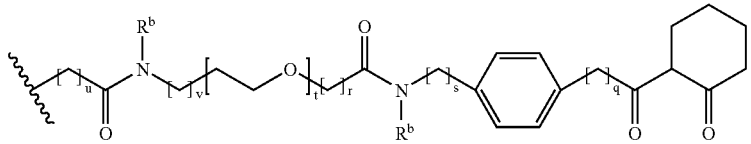

In certain of these embodiments, u is 0, 1, 2, 3, 5, or 5; v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, u is 0; v is 0; t is 1, 2, 3, 4, 5, or 6; r is 1 or 2; s is 3; and q is 0, 1, 2, or 3. In some embodiments, u is 0 or 1; v is 0; t is 1, 2, or 3, r is 1; s is 1 or 2; and q is 1 or 2.

In certain embodiments of Formula I, L has the structure:

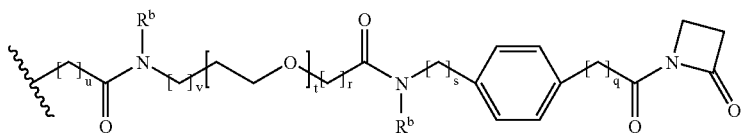

In certain of these embodiments, u is 0, 1, 2, 3, 5, or 5; v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, or 3; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, u is 0; v is 0; t is 1, 2, 3, 4, 5, or 6; r is 1 or 2; s is 3; and q is 0, 1, 2, or 3. In some embodiments, u is 0 or 1; v is 0; t is 1, 2, or 3, r is 1; s is 1 or 2; and q is 2 or 3.

In certain embodiments of Formula I, L has the structure:

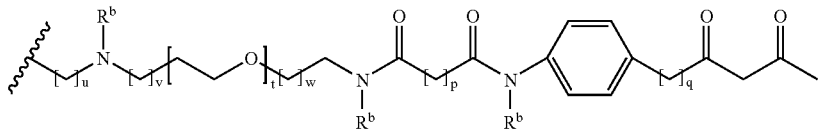

In certain of these embodiments, u is 0, 1, 2, 3, 4, or 5; v is 0, 1, 2, 3, 4, or 5; t is 1, 2, 3, 4, 5, or 6; w is 1, 2, 3, 4, or 5; p is 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, u is 0; v is 0; t is 1, 2, 3, 4, 5, or 6; w is 1; p is 3; and q is 0, 1, 2, or 3. In still some embodiments, u is 0 or 1; v is 0; t is 1 or 2; w is 1; p is 1 or 2; and q is 1 or 2.

In certain embodiments of Formula I, L has the structure:

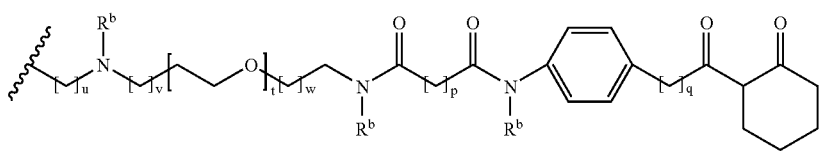

In certain of these embodiments, u is 0, 1, 2, 3, 4, or 5; v is 0, 1, 2, 3, 4, or 5; t is 1, 2, 3, 4, 5, or 6; w is 1, 2, 3, 4, or 5; p is 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, u is 0; v is 0; t is 1, 2, 3, 4, 5, or 6; w is 1; p is 3; and q is 0, 1, 2, or 3. In some embodiments, u is 0 or 1; v is 0; t is 1 or 2; w is 1; p is 1 or 2; and q is 1 or 2.

In certain embodiments of Formula I, L has the structure:

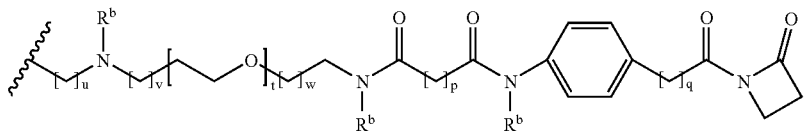

In certain of these embodiments, u is 0, 1, 2, 3, 4, or 5; v is 0, 1, 2, 3, 4, or 5; t is 1, 2, 3, 4, 5,or 6; w is 1, 2, 3, 4,or 5; p is 1, 2, 3, 4,or 5; q is 0, 1, 2,or 3; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, u is 0; v is 0; t is 1, 2, 3, 4, 5, or 6; w is 1; p is 3; and q is 0, 1, 2, or 3. In some embodiments, u is 0 or 1; v is 0; t is 1 or 2; w is 1; p is 1 or 2; and q is 2 or 3.

In certain embodiments of Formula I, L has the structure:

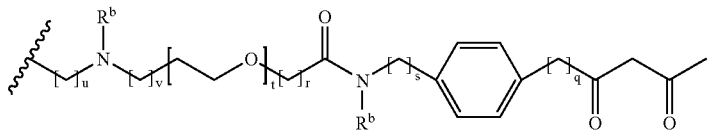

In certain of these embodiments, u is 0, 1, 2, 3, 5, or 5; v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, u is 0; v is 0; t is 1, 2, 3, 4, 5, or 6; r is 1 or 2; s is 3; and q is 0, 1, 2, or 3. In some embodiments, u is 0 or 1; v is 0; t is 1, 2, or 3, r is 1; s is 1 or 2; and q is 1 or 2.

In certain embodiments of Formula I, L has the structure:

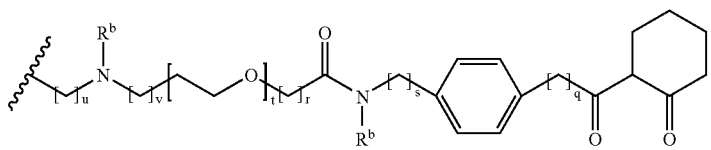

In certain of these embodiments, u is 0, 1, 2, 3, 5, or 5; v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, u is 0; v is 0; t is 1, 2, 3, 4, 5, or 6; r is 1 or 2; s is 3; and q is 0, 1, 2, or 3. In some embodiments, u is 0 or 1; v is 0; t is 1, 2, or 3, r is 1; s is 1 or 2; and q is 1 or 2.

In certain embodiments of Formula I, L has the structure:

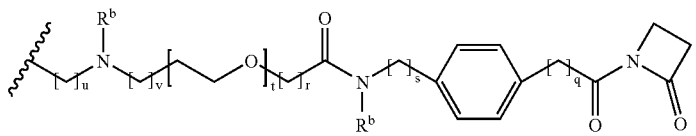

In certain of these embodiments, u is 0, 1, 2, 3, 5, or 5; v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, or 3; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, u is 0; v is 0; t is 1, 2, 3, 4, 5, or 6; r is 1 or 2; s is 3; and q is 0, 1, 2, or 3. In some embodiments, u is 0 or 1; v is 0; t is 1, 2, or 3, r is 1; s is 1 or 2; and q is 2 or 3.

In certain embodiments of Formula I, L has the structure:

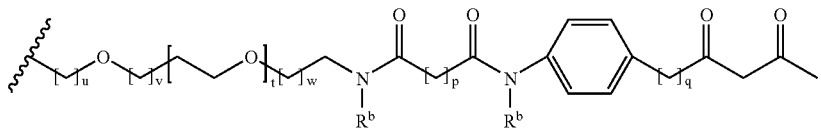

In certain of these embodiments, u is 0, 1, 2, 3, 4, or 5; v is 0, 1, 2, 3, 4, or 5; t is 1, 2, 3, 4, 5, or 6; w is 1, 2, 3, 4, or 5; p is 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, u is 0; v is 0; t is 1, 2, 3, 4, 5, or 6; w is 1; p is 3; and q is 0, 1, 2, or 3. In still other embodiments, u is 0 or 1; v is 0; t is 1 or 2; w is 1; p is 1 or 2; and q is 1 or 2.

In certain embodiments of Formula I, L has the structure:

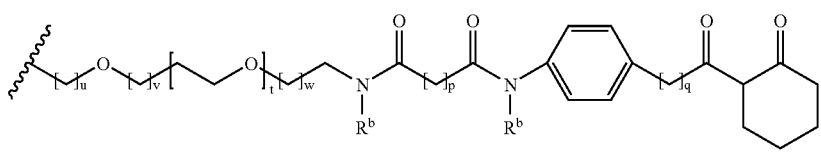

In certain of these embodiments, u is 0, 1, 2, 3, 4, or 5; v is 0, 1, 2, 3, 4, or 5; t is 1, 2, 3, 4, 5, or 6; w is 1, 2, 3, 4, or 5; p is 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, u is 0; v is 0; t is 1, 2, 3, 4, 5, or 6; w is 1; p is 3; and q is 0, 1, 2, or 3. In some embodiments, u is 0 or 1; v is 0; t is 1 or 2; w is 1; p is 1 or 2; and q is 1 or 2.

In certain embodiments of Formula I, L has the structure:

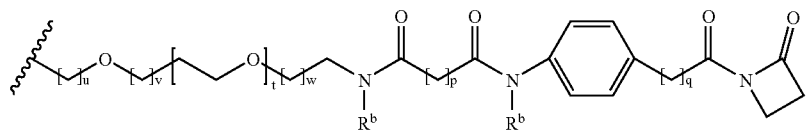

In certain of these embodiments, u is 0, 1, 2, 3, 4, or 5; v is 0, 1, 2, 3, 4, or 5; t is 1, 2, 3, 4, 5, or 6; w is 1, 2, 3, 4, or 5; p is 1, 2, 3, 4, or 5; q is 0, 1, 2, or 3; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, u is 0; v is 0; t is 1, 2, 3, 4, 5, or 6; w is 1; p is 3; and q is 0, 1, 2, or 3. In some embodiments, u is 0 or 1; v is 0; t is 1 or 2; w is 1; p is 1 or 2; and q is 2 or 3.

In certain embodiments of Formula I, L has the structure:

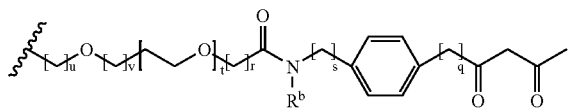

In certain of these embodiments, u is 0, 1, 2, 3, 5, or 5; v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, 3, 4, or 5; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, u is 0; v is 0; t is 1, 2, 3, 4, 5, or 6; r is 1 or 2; s is 3; and q is 0, 1, 2, or 3. In some embodiments, u is 0 or 1; v is 0; t is 1, 2, or 3, r is 1; s is 1 or 2; and q is 1 or 2.

In certain embodiments of Formula I, L has the structure:

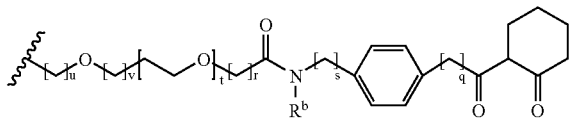

In certain of these embodiments, u is 0, 1, 2, 3, 5, or 5; v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, 3, 4, or 5; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, u is 0; v is 0; t is 1, 2, 3, 4, 5, or 6; r is 1 or 2; s is 3; and q is 0, 1, 2, or 3. In some embodiments, u is 0 or 1; v is 0; t is 1, 2, or 3, r is 1; s is 1 or 2; and q is 1 or 2.

In certain embodiments of Formula I, L has the structure:

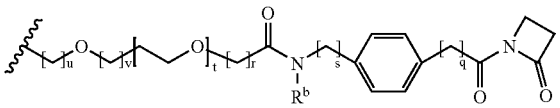

In certain of these embodiments, u is 0, 1, 2, 3, 5, or 5; v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, or 3; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, u is 0; v is 0; t is 1, 2, 3, 4, 5, or 6; r is 1 or 2; s is 3; and q is 0, 1, 2, or 3. In some embodiments, u is 0 or 1; v is 0; t is 1, 2, or 3, r is 1; s is 1 or 2; and q is 2 or 3.

As used herein, "$AA_1$-$AA_2$-$AA_n$" refers to an AA targeting agent wherein "$AA_1$" is the first amino acid in the AA targeting agent sequence, as measured from the N-terminus, "$AA_2$" is the second amino acid in the AA targeting agent sequence, as measured from the N-terminus, and "$AA_n$" is the $n^{th}$ amino acid in the AA targeting agent sequence, as measured from the N-terminus.

Certain embodiments in accordance with Formula I have the structure:

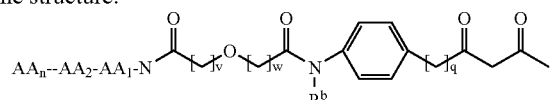

In certain of these embodiments, v is 1, 2, 3, 4, or 5; w is 1, 2, 3, 4, or 5; q is 0, 1, 2, 3, 4, or 5; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 1, 2, or 3; w is 1, 2, or 3; and q is 0, 1, 2, or 3. In some embodiments, v is 1 or 2; w is 1 or 2; and q is 1 or 2.

Certain embodiments in accordance with Formula I have the structure:

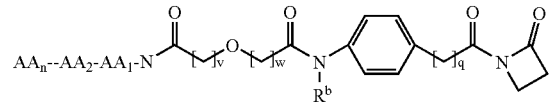

In certain of these embodiments, v is 1, 2, 3, 4, or 5; w is 1, 2, 3, 4, or 5; q is 0, 1, 2, or 3; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 1, 2, or 3; w is 1, 2, or 3; and q is 0, 1, 2, 3. In some embodiments, v is 1 or 2; w is 1 or 2; and q is 2 or 3.

Certain embodiments in accordance with Formula I have the structure:

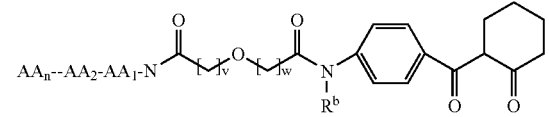

In certain of these embodiments, v is 1, 2, 3, 4, or 5; w is 1, 2, 3, 4, or 5; q is 0, 1, 2, 3, 4, or 5; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl In certain embodiments, v is 1, 2, or 3; w is 1, 2, or 3; and q is 0, 1, 2, 3. In some embodiments, v is 1 or 2; w is 1 or 2; and q is 2 or 3.

Certain embodiments in accordance with Formula I have the structure:

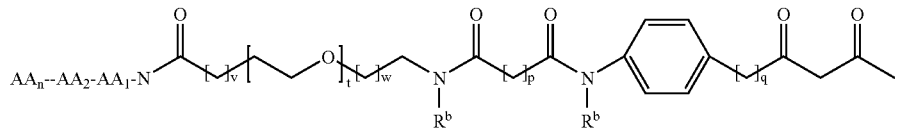

In certain of these embodiments, v is 0, 1, 2, 3, 4, or 5; t is 1, 2, 3, 4, 5, or 6; w is 1, 2, 3, 4, or 5; p is 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; p is 3; and q is 0, 1, 2, or 3. In some embodiments, v is 0; t is 1 or 2; w is 1; p is 1 or 2; and q is 1 or 2.

Certain embodiments in accordance with Formula I have the structure:

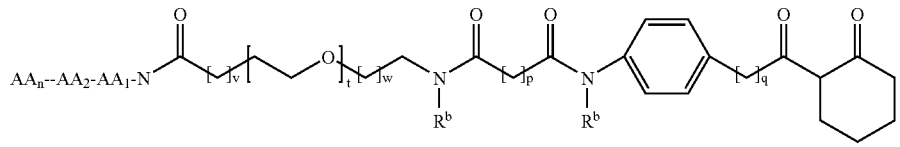

In certain of these embodiments, v is 0, 1, 2, 3, 4, or 5; t is 1, 2, 3, 4, 5, or 6; w is 1, 2, 3, 4, or 5; p is 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; p is 3; and q is 0, 1, 2, or 3. In some embodiments, v is 0; t is 1 or 2; w is 1; p is 1 or 2; and q is 1 or 2.

Certain embodiments in accordance with Formula I have the structure:

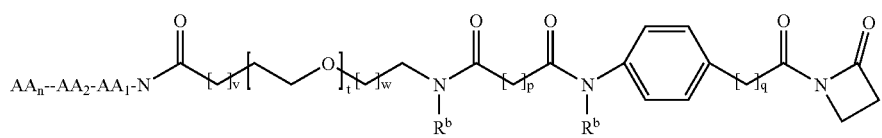

In certain of these embodiments, v is 0, 1, 2, 3, 4, or 5; t is 1, 2, 3, 4, 5, or 6; w is 1, 2, 3, 4, or 5; p is 1, 2, 3, 4, or 5; q is 0, 1, 2, or 3; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0, 1, 2, 3, 4, or 5; t is 1, 2, 3, 4, 5, or 6; w is 1, 2, 3, 4, or 5; p is 1, 2, 3, 4, or 5; and q is 0, 1, 2, or 3. In certain embodiments, v is 0; t is 1, 2, 3, 4, 5, or 6; w is 1; and p is 3, and in some embodiments, v is 0; t is 1 or 2; w is 1; p is 1 or 2; and q is 2 or 3.

Certain embodiments in accordance with Formula I have the structure:

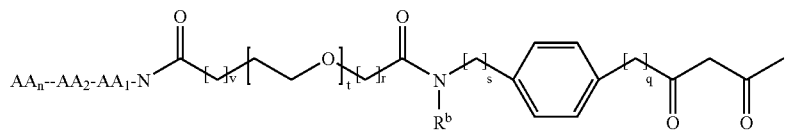

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, 3, 4, or 5; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; s is 3; and q is 0, 1, 2, or 3. In some embodiments, v is 0; t is 1, 2, or 3, r is 1; s is 1 or 2; and q is 1 or 2.

Certain embodiments in accordance with Formula I have the structure:

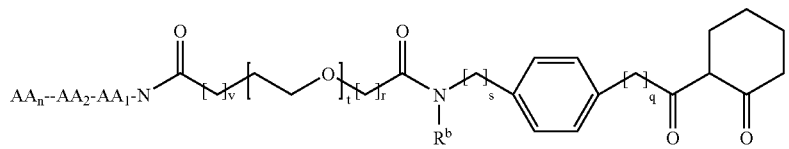

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, 3, 4, or 5; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; s is 3; and q is 0, 1, 2, or 3. In some embodiments, v is 0; t is 1, 2 or 3, r is 1; s is 1 or 2; and q is 1 or 2.

Certain embodiments in accordance with Formula I have the structrue:

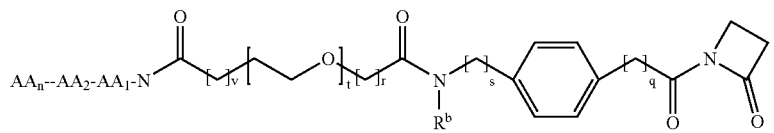

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, or 3; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; s is 3; and q is 0, 1, 2, or 3. In some embodiments, v is 0; t is 1, 2, or 3, r is 1; s is 1 or 2; and q is 2 or 3.

Certain embodiments in accordance with Formula I have the structure:

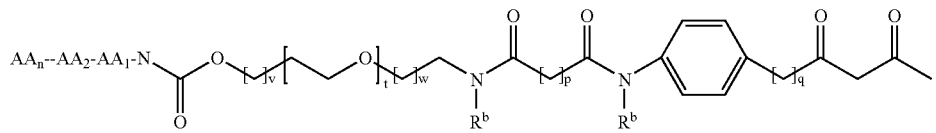

In certain of these embodiments, v is 0, 1, 2, 3, 4, or 5; t is 1, 2, 3, 4, 5, or 6; w is 1, 2, 3, 4, or 5; p is 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; p is 3; and q is 0, 1, 2, or 3. In some embodiments, v is 0; t is 1 or 2; w is 1; p is 1 or 2; and q is 1 or 2.

Certain embodiments in accordance with Formula I have the structure:

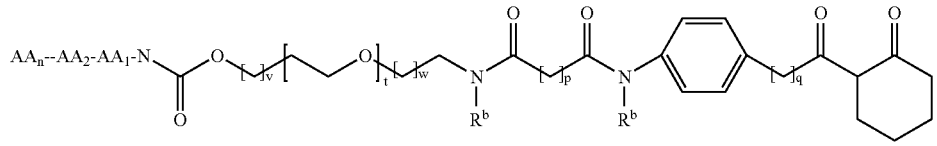

In certain of these embodiments, v is 0, 1, 2, 3, 4, or 5; t is 1, 2, 3, 4, 5, or 6; w is 1, 2, 3, 4, or 5; p is 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; p is 3; and q is 0, 1, 2, or 3. In some embodiments, v is 0; t is 1 or 2; w is 1; p is 1 or 2; and q is 1 or 2.

Certain embodiments in accordance with Formula I have the structure:

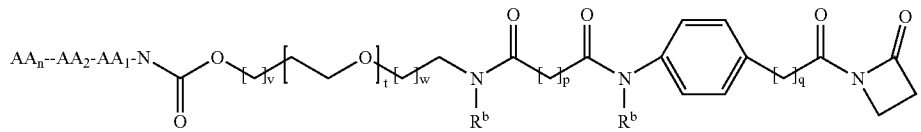

In certain of these embodiments, v is 0, 1, 2, 3, 4, or 5; t is 1, 2, 3, 4, 5, or 6; w is 1, 2, 3, 4, or 5; p is 1, 2, 3, 4, or 5; q is 0, 1, 2, or 3; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; p is 3; and q is 0, 1, 2, or 3. In some embodiments, v is 0; t is 1 or 2; w is 1; p is 1 or 2; and q is 2 or 3.

Certain embodiments in accordance with Formula I have the structure:

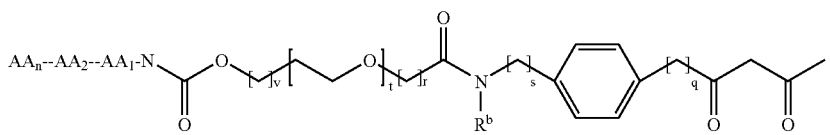

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, 3, 4, or 5; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; s is 3; and q is 0, 1, 2, or 3. In some embodiments, v is 0; t is 1, 2, or 3, r is 1; s is 1 or 2; and q is 1 or 2.

Certain embodiments in accordance with Formula I have the structure:

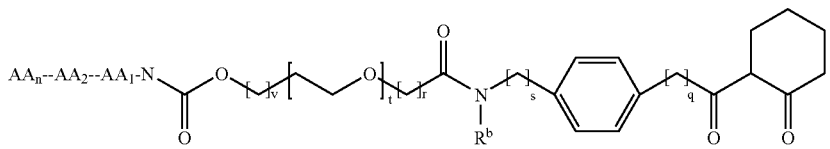

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, 3, 4, or 5; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; s is 3; and q is 0, 1, 2, or 3. In some embodiments, v is 0; t is 1, 2, or 3, r is 1; s is 1 or 2; and q is 1 or 2.

Certain embodiments in accordance with Formula I have the structure:

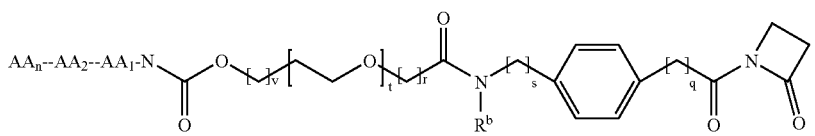

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, or 3; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; s is 3; and q is 0, 1, 2, or 3. In some embodiments, v is 0; t is 1, 2, or 3, r is 1; s is 1 or 2; and q is 2 or 3.

Certain embodiments in accordance with Formula I have the structure:

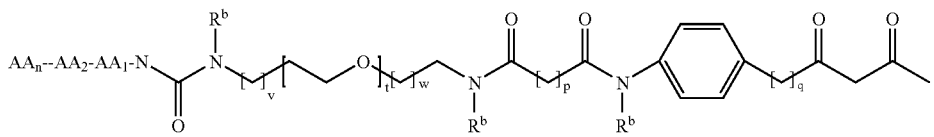

In certain of these embodiments, v is 0, 1, 2, 3, 4, or 5; t is 1, 2, 3, 4, 5, or 6; w is 1, 2, 3, 4, or 5; p is 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; p is 3; and q is 0, 1, 2, or 3. In some embodiments, v is 0; t is 1 or 2; w is 1; p is 1 or 2; and q is 1 or 2.

Certain embodiments in accordance with Formula I have the structure:

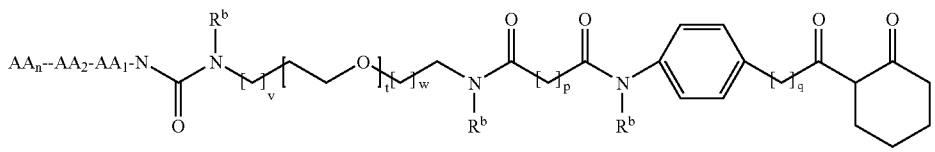

In certain of these embodiments, v is 0, 1, 2, 3, 4, or 5; t is 1, 2, 3, 4, 5, or 6; w is 1, 2, 3, 4, or 5; p is 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; p is 3; and q is 0, 1, 2, or 3. In some embodiments, v is 0; t is 1 or 2; w is 1; p is 1 or 2; and q is 1 or 2.

Certain embodiments in accordance with Formula I have the structure:

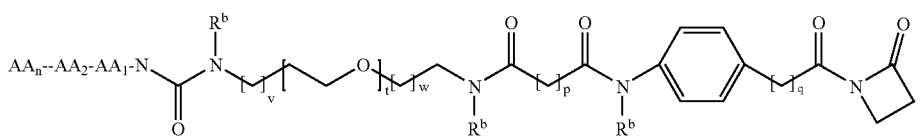

In certain of these embodiments, v is 0, 1, 2, 3, 4, or 5; t is 1, 2, 3, 4, 5, or 6; w is 1, 2, 3, 4, or 5; p is 1, 2, 3, 4, or 5; q is 0, 1, 2, or 3; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; p is 3; and q is 0, 1, 2, or 3. In some embodiments, v is 0; t is 1 or 2; w is 1; p is 1 or 2; and q is 2 or 3.

Certain embodiments in accordance with Formula I have the structure:

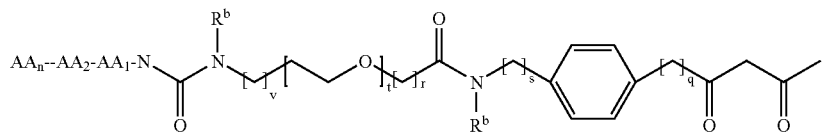

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; s is 3; and q is 0, 1, 2, or 3. In some embodiments, v is 0; t is 1, 2, or 3, r is 1; s is 1 or 2; and q is 1 or 2.

Certain embodiments in accordance with Formula I have the structure:

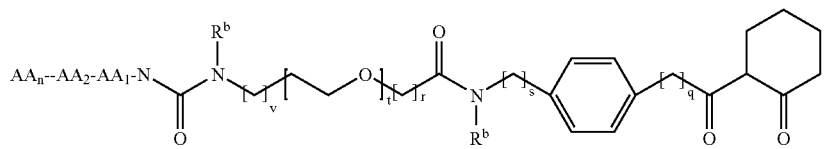

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; s is 3; and q is 0, 1, 2, or 3. In some embodiments, v is 0; t is 1, 2, or 3, r is 1; s is 1 or 2; and q is 1 or 2.

Certain embodiments in accordance with Formula I have the structure:

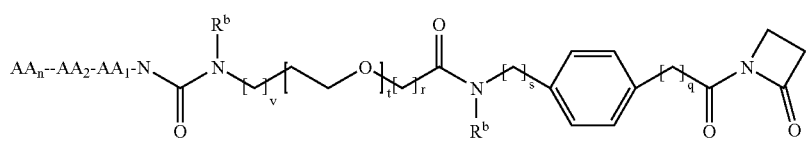

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, or 3; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; s is 3; and q is 0, 1, 2, or 3. In some embodiments, v is 0; t is 1, 2, or 3, r is 1; s is 1 or 2; and q is 2 or 3.

Certain embodiments in accordance with Formula I have the structure:

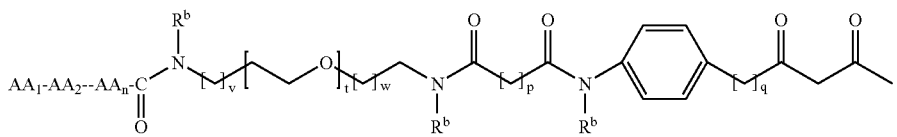

In certain of these embodiments, v is 0, 1, 2, 3, 4, or 5; t is 1, 2, 3, 4, 5, or 6; w is 1, 2, 3, 4, or 5; p is 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; p is 3; and q is 0, 1, 2, or 3. In some embodiments, v is 0; t is 1 or 2; w is 1; p is 1 or 2; and q is 1 or 2.

Certain embodiments in accordance with Formula I have the structure:

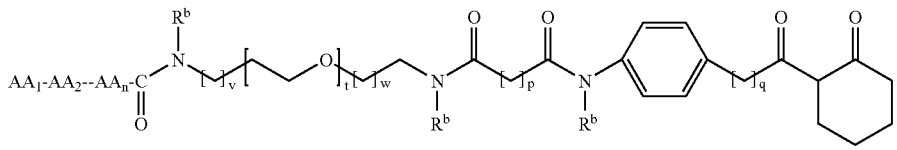

In certain of these embodiments, v is 0, 1, 2, 3, 4, or 5; t is 1, 2, 3, 4, 5, or 6; w is 1, 2, 3, 4, or 5; p is 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; p is 3; and q is 0, 1, 2, or 3. In some embodiments, v is 0; t is 1 or 2; w is 1; p is 1 or 2; and q is 1 or 2.

Certain embodiments in accordance with Formula I have the structure:

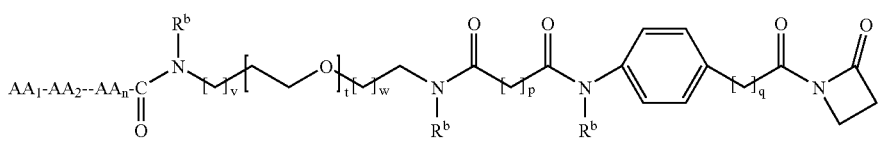

In certain of these embodiments, v is 0, 1, 2, 3, 4, or 5; t is 1, 2, 3, 4, 5, or 6; w is 1, 2, 3, 4, or 5; p is 1, 2, 3, 4, or 5; q is 0, 1, 2, or 3; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; p is 3; and q is 0, 1, 2, or 3. In some embodiments, v is 0; t is 1 or 2; w is 1; p is 1 or 2; and q is 2 or 3.

Certain embodiments in accordance with Formula I have the structure:

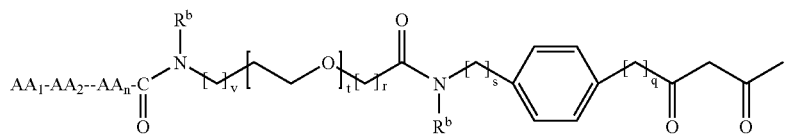

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; s is 3; and q is 0, 1, 2, or 3. In some embodiments, v is 0; t is 1, 2, or 3, r is 1; s is 1 or 2; and q is 1 or 2.

Certain embodiments in accordance with Formula I have the structure:

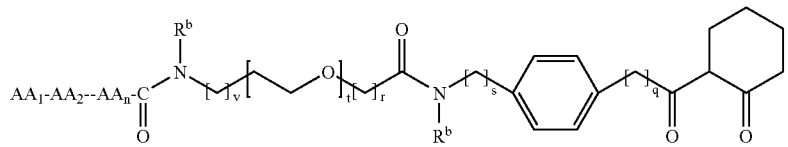

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; s is 3; and q is 0, 1, 2, or 3. In some embodiments, v is 0; t is 1, 2, or 3, r is 1; s is 1 or 2; and q is 1 or 2.

Certain embodiments in accordance with Formula I have the structure:

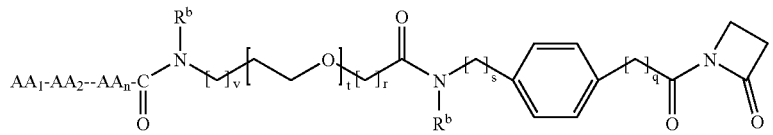

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, or 3; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl In certain embodiments, v is 0; t is 1, 2, 3, 4, 5, or 6; r is 1 or 2; s is 3; and q is 0, 1, 2, or 3. In some embodiments, v is 0; t is 1, 2, or 3, r is 1; s is 1 or 2; and q is 2 or 3.

Certain embodiments in accordance with Formula I have the structure:

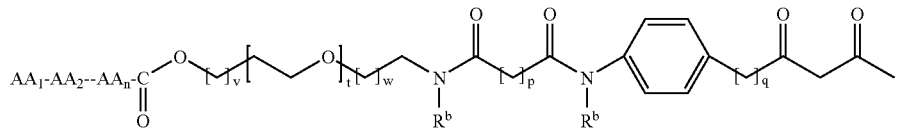

In certain of these embodiments, v is 0, 1, 2, 3, 4, or 5; t is 1, 2, 3, 4, 5, or 6; w is 1, 2, 3, 4, or 5; p is 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; p is 3; and q is 0, 1, 2, or 3. In some embodiments, v is 0; t is 1 or 2; w is 1; p is 1 or 2; and q is 1 or 2.

Certain embodiments in accordance with Formula I have the structure:

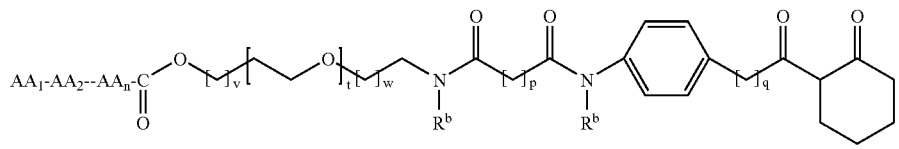

In certain of these embodiments, v is 0, 1, 2, 3, 4, or 5; t is 1, 2, 3, 4, 5, or 6; w is 1, 2, 3, 4, or 5; p is 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; p is 3; and q is 0, 1, 2, or 3. In some embodiments, v is 0; t is 1 or 2; w is 1; p is 1 or 2; and q is 1 or 2.

Certain embodiments in accordance with Formula I have the structure:

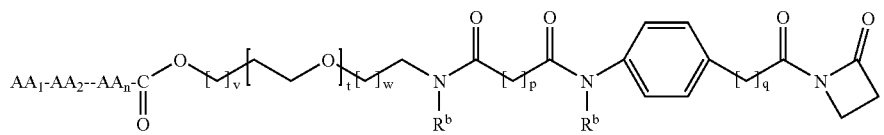

In certain of these embodiments, v is 0, 1, 2, 3, 4, or 5; t is 1, 2, 3, 4, 5, or 6; w is 1, 2, 3, 4, or 5; p is 1, 2, 3, 4, or 5; q is 0, 1, 2, or 3; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; p is 3; and q is 0, 1, 2, or 3. In some embodiments, v is 0; t is 1 or 2; w is 1; p is 1 or 2; and q is 2 or 3.

Certain embodiments in accordance with Formula I have the structure:

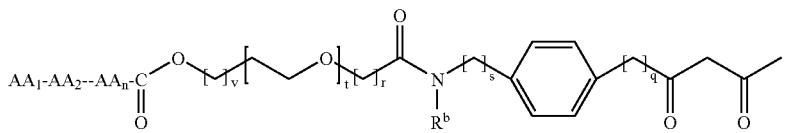

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, 3, 4, or 5; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; s is 3; and q is 0, 1, 2, or 3. In some embodiments, v is 0; t is 1, 2, or 3, r is 1; s is 1 or 2; and q is 1 or 2.

Certain embodiments in accordance with Formula I have the structure:

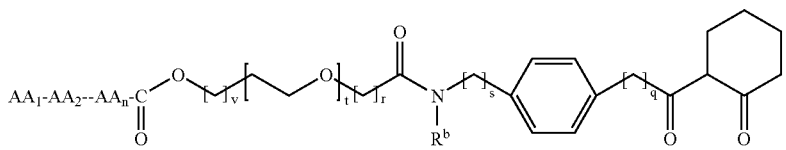

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, 3, 4, or 5; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; s is 3; and q is 0, 1, 2, or 3. In some embodiments, v is 0; t is 1, 2, or 3, r is 1; s is 1 or 2; and q is 1 or 2.

Certain embodiments in accordance with Formula I have the structure:

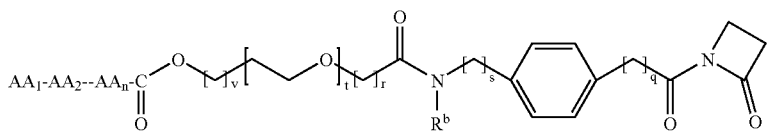

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, or 3; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; s is 3; and q is 0, 1, 2, or 3. In some embodiments, v is 0; t is 1, 2, or 3, r is 1; s is 1 or 2; and q is 2 or 3.

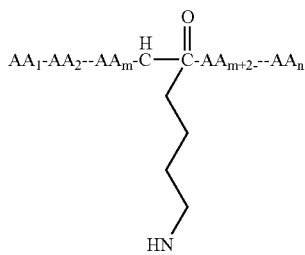

as used herein refers to an AA targeting agent wherein "$AA_1$" is the first amino acid in an AA targeting agent sequence as measured from the N-terminus, "$AA_2$" is the second amino acid in an AA targeting agent sequence as measured from the N-terminus, and "$AA_n$" is the $n^{th}$ amino acid in an AA targeting agent sequence as measured from the N-terminus. The targeting agent further comprises a Lys residue at arbitrary position m+1 as measured from the N-terminus. It will be appreciated that in addition to linking to a Lys side chain in the body of an AA targeting agent, it is also possible to link to a Lys side chain on the N-terminus or C-terminus of an AA targeting agent.

Certain embodiments in accordance with Formula I have the structure:

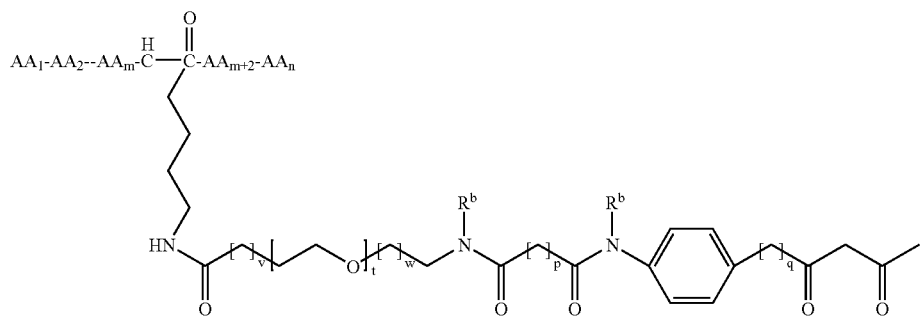

In certain of these embodiments, v is 0, 1, 2, 3, 4, or 5; t is 1, 2, 3, 4, 5, or 6; w is 1, 2, 3, 4, or 5; p is 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; p is 3; and q is 0, 1, 2, or 3. In some embodiments, v is 0; t is 1 or 2; w is 1; p is 1 or 2; and q is 1 or 2.

Certain embodiments in accordance with Formula I have the structure:

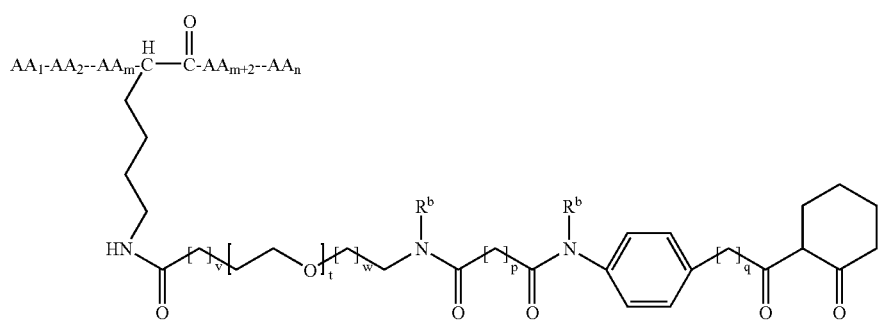

In certain of these embodiments, v is 0, 1, 2, 3, 4, or 5; t is 1, 2, 3, 4, 5, or 6; w is 1, 2, 3, 4, or 5; p is 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; p is 3; and q is 0, 1, 2, or 3. In some embodiments, v is 0; t is 1 or 2; w is 1; p is 1 or 2; and q is 1 or 2.

Certain embodiments in accordance with Formula I have the structure:

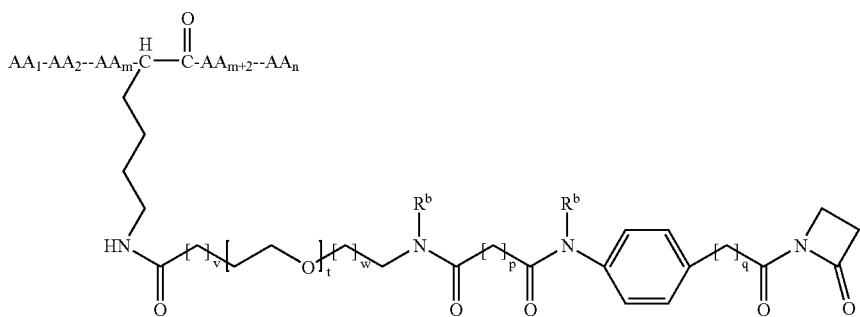

In certain of these embodiments, v is 0, 1, 2, 3, 4, or 5; t is 1, 2, 3, 4, 5, or 6; w is 1, 2, 3, 4, or 5; p is 1, 2, 3, 4, or 5; q is 0, 1, 2, or 3; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; p is 3; and q is 0, 1, 2, or 3. In some embodiments, v is 0; t is 1 or 2; w is 1; p is 1 or 2; and q is 2 or 3.

Certain embodiments in accordance with Formula I have the structure:

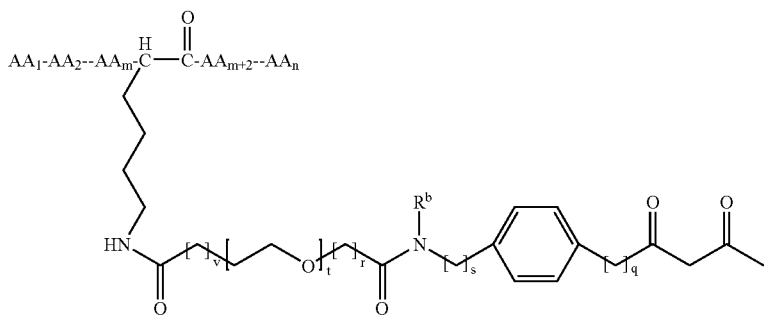

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, 3, 4, or 5; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; s is 3; and q is 0, 1, 2, or 3. In some embodiments, v is 0; t is 1, 2, or 3, r is 1; s is 1 or 2; and q is 1 or 2.

Certain embodiments in accordance with Formula I have the structure:

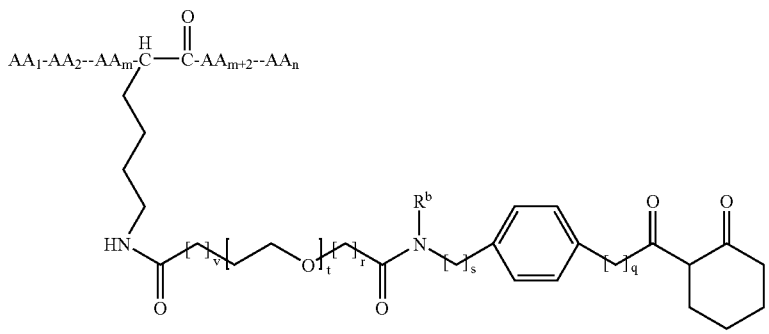

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, 3, 4, or 5; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; s is 3; and q is 0, 1, 2, or 3. In some embodiments, v is 0; t is 1, 2, or 3, r is 1; s is 1 or 2; and q is 1 or 2.

Certain embodiments in accordance with Formula I have the structure:

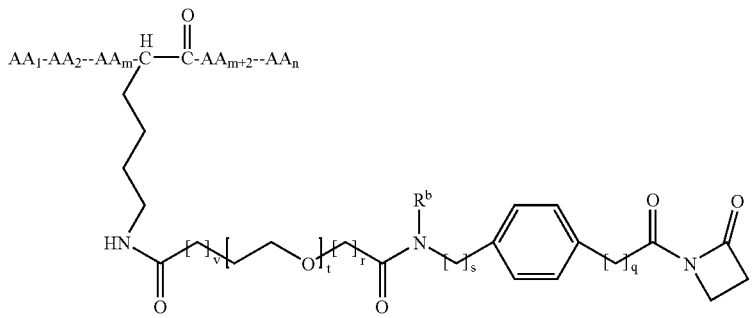

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, or 3; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; s is 3; and q is 0, 1, 2, or 3. In some embodiments, v is 0; t is 1, 2 or 3, r is 1; s is 1 or 2; and q is 2 or 3.

Certain embodiments in accordance with Formula I have the structure:

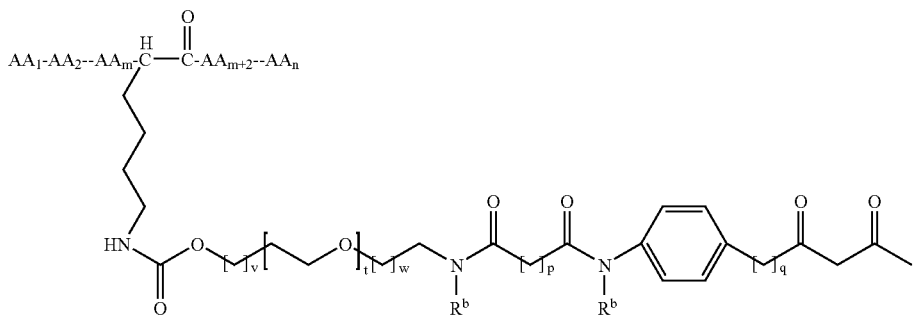

In certain of these embodiments, v is 0, 1, 2, 3, 4, or 5; t is 1, 2, 3, 4, 5, or 6; w is 1, 2, 3, 4, or 5; p is 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; p is 3; and q is 0, 1, 2, or 3. In some embodiments, v is 0; t is 1 or 2; w is 1; p is 1 or 2; and q is 1 or 2.

Certain embodiments in accordance with Formula I have the structure:

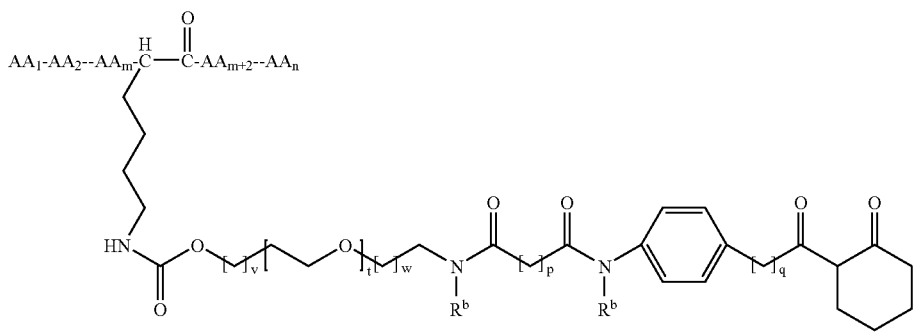

In certain of these embodiments, v is 0, 1, 2, 3, 4, or 5; t is 1, 2, 3, 4, 5, or 6; w is 1, 2, 3, 4, or 5; p is 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; p is 3; and q is 0, 1, 2, or 3. In some embodiments, v is 0; t is 1 or 2; w is 1; p is 1 or 2; and q is 1 or 2.

Certain embodiments in accordance with Formula I have the structure:

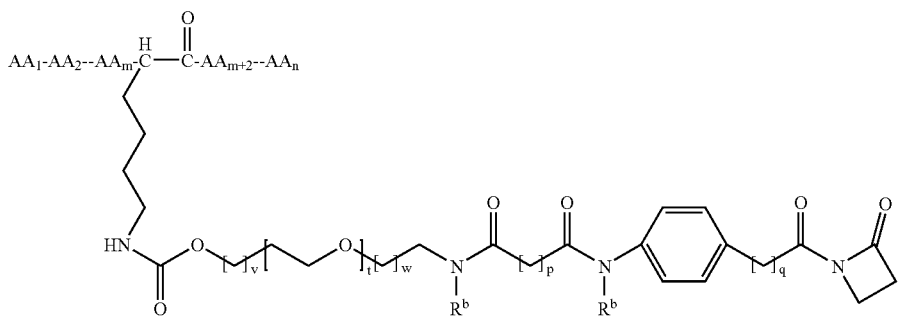

In certain of these embodiments, v is 0, 1, 2, 3, 4, or 5; t is 1, 2, 3, 4, 5, or 6; w is 1, 2, 3, 4, or 5; p is 1, 2, 3, 4, or 5; q is 0, 1, 2, or 3; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; p is 3; and q is 0, 1, 2, or 3. In some embodiments, v is 0; t is 1 or 2; w is 1; p is 1 or 2; and q is 2 or 3.

Certain embodiments in accordance with Formula I have the structure:

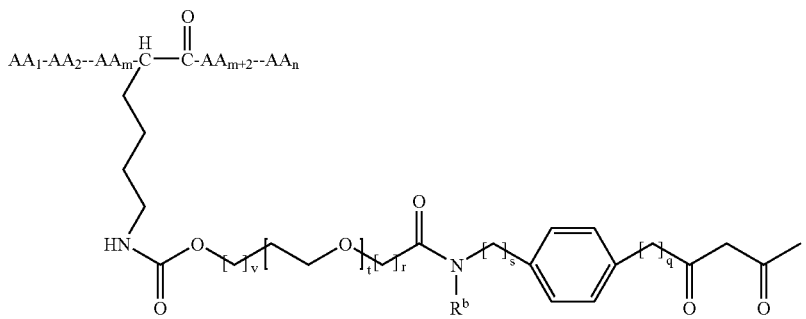

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, 3, 4, or 5; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; s is 3; and q is 0, 1, 2, or 3. In some embodiments, v is 0; t is 1, 2, or 3, r is 1; s is 1 or 2; and q is 1 or 2.

Certain embodiments in accordance with Formula I have the structure:

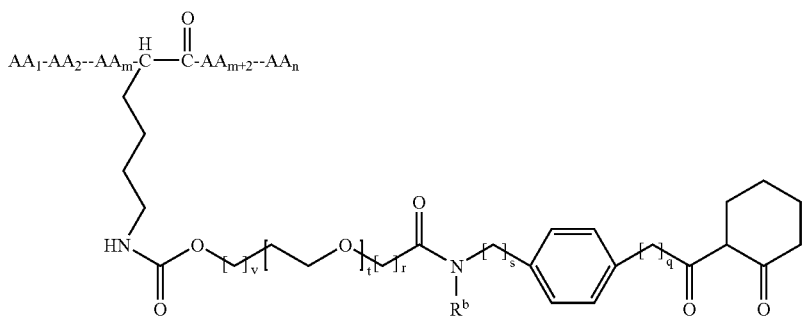

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, 3, 4, or 5; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; s is 3; and q is 0, 1, 2, or 3. In some embodiments, v is 0; t is 1, 2, or 3, r is 1; s is 1 or 2; and q is 1 or 2.

Certain embodiments in accordance with Formula I have the structure:

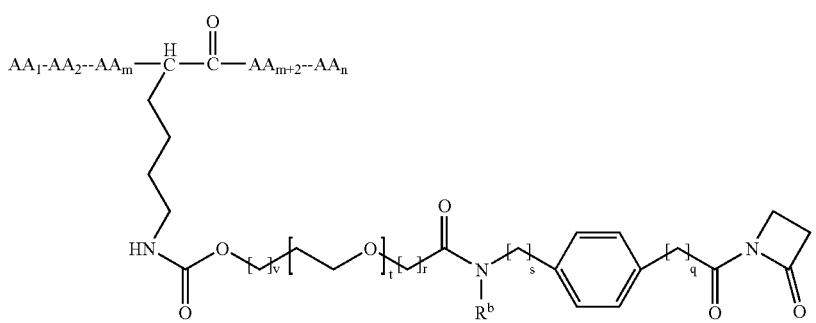

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, or 3; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; s is 3; and q is 0, 1, 2, or 3. In some embodiments, v is 0; t is 1, 2, or 3, r is 1; s is 1 or 2; and q is 2 or 3.

Certain embodiments in accordance with Formula I have the structure:

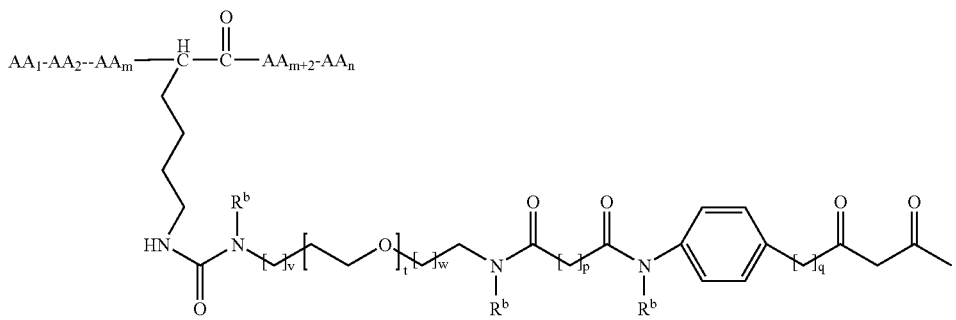

In certain of these embodiments, v is 0, 1, 2, 3, 4, or 5; t is 1, 2, 3, 4, 5, or 6; w is 1, 2, 3, 4, or 5; p is 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; p is 3; and q is 0, 1, 2, or 3. In some embodiments, v is 0; t is 1 or 2; w is 1; p is 1 or 2; and q is 1 or 2.

Certain embodiments in accordance with Formula I have the structure:

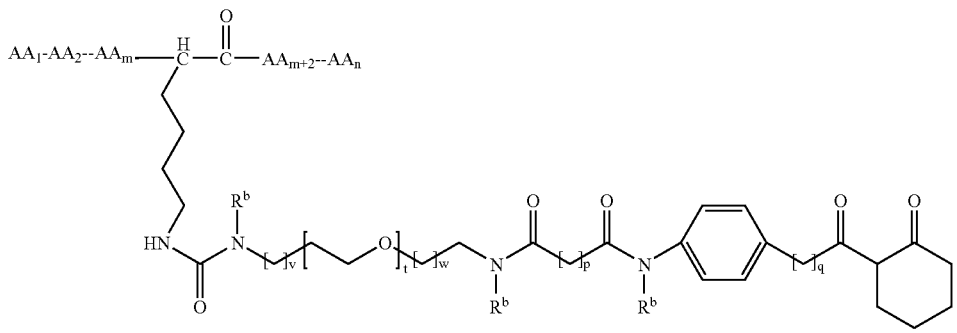

In certain of these embodiments, v is 0, 1, 2, 3, 4, or 5; t is 1, 2, 3, 4, 5, or 6; w is 1, 2, 3, 4, or 5; p is 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiment v is 0; t is 1, 2, 3, 4, 5, or 6; w is 1; p is 3; and q is 0, 1, 2, or 3. In some embodiments, v is 0; t is 1 or 2; w is 1; p is 1 or 2; and q is 1 or 2.

Certain embodiments in accordance with Formula I have the structure:

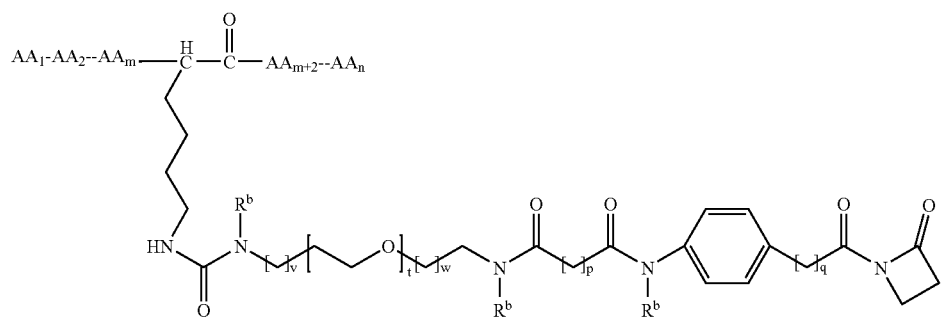

In certain of these embodiments, v is 0, 1, 2, 3, 4, or 5; t is 1, 2, 3, 4, 5, or 6; w is 1, 2, 3, 4, or 5; p is 1, 2, 3, 4, or 5; q is 0, 1, 2, or 3; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; p is 3; and q is 0, 1, 2, or 3. In some embodiments, v is 0; t is 1 or 2; w is 1; p is 1 or 2; and q is 2 or 3.

Certain embodiments in accordance with Formula I have the structure:

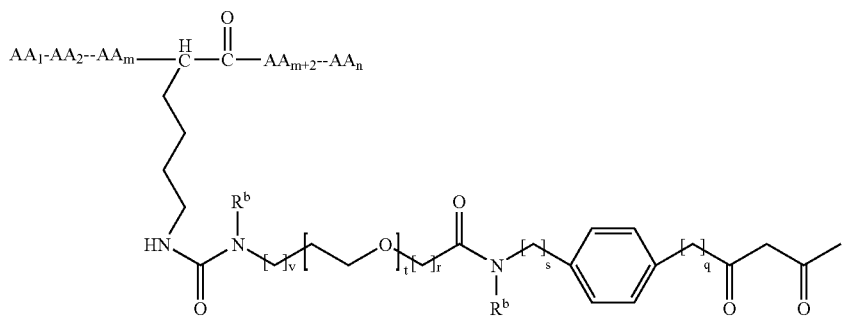

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; s is 3; and q is 0, 1, 2, or 3. In some embodiments, v is 0; t is 1, 2, or 3, r is 1; s is 1 or 2; and q is 1 or 2.

Certain embodiments in accordance with Formula I have the structure:

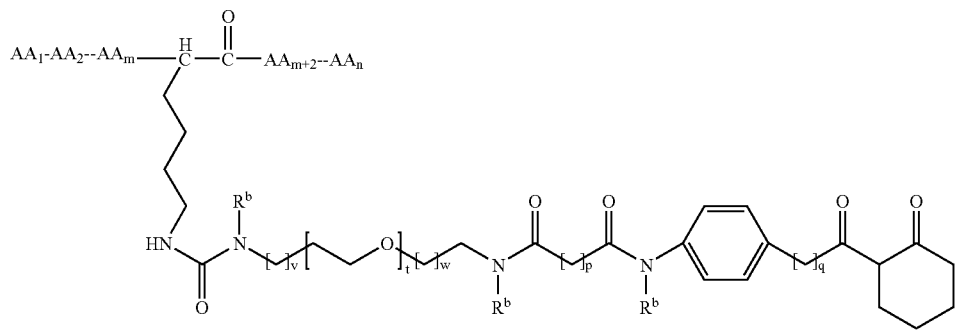

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; s is 3; and q is 0, 1, 2, or 3. In some embodiments, v is 0; t is 1, 2, or 3, r is 1; s is 1 or 2; and q is 1 or 2.

Certain embodiments in accordance with Formula I have the structure:

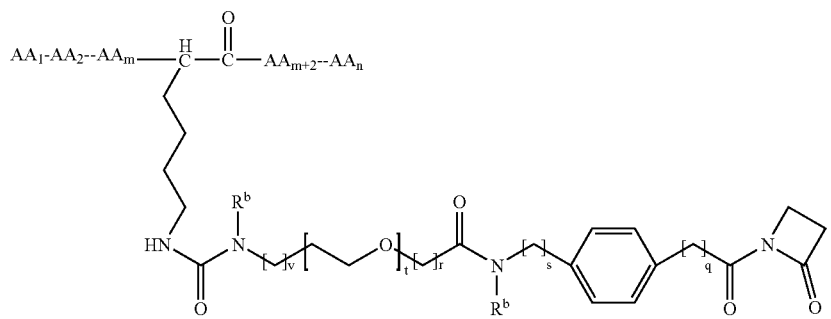

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, or 3; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; s is 3; and q is 0, 1, 2, or 3. In some embodiments, v is 0; t is 1, 2, or 3, r is 1; s is 1 or 2; and q is 2 or 3.

The administration of an AA targeting compound to an immunocompetent individual may result in the production of antibodies against the conjugate. Such antibodies may be directed to the variable region, including the antibody idiotype, as well as to the targeting agent or any linker used to conjugate the targeting agent to the antibody. Reducing the immunogenicity of an AA targeting compound can be accomplished by methods well known in the art, such as by attaching long chain polyethylene glycol (PEG)-based spacers and the like to the AA targeting compound. Long chain PEG and other polymers are known for their ability to mask foreign epitopes, resulting in the reduced immunogenicity of therapeutic proteins that display foreign epitopes (N. V. Katre, J.

Immunol. 144:209-213 (1990); G. E. Francis et al., Int. J. Hematol. 68:1-18 (1998). Alternatively, or in addition, the individual administered the antibody-AA targeting agent conjugate may be administered an immunosuppressant such as cyclosporin A, anti-CD3 antibody, and the like.

In one embodiment, an AA targeting compound is as shown by Formula II, and includes stereoisomers, tautomers, solvates, prodrugs, and pharmaceutically acceptable salts thereof.

Antibody-L'-[AA targeting agent]      (II)

Figure 10:
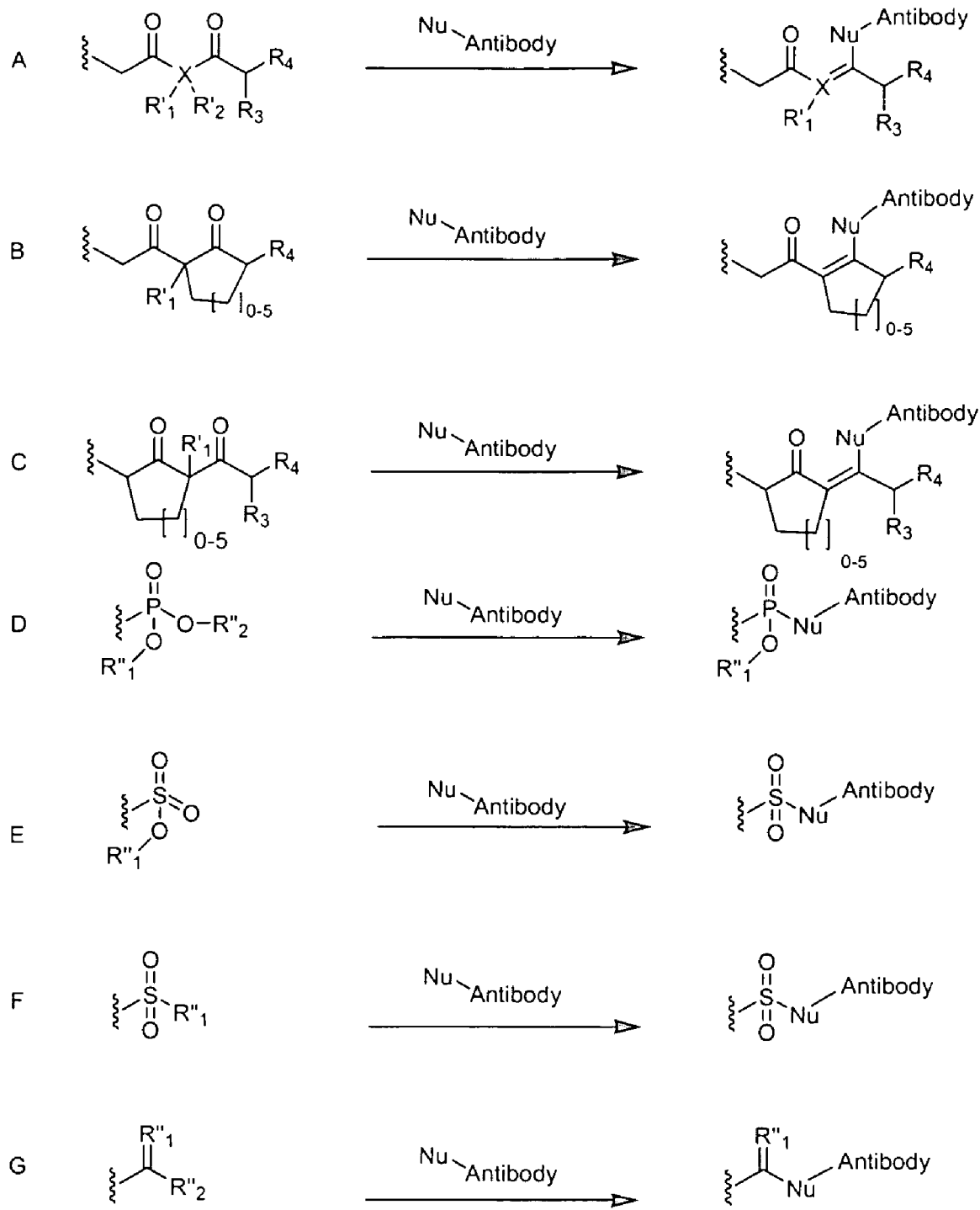
FIG. 10 shows the addition of a nucleophilic ("nu") side chain in an antibody combining site to compounds A-G in FIG. 8. Antibody-Nu-refers to a covalent bond to an amino acid side chain bearing a nucleophile in a combining site of an antibody.
Figure 11:
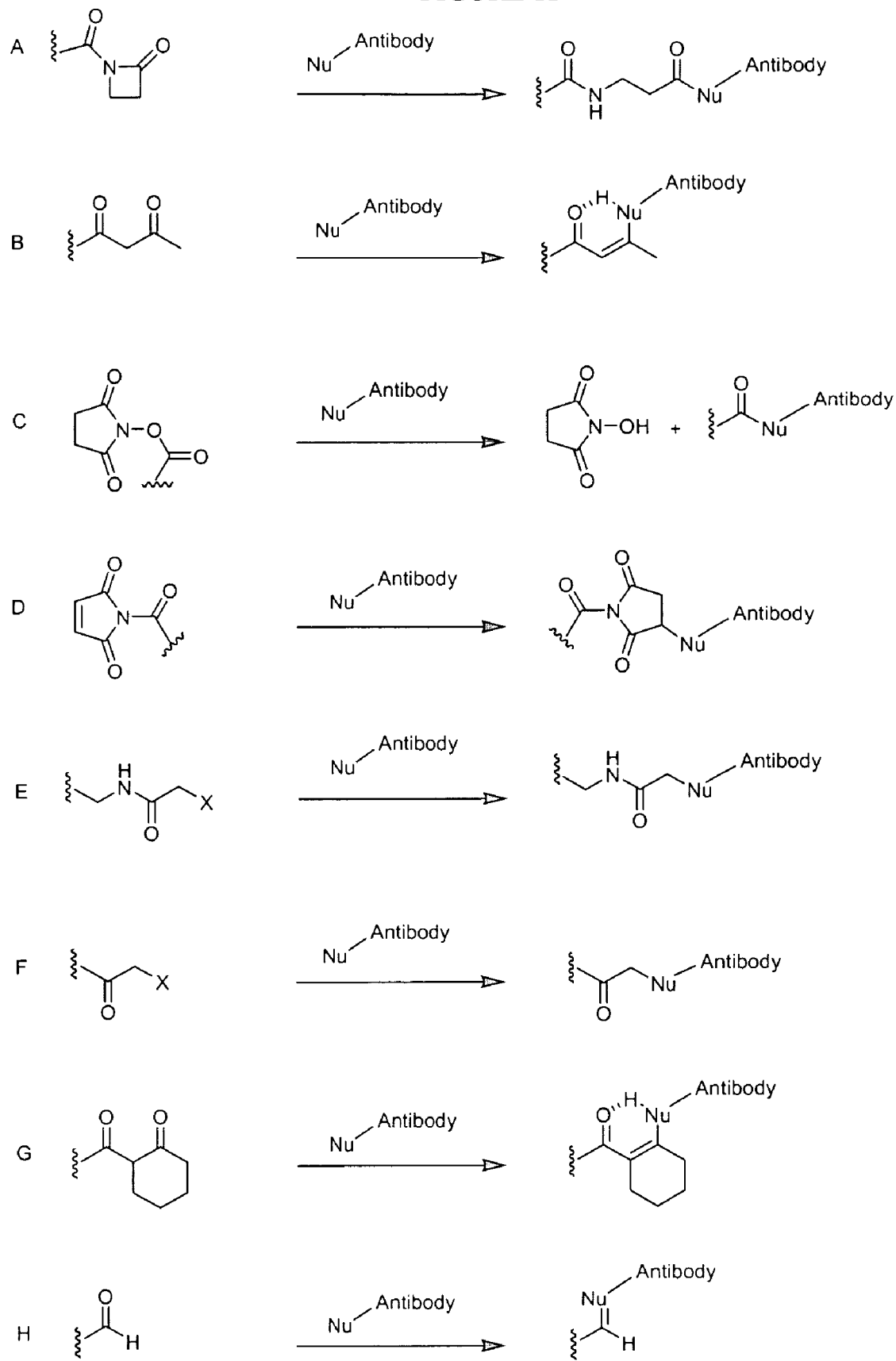
FIG. 11 shows the addition of a nucleophilic side chain in an antibody combining to compounds A-H in FIG. 9. Antibody-Nu-refers to a covalent bond to an amino acid side chain bearing a nucleophile in a combining site of an antibody.

In compounds of Formula II, [AA targeting agent] is defined as in Formula I. L' is a linker moiety linking an antibody to the targeting agent and having the formula —X—Y-Z'-. In compounds of Formula II, X and Y are defined as in Formula I, and Antibody is an antibody as defined herein. FIGS. 10 and 11, respectively, illustrate the addition mechanism of a reactive, nucleophilic side chain in a combining site of an antibody to the Z moieties illustrated in FIGS. 8 and 9.

In certain embodiments, wherein Antibody is an aldolase catalytic antibody, Z'- Antibody has the structure:

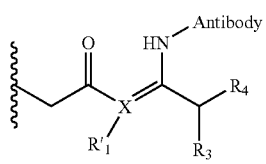

wherein HN-Antibody refers to an arbitrary side chain in the combining site of an antibody bearing an amino group.

In certain embodiments, wherein Antibody is an aldolase catalytic antibody, Z'- Antibody has the structure:

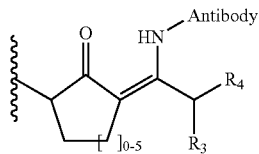

wherein HN-Antibody refers to an arbitrary side chain in the combining site of an antibody bearing an amino group.

In certain embodiments, wherein Antibody is an aldolase catalytic antibody, Z'- Antibody has the structure:

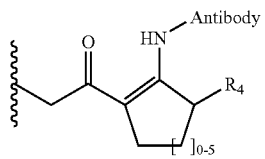

wherein HN-Antibody refers to an arbitrary side chain in the combining site of an antibody bearing an amino group.

In certain embodiments, wherein Antibody is an aldolase catalytic antibody, Z'- Antibody has the structure:

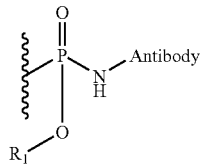

wherein HN-Antibody refers to an arbitrary side chain in the combining site of an antibody bearing an amino group.

In certain embodiments, wherein Antibody is an aldolase catalytic antibody, Z'- Antibody has the structure:

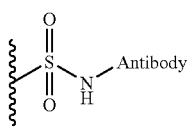

wherein HN-Antibody refers to an arbitrary side chain in the combining site of an antibody bearing an amino group.

In certain embodiments, wherein Antibody is an aldolase catalytic antibody, Z'- Antibody has the structure:

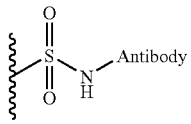

wherein HN-Antibody refers to an arbitrary side chain in the combining site of an antibody bearing an amino group.

In certain embodiments, wherein Antibody is an aldolase catalytic antibody, Z'- Antibody has the structure:

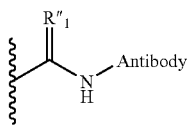

wherein HN-Antibody refers to an arbitrary side chain in the combining site of an antibody bearing an amino group.

In certain embodiments, wherein Antibody is an aldolase catalytic antibody, Z'- Antibody has the structure:

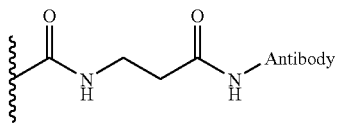

wherein HN-Antibody refers to an arbitrary side chain in the combining site of an antibody bearing an amino group.

In certain embodiments, wherein Antibody is an aldolase catalytic antibody, Z'- Antibody has the structure:

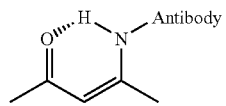

wherein HN-Antibody refers to an arbitrary side chain in the combining site of an antibody bearing an amino group.

In certain embodiments, wherein Antibody is an aldolase catalytic antibody, Z'- Antibody has the structure:

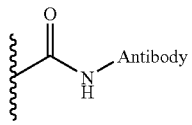

wherein HN-Antibody refers to an arbitrary side chain in the combining site of an antibody bearing an amino group.

In certain embodiments, wherein Antibody is an aldolase catalytic antibody, Z'- Antibody has the structure:

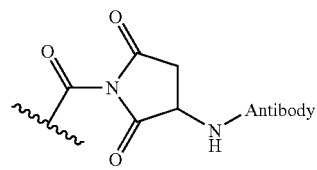

wherein HN-Antibody refers to an arbitrary side chain in the combining site of an antibody bearing an amino group.

In certain embodiments, wherein Antibody is an aldolase catalytic antibody, Z'- Antibody has the structure:

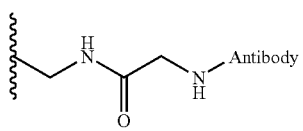

wherein HN-Antibody refers to an arbitrary side chain in the combining site of an antibody bearing an amino group.

In certain embodiments, wherein Antibody is an aldolase catalytic antibody, Z'- Antibody has the structure:

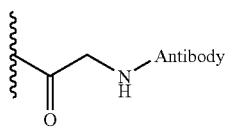

wherein HN-Antibody refers to an arbitrary side chain in the combining site of an antibody bearing an amino group.

In certain embodiments, wherein Antibody is an aldolase catalytic antibody, Z'- Antibody has the structure:

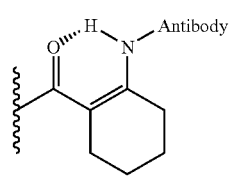

wherein HN-Antibody refers to an arbitrary side chain in the combining site of an antibody bearing an amino group.

In certain embodiments, wherein Antibody is an aldolase catalytic antibody, Z'- Antibody has the structure:

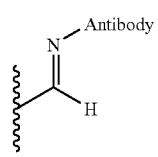

wherein HN-Antibody refers to an arbitrary side chain in the combining site of an antibody bearing an amino group.

In compounds having Formula II, Z' is an attachment moiety comprising a covalent bond and 0-20 carbon atoms to which the Antibody is attached. This is shown below for the case where the linker has a diketone moiety as the reactive group and linkage occurs with the side chain amino group of a lysine residue in the antibody combining site. The Antibody is shown schematically as bivalent with a reactive amino acid side chain for each combining site indicated.

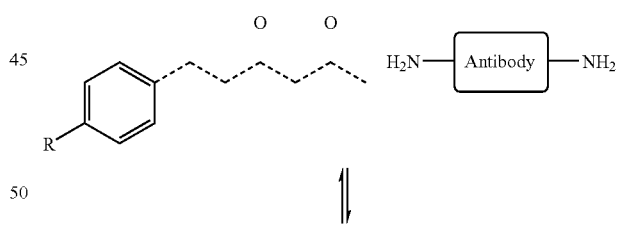

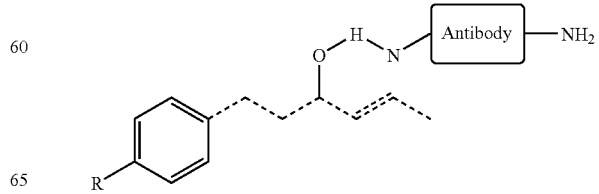

Another embodiment shown below is for the case where the linker has a beta lactam moiety as the reactive group and linkage occurs with the side chain amino group of a lysine residue in the antibody combining site. The Antibody is shown schematically as bivalent with a reactive amino acid side chain for each combining site indicated.

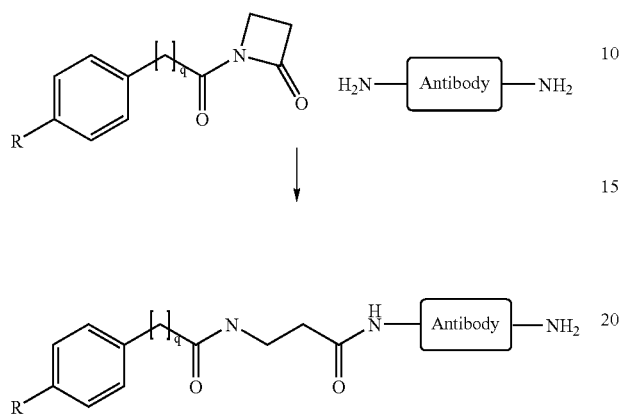

Certain embodiments in accordance with Formula II have the structure:

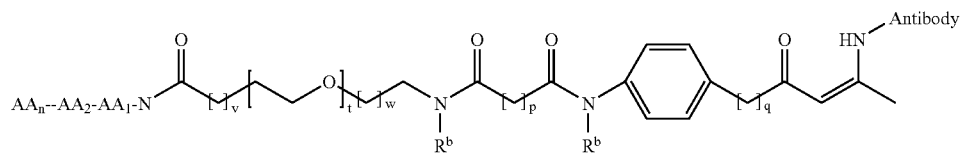

In certain of these embodiments, v is 0, 1, 2, 3, 4, or 5; t is 1, 2, 3, 4, 5, or 6; w is 1, 2, 3, 4, or 5; p is 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; p is 3; and q is 0, 1, 2, or 3. In some embodiments, v is 0; t is 1 or 2; w is 1; p is 1 or 2; and q is 2 or 3.

Certain embodiments in accordance with Formula II have the structure:

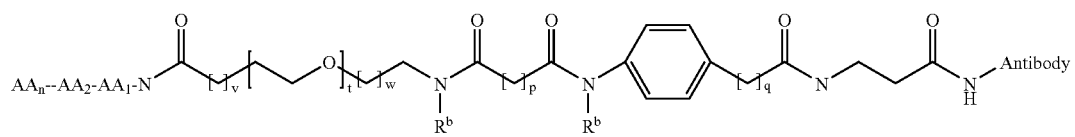

In certain of these embodiments, v is 0, 1, 2, 3, 4, or 5; t is 1, 2, 3, 4, 5, or 6; w is 1, 2, 3, 4, or 5; p is 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; p is 3; and q is 0, 1, 2, or 3. In some embodiments, v is 0; t is 1 or 2; w is 1; p is 1 or 2; and q is 1 or 2.

Certain embodiments in accordance with Formula II have the structure:

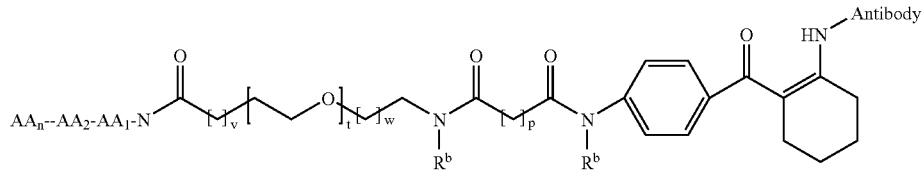

In certain of these embodiments, v is 0, 1, 2, 3, 4, or 5; t is 1, 2, 3, 4, 5, or 6; w is 1, 2, 3, 4, or 5; and p is 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; and p is 3. In some embodiments, v is 0; t is 1 or 2; w is 1; and p is 1 or 2.

Certain embodiments in accordance with Formula II have the structure:

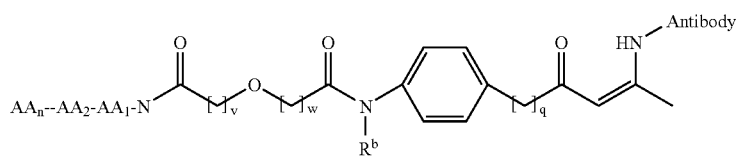

In certain of these embodiments, v is 1, 2, 3, 4, or 5; w is 1, 2, 3, 4, or 5; q is 0, 1, 2, 3, 4, or 5; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 1, 2, or 3; w is 1, 2, or 3; and q is 0, 1, 2, 3. In some embodiments, v is 1 or 2; w is 1 or 2; and q is 1 or 2.

Certain embodiments in accordance with Formula II have the structure:

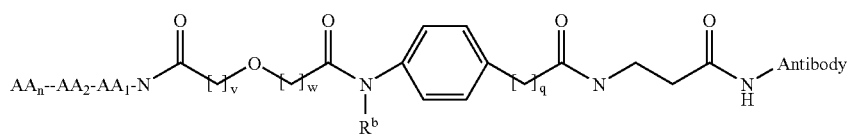

In certain of these embodiments, v is 1, 2, 3, 4, or 5; w is 1, 2, 3, 4, or 5; q is 0, 1, 2, or 3; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 1, 2, or 3; w is 1, 2, or 3; and q is 0, 1, 2, 3. some embodiments, v is 1 or 2; w is 1 or 2; and q is 2 or 3.

Certain embodiments in accordance with Formula II have the structure:

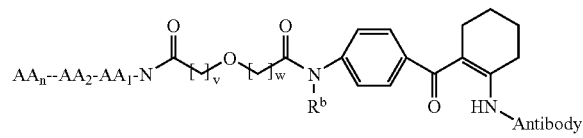

In certain of these embodiments, v is 1, 2, 3, 4, or 5; w is 1, 2, 3, 4, or 5; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 1, 2, or 3; and w is 1, 2, or 3. In some embodiments, v is 1 or 2 and w is 1 or 2.

Certain embodiments in accordance with Formula II have the structure:

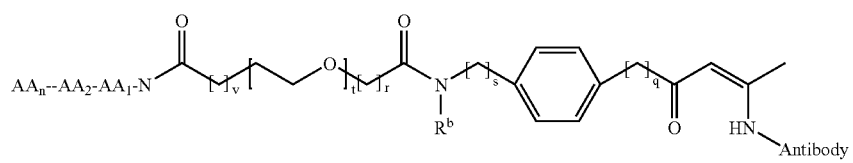

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, 3, 4, or 5; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; s is 3 and q is 0, 1, 2, or 3. In some embodiments, v is 0; t is 1, 2, or 3, r is 1; s is 1 or 2; and q is 1 or 2.

Certain embodiments in accordance with Formula II have the structure:

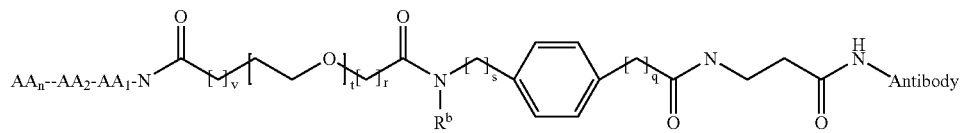

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, or 3; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; s is 3 and q is 0, 1, 2, or 3. In some embodiments, v is 0; t is 1, 2, or 3, r is 1; s is 1 or 2; and q is 2 or 3.

Certain embodiments in accordance with Formula II have the structure:

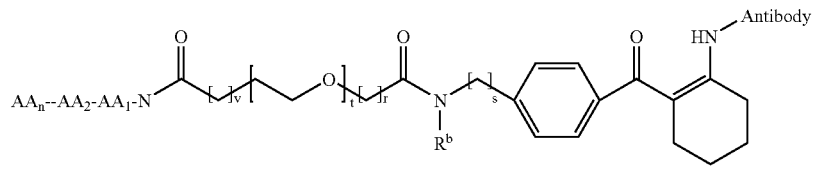

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; and s is 3. In some embodiments, v is 0; t is 1, 2, or 3, r is 1; and s is 1 or 2.

Certain embodiments in accordance with Formula II have the structure:

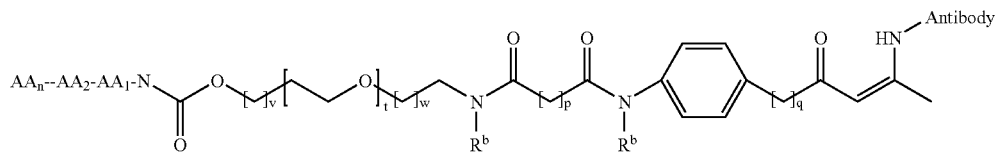

In certain of these embodiments, v is 0, 1, 2, 3, 4, or 5; t is 1, 2, 3, 4, 5, or 6; w is 1, 2, 3, 4, or 5; p is 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; p is 3; and q is 0, 1, 2, or 3. In some embodiments, v is 0; t is 1 or 2; w is 1; p is 1 or 2; and q is 1 or 2.

Certain embodiments in accordance with Formula II have the structure:

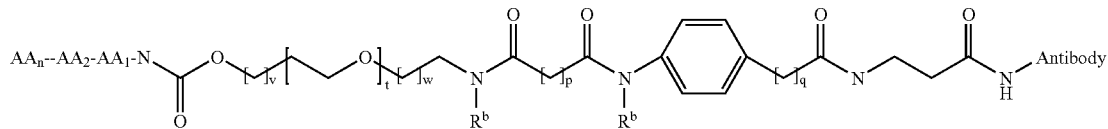

In certain of these embodiments, v is 0, 1, 2, 3, 4, or 5; t is 1, 2, 3, 4, 5, or 6; w is 1, 2, 3, 4, or 5; p is 1, 2, 3, 4, or 5; q is 0, 1, 2, or 3; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; p is 3; and q is 0, 1, 2, or 3. In some embodiments, v is 0; t is 1 or 2; w is 1; p is 1 or 2; and q is 2 or 3.

Certain embodiments in accordance with Formula II have the structure:

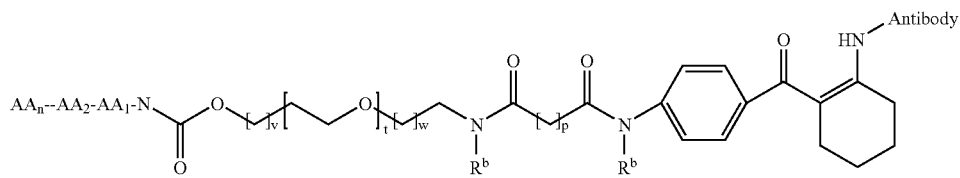

In certain of these embodiments, v is 0, 1, 2, 3, 4, or 5; t is 1, 2, 3, 4, 5, or 6; w is 1, 2, 3, 4, or 5; p is 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; and p is 3. In some embodiments, v is 0; t is 1 or 2; w is 1; and p is 1 or 2.

Certain embodiments in accordance with Formula II have the structure:

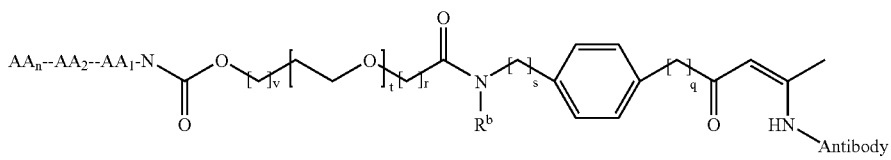

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, 3, 4, or 5; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; s is 3 and q is 0, 1, 2, or 3. In some embodiments, v is 0; t is 1, 2, or 3, r is 1; s is 1 or 2; and q is 1 or 2.

Certain embodiments in accordance with Formula II have the structure:

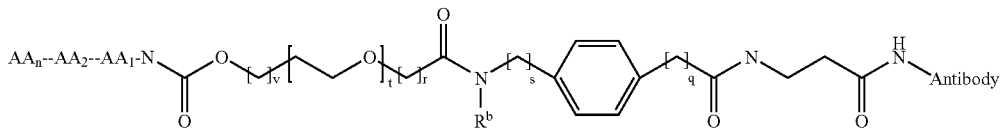

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, or 3; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; s is 3 and q is 0, 1, 2, or 3. In some embodiments, v is 0; t is 1, 2, or 3, r is 1; s is 1 or 2; and q is 2 or 3.

Certain embodiments in accordance with Formula II have the structure:

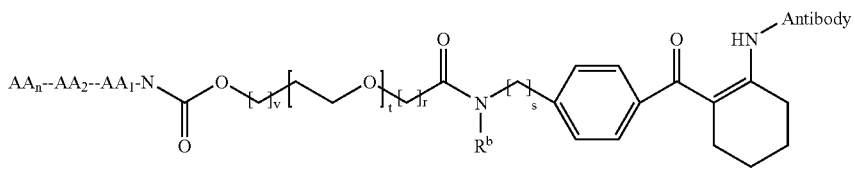

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; and s is 3. In some embodiments, v is 0; t is 1, 2, or 3, r is 1; and s is 1 or 2.

Certain embodiments in accordance with Formula II have the structure:

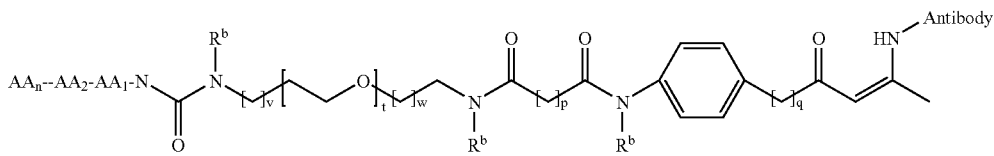

In certain of these embodiments, v is 0, 1, 2, 3, 4, or 5; t is 1, 2, 3, 4, 5, or 6; w is 1, 2, 3, 4, or 5; p is 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; p is 3; and q is 0, 1, 2, or 3. In some embodiments, v is 0; t is 1 or 2; w is 1; p is 1 or 2; and q is 1 or 2.

Certain embodiments in accordance with Formula II have the structure:

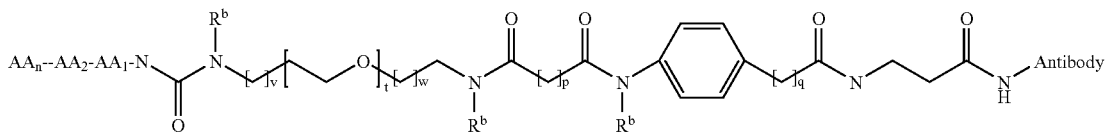

In certain of these embodiments, v is 0, 1, 2, 3, 4, or 5; t is 1, 2, 3, 4, 5, or 6; w is 1, 2, 3, 4, or 5; p is 1, 2, 3, 4, or 5; q is 0, 1, 2, or 3; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; p is 3; and q is 0, 1, 2, or 3. In some embodiments, v is 0; t is 1 or 2; w is 1; p is 1 or 2; and q is 2 or 3.

Certain embodiments in accordance with Formula II have the structure:

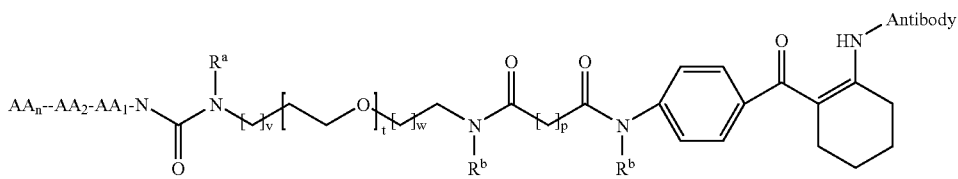

In certain of these embodiments, v is 0, 1, 2, 3, 4, or 5; t is 1, 2, 3, 4, 5, or 6; w is 1, 2, 3, 4, or 5; p is 1, 2, 3, 4, or 5; and $R^b$ at each occurrence are independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; and p is 3. In some embodiments, v is 0; t is 1 or 2; w is 1; and p is 1 or 2.

Certain embodiments in accordance with Formula II have the structure:

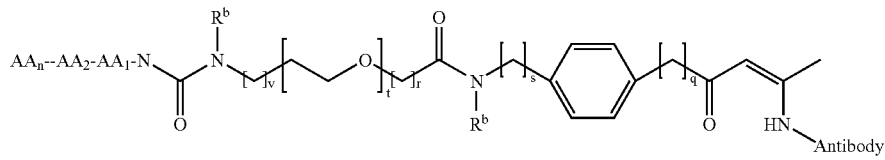

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; s is 3 and q is 0, 1, 2, or 3. In some embodiments, v is 0; t is 1, 2, or 3, r is 1; s is 1 or 2; and q is 1 or 2.

Certain embodiments in accordance with Formula II have the structure:

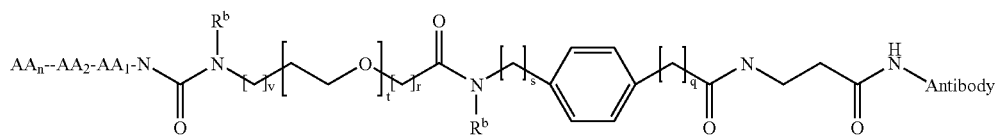

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, or 3; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; s is 3 and q is 0, 1, 2, or 3. In some embodiments, v is 0; t is 1, 2, or 3, r is 1; s is 1 or 2; and q is 2 or 3.

Certain embodiments in accordance with Formula II have the structure:

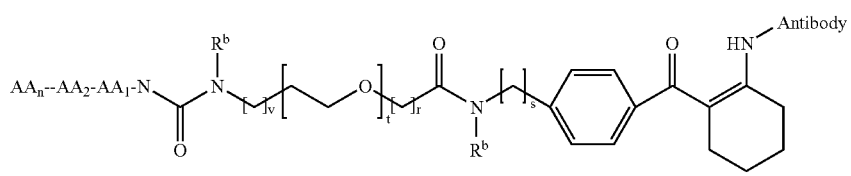

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; and s is 3. In some embodiments, v is 0; t is 1, 2, or 3, r is 1; and s is 1 or 2.

Certain embodiments in accordance with Formula II have the structure:

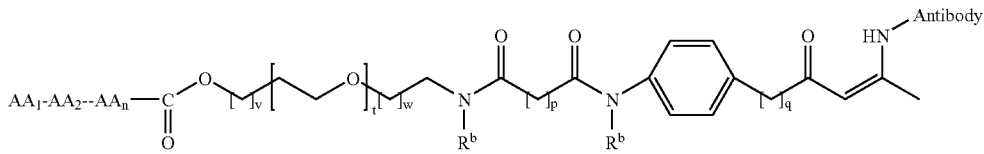

In certain of these embodiments, v is 0, 1, 2, 3, 4, or 5 ; t is 1, 2, 3, 4, 5, or 6; w is 1, 2, 3, 4, or 5; p is 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; p is 3; and q is 0, 1, 2, or 3. In some embodiments, v is 0; t is 1 or 2; w is 1; p is 1 or 2; and q is 1 or 2.

Certain embodiments in accordance with Formula II have the structure:

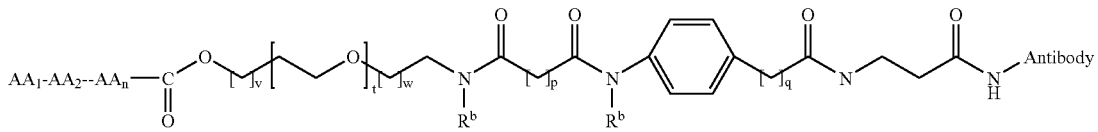

In certain of these embodiments, v is 0, 1, 2, 3, 4, or 5; t is 1, 2, 3, 4, 5, or 6; w is 1, 2, 3, 4, or 5; p is 1, 2, 3, 4, or 5; q is 0, 1, 2, or 3; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; p is 3; and q is 0, 1, 2, or 3. In some embodiments, v is 0; t is 1 or 2; w is 1; p is 1 or 2; and q is 2 or 3.

Certain embodiments in accordance with Formula II have the structure:

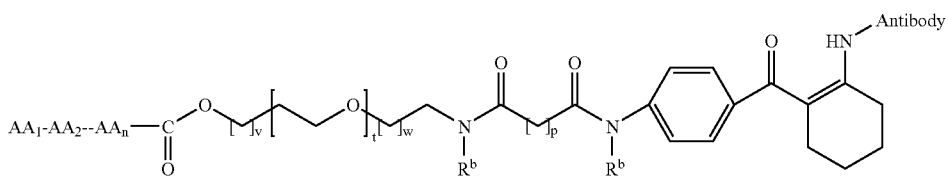

In certain of these embodiments, v is 0, 1, 2, 3, 4, or 5; t is 1, 2, 3, 4, 5, or 6; w is 1, 2, 3, 4, or 5; p is 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; and p is 3. In some embodiments, v is 0; t is 1 or 2; w is 1; and p is 1 or 2.

Certain embodiments in accordance with Formula II have the structure:

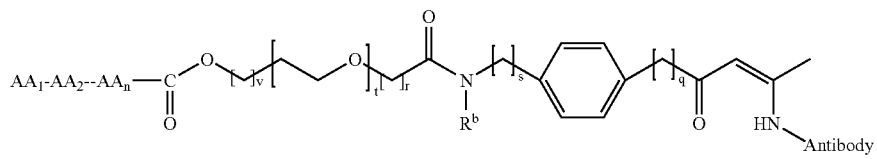

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, 3, 4, or 5; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; s is 3 and q is 0, 1, 2, or 3. In some embodiments, v is 0; t is 1, 2, or 3, r is 1; s is 1 or 2; and q is 1 or 2.

Certain embodiments in accordance with Formula II have the structure:

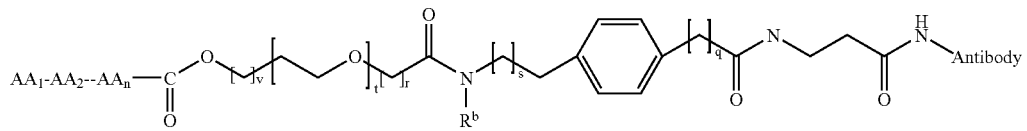

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, or 3; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; s is 3 and q is 0, 1, 2, or 3. In some embodiments, v is 0; t is 1, 2, or 3, r is 1; s is 1 or 2; and q is 2 or 3.

Certain embodiments in accordance with Formula II have the structure:

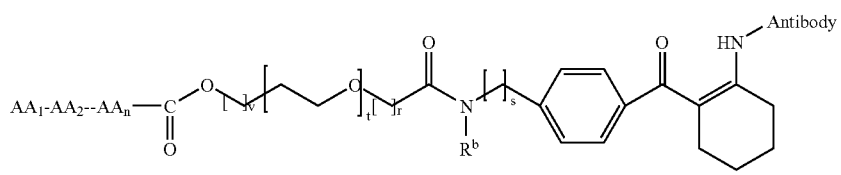

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; and s is 3. In some embodiments, v is 0; t is 1, 2, or 3, r is 1; and s is 1 or 2.

Certain embodiments in accordance with Formula II have the structure:

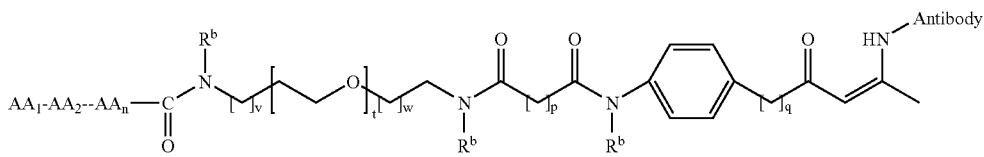

In certain of these embodiments, v is 0, 1, 2, 3, 4, or 5; t is 1, 2, 3, 4, 5, or 6; w is 1, 2, 3, 4, or 5; p is 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; p is 3; and q is 0, 1, 2, or 3. In some embodiments, v is 0; t is 1 or 2; w is 1; p is 1 or 2; and q is 1 or 2.

Certain embodiments in accordance with Formula II have the structure:

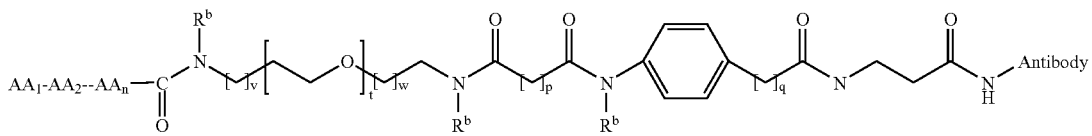

In certain of these embodiments, v is 0, 1, 2, 3, 4, or 5; t is 1, 2, 3, 4, 5, or 6; w is 1, 2, 3, 4, or 5; p is 1, 2, 3, 4, or 5; q is 0, 1, 2, or 3; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; p is 3; and q is 0, 1, 2, or 3. In some embodiments, v is 0; t is 1 or 2; w is 1; p is 1 or 2; and q is 2 or 3.

Certain embodiments in accordance with Formula II have the structure:

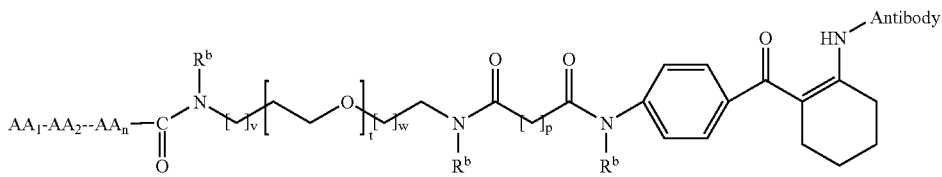

In certain of these embodiments, v is 0, 1, 2, 3, 4, or 5; t is 1, 2, 3, 4, 5, or 6; w is 1, 2, 3, 4, or 5; p is 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; and p is 3. In some embodiments, v is 0; t is 1 or 2; w is 1; and p is 1 or 2.

Certain embodiments in accordance with Formula II have the structure:

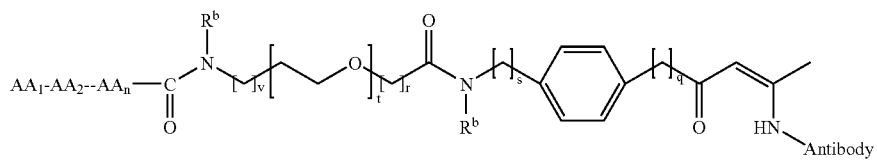

In certain of these embodiments v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; s is 3 and q is 0, 1, 2, or 3. In some embodiments, v is 0; t is 1, 2, or 3, r is 1; s is 1 or 2; and q is 1 or 2.

Certain embodiments in accordance with Formula II have the structure:

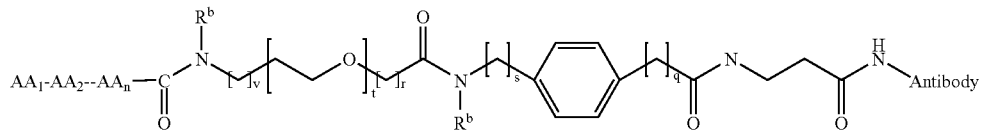

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, or 3; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; s is 3 and q is 0, 1, 2, or 3. In some embodiments, v is 0; t is 1, 2, or 3, r is 1; s is 1 or 2; and q is 2 or 3.

Certain embodiments in accordance with Formula II have the structure:

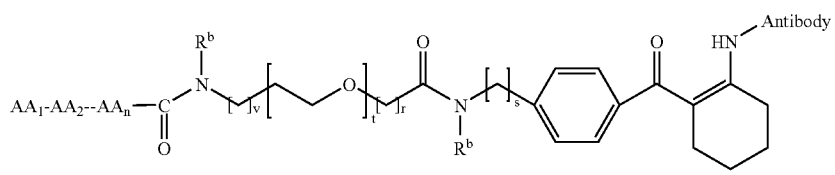

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; and s is 3. In some embodiments, v is 0; t is 1, 2, or 3, r is 1; and s is 1 or 2.

Certain embodiments in accordance with Formula II have the structure:

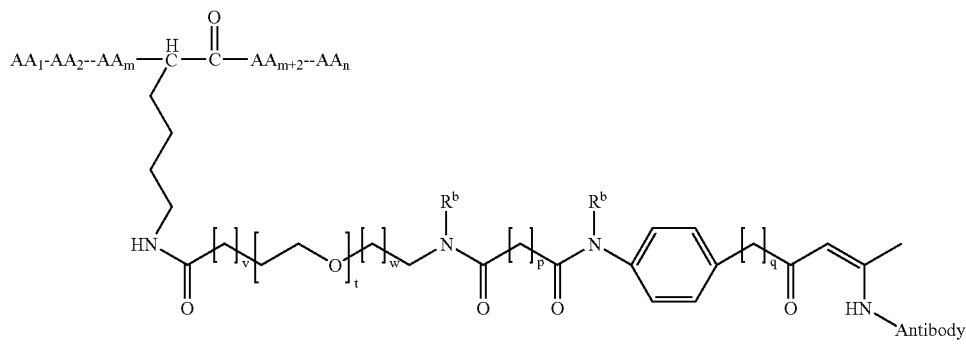

In certain of these embodiments, v is 0, 1, 2, 3, 4, or 5; t is 1, 2, 3, 4, 5, or 6; w is 1, 2, 3, 4, or 5; p is 1, 2, 3, 4, or 5; q is 0, 1, 2, 3, 4, or 5; and $R^b$ at each occurrence is independently hydrogen, substituted or unsubstituted $C_{1-10}$ alkyl substituted or unsubstituted $C_{3-7}$ cycloalkyl-$C_{0-6}$ alkyl, or substituted or unsubstituted aryl-$C_{0-6}$ alkyl In certain embodiments, v is 0; t is 1, 2, 3, 4, 5, or 6; w is 1; p is 3; and q is 0, 1, 2, or 3. In some embodiments, v is 0; t is 1 or 2; w is 1; p is 1 or 2; and q is 1 or 2.

Certain embodiments in accordance with Formula II have the structure:

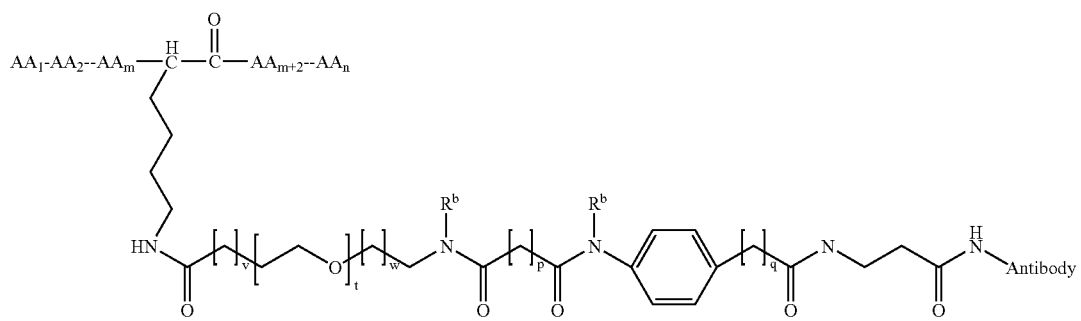

In certain of these embodiments, v is 0, 1, 2, 3, 4, or 5; t is 1, 2, 3, 4, 5, or 6; w is 1, 2, 3, 4, or 5; p is 1, 2, 3, 4, or 5; q is 0, 1, 2, or 3; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; p is 3; and q is 0, 1, 2, or 3. In some embodiments, v is 0; t is 1 or 2; w is 1; p is 1 or 2; and q is 2 or 3.

Certain embodiments in accordance with Formula II have the structure:

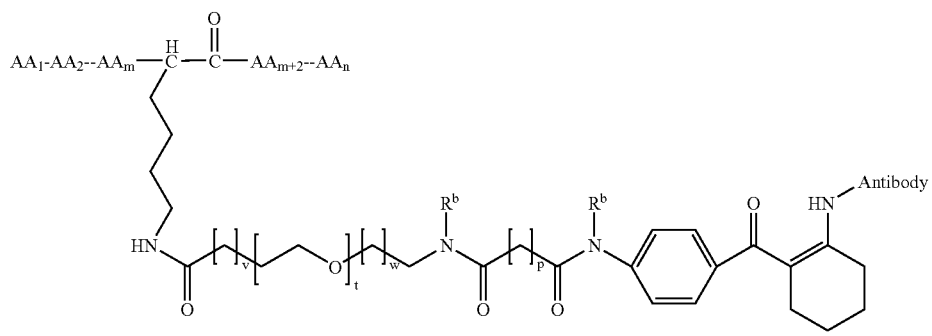

In certain of these embodiments, v is 0, 1, 2, 3, 4, or 5; t is 1, 2, 3, 4, 5, or 6; w is 1, 2, 3, 4, or 5; p is 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; and p is 3. In some embodiments, v is 0; t is 1 or 2; w is 1; and p is 1 or 2.

Certain embodiments in accordance with Formula II have the structure:

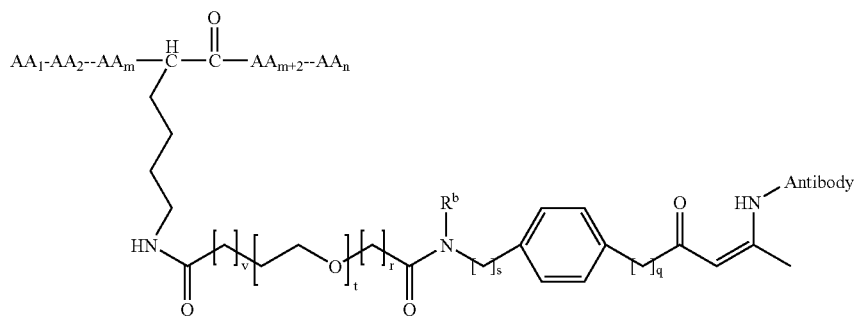

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, 3, 4, or 5; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; s is 3; and q is 0, 1, 2, or 3. In some embodiments, v is 0; t is 1, 2 or 3, r is 1; s is 1 or 2; and q is 1 or 2.

Certain embodiments in accordance with Formula II have the structure:

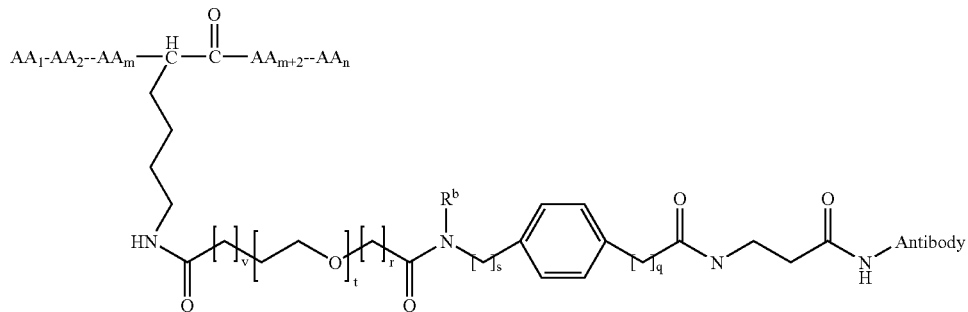

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, or 3; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; s is 3; and q is 0, 1, 2, or 3. In some embodiments, v is 0; t is 1, 2, or 3, r is 1; s is 1 or 2; and q is2or 3.

Certain embodiments in accordance with Formula II have the structure:

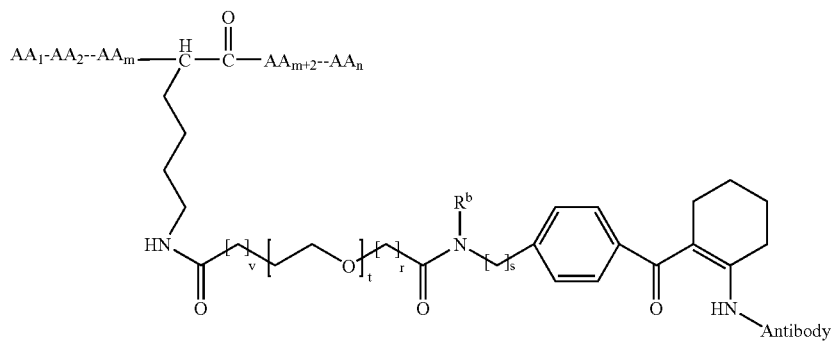

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; and s is 3. In some embodiments, v is 0; t is 1, 2, or 3, r is 1; and s is 1 or 2.

Certain embodiments in accordance with Formula II have the structure:

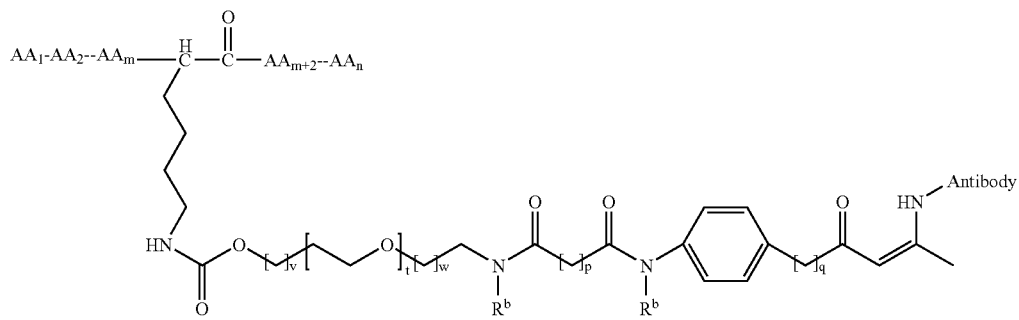

In certain of these embodiments, v is 0, 1, 2, 3, 4, or 5; t is 1, 2, 3, 4, 5, or 6; w is 1, 2, 3, 4, or 5; p is 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; p is 3; and q is 0, 1, 2, or 3. In some embodiments, v is 0; t is 1 or 2; w is 1; p is 1 or 2; and q is 1 or 2.

Certain embodiments in accordance with Formula II have the structure:

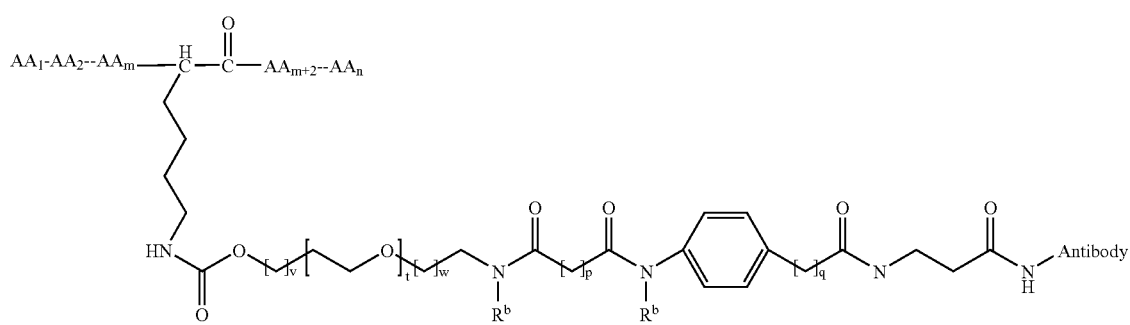

In certain of these embodiments, v is 0, 1, 2, 3, 4, or 5; t is 1, 2, 3, 4, 5, or 6; w is 1, 2, 3, 4, or 5; p is 1, 2, 3, 4, or 5; q is 0, 1, 2, or 3; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; p is 3; and q is 0, 1, 2, or 3. In some embodiments, v is 0; t is 1 or 2; w is 1; p is 1 or 2; and q is 2 or 3.

Certain embodiments in accordance with Formula II have the structure:

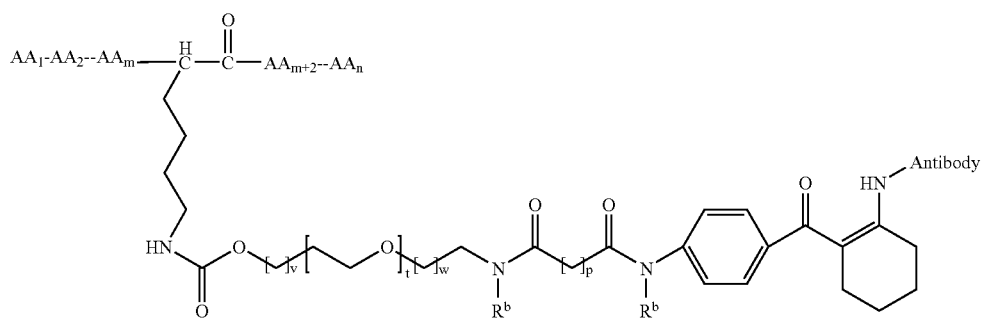

In certain of these embodiments, v is 0, 1, 2, 3, 4, or 5; t is 1, 2, 3, 4, 5, or 6; w is 1, 2, 3, 4, or 5; p is 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; and p is 3. In some embodiments, v is 0; t is 1 or 2; w is 1; and p is 1 or 2.

Certain embodiments in accordance with Formula II have the structure:

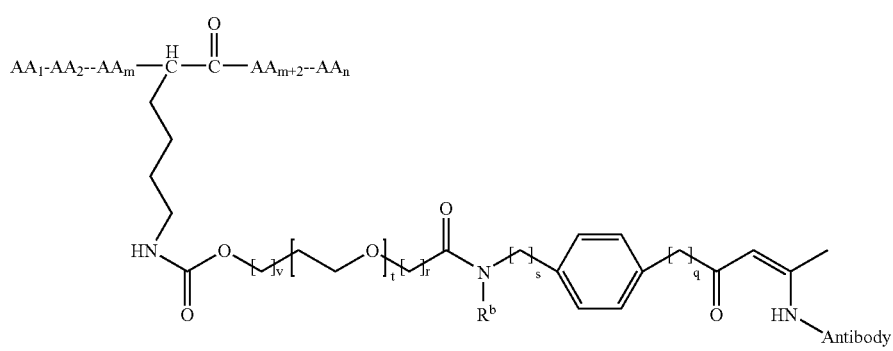

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, 3, 4, or 5; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; s is 3; and q is 0, 1, 2, or 3. In some embodiments, v is 0; t is 1, 2, or 3, r is 1; s is 1 or 2; and q is 1 or 2.

Certain embodiments in accordance with Formula II have the structure:

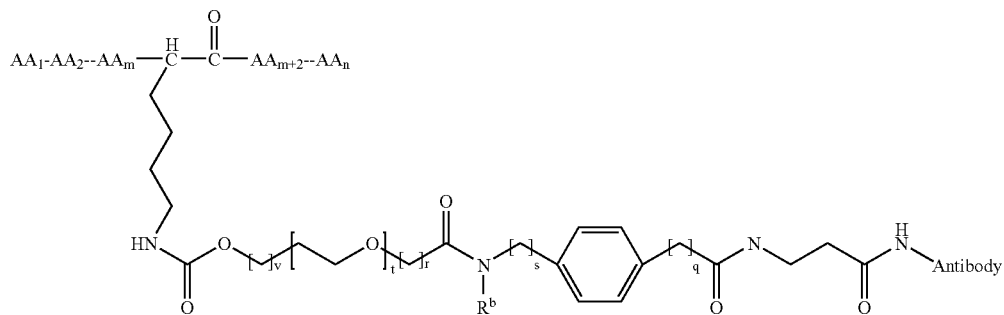

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, or 3; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; s is 3; and q is 0, 1, 2, or 3. In some embodiments, v is 0; t is 1, 2, or 3, r is 1; s is 1 or 2; and q is 2 or 3.

Certain embodiments in accordance with Formula II have the structure:

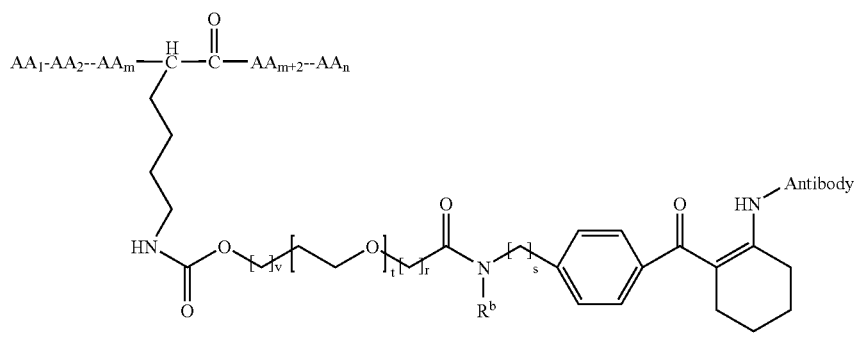

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; and $R^b$ is hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; and s is 3. In some embodiments, v is 0; t is 1, 2, or 3, r is 1; and s is 1 or 2.

Certain embodiments in accordance with Formula II have the structure:

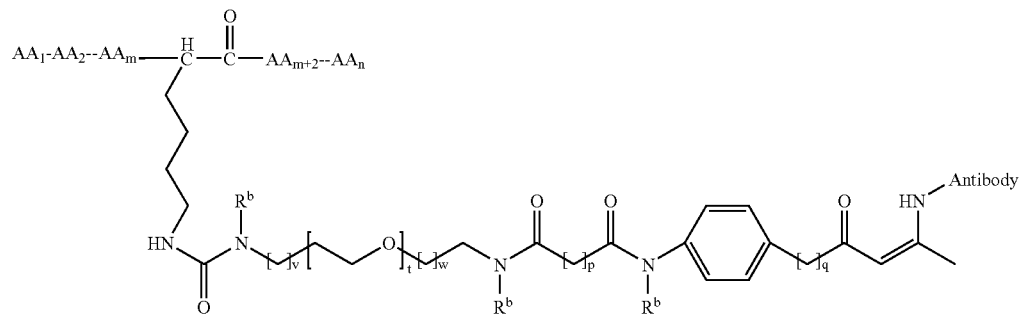

In certain of these embodiments, v is 0, 1, 2, 3, 4, or 5; t is 1, 2, 3, 4, 5, or 6; w is 1, 2, 3, 4, or 5; p is 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; p is 3; and q is 0, 1, 2, or 3. In some embodiments, v is 0; t is 1 or 2; w is 1; p is 1 or 2; and q is 1 or 2.

Certain embodiments in accordance with Formula II have the structure:

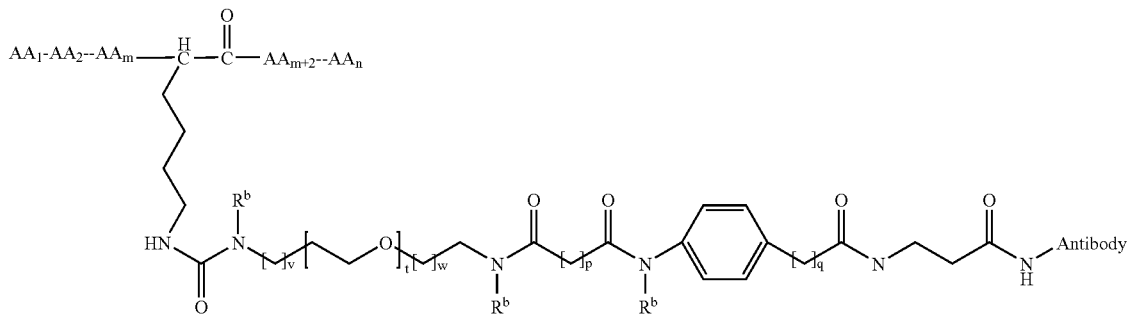

In certain of these embodiments, v is 0, 1, 2, 3, 4, or 5; t is 1, 2, 3, 4, 5, or 6; w is 1, 2, 3, 4, or 5; p is 1, 2, 3, 4, or 5; q is 0, 1, 2, or 3; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; p is 3; and q is 0, 1, 2, or 3. In some embodiments, v is 0; t is 1 or 2; w is 1; p is 1 or 2; and q is 2 or 3.

Certain embodiments in accordance with Formula II have the structure:

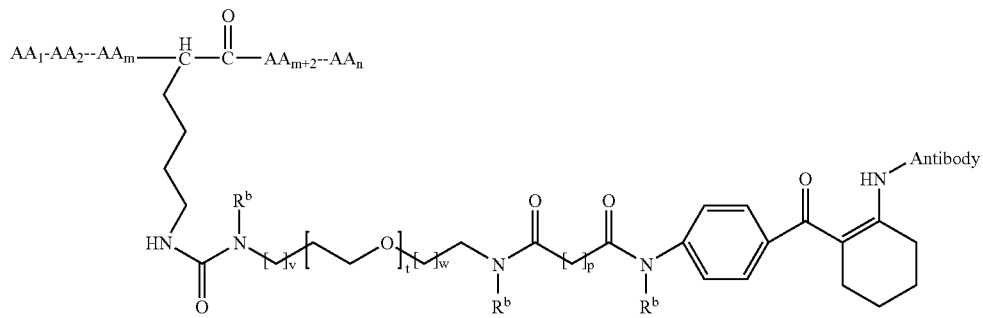

In certain of these embodiments, v is 0, 1, 2, 3, 4, or 5; t is 1, 2, 3, 4, 5, or 6; w is 1, 2, 3, 4, or 5; p is 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; w is 1; and p is 3. In some embodiments, v is 0; t is 1 or 2; w is 1; and p is 1 or 2.

Certain embodiments in accordance with Formula II have the structure:

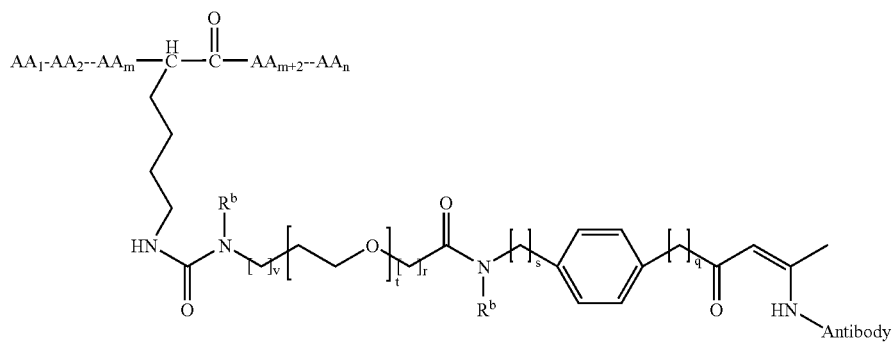

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; s is 3; and q is 0, 1, 2, or 3. In some embodiments, v is 0; t is 1, 2, or 3, r is 1; s is 1 or 2; and q is 1 or 2.

Certain embodiments in accordance with Formula II have the structure:

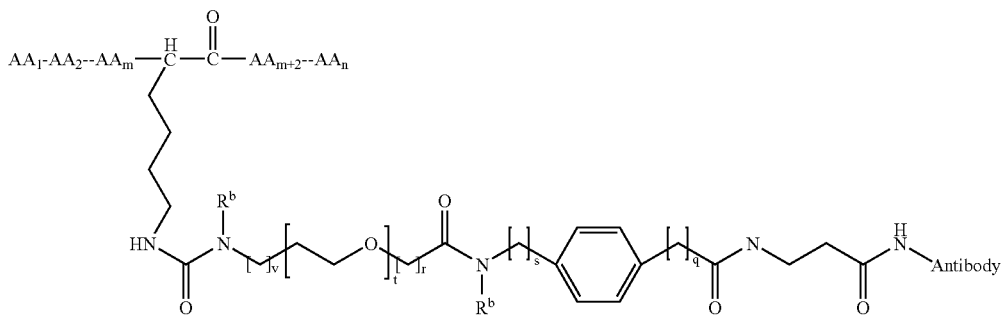

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; q is 0, 1, 2, or 3; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; s is 3; and q is 0, 1, 2, or 3. In some embodiments, v is 0; t is 1, 2, or 3, r is 1; s is 1 or 2; and q is 2 or 3.

Certain embodiments in accordance with Formula II have the structure:

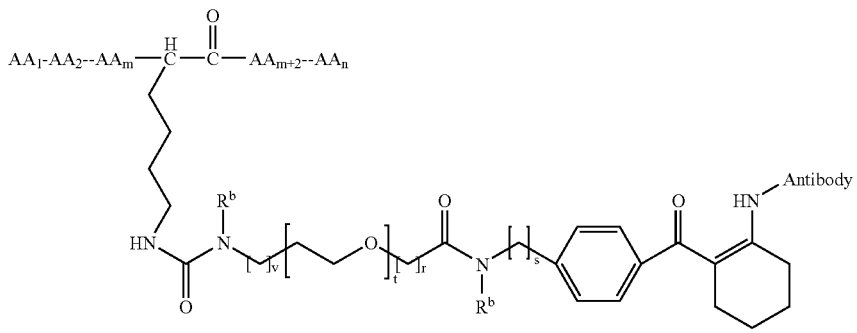

In certain of these embodiments, v is 0, 1, 2, 3, 4, or 5; t is 1, 2, 3, 4, 5, or 6; r is 1, 2, 3, 4, or 5; s is 0, 1, 2, 3, 4, or 5; and $R^b$ at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl. In certain embodiments, v is 0; t is 1, 2, 3, 4, 5, or 6; r is 1 or 2; and s is 3. In some embodiments, v is 0; t is 1, 2, or 3, r is 1; and s is 1 or 2.

Alternatively, the linker may have an amine or hydrazide as the reactive group and the Antibody may be engineered to have a diketone moiety. An unnatural diketone-containing amino acid may be readily incorporated into an antibody combining site using techniques well known in the art; proteins containing unnatural amino acids have been produced in yeast and bacteria. See, e.g., J. W. Chin et al., Science 301: 964-966 (2003); L. Wang et al., Science 292:498-500 (2001); J. W. Chin et al., J. Am. Chem. Soc. 124:9026-9027 (2002); L. Wang, et al., J. Am. Chem. Soc. 124:1836-1837 (2002); J. W. Chin and P. G. Schultz, Chembiochem. 3:1135-1137 (2002); J. W. Chin et al., Proc. Natl. Acad. Sci. U.S.A. 99:11020-11024 (2002); L. Wang and P. G. Schultz, Chem. Commun. (1):1-11 (2002); Z. Zhang et al., Angew. Chem. Int. Ed. Engl. 41:2840-2842 (2002); L. Wang, Proc. Natl. Acad. Sci. U.S.A. 100:56-61 (2003). Thus, for example, to insert an unnatural amino acid containing a diketone moiety into the yeast *Saccharomyces cerevisiae* requires the addition of new components to the protein biosynthetic machinery including a unique codon, tRNA, and aminoacyl-tRNA synthetase (aa RS). For example, the amber suppressor tyrosyl-tRNA synthetase (TyrRS)-$tRNA_{CUA}$ pair from *E. coli* may be used as reported for eukaryotes in J. W. Chin et al., Science 301:964-966 (2003). The amber codon is used to code for the unnatural amino acid of interest. Libraries of mutant TyrRS and $tRNA_{CUA}$ may then be produced and selected for those aaRS-$tRNA_{CUA}$ pairs in which the TyrRS charges the $tRNA_{CUA}$ with the unnatural amino acid of interest, e.g., the diketone-containing amino acid. Subsequently, antibodies incorporating the diketone-containing amino acid may be produced by cloning and expressing a gene containing the amber codon at one or more antibody combining sites.

In some embodiments of compounds of Formula II, the Antibody is a full length antibody. In other embodiments, the Antibody is Fab, Fab' F(ab')$_2$, Fv, $V_H$, $V_L$, or scFv. In certain embodiments, the Antibody is a human antibody, humanized antibody or chimeric human antibody. In certain embodiments, the Antibody is a catalytic antibody. In one embodiment, the Antibody is a humanized version of a murine 38c2 comprising a constant region from a human IgG, IgA, IgM, IgD, or IgE antibody. In another embodiment, Antibody is a chimeric antibody comprising the variable region from murine 38c2 and a constant region from a human IgG, IgA, IgM, IgD, or IgE antibody.

In some cases, two or more AA targeting agents may be linked to a single full length bivalent Antibody. This is shown below as Formula III:

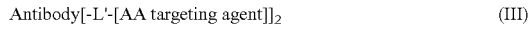

Antibody[-L'-[AA targeting agent]]$_2$      (III)

Also provided are stereoisomers, tautomers, solvates, prodrugs, and pharmaceutically acceptable salts thereof.

In compounds of Formula III, [AA targeting agent], L' and Antibody are each defined as in Formula II.

Targeting compounds such as those of Formula II may also be readily synthesized by covalently linking a targeting agent-linker compound as described herein to a combining site of a multivalent antibody. For example, an AA targeting-agent linker conjugate, where the linker includes a diketone reactive moiety, can be incubated with 0.5 equivalents of an aldolase antibody, such as h38C2 IgG1 to produce an AA targeting compound. Alternatively, an AA targeting compound such as those of Formula III may be produced by covalently linking an AA targeting agent-linker compound as described herein to each combining site of a bivalent antibody.

Methods of Use for AA Targeting Compounds

One aspect of the invention provides methods for modulating thrombospondin activity in vivo comprising administering an effective amount of an AA targeting compound as described herein to a subject. There are further provided methods for treating abnormal angiogenesis or an angiogenesis-mediated condition in a subject. Such methods include administering to the subject a therapeutically effective amount of an AA targeting compound as described herein. As used herein, an angiogenesis-mediated condition is a condition that is caused by abnormal angiogenesis activity or one in which compounds that modulate angiogenesis activity have therapeutic use. Diseases and conditions that may be treated include cancer, arthritis, psoriasis, angiogenesis of the eye associated with infection or surgical intervention, macular degeneration or diabetic retinopathy. In particular, methods of treating cancer include carcinomas of the breast, colon, rectum, lung, oropharynx, hypopharynx, esophagus, stomach, pancreas, liver, gallbladder and bile ducts, small intestine, urinary tract, female genital tract, male, genital tract, endocrine glands, and skin; hemangiomas; melanomas; sarcomas; tumors of the brain, nerves, eyes, and meninges; leukemia; or lymphoma.

Pharmaceutical Compositions and Methods of Administration

Another aspect of the invention provides pharmaceutical compositions of the AA targeting compounds. The AA targeting compounds can be mixed with pharmaceutically-acceptable carriers to form a pharmaceutical composition for administration to a cell or subject, either alone, or in combination with one or more other modalities of therapy.

A pharmaceutical composition is generally formulated to be compatible with its intended route of administration. Those skilled in the art will know that the choice of the pharmaceutical medium and the appropriate preparation of the composition will depend on the intended use and mode of administration. Examples of routes of administration include parenteral (e.g. intravenous, intramuscular, intramedullary, intradermal, subcutaneous), oral (e.g. inhalation, ingestion), intranasal, transdermal (e.g. topical), transmucosal, and rectal administration. Administration routes of AA targeting compounds may also include intrathecal, direct intraventricular and intraperitoneal delivery. The AA targeting compounds may be administered through any of the parenteral routes either by direct injection of the formulation or by infusion of a mixture of the targeting AA compound formulation with an infusion matrix such as normal saline, D5W, lactated Ringers solution or other commonly used infusion media.

The AA targeting compounds may be administered using techniques well known to those in the art. Preferably, agents are formulated and administered systemically. Techniques for formulation and administration may be found in "Remington's Pharmaceutical Sciences," 18$^{th}$ Ed., 1990, Mack Publishing Co., Easton, Pa. For injection, AA targeting compounds may be formulated in aqueous solutions, emulsions or suspensions. AA targeting compounds are preferably formulated in aqueous solutions containing physiologically compatible buffers such as citrate, acetate, histidine or phosphate. Where necessary, such formulations may also contain various tonicity adjusting agents, solubilizing agents and/or stabilizing agents (e.g. salts such as sodium chloride or sugars such as sucrose, mannitol, and trehalose, or proteins such as albumin or amino acids such as glycine and histidine or surfactants such as polysorbates (Tweens) or cosolvents such as ethanol, polyethylene glycol and propylene glycol.

The pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates, other organic acids, chelating agents [such as ethylenediamine tetraacetic acid (EDTA)]; solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (sucrose or sorbitol); tonicity enhancing agents (such as alkali metal halides (preferably sodium or potassium chloride, mannitol sorbitol); delivery vehicles; diluents; excipients and/or pharmaceutical adjuvants. (Remington's Pharmaceutical Sciences, 18th Edition, A. R. Gennaro, ed., Mack Publishing Company, 1990).

When parenteral administration is contemplated, the therapeutic compositions may be in the form of a pyrogen-free, parenterally acceptable aqueous solution comprising an AA targeting compound in a pharmaceutically acceptable vehicle. One vehicle for parenteral injection is sterile distilled water in which an AA targeting compound is formulated as a sterile, isotonic solution. Yet another formulation can involve the formulation an AA targeting compound with an agent, such as injectable microspheres, bio-degradable particles, polymeric compounds (polylactic acid, polyglycolic acid), beads, or liposomes, that provides for the controlled or sustained release of the product which may then be delivered via a depot injection. Hyaluronic acid may also be used, and this may have the effect of promoting sustained duration in the circulation. Other suitable means for the introduction of the desired molecule include implantable drug delivery devices.

In another aspect, pharmaceutical formulations suitable for parenteral administration may be formulated in aqueous solutions, preferably in physiologically compatible buffers such as Hanks' solution, Ringer's solution, or a physiologically buffered saline. Aqueous injection suspensions may contain substances that increase the viscosity of the suspension, such as sodium carboxymethyl cellulose, sorbitol, or dextran. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

The pharmaceutical composition to be used for in vivo administration typically must be sterile. This may be accomplished by filtration through sterile filtration membranes. Where the composition is lyophilized, sterilization using this method may be conducted either prior to or following lyophilization and reconstitution. The composition for parenteral administration may be stored in lyophilized form or in solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or a dehydrated or lyophilized powder. Such formulations may be stored either in a ready-to-use form or in a form (e.g., lyophilized) requiring reconstitution prior to administration.

One embodiment is directed to kits for producing a single-dose administration unit. The kits may each contain both a first container having an AA targeting compound and a second container having an aqueous formulation. Also included within the scope of this invention are kits containing single and multi-chambered pre-filled syringes.

In treating mammals, including humans, having a disorder with an angiogenic component to the disorder, a therapeutically effective amount of an AA targeting compound or a pharmaceutically acceptable derivative is administered. The frequency of dosing will depend upon the pharmacokinetic parameters of the AA targeting compound in the formulation used. Typically, a composition is administered until a dosage is reached that achieves the desired effect. The composition may therefore be administered as a single dose, or as multiple doses (at the same or different concentrations/dosages) over time, or as a continuous infusion. Routes and frequency of administration of a composition as well as dosage may vary from individual to individual and may be readily established using standard techniques. Further refinement of the appropriate dosage is routinely made. Appropriate dosages may be developed by one skilled in the art through the use of appropriate dose-response data.

An appropriate dosage and treatment regimen provides the active compound(s) in an amount sufficient to provide therapeutic and/or prophylactic benefit. Such a response can be monitored by establishing an improved clinical outcome (e.g. reduced number of blood vessels in a target area, decreased tumor size or volume, in treated patients as compared to non-treated patients. Typically, a suitable dose is an amount of a compound that, when administered as described herein, is capable of promoting an anti-angiogenesis response, and/or is at least 10-50% above the basal or untreated level.

In some embodiments, the most effective mode of administration and dosage regimen for the invention compositions depends upon the severity and course of the disease, the patient's health and response to treatment, and the judgment of the treating physician. Accordingly, the dosages of the invention compositions should be titrated to the individual patient. An effective dose of the compounds is in the range of from about 0.1 ug to about 40 mg per kilogram per day. An AA targeting compound may be administered as a daily intravenous infusion from about 0.1 mg/kg body weight to about 15 mg/kg body weight. Accordingly, one embodiment provides a dose of about 0.5 mg/kg body weight. Another embodiment provides a dose of about 0.75 mg/kg body weight. Another embodiment provides a dose of about 1.0 mg/kg body weight. Another embodiment provides a dose of about 2.5 mg/kg body weight. Another embodiment provides a dose of about 5 mg/kg body weight. Another embodiment provides a dose of about 10.0 mg/kg body weight. Another embodiment provides a dose of about 15.0 mg/kg body weight. Doses of an AA targeting compound or a pharmaceutically acceptable derivative should be administered in intervals of from about once per day to 2 times per week, or alternatively, from about once every week to once per month. In one embodiment, a dose is administered to achieve peak plasma concentrations of an AA targeting compound or a pharmaceutically acceptable derivative thereof from about 0.002 mg/ml to 30 mg/ml. This may be achieved by the sterile injection of a solution of the administered ingredients in an appropriate formulation (any suitable formulation solutions known to those skilled in the art of chemistry may be used). Desirable blood levels may be maintained by a continuous infusion of an AA targeting compound as ascertained by plasma levels measured by a validated analytical methodology.

One method for administering an AA targeting compound to an individual comprises administering an AA targeting agent—linker conjugate to the individual and allowing it to form a covalent compound with a combining site of an appropriate antibody in vivo. The antibody portion of an AA targeting compound that forms in vivo may be administered to the individual before, at the same time, or after administration of the targeting agent—linker conjugate. As already discussed, an AA targeting agent may include a linker/reactive moiety, or the antibody combining site may be suitably modified to covalently link to the targeting agent. Alternatively, or in addition, an antibody may be present in the circulation of the individual following immunization with an appropriate immunogen. For example, catalytic antibodies may be generated by immunizing with a reactive intermediate of the substrate conjugated to a carrier protein. See R. A. Lerner and C. F. Barbas $3^{rd}$, Acta Chem. Scand. 50:672-678 (1996). In particular, aldolase catalytic antibodies may be generated by administering with keyhole limpet hemocyanin linked to a diketone moiety as described by P. Wirsching et al., Science 270:1775-1782 (1995) (commenting on J. Wagner et al., Science 270:1797-1800 (1995)).

The invention also provides a method of visualizing or localizing a thrombospondin receptor or anti-angiogenesis target (i.e. AA-targeting agent receptor) in tissues and cells. In one embodiment, biopsied tissues may be examined for presence of AA-targeting agent receptor. In another embodiment, neovascularization in a subject may be imaged by administering to the subject an AA targeting agent or compound including a detectable label. As used herein, the term "detectable label" refers to any molecule which can be administered in vivo and subsequently detected. Exemplary detectable labels include radiolabels and fluorescent molecules. Exemplary radionuclides include indium-111, technetium-99, carbon-11, and carbon-13. Fluorescent molecules include, without limitation, fluorescein, allophycocyanin, phycoerythrin, rhodamine, and Texas red.

Combination Therapies

The vasculature within a tumor generally undergoes active angiogenesis, resulting in the continual formation of new blood vessels to support the growing tumor. Such angiogenic blood vessels are distinguishable from mature vasculature in that angiogenic vasculature expresses unique endothelial cell surface markers, including the .alpha.sub.v.beta.sub.3 integrin. (Brooks, Cell 79:1157-1164 (1994); WO 95/14714, Int. Filing Date Nov. 22, 1994) and receptors for angiogenic growth factors (Mustonen and Alitalo, J. Cell Biol. 129:895-898 (1995); Lappi, Semin. Cancer Biol. 6:279-288 (1995)).

The invention also includes administration of one or more AA targeting agents in combination with one or more oncology therapeutics, each being administered according to a regimen suitable for that therapeutic. The components of the combination therapy may be administered concurrently or non-concurrently. As used herein, the terms "concurrently administered" and "concurrent administration" encompass substantially simultaneous administration of one or more AA targeting compounds and one other oncology therapeutic.

As used herein, the term, "non-concurrent" administration encompasses administering one or more AA targeting compounds at different times, in any order, whether overlapping or not. This includes, but is not limited to, sequential treatment (such as pretreatment, post-treatment, or overlapping treatment) with the components of the combination, as well as regimens in which the drugs are alternated, or wherein one component is administered long-term and the other(s) are administered intermittently. Components may be administered in the same or in separate compositions, and by the same or different routes of administration.

Suitable oncology therapeutics and combinations that may be used in combination with an AA targeting compounds are listed in Tables 4-6.

TABLE 4

Approved oncology drugs and indications

| Generic | Trade Name | Indication | Company |
| --- | --- | --- | --- |
| Aldesleukin | Proleukin | Proleukin is indicated for the treatment of adults with metastatic renal cell carcinoma (metastatic RCC) and for the treatment of adults with metastatic melanoma. | Chiron Corp |
| Alemtuzumab | Campath | Campath is indicated for the treatment of B-cell chronic lymphocytic leukemia (B-CLL) in patients who have been treated with alkylating agents and who have failed fludarabine therapy. | Millennium and ILEX Partners, LP |
| Alitretinoin | Panretin | Topical treatment of cutaneous lesions in patients with AIDS-related Kaposi's sarcoma. | Ligand Pharmaceuticals |
| Allopurinol | Zyloprim | Patients with leukemia, lymphoma and solid tumor malignancies who are receiving cancer therapy which causes elevations of serum and urinary uric acid levels and who cannot tolerate oral therapy. | GlaxoSmithKline |
| Palonosetron | Aloxi | For the treatment of nausea | MGI Pharmaceuticals |
| Altretamine | Hexalen | Single agent palliative treatment of patients with persistent or recurrent ovarian cancer following first-line therapy with a cisplatin and/or alkylating agent based combination. | US Bioscience |
| Amifostine | Ethyol | To reduce the cumulative renal toxicity associated with repeated administration of cisplatin in patients with advanced ovarian cancer | US Bioscience |
| Amifostine | Ethyol | Reduces platinum toxicity in non-small cell lung cancer | US Bioscience |
| Amifostine | Ethyol | To reduce post-radiation xerostomia for head and neck cancer where the radiation port includes a substantial portion of the parotid glands. | US Bioscience |

TABLE 4-continued

Approved oncology drugs and indications

| Generic | Trade Name | Indication | Company |
| --- | --- | --- | --- |
| Anastrozole | Arimidex | Adjuvant treatment of postmenopausal women with hormone receptor positive early breast cancer | AstraZeneca |
| Anastrozole | Arimidex | Treatment of advanced breast cancer in postmenopausal women with disease progression following tamoxifen therapy. | AstraZeneca Pharmaceuticals |
| Anastrozole | Arimidex | For first-line treatment of postmenopausal women with hormone receptor positive or hormone receptor unknown locally advanced or metastatic breast cancer. | AstraZeneca Pharmaceuticals |
| Nelarabine | Arranon | For the treatement of T cell acute lymphoblatic leukemia | GlaxoSmithKline |
| Arsenic trioxide | Trisenox | Second line treatment of relapsed or refractory APL following ATRA plus an anthracycline. | Cell Therapeutic |
| Asparaginase | Elspar | ELSPAR is indicated in the therapy of patients with acute lymphocytic leukemia. This agent is useful primarily in combination with other chemotherapeutic agents in the induction of remissions of the disease in pediatric patients. | Merck & Co, Inc |
| Bevacizumab | Avastin | For the treatment of metastatic colorectal cancer | Genentech |
| Bexarotene capsules | Targretin | For the treatment by oral capsule of cutaneous manifestations of cutaneous T-cell lymphoma in patients who are refractory to at least one prior systemic therapy. | Ligand Pharmaceuticals |
| Bexarotene gel | Targretin | For the topical treatment of cutaneous manifestations of cutaneous T-cell lymphoma in patients who are refractory to at least one prior systemic therapy. | Ligand Pharmaceuticals |
| Bleomycin | Blenoxane | Palliative agent for the management of the following neoplasms: Squamous Cell Carcinoma (head and neck including mouth, tongue, tonsil, nasopharynx, oropharynx, sinus, palate, lip, buccal mucosa, gingivae, epiglottis, skin, larynx, penis, cervix, and vulva. Lymphomas (Hodgkin's Disease, non-Hodgkin's lymphoma). Testicular Carcinoma (Embryonal cell, choriocarcinoma, and teratocarcinoma). | Bristol-Myers Squibb |
| Bleomycin | Blenoxane | Sclerosing agent for the treatment of malignant pleural effusion (MPE) and prevention of recurrent pleural effusions. | Bristol-Myers Squibb |
| Busulfan intravenous | Busulfex | Use in combination with cyclophosphamide as conditioning regimen prior to allogeneic hematopoietic progenitor cell transplantation for chronic myelogenous leukemia. | Orphan Medical, Inc. |
| Busulfan oral | Myleran | Palliative therapy for Chronic Myelogenous Leukemia - | GlaxoSmithKline |
| Calusterone | Methosarb | Synthetic androgen for the treatment of androgen sensitive cancers | Pharmacia & Upjohn Company |
| Capecitabine | Xeloda | Treatment of metastatic breast cancer resistant to both paclitaxel and an anthracycline containing chemotherapy regimen or resistant to paclitaxel and for whom further anthracycline therapy may be contraindicated, e.g., patients who have received cumulative doses of 400 mg/m2 of doxorubicin or doxorubicin equivalents | Roche |
| Capecitabine | Xeloda | Initial therapy of patients with metastatic colorectal carcinoma when treatment with fluoropyrimidine therapy alone is preferred. Combination chemotherapy has shown a survival benefit compared to 5-FU/LV alone. A survival benefit over 5_FU/LV has not been demonstrated with Xeloda monotherapy. | Roche |
| Capecitabine | Xeloda | Treatment in combination with docetaxel of patients with metastatic breast cancer after failure of prior anthracycline containing chemotherapy | Roche |

TABLE 4-continued

Approved oncology drugs and indications

| Generic | Trade Name | Indication | Company |
|---|---|---|---|
| Carboplatin | Paraplatin | Palliative treatment of patients with ovarian carcinoma recurrent after prior chemotherapy, including patients who have been previously treated with cisplatin. | Bristol-Myers Squibb |
| Carboplatin | Paraplatin | Initial chemotherapy of advanced ovarian carcinoma in combination with other approved chemotherapeutic agents. | Bristol-Myers Squibb |
| Carmustine | BCNU, BiCNU | Palliative therapy as a single agent or in established combination therapy with other approved chemotherapeutic agents in the following: Brain tumors (glioblastoma, brainstem glioma, medulloblastoma, astrocytoma, ependymoma, and metastatic brain tumors); Multiple myeloma; Hodgkin's Disease; and Non-Hodgkin's lymphomas. | Bristol-Myers Squibb |
| Carmustine with Polifeprosan 20 Implant | Giladel Wafer | For use in addition to surgery to prolong survival in patients with recurrent glioblastoma multiforme who qualify for surgery. | Guilford Pharmaceuticals Inc. |
| Celecoxib | Celebrex | Reduction of polyp number in patients with the rare genetic disorder of familial adenomatous polyposis. | Searle |
| Cetuximab | Erbitux | For the treatement of EGFR expressing metastatic colorectal cancer | |
| Chlorambucil | Leukeran | Chronic Lymphocytic Leukemia-palliative therapy | GlaxoSmithKline |
| Chlorambucil | Leukeran | Treatment for CLL or indolent NHL. | GlaxoSmithKline |
| Cinacalchet | Sensipar | For the treatment of secondary hypparathyroidism | Amgen |
| Cisplatin | Platinol | Metastatic testicular-in established combination therapy with other approved chemotherapeutic agents in patients with metastatic testicular tumors whoc have already received appropriate surgical and/or radiotherapeutic procedures. An established combination therapy consists of Platinol, Blenoxane and Velbam. | Bristol-Myers Squibb |
| Cisplatin | Platinol | Metastatic ovarian tumors - in established combination therapy with other approved chemotherapeutic agents: Ovarian-in established combination therapy with other approved chemotherapeutic agents in patients with metastatic ovarian tumors who have already received appropriate surgical and/or radiotherapeutic procedures. An established combination consists of Platinol and Adriamycin. Platinol, as a single agent, is indicated as secondary therapy in patients with metastatic ovarian tumors refractory to standard chemotherapy who have not previously received Platinol therapy. | Bristol-Myers Squibb |
| Cisplatin | Platinol | Transitional cell bladder cancer which is no longer amenable to local treatments such as surgery and/or radiotherapy. | Bristol-Myers Squibb |
| Cladribine | Leustatin, 2-CdA | Treatment of active hairy cell leukemia. | R. W. Johnson Pharmaceutical Research Institute |
| Clofarabine | Clolar | Treatment for acute lymphblastic leukemia | Genzyme |
| Cyclophosphamide | Cytoxan, Neosar | Treatment for ovary, breast, bladder and CLL. | Bristol-Myers Squibb |
| Cytarabine | Cytosar-U | Treatment for AML | Pharmacia & Upjohn Company |
| Cytarabine Liposomal | DepoCyt | Intrathecal therapy of lymphomatous meningitis | Skye Pharmaceuticals |
| Dacarbazine | DTIC-Dome | Treatment for melanoma and Hodgkins lymphoma | Bayer |
| Dactinomycin, actinomycin D | Cosmegan | Treatment for pediatric leukemias | Merck |
| Darbepoetin alfa | Aranesp | Treatment of anemia associated with chronic renal failure. | Amgen, Inc. |
| Darbepoetin alfa | Aranesp | Aranesp is indicated for the treatment of anemia in patients with non-myeloid malignancies where anemia is due to the | Amgen, Inc. |

TABLE 4-continued

Approved oncology drugs and indications

| Generic | Trade Name | Indication | Company |
|---|---|---|---|
| | | effect of concomitantly administered chemotherapy. | |
| Daunorubicin liposomal | DanuoXome | First line cytotoxic therapy for advanced, HIV related Kaposi's sarcoma. | Nexstar, Inc. |
| Daunorubicin, daunomycin | Daunorubicin | Leukemia/myelogenous/monocytic/erythroid of adults/remission induction in acute lymphocytic leukemia of children and adults. | Bedford Labs |
| Daunorubicin, daunomycin | Cerubidine | In combination with approved anticancer drugs for induction of remission in adult ALL. | Wyeth Ayerst |
| Danileukin diftitox | Ontak | Treatment of patients with persistent or recurrent cutaneous T-cell lymphoma whose malignant cells express the CD25 component of the IL-2 receptor | Seragen, Inc. |
| Dexrazoxane | Zinecard | Prevention of cardiomyopathy associated with doxorubicin administration | Pharmacia & Upjohn Company |
| Dexrazoxane | Zinecard | Used for reducing the incidence and severity of cardiomyopathy associated with doxorubicin administration in women with metastatic breast cancer who have received a cumulative doxorubicin dose of 300 mg/m2 and who will continue to receive doxorubicin therapy to maintain tumor control. | Pharmacia & Upjohn Company |
| Docetaxel | Taxotere | Treatment of patients with locally advanced or metastatic breast cancer who have progressed during anthracycline-based therapy or have relapsed during anthracycline-based adjuvant therapy. | Aventis Pharmaceutical |
| Docetaxel | Taxotere | For the treatment of locally advanced or metastatic breast cancer which has progressed during anthracycline-based treatment or relapsed during anthracycline-based adjuvant therapy. | Aventis Pharmaceutical |
| Docetaxel | Taxotera | For locally advanced or metastatic non-small cell lung cancer after failure of prior platinum-based chemotherapy. | Aventis Pharmaceutical |
| Docetaxel | Taxotere | | Aventis Pharmaceutical |
| Docetaxel | Taxotere | Used in combination with cisplatin for the treatment of patients with unresectable, locally advanced or metastatic non-small cell lung cancer who have not previously received chemotherapy for this condition. | Aventis Pharmaceutical |
| Doxorubicin | Adriamycin PFS Injection intravenous injection | Antibiotic, antitumor agent. | Pharmacia & Upjohn Company |
| Doxorubicin liposomal | Doxil | Treatment of AIDS-related Kaposi's sarcoma in patients with disease that has progressed on prior combination chemotherapy or in patients who are intolerant to such therapy. | Sequus Pharmaceuticals, Inc. |
| Doxorubicin liposomal | Doxil | Treatment of metastatic carcinoma of the ovary in patient with disease that is refractory to both paclitaxel and platinum based regimens | Sequus Pharmaceuticals, Inc. |
| Dromostanolone Propionate | Dromostanolone | Sythetic androgen for use in androgen sensitve cancers | Eli Lilly |
| Elliott's B Solution | Elliott's B Solution | Diluent for the intrathecal administration of methotrexate sodium and cytarabine for the prevention or treatment of meningeal leukemia or lymphocytic lymphoma. | Orphan Medical, Inc. |
| Epoetin alfa/beta | Epogen | EPOGEN is indicated for the treatment of anemia. | Amgen, Inc. |
| Erlotinib | Tarceva | For the treatment of advanced metatstaic non-small cell lung cancer | OSI Pharmaceuticals |
| Estramustine | Emcyt | Palliation of prostate cancer | Pharmacia & Upjohn Company |
| Etoposide phosphate | Etopophos | Management of refractory testicular tumors, in combination with other approved chemotherapeutic agents. | Bristol-Myers Squibb |
| Etoposide | Etopophos | Management of small cell lung cancer, first- | Bristol-Myers |

TABLE 4-continued

Approved oncology drugs and indications

| Generic | Trade Name | Indication | Company |
|---|---|---|---|
| phosphate | | line, in combination with other approved chemotherapeutic agents. | Squibb |
| Etoposide phosphate | Etopophos | Management of refractory testicular tumors and small cell lung cancer. | Bristol-Myers Squibb |
| Etoposide, VP-16 | Vepesid | Refractory testicular tumors-in combination therapy with other approved chemotherapeutic agents in patients with refractory testicular tumors who have already received appropriate surgical, chemotherapeutic and radiotherapeutic therapy. | Bristol-Myers Squibb |
| etoposide, VP-16 | VePesid | In combination with other approved chemotherapeutic agents as first line treatment in patients with small cell lung cancer. | Bristol-Myers Squibb |
| Etoposide, VP-16 | Vepesid | In combination with other approved chemotherapeutic agents as first line treatment in patients with small cell lung cancer. | Bristol-Myers Squibb |
| Exemestane | Aromasin | Treatment of advance breast cancer in postmenopausal women whose disease has progressed following tamoxifen therapy. | Pharmacia & Upjohn Company |
| Filgrastim | Neupogen | NEUPOGEN is indicated for reducing the time to neutrophil recovery and the duration of fever, following induction or consolidation hemotherapy treatment of adults with AML. | Amgen, Inc. |
| Floxuridine (intraarterial) | FUDR | An analog for 5-flurouracil. FUDR has been approved in the directed treatment of liver metastases using hepatic arterial infusion. | Roche |
| Fludarabine | Fludara | Palliative treatment of patients with B-cell lymphocytic leukemia (CLL) who have not responded or have progressed during treatment with at least one standard alkylating agent containing regimen. | Berlex Laboratories Inc. |
| Fluorouracil, 5-FU | Adrucil | Prolong survival in combination with leucovorin | ICN Puerto Rico |
| Fulvestrant | Faslodex | the treatment of hormone receptor-positive metastatic breast cancer in postmenopausal women with disease progression following antiestrogen therapy | IPR |
| Gemcitabine | Gemzar | Treatment of patients with locally advanced (nonresectable stage II or III) or metastatic (stage IV) adenocarcinoma of the pancreas. Indicated for first-line treatment and for patients previously treated with a 5-fluorouracil-containing regimen. | Eli Lilly |
| Gemcitabine | Gemzar | For use in combination with cisplatin for the first-line treatment of patients with inoperable, locally advanced (Stage IIIA or IIIB) or metastatic (Stage IV) non-small cell lung cancer. | Eli Lilly |
| Gemtuzumab ozogamicin | Mylotarg | Treatment of CD33 positive acute myeloid leukemia in patients in first relapse who are 60 years of age or older and who are not considered candidates for cytotoxic chemotherapy. | Wyeth Ayerst |
| Goserelin acetate | Zoladex implant | Palliative treatment of advanced breast cancer in pre- and perimenopausal women. | AstraZeneca Pharmaceuticals |
| Goserelin acetate | Zoladex | Used for treatement of prostate cancer | AstraZeneca Pharmaceuticals |
| Hydroxyurea | Hydrea | Decrease need for transfusions in sickle cell anemia | Bristol-Myers Squibb |
| Ibritumomab tiuxetan | Zevalin | Treatment of patients with relapsed or refractory low-grade, follicular, or transformed B-cell non-Hodgkin's lymphoma, including patients with Rituximab refractory follicular non-Hodgkin's lymphoma. | IDEC Pharmaceuticals Corp. |
| Idarubicin | Idamycin | For use in combination with other approved antileukemic drugs for the treatment of acute myeloid leukemia (AML) in adults. | Adria Laboratories |
| Idarubicin | Idamycin | In combination with other approved antileukemic drugs for the treatment of acute non-lymphocytic leukemia in adults. | Pharmacia & Upjohn Company |

TABLE 4-continued

Approved oncology drugs and indications

| Generic | Trade Name | Indication | Company |
|---|---|---|---|
| Ifosfamide | IFEX | Third line chemotherapy of germ cell testicular cancer when used in combination with certain other approved antineoplastic agents. | Bristol-Myers Squibb |
| Imatinib mesylate | Gleevec | Initial therapy of chronic myelogenous leukemia | Novartis |
| Imatrinib mesylate | Gleevac | Treatment of metastatic or unresectable malignant gastrointestinal stromal tumors | Novartis |
| Imatinib mesylate | Gleevec | Initial treatment of newly diagnosed Ph+ chronic myelogenous leukemia (CML). | Novartis |
| Interferon alfa-2a | Roferon-A | Treatment of chronic hepatitis C, hairy cell leukemia and AIDS-related Kaposi's sarcoma in adult patients and for chronic phase, Philadelphia chromosome (Ph) positive chronic myelogenous leukemia (CML) patients who are minimally pretreated (within 1 year of diagnosis). | Hoffmann-La Roche Inc. |
| Interferon alfa-2b | Intron A | Interferon alfa-2b, recombinant for injection is indicated as adjuvant to surgical treatment in patients 18 years of age or older with malignant melanoma who are free of disease but at high risk for systemic recurrence within 56 days of surgery. Interferon alfa-2b, recombinant for Injection is indicated for the initial treatment of clinically aggressive follicular Non-Hodgkin's Lymphoma in conjunction with anthracycline-containing combination chemotherapy in patients 18 years of age or older. Interferon alfa-2b, recombinant for Injection is indicated for intralesional treatment of selected patients 18 years of age or older with condylomata acuminata involving external surfaces of the genital and perianal areas. Interferon alfa-2b, recombinant for Injection is indicated for the treatment of patients 18 years of age or older with hairy cell leukemia. Interferon alfa-2b, recombinant for Injection is indicated for the treatment of selected patients 18 years of age or older with AIDS-Related Kaposi's Sarcoma. The likelihood of response to INTRON A therapy is greater in patients who are without systemic symptoms, who have limited lymphadenopathy and who have a relatively intact immune system as indicated by total CD4 count. | Schering Corp. |
| Irinotecan | Camptosar | Treatment of patients with metastatic carcinoma of the colon or rectum whose disease has recurred or progressed following 5-FU-based therapy. | Pharmacia & Upjohn Company |
| Letrozole | Femara | First-line treatment of postmenopausal women with hormone receptor positive or hormone receptor unknown locally advanced or metastatic breast cancer. | Novartis |
| Letrozole | Femara | Used for treatment of post-menopausal women with early stage breast cancer | Novartis |
| Leucovorin | Wellcovorin, Leucovorin | Leucovorin calcium is indicated fro use in combination with 5-fluorouracil to prolong survival in the palliative treatment of patients with advanced colorectal cancer. | Immunex Corporation |
| Leucovorin | Leucovorin | In combination with fluorouracil to prolong survival in the palliative treatment of patients with advanced colorectal cancer. | Lederle laboratories |
| Levamisole | Ergamisol | Adjuvant treatment in combination with 5-fluorouracil after surgical resection in patients with Dukes' Stage C colon cancer. | Janssen Research Foundation |
| Lomustine, CCNU | CeeNu | An alkylating agent used for the treatment of brain cancer and NHL. | Bristol-Myers Squibb |

TABLE 4-continued

Approved oncology drugs and indications

| Generic | Trade Name | Indication | Company |
|---|---|---|---|
| Mechlorethamine, nitrogen mustard | Mustargen | A nitrogen mustard used in the treatment of lymphoma. | Merck |
| Megestrol acetate | Megace | A synthetic progesterone used for the treatment of estrogen sensitive cancers. | Bristol-Myers Squibb |
| Melphalan, L-PAM | Alkeran | Systemic administration for palliative treatment of patients with multiple myeloma for whom oral therapy is not appropriate. | GlaxoSmithKline |
| Mercaptopurine, 6-MP | Purinethol | Purinethol is indicated for remission induction and maintenance therapy of acute lymphatic leukemia. | GlaxoSmithKline |
| Mesna | Mesnex | Prevention of ifosfamide-induced hemorrhagic cystitis | Asta Medica |
| Methotrexate | Methotrexate | Is used to treat cancer of the breast, head and neck, lung, blood, bone, and lymph, and tumors in the uterus. | Laderle Laboratories |
| Methoxsalen | Uvadex | For the use of UVADEX with the UVAR Photopheresis System in the palliative treatment of the skin manifestations of cutaneous T-cell lymphoma (CTCL) that is unresponsive to other forms of treatment. | Therakos |
| Mitromycin C | Mitozytrex | Therapy of disseminated adenocarcinoma of the stomach or pancreas in proven combinations with other approved chemotherapeutic agents and as palliative treatment when other modalities have failed. | Supergen |
| Mitotane | Lysodren | Used for the treatment of adrenal cancers. | Bristol-Myers Squibb |
| Mitoxantrone | Novantrone | For use in combination with corticosteroids as initial chemotherapy for the treatment of patients with pain related to advanced hormone-refractory prostate cancer. | Immunex Corporation |
| Mitoxantrone | Novantrone | For use with other approved drugs in the initial therapy for acute nonlymphocytic leukemia (ANLL) in adults. | Laderle Laboratories |
| Nandrolone phenpropionate | Durabolin-509 | It is indicated as a treatment for palliation of inoperable metastatic breast cancer in postmenopausal women. | Organon |
| Nofetumomab | Verluma | Verluma is a monoclonal antibody Fab fragment linked to $^{99m}$Tc. Verluma identifies advanced-stage disease in patients with small-cell lung cancer (SCLC). | Boehringer Ingelheim Pharma KG (formerly Dr. Karl Thomae GmbH) |
| Oprelvekin | Neumega | Neumega is indicated for the prevention of severe thrombocytopenia and the reduction of the need for platelet transfusions following myelosuppressive chemotherapy in adult patients with nonmyeloid malignancies who are at high risk of severe thrombocytopenia. | Genetics Institute, Inc. |
| Oxaliplatin | Eloxatin | Used) in combination with infusional 5-FU/LV, is indicated for the treatment of patients with metastatic carcinoma of the colon or rectum whose disease has recurred or progressed during or within 6 months of completion of first line therapy with the combination of bolus 5-FU/LV and irinotecan. | Sanofi Synthelabo |
| Paclitaxel | Paxene | Treatment of advanced AIDS-related Kaposi's sarcoma after failure of first line or subsequent systemic chemotherapy | Baker Norton Pharmaceuticals, Inc. |
| Paclitaxel | Taxol | Treatment of patients with metastatic carcinoma of the ovary after failure of first-line or subsequent chemotherapy. Treatment of breast cancer after failure of combination chemotherapy for metastatic disease or relapse within 6 months of adjuvant chemotherapy. Prior therapy should have included an anthracycline unless clinically contraindicated. New dosing regimen for patients who have failed initial or subsequent chemotherapy for metastatic carcinoma of the ovary | Bristol-Myers Squibb |

TABLE 4-continued

Approved oncology drugs and indications

| Generic | Trade Name | Indication | Company |
|---|---|---|---|
| | | Second line therapy for AIDS related Kaposi's sarcoma. | |
| | | For first-line therapy for the treatment of advanced carcinoma of the ovary in combination with cisplatin. | |
| | | For use in combination with cisplatin, for the first-line treatment of non-small cell lung cancer in patients who are not candidates for potentially curative surgery and/or radiation therapy. | |
| | | For the adjuvant treatment of node-positive breast cancer administered sequentially to standard doxorubicin-containing combination therapy. | |
| | | First line ovarian cancer with 3 hour infusion. | |
| Pamidronate | Aredia | Treatment of osteolytic bone metastases of breast cancer in conjunction with standard antineoplastic therapy. | Novartis |
| Pegademase | Adagen (Pegademase Bovine) | Enzyme replacement therapy for patients with severe combined immunodeficiency asa result of adenosine deaminase deficiency. | Enzon |
| Pegaspargase | Oncaspar | PEG asparginase used in the treatment of ALL. | Enzon, Inc. |
| Pegfilgrastim | Neulasta | Neulasta is indicated to decrease the incidence of infection, as manifested by febrile neutropenia, in patients with non-myeloid malignancies receiving myelosuppressive anti-cancer drugs associated with a clinically significant incidence of febrile neutropenia. | Amgen, Inc. |
| Pemetrexed | Alimta | Treatment of malignant pleural mesothelioma | Eli Lilly |
| Pentostatin | Nipent | Single agent treatment for adult patients with alpha interferon refractory hairy cell leukemia. | Parke-Davis Pharmaceutical Co. |
| Pipobroman | Vercyte | Used in the treatment of CRC. | Abbott Labs |
| Plicamycin, mithramycin | Mithracin | Used in the treatment of testicular cancer. | Pfizer Labs |
| Porfimer sodium | Photofrin | For use in photodynamic therapy (PDT) for palliation of patients with completely obstructing esophageal cancer, or patients with partially obstructing esophageal cancer who cannot be satisfactorily treated with ND-YAG laser therapy. | QLT Phototherapeutics Inc. |
| | | For use in photodynamic therapy for treatment of microinvasive endobronchial nonsmall cell lung cancer in patients for whom surgery and radiotherapy are not indicated. | |
| | | For use in photodynamic therapy (PDT) for reduction of obstruction and palliation of symptoms in patients with completely or partially obstructing endobroncial nonsmall cell lung cancer (NSCLC). | |
| Procarbazine | Matulane | One component of the MOPP regime. | Sigma Tau Pharms |
| Rasburicase | Elitek | ELITEK is indicated for the initial management of plasma uric acid levels in pediatric patients with leukemia, lymphoma, and solid tumor malignancies who are receiving anti-cancer therapy expected to result in tumor lysis and subsequent elevation of plasma uric acid. | Sanofi-Synthelabo, Inc. |
| Rituximab | Rituxan | Used in the treatment NHL. | Genentech, Inc. |
| Sargramostim | Prokine | GM-CSF used in the treatment of NHL, Hodgkins Leukemia and acute lymphoblastic leukemia. | Immunex Corp. |
| Sorafenib | Nexavar | Treatment of RCC | Bayer/Onyx |
| Streptozocin | Zanosar | Antineoplastic agent. | Pharmacia & Upjohn Company |
| Talc | Slerosol | For the prevention of the recurrence of malignant pleural effusion in symptomatic patients. | Bryan |

TABLE 4-continued

Approved oncology drugs and indications

| Generic | Trade Name | Indication | Company |
|---|---|---|---|
| Tamoxifen | Nolvadex | As a single agent to delay breast cancer recurrence following total mastectomy and axillary dissection in postmenopausal women with breast cancer (T1-3, N1, M0). For use in premenopausal women with metastatic breast cancer as an alternative to oophorectomy or ovarian irradiation. For use in women with axillary node-negative breast cancer adjuvant therapy. Metastatic breast cancer in men. | AstraZeneca Pharmaceuticals |
| Temozolomide | Temodar | For treatment of adult patients with refractory anaplastic astrocytoma, i.e., patients at first relapse with disease progression on a nitrosourea and procarbazine containing regimen | Scherine |
| Teniposide, VM-26 | Vumon | In combination with other approved anticancer agents for induction therapy in patients with refractory childhood acute lymphoblastic leukemia (all). | Bristol-Myers Squibb |
| Testolactone | Teslac | Used in the treatment of breast cancer. | Bristol-Myers Squibb |
| Thioguanine, 6-TG | Thioguanine | Antimetabolite used in the treatment of AML, CML, CLL. | GlaxoSmithKline |
| Thiotepa | Thioplex | Thiotepa is a cytotoxic agent of the polyfunctional type, related chemically and pharmacologically to nitrogen mustard. Thiotepa has been tried with varying results in the palliation of a wide variety of neoplastic diseases. However, the most consistent results have been seen in the following tumors: 1. Adenocarcinoma of the breast. 2. Adenocarcinoma of the ovary. 3. For controlling intracavitary effusions secondary to diffuse or localized neoplastic diseases of various serosal cavities. 4. For the treatment of superficial papillary carcinoma of the urinary bladder. While now largely superseded by other treatments, thiotepa has been effective against other lymphomas, such as lymphosarcoma and Hodgkin's disease. | Immunex Corporation |
| Topotecan | Hycamtin | Treatment of patients with metastatic carcinoma of the ovary after failure of initial or subsequent chemotherapy. Treatment of small cell lung cancer sensitive disease after failure of first-line chemotherapy. | GlaxoSmithKline |
| Toremifene | Fareston | Treatment of advanced breast cancer in postmenopausal women. | Chiron Corp. |
| Tositumomab | Bexxar | Accel. Approv. (clinical benefit not established) Treatment of patients with CD20 positive, follicular, non-Hodgkin's lymphoma, with and without transformation, whose disease is refractory to Rituximab and has relapsed following chemotherapy | Corixa Corporation |
| Trastuzumab | Herceptin | HERCEPTIN as a single agent is indicated for the treatment of patients with metastatic breast cancer whose tumors overexpress the HER2 protein and who have received one or more chemotherapy regimens for their metastatic disease. Herceptin in combination with paclitaxel is indicated for treatment of patients with metastatic breast cancer whose tumors overexpress the HER-2 protein and had not received chemotherapy for their metastatic disease | Genentech, Inc. |
| Tretinoin, ATRA | Vesanoid | Induction of remission in patients with acute promyelocytic leukemia (APL) who are refractory to or unable to tolerate anthracycline based cytotoxic chemotherapeutic regimens. | Roche |
| Uracil Mustard | Uracil Mustard Capsules | Used in the treatment of CML, NHL and CLL. | Roberts Labs |

TABLE 4-continued

Approved oncology drugs and indications

| Generic | Trade Name | Indication | Company |
|---|---|---|---|
| Valrubicin | Valstar | For intravesical therapy of BCG-refractory carcinoma in situ (CIS) of the urinary bladder in patients for whom immediate cystectomy would be associated with unacceptable morbidity or mortality. | Anthra → Medeva |
| Vinblastine | Velban | Vinca alkyloid used in the treatment of many types of cancer. | Eli Lilly |
| Vincristine | Oncovin | Vinca alkyloid used in the treatment of many types of cancer. | Eli Lilly |
| Vinorelbine | Navelbine | Single agent or in combination with cisplatin for the first-line treatment of ambulatory patients with unresectable, advanced non-small cell lung cancer (NSCLC). | GlaxoSmithKline |
| Vinorelbine | Navelbine | Navelbine is indicated as a single agent or in combination with cisplatin for the first-line treatment of ambulatory patients with unreseactable, advanced non-small cell lung cancer (NSCLC). In patients with Stage IV NSCLC, Navelbine is indicated as a single agent or in combination with cisplatin. In Stage III NSCLC, Navelbine is indicated in combination with cisplatin. | GlaxoSmithKline |
| Zoledronate | Zometa | Used in the treatment of patients with multiple myeloma and patients with documented bone metastases from solid tumors, in conjunction with standard antineoplastic therapy. Prostate cancer should have progressed after treatment with at least one hormonal therapy | Novartis |

TABLE 5

Advanced antiangiogenic compounds in the clinic

| Product | Mechanism of Action | Clinical Phase | Marketing Co. |
|---|---|---|---|
| Sorafenib | Inhibits VEGFR2, VEGFR3, Raf Kinase and PDGFRa | Pre-registration | Bayer/Onyx |
| Sutent | Inhibits VEGFR1, VEGFR2, VEGFR3, PDGFR, CSF-1, Flt-3, and C-Kit | Pre-registration | Pfizer |
| Thalomid | Antiangiogenic compound of unknown mechanism of action | III | Celgene |
| Revlimid | Antiangiogenic compound of unknown mechanism of action | III | Celgene |
| Vatalanib | Inhibits VEGFR1, VEGFR2, VEGFR3, PDGFR, and C-Kit | III | Novartis/Schering |
| ZD-6474 | Inhibits VEGFR2, and EGFR | III | AstraZeneca |
| Neovastat | Liquid extract derived from Shark cartilage that blocks VEGFR2 and inhibits MMP-1, MMP-9 and MMP-12 | III | AEterna |
| GSK-786024 | Inihibits VEGFR1, VEGFR2 and VEGFR3 | II | GlaxoSmithKline |
| AEE-788 | Inhibits EGFR, HER2 and VEGFR | II | Novartis |
| AG-13736 | Inihibits VEGFR1, VEGFR2 and PDGF | II | Pfizer |
| AMG706 | Inhibits VEGFR1, VEGFR2, VEGFR3, PDGFR, Ret, and C-Kit | II | Amgen |
| AZD-2171 | Inhibits VEGFR1, VEGFR2, VEGFR3, and EGFR | II | AstraZeneca |
| BIBF-1120 | Inhibits VEGFR, FGFR, and PDGFR | II | Boehringer Ingelheim |
| CP-547,632 | Inhibits VEGFR1 and VEGFR2 | II | Pfizer/OSI Pharma |
| Midostaurin | Inhibits FLT3 Kinase, VEGFR2, and various PKC kinases | II | Novartis |
| SU-6668 | Inhibits VEGFR1, PDGF and FGFR | II | Pfizer/Taiho |
| CDP-791 | Inhibits VEFR2 | II | UCB/Imclone Systems |
| PI-88 | Inhibits heparinase, binds to VEGF, FGF1, FGF2 and stimulates the release of TFP1 | II | Progen |
| PCK-3145 | Binds to laminin receptor and VEGFR2, and downregulates MMP9 expression | II | Procyon Biopharma |

TABLE 5-continued

Advanced antiangiogenic compounds in the clinic

| Product | Mechanism of Action | Clinical Phase | Marketing Co. |
| --- | --- | --- | --- |
| Atiprimod | Inhibits IL6 and VEGF secretion | II | Callisto Pharmaceuticals |
| A6 | Eight amino acid, uPA derived peptide that inhibits the activity of uPAR | II | Angstrom Pharmaceuticals |
| Angiostatin | Peptidic angiostatin inhibitor that is a fragment of the clotting factor plasminogen | II | Alchemgen Therapeutics |
| Cilengitide | Cyclic Peptide that is an alpha-v integrin antagonist | II | Merck |
| Enodstatin | Peptidic angiogenesis inhibitor based Collagen XVIII fragment | II | Alchemgen Therapeutics |
| rPF4 | Recombinant form of Platlet Factor 4 | II | Repligen Clinical Partners |
| Vitakin | Antibody antagonist of alpha-v-beta-3 ingrins | II | MedImmune |
| Volociximab | Antibody antagonist of alpha-v-beta-3 ingrins | II | Biogen Idec/Protein Design Labs |
| 2-methoxyestradiol | Estrogen metabolite that inhibits HIF1a translation | II | EntreMed |
| AP-23573 | Inhibits mTOR | II | Ariad Pharmaceuticals |
| Cancertinib | TKI that inhibits EGFR | II | Pfizer |
| Actimid | Thalomid derivative | II | Celgene |
| Combretastatin A4 prodrug | Tubulin destabilizing agent | II | Oxigene |
| Endo Tag 1 | Antineovasculature agent, formation of paclitaxel encapsulated in positively charged liposomes | II | Medigene |
| Enzastaurin | Protein kinase C-beta inhibitor | II | Eli Lilly |
| Ceflatonin | Induces apoptosis | II | ChemGenex Pharmaceuticals |
| Silipide | A complex of silybin and phosphatidiylcholine | II | Indena |
| INGN-241 | Gene therapy based upon the mda-7 gene coding for IL-24 | II | Introgen Therapeutics |
| OSI-461 | Inhibits cGMP phospodiesterase | II | OSI Pharmaceuticals |
| Patupilone | A non-taxane microtubule stabilizing agent | II | Novartis |
| Squalamine | Blocks multiple angiogenic cofactors | II | Genaera |
| Tacedinaline | Cystostatic histone deacetylation inhibitor | II | Pfizer |
| UCN-01 | Inhibitor of serine-threonine kinases, including protein kinase C | II | NCI |
| UK-356202 | Urokinase-like plasminogen activator | II | Pfizer |

TABLE 6

Combination therapies for use in oncology

| | |
| --- | --- |
| ABVD | Doxorubcin, Bleomycin, Vinblastine, and Dacarbazine |
| AC | Doxorubicin and Cyclophosphamide |
| BEP | Bleomycin, Etoposide and Cisplatin |
| CAF | Cyclosphosphamide, Doxorubicin and 5-Fluorouracil (5FU) |
| CAV | Cyclophosphamide, Doxorubicin, Vincristine |
| Carboplatin-Etoposide | Carboplatin and Etoposide |
| ChlVPP | Chlorambucil, Vinblastine, Procarbazine, and Prednisolone |
| CHOP | Cyclophosphamide, Doxorubicin, Vincristine, and Prednisolone |
| CHOP-R | Cyclophosphamide, Doxorubicin, Vincristine, Prednisolone, and Rituximab |
| CMF | Cyclophosphamide, Methotrexate and 5FU |
| CVAMP | Cyclophosphamide, Doxorubicin, Vincristine, and Methyl-prednisolone |
| De Gramont | 5FU and leucovorin |
| DHAP | Dexamethasone, Cytarabine, and Cisplatin |
| DAHP-R | Dexamethasone, Cytarabine, Cisplatin and Rituximab |
| Doxorubicin-Ifostamide | Doxorubicin and Ifostamide |
| EC | Epirubicin and Cyclophosphamide |
| ECF | Epirubicin, Cyclophosphamide, and 5FU |
| ECMF | Epirubicin, Cyclophosphamide, Methotrexate, and 5FU |
| EEX | Epirubicin, Oxaliplatin, and Capecitabine |
| ECX | Epirubicin, Cisplatin, and Capecitabine |
| ESHAP | Etoposide, Methyl-prednisolone, Cytarabine and Cisplatin |
| FEC | 5FU, Epirubicin, and Cyclophosphamide |
| Gemcarbo | Gemcitabine and Carboplatin |
| Gemcitabine-Cisplatin | Gemcitabine and Cisplatin |
| Irinotecan-De Gramont | Irinotecan, 5FU and Leucovorin |
| MIC | Mitomycin, Ifosamide and Cisplatine |
| MM | Methotrexate and Mitoxantrone |
| MMM | Methotrexate, Mitomycin, and Mitoxantrone |
| MVP | Mitomycin, Vinblastine and Cisplatin |
| FOLFOX | 5FU, Oxilaplatin and Leucovorin |
| FOLFIRI | 5FU, Leucovorin and Irinotecan |
| Paclitaxel-Carboplatin | Paclitaxel and Carboplatin |
| PmitCebo | Prednisolone, Mitoxantrone, Cyclophosphamide, Etoposide, Bleomycin and Vincristine |

TABLE 6-continued

Combination therapies for use in oncology

| | |
|---|---|
| VAD | Vincristine, Doxorubicin, and Dexamethasone |
| VAPEC-B | Vincristine, Doxorubicin, Prednisolone, Etoposide, Cyclosphosphamide, and Bleomycin |
| Vinorelabine-Cisplatin | Vinorelabine and Cisplatin |

BAMVEC Migration Assay

Endothelial cell migration is performed as described in P. J. Polverini et al., Methods Enzymol. 198:440-450 (1991). The BAMVECs (bovine adrenal microvascular endothelial cells, VEC Technologies, Rensselaer, N.Y.) are starved overnight in EBM (endothelial basal medium) containing 0.1% BSA. Cell are washed with HBSS and treated with Cellstripper™ (Mediatech, Herndon, Va.) for 10 minutes, then harvested with trypsin and resuspended in EBM with 0.1% BSA at a concentration of $1.5 \times 10^6$ cells per mL. Next, cells are added to the bottom of a modified Boyden chamber (Nucleopore Corp). The chamber is assembled, inverted, and the cells are allowed to adhere for 90 minutes. The test compounds are added to the top part of the wells and incubated 3-4 hours. Membranes are recovered, fixed, stained, and the cells migrated through the filter. The cells are counted at (100×) using 10 fields. 0.25% FBS (fetal bovine serum) (Tissue Culture Biologicals, Tulare, Calif.) is used for a positive control, and 0.1% BSA is used for a negative control. Background migration is subtracted and the data presented is a percentage of FBS-induced migration (% maximal migration).

Matrigel Plug Assay

500 μl of growth factor reduced Matrigel (BD Bioscience), containing 100 ng/ml bFGF (R&D systems), is prepared on ice and injected in the left chest area of nude mouse anesthetized with isofluorane (5 mice per group). The test compounds are dosed i.v., at 30 mg/kg twice a week. After one week, the plugs are extracted and photographed. Five plugs of the same group are aligned together and snap-frozen in one OTC compound block. Five 5 μm sections in different depths are obtained from each block using a Leica CM1850 Cryostat. The slides are immediately fixed in cold acetone for 2 minutes and air dried. CD31 immunohistochemical staining of blood vessels is carried out by using an Anti-Rat IG HRP detection kit (BD Pharmingen) and using the methods provided in the manufacturer's instruction manual. The primary CD31 antibody used is Rat IgG2a, Clone MEC13.3 (BD Pharmingen, cat# 550274,). The CD31 antibody is diluted 1:30-50. The CD31 positive area of every plug is photographed using a Qimaging Micropublisher 5.0 RTV camera coupled with a Nikon Eclipse 80i microscope (20×). ImagePro 5.1 software is used to quantify the CD31 positive area using a common macro throughout the experiment. The total CD31 positive area of five sections of each plug is calculated.

The versatility of the invention is illustrated by the following Examples, which illustrate typical embodiments of the invention and are not limiting of the claims or specification in any way.

EXAMPLES

Example 1

Synthesis of

Sar-Gly-Val-(D-alloIle)-Thr-Nva-Ile-   (SEQ ID NO:1)
Arg-Pro

Solid phase peptide synthesis of the modified peptide on a 100μ mole scale is performed using manual solid-phase synthesis, a Symphony Peptide Synthesizer and Fmoc protected Rink Amide MBHA. The following protected amino acids are sequentially added to resin: Fmoc-Pro-OH, Fmoc-Arg(Pbf)-OH, Fmoc-Ile-OH, Fmoc-Nva-OH, Fmoc-Thr(tBu)-OH, Fmoc-(D-alloIle)-OH, Fmoc-Val-OH, Fmoc-Gly-OH, and Fmoc-Sar-OH. They are dissolved in N,N-dimethylformamide (DMF) and, according to the sequence, activated using O-benzotriazol-1-yl-N,N,N$^1$,N$^1$-tetramethyl-uronium hexafluorophosphate (HBTU) and Diisopropylethylamine (DIEA). Removal of the Fmoc protecting group is achieved using a solution of 20% (V/V) piperidine in N,N-dimethylformamide (DMF) for 20 minutes. Between every coupling, the resin is washed 3 times with N,N-dimethylformamide (DMF) and 3 times with isopropanol. The peptide is cleaved from the resin using 85% TFA/5% TIS/5% thioanisole and 5% phenol, followed by precipitation by dry-ice cold $Et_2O$. The product is purified by a reverse phase HPLC using a $C_{18}$ column.

Example 2

Synthesis of

Sar-Gly-Val-(D-alloIle)-Thr-Nva-Lys-   (SEQ ID NO:3)
Arg-Pro

Solid phase peptide synthesis of the modified peptide on a 100μ mole scale is performed using manual solid-phase synthesis, a Symphony Peptide Synthesizer and Fmoc protected Rink Amide MBHA. The following protected amino acids are sequentially added to resin: Fmoc-Pro-OH, Fmoc-Arg(Pbf)-OH, Fmoc-Lys(Boc)-OH, Fmoc-Nva-OH, Fmoc-Thr(tBu)-OH, Fmoc-(D-allo-Ile)-OH, Fmoc-Val-OH, Fmoc-Gly-OH, and Fmoc-Sar-OH. They are dissolved in N,N-dimethylformamide (DMF) and, according to the sequence, activated using O-benzotriazol-1-yl-N,N,N$^1$,N$^1$-tetramethyl-uronium hexafluorophosphate (HBTU) and Diisopropylethylamine (DIEA). Removal of the Fmoc protecting group is achieved using a solution of 20% (V/V) piperidine in N,N-dimethylformamide (DMF) for 20 minutes. Between every coupling, the resin is washed 3 times with N,N-dimethylformamide (DMF) and 3 times with isopropanol. The peptide is cleaved from the resin using 85% TFA/5% TIS/5% thioanisole and 5% phenol, followed by precipitation by dry-ice cold $Et_2O$. The product is purified by a reverse phase HPLC using a $C_{18}$ column.

Example 3

Synthesis of

```
Pro-Gly-Val-(D-alloIle)-Thr-Nva-Ile-  (SEQ ID NO:10)
Arg-Pro
```

Solid phase peptide synthesis of the modified peptide on a 100μ mole scale is performed using manual solid-phase synthesis, a Symphony Peptide Synthesizer and Fmoc protected Rink Amide MBHA. The following protected amino acids are sequentially added to resin: Fmoc-Pro-OH, Fmoc-Arg(Pbf)-OH, Fmoc-Ile-OH, Fmoc-Nva-OH, Fmoc-Thr(tBu)-OH, Fmoc-(D-allo-Ile)-OH, Fmoc-Val-OH, Fmoc-Gly-OH, and Fmoc-Pro-OH. They are dissolved in N,N-dimethylformamide (DMF) and, according to the sequence, activated using O-benzotriazol-1-yl-N,N,$N^1$,$N^1$-tetramethyl-uronium hexafluorophosphate (HBTU) and Diisopropylethylamine (DIEA). Removal of the Fmoc protecting group is achieved using a solution of 20% (V/V) piperidine in N,N-dimethylformamide (DMF) for 20 minutes. Between every coupling, the resin is washed 3 times with N,N-dimethylformamide (DMF) and 3 times with isopropanol. The peptide is cleaved from the resin using 85% TFA/5% TIS/5% thioanisole and 5% phenol, followed by precipitation by dry-ice cold $Et_2O$. The product is purified by a reverse phase HPLC using a $C_{18}$ column.

Example 4

Figure 12:
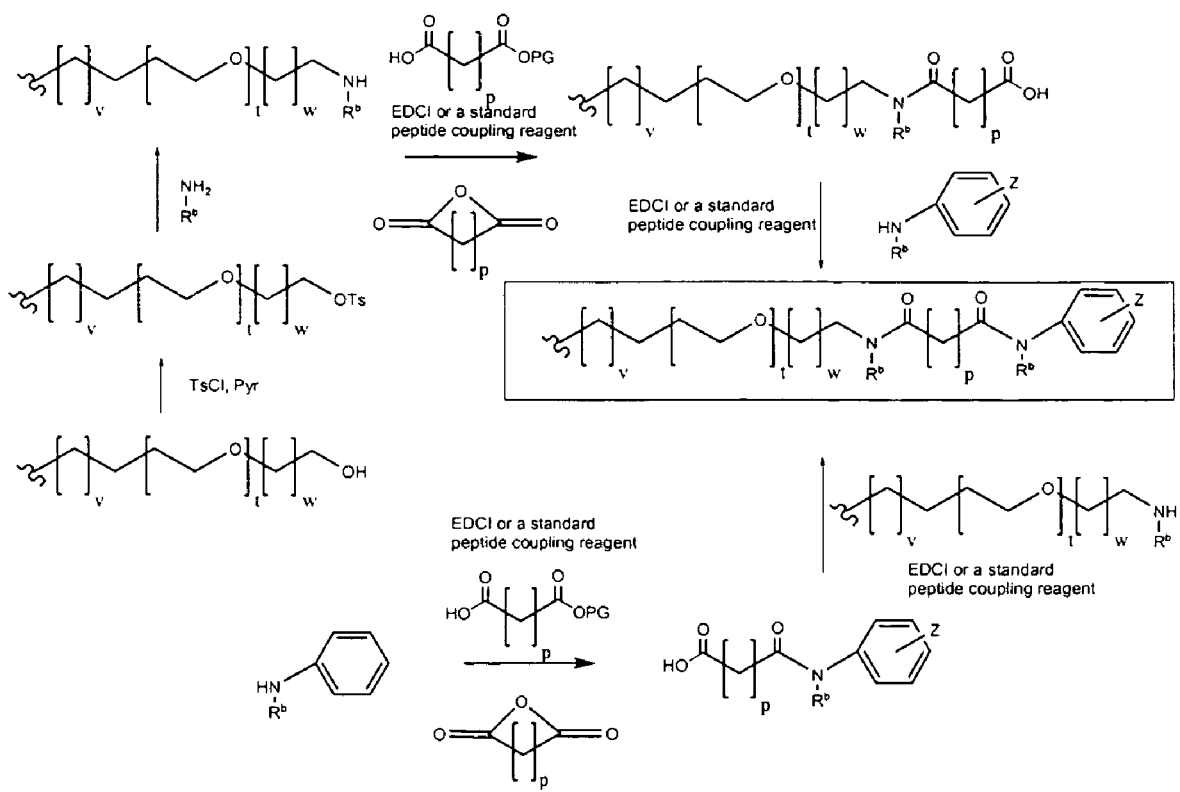

Synthesis of is provided in FIG. 12.

Example 5

Synthesis of is provided in FIG. 13.

Example 6

Synthesis of

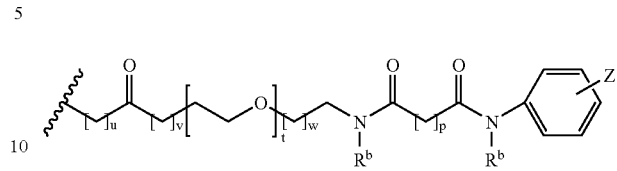

is provided in FIG. 14.

Example 7

Synthesis of is provided in FIG. 15.

Example 8

Synthesis of is provided in FIG. 16.

Example 9

Synthesis of is provided in FIG. 17.

Example 10
Synthesis of
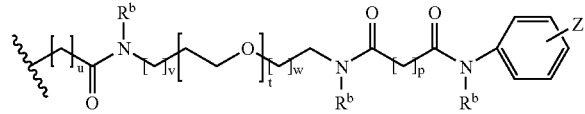
is provided in FIG. 18.
Example 11
Synthesis of
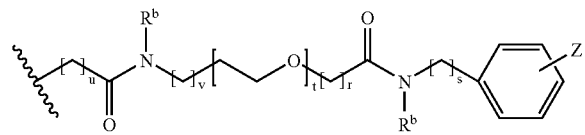
is provided in FIG. 19.
Example 12
Synthesis of
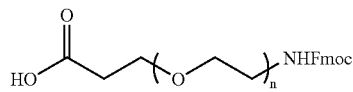
is provided in FIG. 20.
Example 13
Synthesis of
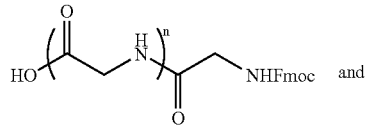
and
-continued
is provided in FIG. 21.
Example 14
Synthesis of
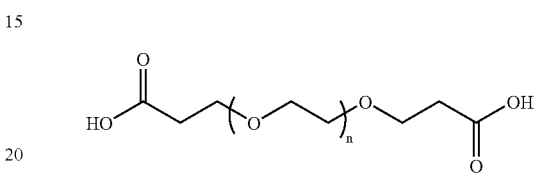
is provided in FIG. 22.
Example 15
Synthesis of
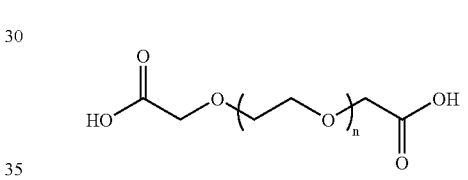
is provided in FIG. 23.
Example 16
Synthesis of
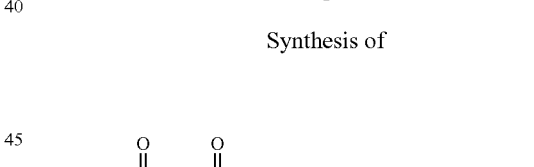
is provided in FIG. 24.
Example 17
Synthesis of
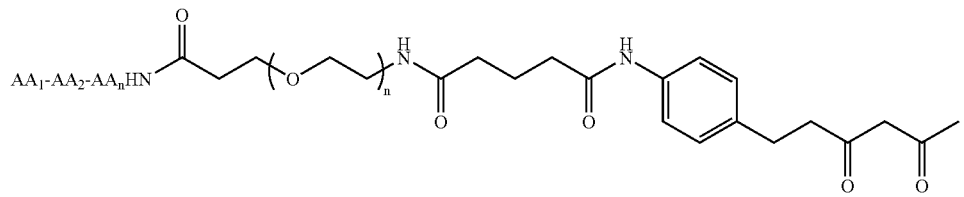

is provided in FIG. 25. While this EXAMPLE uses the compound of EXAMPLE 12, it could also sufficiently employ the compounds of EXAMPLE 13. Further, while this EXAMPLE shows linking to the N-terminus, the free acid on the left side of the compounds of EXAMPLES 12 and 13 may also be linked to any nucleophilic side chain on a peptide, such as the C, K, S, T or Y side chains. As is also shown in this EXAMPLE, the Fmoc protected amino group on the right side of the compounds of EXAMPLES 12 and 13 is used to link to the recognition group, Y, via an amide bond.

Example 18

Synthesis of

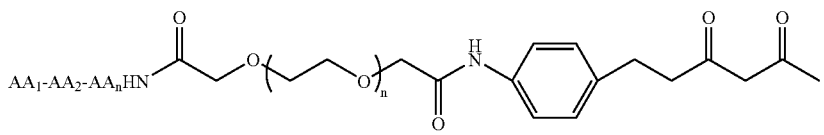

is provided in FIG. 26. While this EXAMPLE uses the compound of EXAMPLE 15, it could also sufficiently employ the compounds of EXAMPLES 14 and 16. Further, while this EXAMPLE shows linking to the N-terminus, the free acid on the left side of the compounds of EXAMPLES 14-16 may also be linked to any nucleophilic side chain on a peptide, such as the C, K, S, T or Y side chains. As is also shown in this EXAMPLE, the free acid on the right side of the compounds of EXAMPLES 14-16 is used to link to the antibody recognition group, Y, via an amide bond.

Example 19

Synthesis of

3-{2-[2-(2-{2-[2-(2-tert-Butoxycarbonyl-ethoxy)-ethoxy]-ethoxy}-ethoxy)-ethoxy]ethoxy}-propionic acid tert-butyl ester

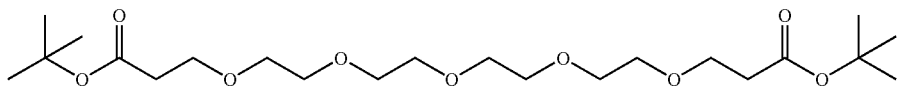

The title compound was prepared using a reported method (O. Seitz and H. Kunz, J. Org. Chem. 62:813-826 (1997)). A small piece of sodium metal was added to a solution of tetra (ethylene glycol) (47.5 g, 244 mmol) in THF (200 ml) and stirred until the sodium was dissolved completely. ʹButyl acrylate (94 g, 730 mmol) was then added and stirring continued for 2 days at RT. Another batch of ʹButyl acrylate (94 g, 730 mmol) was added and stirring continued for another 2 days. The reaction mixture was neutralized with a few drops of 1N HCl and concentrated under reduced pressure. The residue was suspended in water and extracted with ethyl acetate (3×150 ml). Combined organic layers were washed with brine and dried over sodium sulfate. Evaporation of volatiles over reduced pressure provided the crude product as colorless liquid which was purified using a silica gel column (42 g, 51%).

Example 20

Synthesis of

3-{2-[2-(2-{2-[2-(2-Carboxy-ethoxy)-ethoxy]-ethoxy}-ethoxy)-ethoxy]-ethoxy}-propionic acid

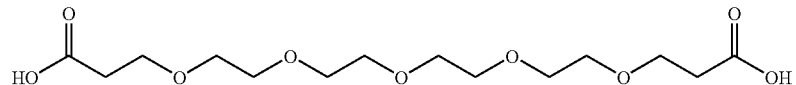

A solution of 3-{2-[2-(2-{2-[2-(2-tert-Butoxycarbonyl-ethoxy)-ethoxy]-ethoxy}-ethoxy)-ethoxy]-ethoxy}-propionic acid tert-butyl ester (6 g, 18.6 mmol) in anisole (20 ml) was cooled in an ice bath and trifluroacetic acid (65 g) was added. After 3 hrs at RT volatiles were removed under reduced pressure and the residue was partitioned between ethyl acetate (50 ml) and 5% sodium bicarbonate solution. The aqueous layer was acidified with 1 N HCl, saturated with NaCl and then extracted with ethyl acetate (3×50 ml). Combined organic layers were washed with brine and dried over sodium sulfate. Removal of volatiles under the reduced pressure provided the product as colorless liquid which solidified upon refrigeration (3.8 g, 82%).

Example 21

Synthesis of 3-(2-{2-[2-(2-{2-[2-(4-{2-[2-(2-Methyl-[1,3]diox-olan-2-ylmethyl)-[1,3]dioxolan-2-yl]-ethyl}-phenyl-carbamoyl)-ethoxy]-ethoxy}-ethoxy)-ethoxy]-ethoxy}-ethoxy)-propionic acid

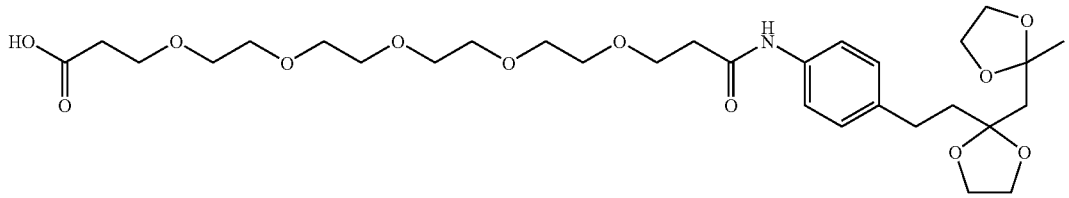

Compound from EXAMPLE 20 (0.6 g, 1.8 mmol) was dissolved in dichloromethane (10 ml) and 4-{2-[2-(2-Methyl-[1,3]dioxolan-2-ylmethyl)-[1,3]dioxolan-2-yl]-ethyl}-phenylamine (0.3 g, 1.4 mmol) followed by EDCI (0.28 g, 1.8 mmol) was added at RT. After 1 hr at RT the RM was washed with water and dried over sodium sulfate. Evaporation of volatiles and purification over silica gel column with 1 to 15% methanol in dichloromethane provided title compound as gum (0.47 g, 32%).

Example 22

Synthesis of

4-{2-[2-(2-Methyl-[1,3]dioxolan-2-ylmethyl)-[1,3]dioxolan-2-yl]-ethyl}-phenylamine

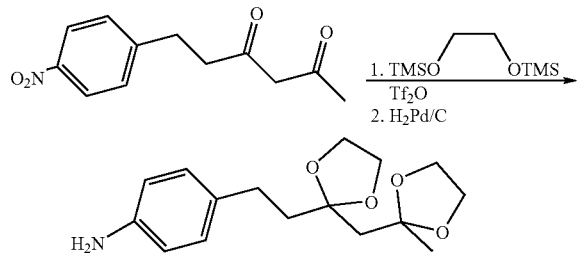

A clean oven dried flask was charged with the 6-(4-nitro-phenyl)-hexane-2,4-dione (3.7 g, 15.72 mmol), dry $CH_2Cl_2$ (20 ml) followed by bisTMS ethylene glycol (38.5 ml, 157.3 ml) were added to the flask and the resulting solution was cooled to −5° C. with stirring under argon. TMSOTf (300 µl) was added to the reaction mixture and the solution was stirred at −5° C. for 6 h. Reaction was quenched with pyridine (10 ml) and poured into sat. $NaHCO_3$. The mixture was extracted with EtOAc and the organic layer was washed with water, brine, dried ($Na_2SO_4$) and concentrated to give a yellow solid. The solid was triturated with hexanes to give a free flowing pale yellow solid (3.5 g, 72%) which was dissolved in EtOAc (50 ml) and hydrogenated on a Parr shaker starting with 50 psi of hydrogen pressure. After two hours the reaction was filtered through a pad of celite, the celite was washed thoroughly with $CH_2Cl_2$MeOH and combined organics were concentrated to give title compound (1.46 g, 100%) as an oil that solidifies upon standing.

Example 23

Synthesis of

Synthesis of 4-[4-(3,5-Dioxo-hexyl)-phenylcarbamoyl]-butyric acid 2,5-dioxo pyrrolidin-1-yl ester (10)

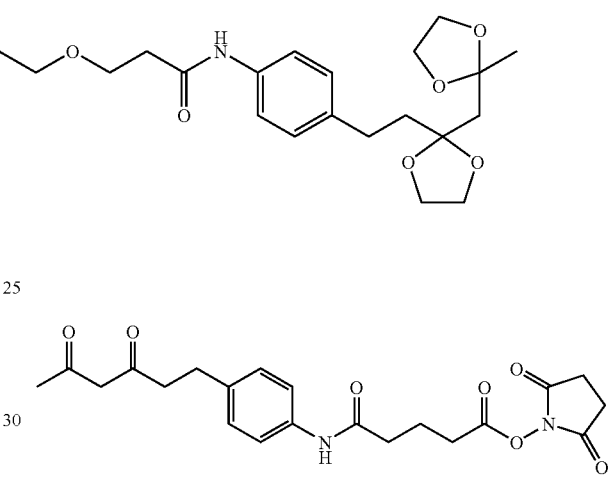

Step 1: 6-(4-Nitro-phenyl)-hexane-2,4-dione (11)

To a reaction vessel (heat and vacuum dried and equipped with a magnetic spin bar) was added tetrahydrofuran and lithium diisopropylamide (2M heptane/ethylbenzene/tetrahydrofuran; 69.4 mL, 138.9 mmol). The solution cooled to −78° C. Pentane-2,4-dione (7.13 mL, 69.4 mmol) was added dropwise and the solution stirred 30 minutes at −78° C. 4-nitrobenzyl bromide (15.0 g, 69.4 mmol) was added in one portion. The solution was removed from the dry-ice/acetone bath, allowed to warm to room temperature and stirred 16 hours. The solution was cooled to approximately 0° C. and the reaction quenched with 1 M HCl. Tetrahydrofuran was removed under reduced pressure. The crude material was taken up into dichloromethane and washed with 1M HCl and brine. The aqueous layers were again washed with dichloromethane. The combined dichloromethane layers were dried ($Na_2SO_4$) and removed under reduced pressure. Gradient flash column chromatography (FCC) was performed using 5% to 15% ethyl acetate/hexanes to afford title compound (8.5 g, 52%; yellow solid). $^1$H NMR ($CDCl_3$): δ 8.14 (d, J=9.0 Hz, 2 H), δ 7.43 (d, J=8.4 Hz, 2 H), δ 5.45 (s, 1H), δ 3.06 (t, J=7.5 Hz, 2H), δ 2.64 (t, J=7.8 Hz, 2H), δ 2.04 (s, 3H).

Step 2: 4-[4-(3,5-Dioxo-hexyl)-phenylcarbamoyl]-butyric acid (12)

200 mL tetrahydrofuran, 6-(4-nitro-phenyl)-hexane-2,4-dione (8.0 g, 34.0 mmol) and dihydro-pyran-2,6-dione (3.88 g, 34.0 mmol) were added to a reaction vessel. The reaction vessel was purged three times with argon. Approximately 200 mg palladium (10 wt % on activated carbon) was added. The reaction vessel was purged again with argon and excess hydrogen introduced via a balloon. Solution stirred 16 hours at room temperature. Hydrogen removed under reduced pressure and catalyst removed by filtration through celite. Tetrahydrofuran removed under reduced pressure to afford title compound (10.5 g, 97%, yellow solid).

Step 3: 4-[4-(3,5-Dioxo-hexyl)-phenylcarbamoyl]-butyric acid 2,5-dioxo pyrrolidin-1-yl ester (10)

To a reaction vessel (heat and vacuum dried and equipped with a magnetic spin bar) was added 4-[4-(3,5-dioxo-hexyl)-phenylcarbamoyl]-butyric acid (10.53 g, 33.0 mmol), N-hydroxysuccinimide (3.8 g, 33.0 mmol) and 1-[3-(dimethylamino)propyl]-3-ethylcarbodiimide hydrochloride (6.3 g, 33.0 mmol) and dichloromethane (250 mL). The solution was stirred under nitrogen at room temperature for 16 hours then washed with 10% citric acid, brine and dried ($Na_2SO_4$). Dichloromethane was removed under reduced pressure. FCC with 70% ethyl acetate/hexanes gave title compound (7.4 g, yellow solid, 54%). $^1$H NMR ($CDCl_3$): δ 7.87 (s, 1H), δ 7.43 (d, J=8.4 Hz, 2H), δ 7.12 (d, J=8.4 Hz, 2H), δ 5.46 (s, 1H), δ 2.89 (t (& m), J=8.1 Hz (for the t), 7H), δ 2.73 (t, J=6.0 Hz, 2H), δ 2.56 (t, J=7.2 Hz, 2H), δ 2.47 (t, J=6.9 Hz, 2H), δ 2.21 (p, J=6.6 Hz, 2H), δ 2.04 (s, 3H).

Example 24

Synthesis of

Synthesis of 3-{2-[2-(2-{4-[4-(3,5-Dioxo-hexyl)-phenylcarbamoyl]-butyrylamino}-ethoxy)-ethoxy]-ethoxy}-propionic acid 2,5-dioxo-pyrrolidin-1-yl ester, (20)

extracted with $CH_2Cl_2$ (2×100 mL). The combined organic layer was washed with HCl (1N, 100 mL), water (100 mL), and dried over $Na_2SO_4$ and the solvent was removed in vacuo to give an oil which corresponds to the title compound that would be used as is for the next step. (M+1)=433.

Step 3: 3-{2-[2-(2-Amino-ethoxy)-ethoxy]-ethoxy}-propionic acid tert-butyl ester $NaN_3$ (35 g, 538 mmol) was added to a stirring solution of 3-{2-[2-(2-tosylsulfonyloxy-ethoxy)-ethoxy]-ethoxy}-propionic acid tert-butyl ester (20 g, 46 mmol) in DMF (150 mL) and the reaction was stirred overnight. Reaction was diluted with water (200 mL) and extracted with EtOAc (4×100 mL). The organic layer was washed with water (100 mL) and brine (100 mL) and dried over $Na_2SO_4$. The solvent was removed in vacuo to give an oil. Column chromatography EtOAc/Hex (1:4) gave an oil which corresponds to the 3-{2-[2-(2-azido-ethoxy)-ethoxy]-ethoxy}-propionic acid tert-butyl ester, (M+1)=304. This oil was hydrogenated using Pd (5% on carbon) in EtOAc under hydrogen (1 atm.) over 3 days. The catalyst was removed by filtration and solvent removed in vacuo to give an oil corresponding to the title compound, (M+1)=278.

Step 4: 3-{2-[2-(2-{4-[4-(3,5-Dioxo-hexyl)-phenylcarbamoyl]-butyrylamino}-ethoxy)-ethoxy]-ethoxy}-propionic acid tert-butyl ester A solution of 4-[4-(3,5-dioxo-hexyl)-phenylcarbamoyl]-butyric acid 2,5-dioxo-pyrrolidin-1-yl ester (1.5 g, 3.6 mmol), 3-{2-[2-(2-amino-ethoxy)-ethoxy]-ethoxy}-propi-

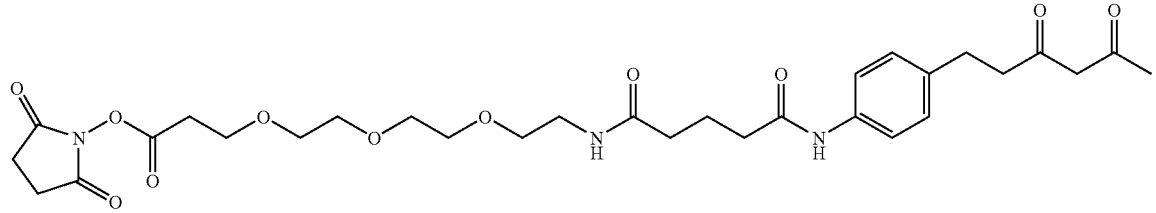

Step 1: 3-{2-[2-(2-Hydroxy-ethoxy)-ethoxy]-ethoxy}-propionic acid tert-butyl ester Na metal (catalytic) was added to a stirring solution of acrylic acid tert-butyl ester (6.7 mL, 46 mmol), and 2-[2-(2-hydroxy-ethoxy)-ethoxy]-ethanol (20.7 g, 138 mmol) in THF (100 mL) at 0° C. and the mixture was stirred overnight. Solvent was removed and the remaining oil dissolved in EtOAc (100 mL). The organic layer was washed with water (3×50 mL), and dried over $Na_2SO_4$ and the solvent removed in vacuo to give an oil which corresponds to the title compound that would be used as is for the next step. (M+1)=279.

Step 2: 3-{2-[2-(2-Tosylsulfonyloxy-ethoxy)-ethoxy]-ethoxy}-propionic acid tert-butyl ester Tosyl chloride (22.3 g, 117 mmol) was added in portions to a stirring solution of 3-{2-[2-(2-hydroxy-ethoxy)-ethoxy]-ethoxy}-propionic acid tert-butyl ester (16.3 g, 58.6 mmol) and pyridine 60 mL in (240 mL) and the mixture was stirred overnight. The reaction was quenched with water (300 mL) and the organic layer was separated. The aqueous layer was onic acid tert-butyl ester (1.0 g, 3.6 mmol) and DIEA (1.3 μL, 7.2 mmol) in $CH_2Cl_2$ (10 mL) was stirred at rt overnight. The solvent was removed in vacuo and the residual oil purified using column chromatography EtOAc/MeOH (95:5) to give the title compound as a transparent oil, (M+1)=579.

Step 5: 3-{2-[2-(2-{4-[4-(3,5-Dioxo-hexyl)-phenyl-carbamoyl]-butyrylamino}-ethoxy)-ethoxy]-ethoxy}-propionic acid 2,5-dioxo-pyrrolidin-1-yl ester 3-{2-[2-(2-{4-[4-(3,5-Dioxo-hexyl)-phenylcarbamoyl]-butyrylamino}-ethoxy)-ethoxy]-ethoxy}-propionic acid tert-butyl ester (400 mg, 0.692 mmol) was dissolved in TFA/$CH_2Cl_2$ (1:1, 3 mL) and the mixture stirred overnight. The solvent was removed to give an oil as the acid intermediate. This oil was dissolved in $CH_2Cl_2$ (4 mL) containing DIEA (569 μL, 3.09 mmol), N-hydroxysuccinimide (119 mg, 1.03 mmol) and EDC (197 mg, 1.0 mmol) and the mixture stirred over the night. The solvent was removed and the residual oil was purified using column chromatography EtOAc/MeOH (95:5) to give an oil as the title compound, (M+1)=620.

Example 25

Synthesis of AA Targeting Compound

Compound of EXAMPLES 17 or 18 can be linked to antibody 38C2 by the following procedure: One mL antibody 38C2 in phosphate buffered saline (10 mg/mL) is added to 12 μL of a 10 mg/mL stock solution of AA targeting agent and the resulting mixture maintained at room temperature for 2 hours prior to use.

Example 26

Synthesis of

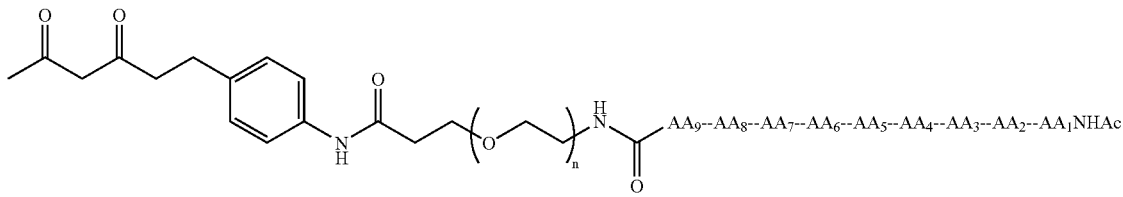

is provided in FIG. 27. While this EXAMPLE uses the compound of EXAMPLE 12, it could also sufficiently employ the compounds of EXAMPLE 13.

Example 27

C. Rader, et al., J. Mol. Biol. 332:889-899 (2003) details one method of making h38c2. The following details the results, materials and methods in this reference.

Humanization Human $V_k$ gene DPK-9 and human $J_k$ gene JK4 were used as frameworks for the humanization of the kappa light chain variable domain, and human $V_H$ gene DP-47 and human $J_H$ gene $J_H4$ are used as frameworks for the humanization of the heavy chain variable domain of m38C2. All complementarity determining region (CDR) residues as defined by Kabat et al., as well as defined framework residues in both light chain and heavy chain variable domain, were grafted from m38C2 onto the human framework. The selection of grafted framework residues may be based on the crystal structure of mouse mAb 33F12 Fab (PDB 1AXT). mAb 33F12 Fab shares a 92% sequence homology with m38c2 in the variable domains and identical CDR lengths. Furthermore, both 33F12 and m38C2 have similar catalytic activity. Framework residues consisted of five residues in the light chain and seven residues in the heavy chain (FIG. 7A) and encompassed the residues that are likely to participate directly or indirectly in the catalytic activity of m38C2. These include the reactive lysine of m38C2, $Lys^{H93}$, which is positioned in framework region 3 (FR3) of the heavy chain. Six residues, $Se^{H35}$, $Val^{H37}$, $Trp^{H47}$, $Trp^{H103}$, and $Phe^{L98}$, which are conserved between mouse mAbs 33F12 and 38C2, are within a 5-Å radius of the E amino group of $Lys^{H93}$. These residues were also conserved in the humanization. $LyS^{H93}$ lies at the bottom of a highly hydrophobic substrate binding sites of mouse mAbs 33F12 and 38C2. In addition to CDR residues, a number of framework residues line this pocket. Among these, $Leu^{L37}$, $Gln^{L42}$, $Ser^{L43}$, $Val^{L85}$, $Phe^{L87}$, $Val^{H5}$, $Ser^{H40}$, $Glu^{H42}$, $Gly^{H88}$, $Ile^{H89}$, and $Thr^{H94}$ were grafted onto the human framework.

Expression By fusing the humanized variable domains to human constant domains $C_k$ and $C_{\gamma1}1$, h38C2 was initially generated as Fab expressed in E. coli. Next, h38c2 IgG was formed from h38c2 Fab using the PIGG vector engineered for human IgG1 expression in mammalian cells. Supernatants from transiently transfected human 293T cells were subjected to affinity chromatography on recombinant protein A, yielding approximately 1 mg/L h38C2 IgG1. Purity was established by SDS-PAGE followed by Coomassie blue staining.

β-Diketone Compounds—

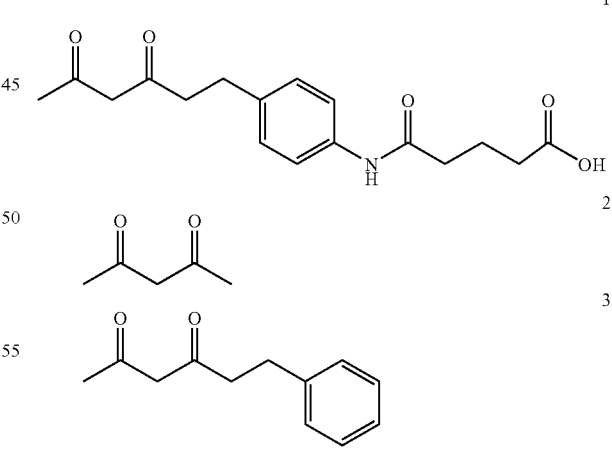

The enaminone formed by the covalent addition of a β-diketone with m38c2 has a characteristic UV absorbance at $\lambda_{max}$=318 nm. Like m38C2 IgG, h38C2 IgG showed the characteristic enaminone absorbance after incubation with β-diketone. As a negative control, recombinant human anti-HIV-1 gp120 mAb b12 with the same IgG1 isotype as h38C2 but without reactive lysine, did not reveal enaminone absorbance after incubation with β-diketone 2. For a quantitative comparison of the binding of β-diketones to m38C2 and h38C2, the authors used a competition ELISA. The antibodies were incubated with increasing concentrations of β-diketones 2 and 3 and assayed against immobilized BSA-conjugated β-diketone 1. The apparent equilibrium dissociation constants were 38 μM (m38C2) and 7.6 μM (h38C2) for β-diketone 2 and 0.43 μM (m38C2) and 1.0 μM (h38C2) for β-diketone 3, revealing similar β-diketone binding properties for mouse and humanized antibody (FIG. 6).

Molecular modeling—A molecular model of h38C2 Fab was constructed by homology modeling using the crystal structure of a related aldolase antibody, mouse 33F12 Fab (Protein Data Bank ID: 1AXT), as a template. The crystal structure of mouse 33F12 Fab was previously determined at a resolution of 2.15 Å[4] Alignment of mouse 33F12 and 38C2 amino acid sequences using the HOMOLOGY module within INSIGHT II software (Accelrys) confirmed that both sequences are highly homologous. They differ from each other by 19 out of 226 amino acids in the two variable domains, and their CDRs share the same lengths. In addition to the high sequence homology, both structures exhibit considerable structural similarity, as observed by a low-resolution crystal structure of 38C2. Residues in the model were mutated to conform to the h38C2 amino acid sequence and sidechains were placed based on standard rotamers. This model was then minimized with the DISCOVER module in INSIGHT II using 100 steps each of steepest descent minimization followed by conjugate gradient minimization.

Construction of h38C2 Fab—The sequences of the variable light and heavy chain domains of m38C2 (SEQ ID NOs: 32 and 33, respectively) as well as the sequences of human germline sequences DPK-9 (SEQ ID NO:36), JK4 (SEQ ID NO:38), DP-47 (SEQ ID NO:37), and JH4 (SEQ ID NO:39) (V BASE; http://vbase.mrc-cpe.cam.ac.uk/) were used to design overlapping oligonucleotides for the synthetic assembly of humanized $V_k$ and $V_H$, respectively. N-glycosylation sites with the sequence NXS/T as well as internal restriction sites HindIII, XbaI, SacI, ApaI, and SfiI were avoided. PCR was carried out by using the Expand High Fidelity PCR System (Roche Molecular Systems). The humanized $V_k$ oligonucleotides were: L flank sense (Rader, C., Ritter, G., Nathan, S., Elia, M., Gout, I., Junbluth, A. A., J. Biol. Chem. 275: 13668-13676 (2000)); h38C2L1 (sense; 5'-GAGCTC-CAGATGACCCAGTCTCCATCCTCCCT-GTCTGCATCTGTAGGTGACC GCGTCACCAT-CACTTG-3') (SEQ ID NO:18); h38C2L2 (antisense; 5'-ATTCAGATATGGGCTGCCATAAGTGTG-CAGGAGGCTCTGACTGGAGCGGCA AGTGATGGT-GACGCGGTC-3') (SEQ ID NO:19); h38C2L3 (sense; 5'-TATGGCAGCCCATATCTGAATTGG-TATCTCCAGAAACCAGGCCAGTCTCCTA AGCTCCT-GATCTAT-3') (SEQ ID NO:20); h38C2L4 (antisense; 5'-CT-GAAACGTGATGGGACACCACTGAAACGATTGGAC ACTTTATAGATCAGG AGCTTAGGAGACTG-3') (SEQ ID NO:21); h38C2L5 (sense; 5'-AGTGGTGTCCCAT-CACGTTTCAGTGGCAGTGGTTCTGGCA-CAGATTTCACTC TCACCATCAGCAGTCTGCAACCT-GAAGATTTTGCAGTG-3') (SEQ ID NO:22); h38C2L6 (antisense; 5'-GATCTCCACCTTGGTCCCTCCGC-CGAAAGTATAAGGGAGGTGGGTGCCCTG ACTACA-GAAGTACACTGCAAAATCTTCAGGTTGCAG-3') (SEQ ID NO:23); L antisense flank (C. Rader et al., J. Biol. Chem. 275:13668-13676 (2000)). The humanized $V_H$ oligonucleotides were: H flank sense (C. Rader et al., J. Biol. Chem. 275:13668-13676 (2000)); h38C2H1 (sense; 5'-GAGGTG-CAGCTGGTGGAGTCTGGCGGTGGCTTGG-TACAGCCTGGCGGTTCC CTGCGCCTCTCCTGTG-CAGCCTCTGGCT-3') (SEQ ID NO:24); h38C2H2 (antisense; 5'-CTCCAGGCCCTTCTCTGGAGACTGGCG-GACCCAGCTCATCCAATAGTTGCTA AAGGTGAAGC-CAGAGGCTGCACAGGAGAG-3') (SEQ ID NO:25); h38C2H3 (sense; 5'-TCTCCAGAGAAGGGCCTG-GAGTGGGTCTCAGAGATTCGTCTGCGCAGTGAC AACTACGCCACGCACTATGCAGAGTCTGTC-3') (SEQ ID NO:26); h38C2H4 (antisense; 5'-CAGATACAGCGTGT-TCTTGGAATTGTCACGGGAGATGGT-GAAGCGGCCCTT GACAGACTCTGCATAGTGCGTG-3') (SEQ ID NO:27); h38C2H5 (sense; 5'-CAATTCCAAGAACACGCTGTATCTG-CAAATGAACAGCCTGCGCGCCGAGGA CACGGGCATTTATTACTGTAAAACG-3') (SEQ ID NO:28); h38C2H6 (antisense; 5'-TGAGGAGACGGTGAC-CAGGGTGCCCTGGCCCCAGTAGCT-GAAACTGTAGAA GTACGTTTTACAGTAATAAATGC-CCGTG-3') (SEQ ID NO:29); H flank antisense (C. Rader et al., J. Biol. Chem. 275:13668-13676 (2000)). Following assembly, humanized $V_k$ and $V_H$ were fused to human $C_k$ and $C_{\gamma 1}1$, respectively, and the resulting light chain and heavy chain fragment were fused and SfiI-cloned into phagemid vector pComb3X as described (C. Rader et al, J. Biol. Chem. 275:13668-13676 (2000); C. F. Barbas 3rd et al., Phage Display. A laboratory manual, Cold Spring Harbor Laboratory, Cold Spring Harbor N.Y. (2001)). To enrich for clones with the correct h38C2 sequence, Fab were displayed on phage and selected by one round of panning against the immobilized β-diketone 1 (JW) conjugated to BSA. Soluble Fab were produced from single clones and tested for binding to immobilized JW-BSA by ELISA using donkey anti-human F(ab')₂ polyclonal antibodies conjugated to horseradish peroxidase (Jackson ImmunoResearch Laboratories) as secondary antibody. Light chain and heavy chain encoding sequences of positive clones were analyzed by DNA sequencing using the primers OMPSEQ and PELSEQ (C. F. Barbas 3rd et al., Phage Display: A laboratory manual, Cold Spring Harbor Laboratory, Cold Spring Harbor N.Y., (2001)), respectively, to confirm the assembled $V_k$ and $V_H$ sequences of h38C2.

Construction, production, and purification of h38C2 IgG1—The recently described vector PIGG (C. Rader et al, FASEB J., 16:2000-2002 (2002)) was used for mammalian expression of h38C2 IgG1. The mammalian expression vector PIGG-h38c2 is illustrated in FIG. 23. The 9 kb vector comprises heavy chain γ1 and light chain κ expression cassettes driven by a bidirectional CM promoter construct. Using primers PIGG-h38C2H (sense; 5'-GAGGAGGAGGAG-GAGGAGCTCACTCCGAGGTGCAGCTG-GTGGAGTCTG-3') (SEQ ID NO:30) and GBACK (C. F. Barbas 3rd et al, Phage Display; A laboratory manual, Cold Spring Harbor Laboratory, Cold Spring Harbor N.Y. (2001)), the VH coding sequence from h38C2 Fab in phagemid vector pComb3X was amplified, digested with SacI and ApaI, and cloned into the appropriately digested vector PIGG. Using primers PIGG-h38C2L (sense: 5'-GAGGAGGAGGAG-GAGAAGCTTGTTGCTCTGGATCTCTGGT-GCCTACGGGA GCTCCAGATGACCCAGTCTCC-3') (SEQ ID NO:31) and LEADB (C. F. Barbas 3rd et al, Phage Display. A laboratory manual, Cold Spring Harbor Laboratory, Cold Spring Harbor N.Y. (2001)) the light chain coding sequence from h38C2 Fab in phagemid vector pComb3X was amplified, digested with HindIII and XbaI, and cloned into the appropriately digested vector PIGG that already contained the h38C2 heavy chain. Intermediate and final PIGG vector constructs were amplified in E. coli strain SURE (Stratagene) and prepared with the QIAGEN Plasmid Maxi Kit. h38C2 IgG1 were produced from the prepared final PIGG vector construct by transient transfection of human 293T cells using Lipofectamine 2000 (Invitrogen). Transfected cells were maintained in GIBCO 10% ultra-low IgG (<0.1%) FCS (Invitrogen) in RPMI 1640 (Hyclone) for 2 weeks. During this time, the medium was collected and replaced three times. The collected medium was subjected to affinity chromatography on a recombinant Protein A HiTrap column (Amersham Biosciences). This purification step yielded 2.45 mg h38C2 IgG1 from 2,300 mL collected medium as determined by measuring the optical density at 280 nm using an Eppendorf BioPhotometer. Following dialysis against PBS in a Slide-A-Lyzer 10K dialysis cassette (Pierce), the antibody was concentrated to 760 μg/mL using an Ultrafree-15 Centrifugal Filter Device (UFV2BTK40; Millipore), and sterile filtered through a 0.2-μm Acrodisc 13MM S-200 Syringe Filter (Pall). The final yield was 2.13 mg (87%). Purified h38C2 IgG1 was confirmed by nonreducing SDS-PAGE followed by Coomassie Blue staining.

Enaminone formation—Antibody (h38C2 IgG1 or b12 IgG1) was added to β-diketone 2 to a final concentration of 25 μM antibody binding site and 125 μM β-diketone. This mixture was incubated at room temperature for 10 minutes before a UV spectrum was acquired on a SpectraMax Plus 384 UV plate reader (Molecular Devices) using SOFTmax Pro software (version 3.1.2).

Binding assays—Unless noted otherwise, all solutions were phosphate buffered saline (pH 7.4). A 2× solution of either β-diketone 2 or 3 (50 μL) was added to 50 μL of the antibody (either h38C2 or m38C2) and allowed to incubate at 37° C. for 1 hr. Solutions were mixed by pipetting. Final concentrations of antibody were 0.4 to 8 nM antibody binding site, and final concentrations of β-diketones 2 and 3 were $10^{-9}$ to $10^{-2}$ M and $10^{-10}$ to $10^{-4}$ M, respectively. Each well of a Costar 3690 96-well plate (Corning) was coated with 100 ng of the BSA conjugate of β-diketone 1 in TBS. Wells were then blocked with 3% (w/v) BSA in TBS. Then, 50 μL of the antibody/β-diketone mixture was added, followed by 50 μL of a 1:1,000 dilution of either goat anti-human Fc IgG polyclonal antibodies (Pierce) or rabbit anti-mouse Fc IgG polyclonal antibodies (Jackson ImmunoResearch Laboratories) conjugated to horseradish peroxidase. This was followed by 50 μL ABTS substrate solution. Between each addition, the plate was covered, incubated at 37° C. for 1 hr, and then washed five times with deionized H$_2$O. The absorbance at 405 nm was monitored as described above until the reaction with no β-diketone reached an appropriate value (0.5<A$_{405}$<1.0). For each well, the fractional inhibition of ELISA signal ($v_i$) was calculated using equation i:

$$v_i = (A_o - A_i)/(A_o) \quad \text{(i)}$$

where $A_o$ is the ELISA absorbance obtained in the absence of β-diketone and $A_i$ is the absorbance obtained in the presence of β-diketone. For monovalent binding proteins, the fraction of antibody bound to soluble β-diketone (f) is equal to $v_i$. However, the IgG antibody is bivalent, and the ELISA signal is inhibited only by the presence of doubly liganded antibody and not by monovalent binding. Therefore, the Stevens correction for a bivalent antibody was used:

$$f_i = (v_i)^{1/2} \quad \text{(ii)}$$

The following relationship was used to determine the apparent equilibrium dissociation constant (modified from [ref. 37]):

$$f_i = f_{min} + (f_{max} - f_{min})(1 + K_D/a_0)^{-1} \quad \text{(iii)}$$

where $a_0$ corresponds to the total β-diketone concentration, $K_D$ is the equilibrium dissociation constant, and $f_{min}$ and $f_{max}$ represent the experimentally determined values when the antibody binding sites are unoccupied or saturated, respectively. Because this equation is only valid when the $K_D$ values are at least 10× higher than the antibody concentration, it was verified that the $K_D$ values determined from equation iii met this criterion. Data were fit using a nonlinear least-squares fitting procedure of KaleidaGraph (version 3.0.5, Abelbeck software) with $K_D$, $f_{max}$, and $f_{min}$ as the adjustable parameters and normalized using equation iv:

$$f_{norm} = (f_i - f_{min})/(f_{max} - f_{min}) \quad \text{(iv)}$$

Example 28

The BAMVEC cell migration assay and Matrigel plug angiogenesis assay were peformed on the following compounds according the protocols detailed above. Compounds and their corresponding assay results are presented. Antibody is h38c2 IgG1.

Compound-1

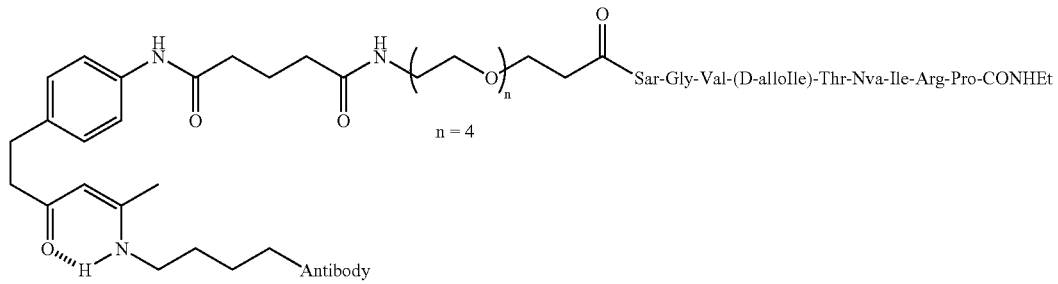

BAMVEC Migration IC$_{50}$<100 μM

Matrigel plug angiogenesis assay: >35% inhibition at 10 mg/Kg, twice a week dose Compound-2
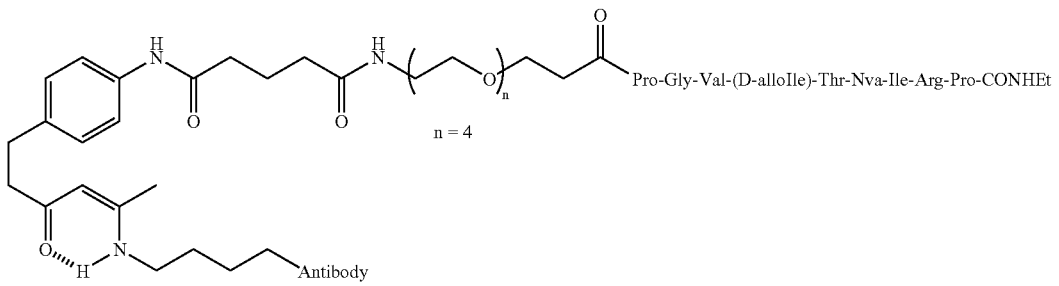
BAMVEC Migration IC$_{50}$<100 µM
Matrigel plug angiogenesis assay: >35% inhibition at
  3 mg/Kg, twice a week dose
Compound-3
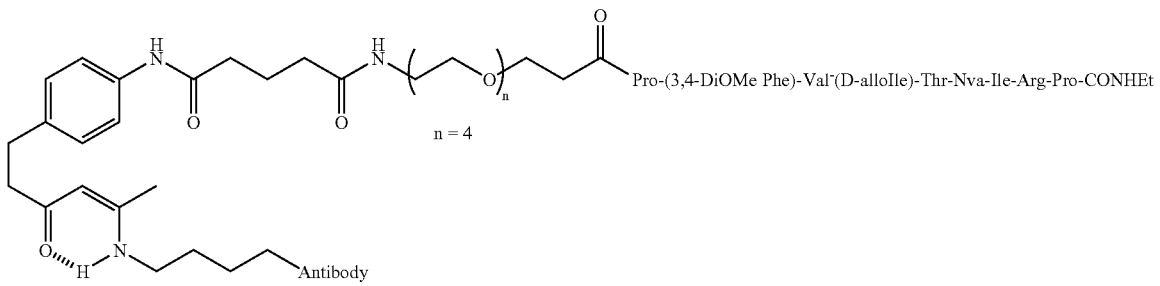
BAMVEC Migration IC$_{50}$<100 µM
Matrigel plug angiogenesis assay: >35% inhibition at
  3 mg/Kg, twice a week dose
Compound-4
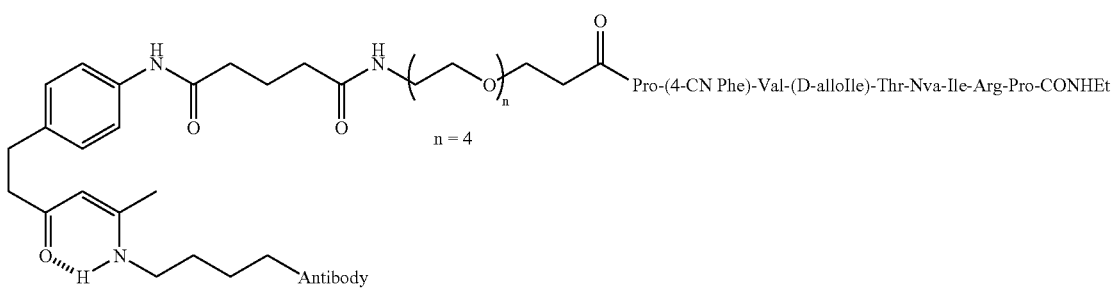

BAMVEC Migration IC$_{50}$<100 μM
Matrigel plug angiogenesis assay =20% inhibition at 10 mg/Kg, twice a week dose
Compound-5
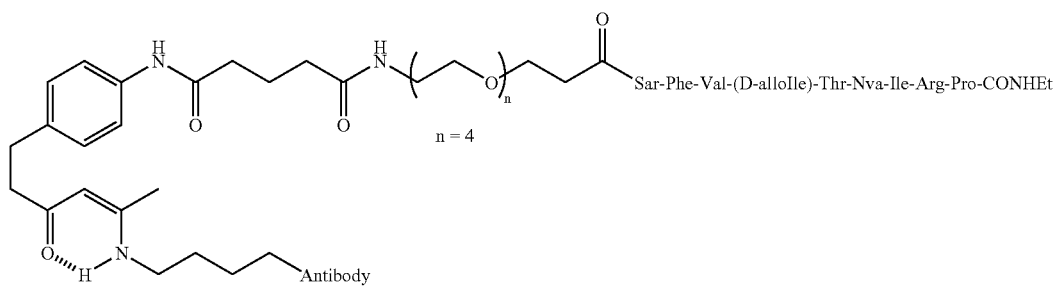
BAMVEC Migration IC$_{50}$=<100 μM
Matrigel plug angiogenesis assay: >35% inhibition at 10 mg/Kg, twvice a week dose
Compound-6
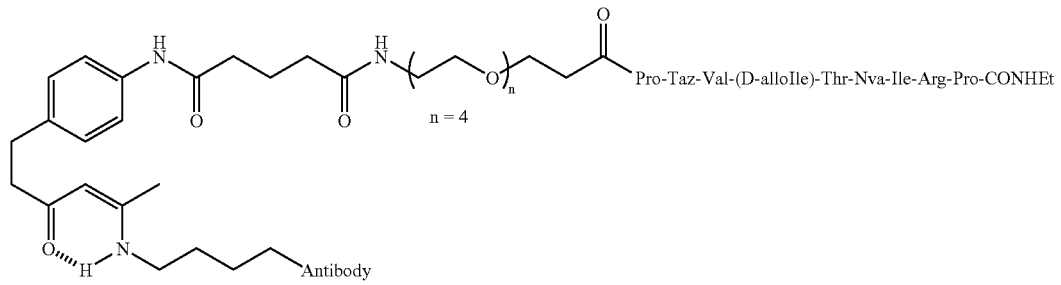
BAMVEC Migration IC$_{50}$<100 μM
Matrigel plug angiogenesis assay: >35% inhibition at 10 mg/Kg, twice a week dose
Compound-7
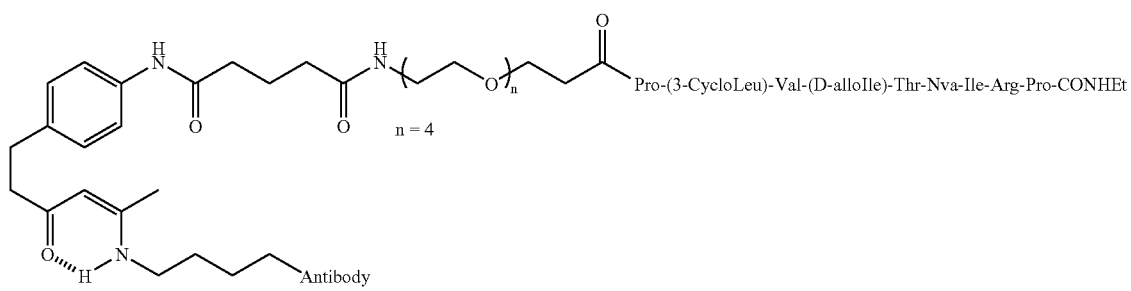

BAMVEC Migration IC$_{50}$<100 μM
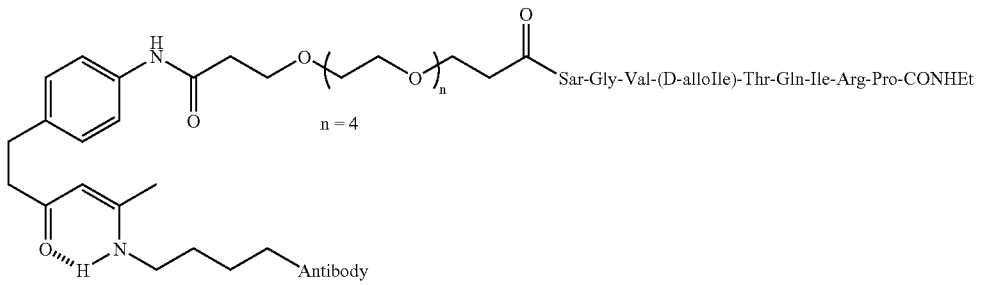
Compound 8
BAMVEC Migration IC$_{50}$<100 μM
Matrigel plug angiogenesis assay: >35% inhibition at 10 mg/kg dose
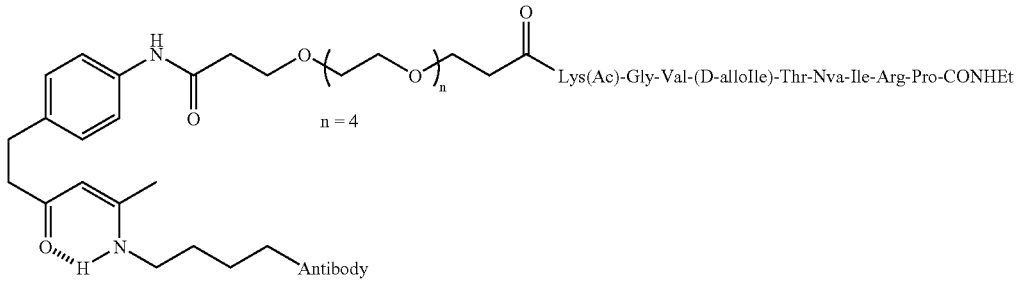
Compound 9
BAMVEC Migration IC$_{50}$<100 μM
Matrigel plug angiogenesis assay:
>35% inhibition at 10 mg/kg, twice a week dose
>35% inhibition at 3 mg/Kg, twice a week dose
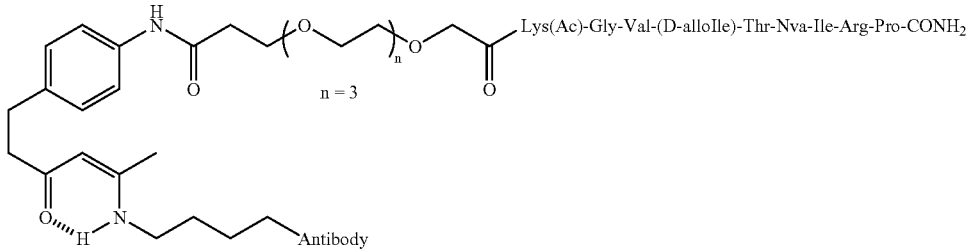
Compound 10

BAMVEC Migration IC$_{50}$<100 μM
Matrigel plug angiogenesis assay:
>35% inhibition at 10 mg/Kg, twice a week dose
>35% inhibition at 3 mg/Kg, twice a week dose
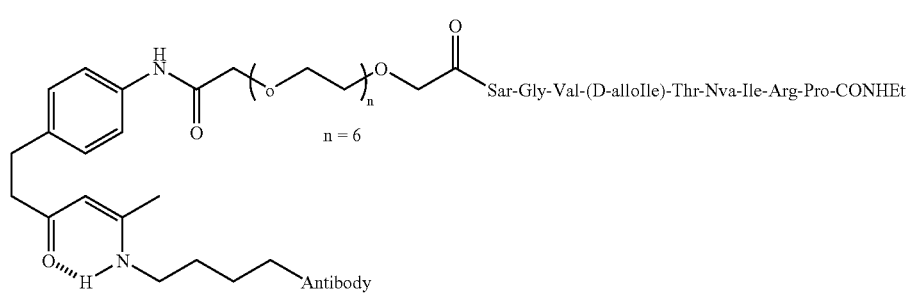
Compound 11
BAMVEC Migration IC$_{50}$<100 μM
Matrigel plug angiogenesis assay: 35% inhibition at 10 mg/Kg, twice a week dose
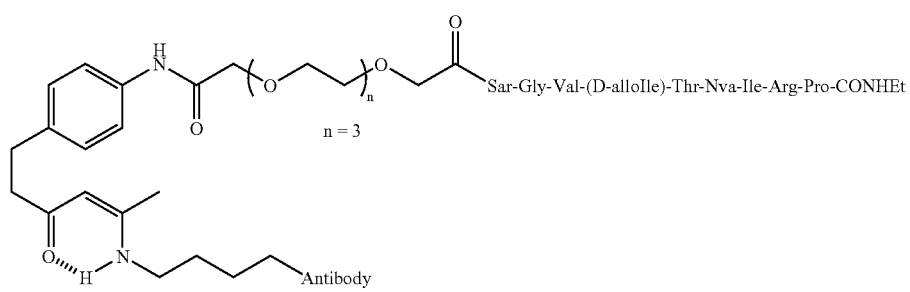
Compound 12
BAMVEC Migration IC$_{50}$<100 μM
Matrigel plug angiogenesis assay: >35% inhibition at 10 mg/Kg
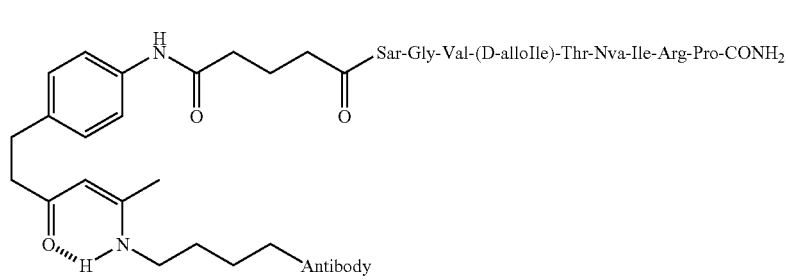
Compound 13

BAMVEC Migration IC$_{50}$<100 μM
Matrigel plug angiogenesis assay: >35% inhibition at 10 mg/kg dose
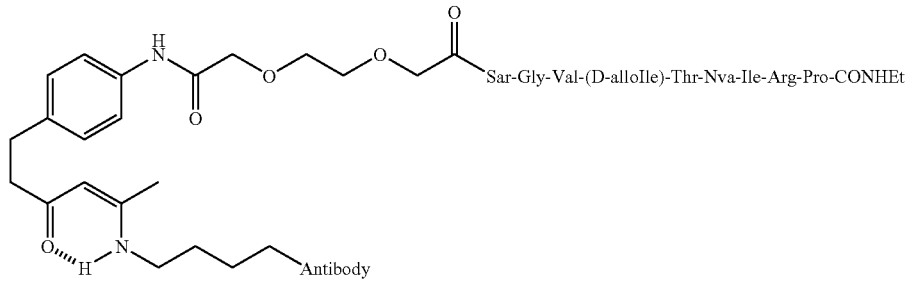
Compound 14
Matrigel plug angiogenesis assay: >35% inhibition at 3 mg/kg dose
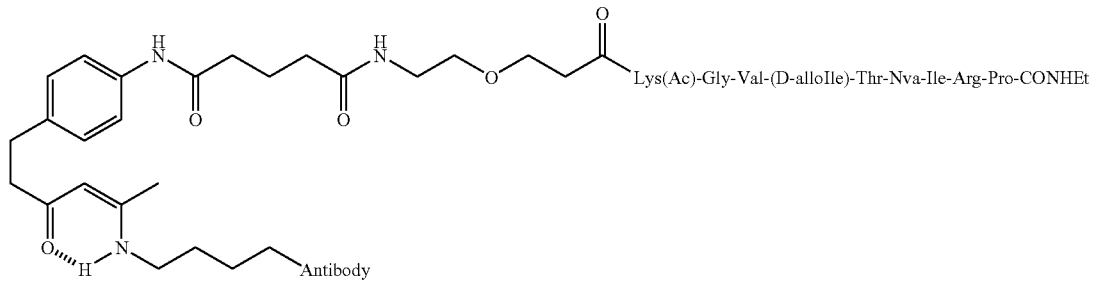
Compound 15
BAMVEC Migration IC$_{50}$<100 μM
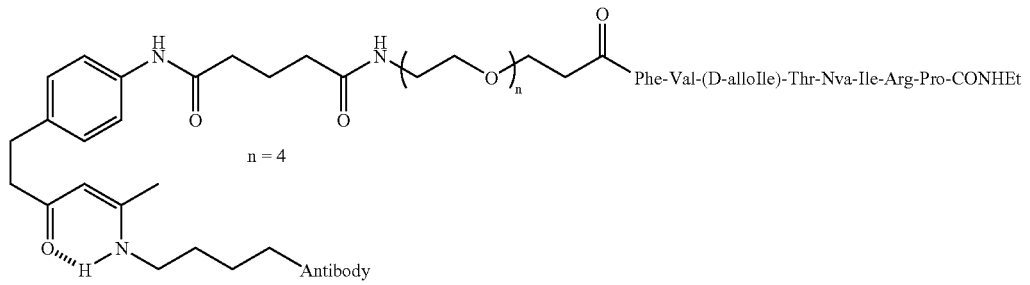
Compound 16

BAMVEC Migration IC$_{50}$<100 μM
Matrigel plug angiogenesis assay:>35% inhibition with 10 mg/Kg dose
Compound 17
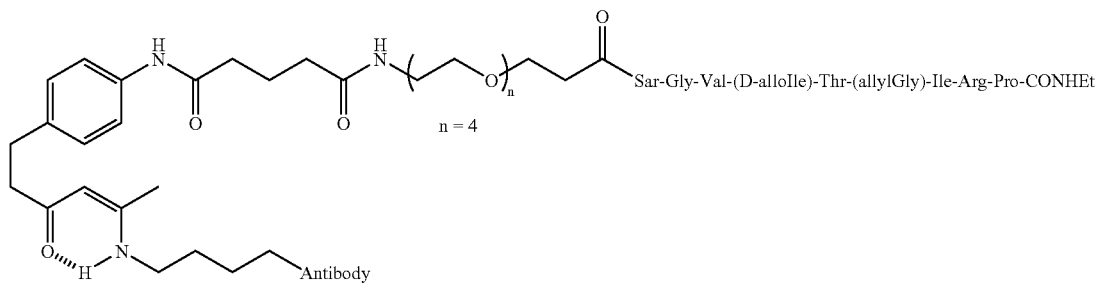
BAMVEC Migration IC$_{50}$<100 μM
Compound 18
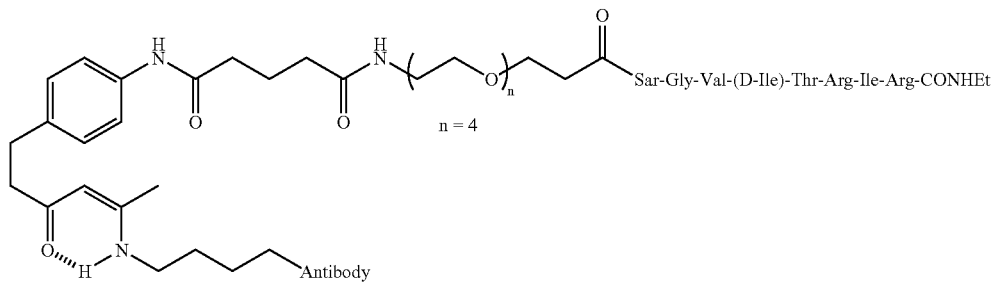
BAMVEC Migration IC$_{50}$<100 μM
Compound 19
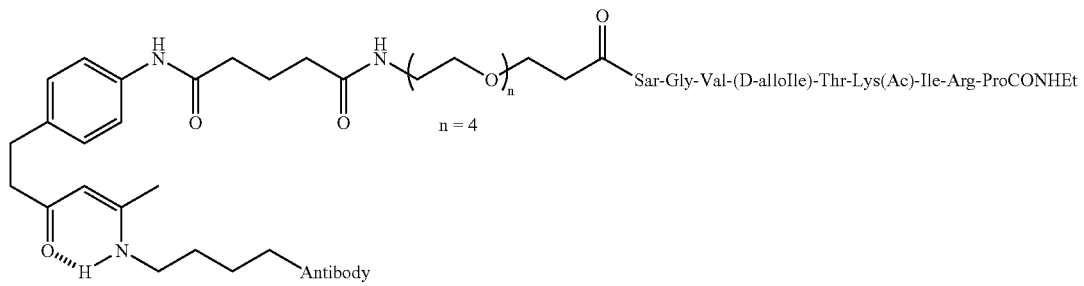

BAMVEC Migration IC$_{50}$<100 µM

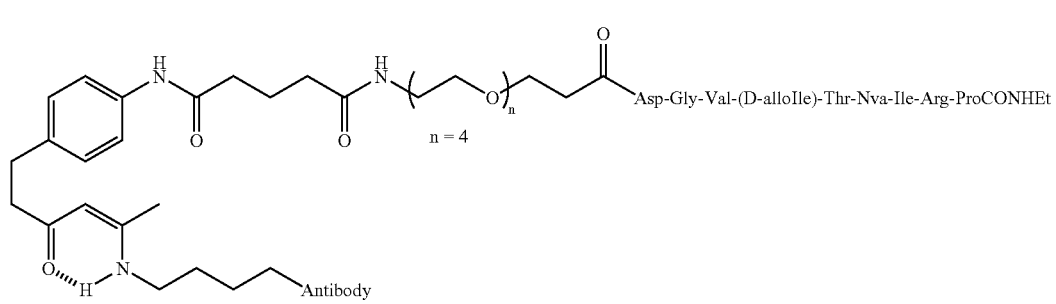

Compound 20

BAMVEC Migration IC$_{50}$<100 µM

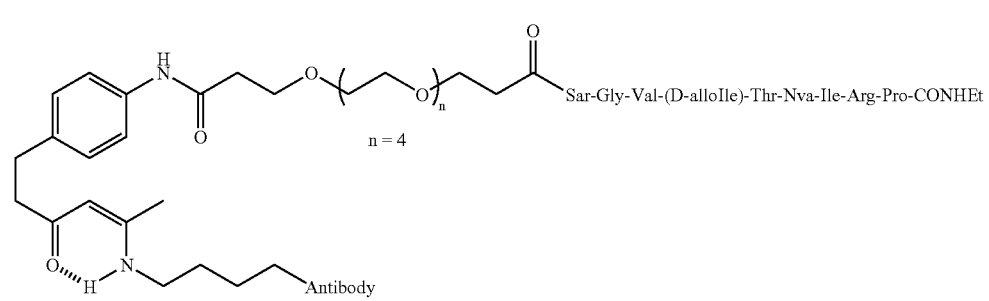

Compound 21

BAMVEC Migration IC$_{50}$<100 µM
Matrigel plug angiogenesis assay:
>35% inhibition at 10 mg/kg, twice a week dose,
>35% inhibition at 3 mg/Kg, twice a week dose Example 29

Synthesis of

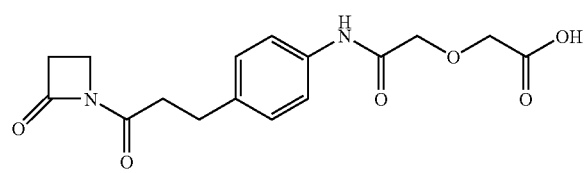

is provided in FIG. 28.

The invention thus has been disclosed broadly and illustrated in reference to representative embodiments described above. Those skilled in the art will recognize that various modifications can be made to the present invention without departing from the spirit and scope thereof. All publications, patent applications, and issued patents, are herein incorporated by reference to the same extent as if each individual publication, patent application or issued patent were specifically and individually indicated to be incorporated by reference in its entirety. Definitions that are contained in text incorporated by reference are excluded to the extent that they contradict definitions in this disclosure.

---

The invention claimed is:
1. A compound having the formula:

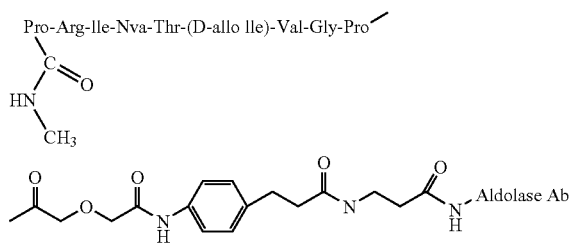

or a pharmaceutically acceptable salt thereof.

2. A compound having the formula:

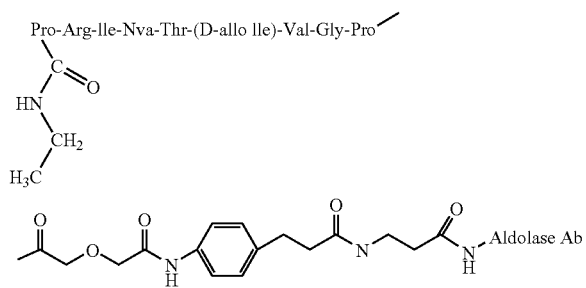

or a pharmaceutically acceptable salt thereof.

3. The compound of claim 1, wherein said aldolase antibody is h38c2 IgG1.

4. The compound of claim 1, wherein said aldolase antibody comprises a light chain comprising the amino acid sequence set forth in SEQ ID NO:40 and a heavy chain comprising the amino acid sequence set forth in SEQ ID NO:41.

5. The compound of claim 2, wherein said aldolase antibody is h38c2 IgG1.

6. The compound of claim 2, wherein said aldolase antibody comprises a light chain comprising the amino acid sequence set forth in SEQ ID NO:40 and a heavy chain comprising the amino acid sequence set forth in SEQ ID NO:41.

7. A pharmaceutical composition comprising a therapeutically effective amount of the compound of claim 1.

8. A pharmaceutical composition comprising a therapeutically effective amount of the compound of claim 2.

9. The pharmaceutical composition of claim 7, further comprising a therapeutically effective amount of one or more chemotherapeutic agents.

10. The pharmaceutical composition of claim 9, wherein the one or more chemotherapeutic agents are selected from the group consisting of 5-flurouracil, irinotecan, oxaliplatin, bevacizumab, and cetuximab.

11. The pharmaceutical composition of claim 8, further comprising a therapeutically effective amount of one or more chemotherapeutic agents.

12. The pharmaceutical composition of claim 11, wherein the one or more chemotherapeutic agents are selected from the group consisting of 5-flurouracil, irinotecan, oxaliplatin, bevacizumab, and cetuximab.

* * * * *